US012286660B2

United States Patent
Koepke

(10) Patent No.: US 12,286,660 B2
(45) Date of Patent: *Apr. 29, 2025

(54) MICROBIAL FERMENTATION FOR THE PRODUCTION OF TERPENES

(71) Applicant: LanzaTech NZ, Inc., Skokie, IL (US)

(72) Inventor: Michael Koepke, Chicago, IL (US)

(73) Assignee: LanzaTech, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/823,471

(22) Filed: Aug. 30, 2022

(65) Prior Publication Data

US 2023/0013524 A1    Jan. 19, 2023

Related U.S. Application Data

(63) Continuation of application No. 17/095,064, filed on Nov. 11, 2020, now Pat. No. 11,459,589, which is a continuation of application No. 15/867,306, filed on Jan. 10, 2018, now Pat. No. 10,913,958, which is a continuation of application No. 14/656,827, filed on Mar. 13, 2015, now abandoned, which is a continuation of application No. 13/909,012, filed on Jun. 3, 2013, now abandoned.

(60) Provisional application No. 61/654,412, filed on Jun. 1, 2012.

(51) Int. Cl.
| | | |
|---|---|---|
| C12P 5/00 | (2006.01) | |
| C12N 1/21 | (2006.01) | |
| C12N 9/04 | (2006.01) | |
| C12N 9/10 | (2006.01) | |
| C12N 9/12 | (2006.01) | |
| C12N 9/88 | (2006.01) | |
| C12N 15/52 | (2006.01) | |
| C12N 15/74 | (2006.01) | |
| C12P 7/42 | (2006.01) | |
| C12P 9/00 | (2006.01) | |

(52) U.S. Cl.
CPC ............ *C12P 5/007* (2013.01); *C12N 9/0006* (2013.01); *C12N 9/1022* (2013.01); *C12N 9/1025* (2013.01); *C12N 9/1029* (2013.01); *C12N 9/1085* (2013.01); *C12N 9/1205* (2013.01); *C12N 9/1229* (2013.01); *C12N 9/88* (2013.01); *C12N 15/52* (2013.01); *C12N 15/74* (2013.01); *C12P 7/42* (2013.01); *C12P 9/00* (2013.01); *C12Y 101/01088* (2013.01); *C12Y 101/01267* (2013.01); *C12Y 117/07001* (2013.01); *C12Y 202/01007* (2013.01); *C12Y 203/01009* (2013.01); *C12Y 203/0301* (2013.01); *C12Y 205/0101* (2013.01); *C12Y 205/0109* (2013.01); *C12Y 207/01036* (2013.01); *C12Y 207/01148* (2013.01); *C12Y 207/04002* (2013.01); *C12Y 207/0706* (2013.01); *C12Y 401/01033* (2013.01); *C12Y 402/03027* (2013.01); *C12Y 402/03046* (2013.01); *C12Y 406/01012* (2013.01); *C12Y 503/03002* (2013.01); *Y02E 50/30* (2013.01)

(58) Field of Classification Search
None
See application file for complete search history.

(56) References Cited

U.S. PATENT DOCUMENTS

| 7,927,862 | B2* | 4/2011 | Millis | ........................ | C12P 7/04 |
| | | | | | 435/254.2 |
| 9,752,163 | B2 | 9/2017 | Marliere | | |
| 2009/0082495 | A1* | 3/2009 | Zimmer | ................ | B60C 1/0016 |
| | | | | | 524/109 |
| 2012/0045807 | A1 | 2/2012 | Simpson | | |
| 2012/0157725 | A1* | 6/2012 | McAuliffe | ............... | B01J 31/10 |
| | | | | | 585/254 |
| 2013/0122562 | A1 | 5/2013 | Aldor | | |
| 2014/0234926 | A1* | 8/2014 | Beck | ........................ | C12P 7/065 |
| | | | | | 435/146 |
| 2014/0256008 | A1 | 9/2014 | Boisart, Sr. | | |
| 2017/0198311 | A1 | 7/2017 | Beck | | |

FOREIGN PATENT DOCUMENTS

| CA | 3012054 | A1 | 9/2017 |
| CN | 1630718 | A | 6/2005 |
| EP | 2516656 | B1 | 6/2014 |
| WO | 2007117157 | A1 | 10/2007 |
| WO | 2008115080 | A1 | 9/2008 |
| WO | 2009094485 | A1 | 7/2009 |
| WO | 2009151342 | A1 | 12/2009 |
| WO | 2010148150 | A1 | 12/2010 |

(Continued)

OTHER PUBLICATIONS

Abrini et al., Clostridium autoethanogenum, Arch. Microbiol. 161, 1994, 345-51. (Year: 1994).*

Mau et al., Cytochrome P450 oxygenases of monoterpene metabolism, Phytochem. Rev. 5 , 2006, 373-83. (Year: 2006).*

(Continued)

Primary Examiner — Todd M Epstein

(57) ABSTRACT

The invention provides a method for producing a terpene or a precursor thereof by microbial fermentation. Typically, the method involves culturing a recombinant bacterium in the presence of a gaseous substrate whereby the bacterium produces a terpene or a precursor thereof, such as mevalonic acid, isopentenyl pyrophosphate, dimethylallyl pyrophosphate, isoprene, geranyl pyrophosphate, farnesyl pyrophosphate, and/or farnesene. The bacterium may comprise one or more exogenous enzymes, such as enzymes in mevalonate, DXS, or terpene biosynthesis pathways.

2 Claims, 20 Drawing Sheets
Specification includes a Sequence Listing.

(56) References Cited

FOREIGN PATENT DOCUMENTS

| WO | 2011112103 | A1 | 9/2011 |
|---|---|---|---|
| WO | 2012015317 | A1 | 2/2012 |
| WO | 2012019169 | A1 | 2/2012 |
| WO | 2012026833 | A1 | 3/2012 |
| WO | 2012034023 | A2 | 3/2012 |
| WO | 2012024522 | A3 | 5/2012 |
| WO | 2013036147 | A2 | 3/2013 |
| WO | 2013180581 | A1 | 12/2013 |
| WO | 2013180584 | A1 | 12/2013 |
| WO | 2013185123 | A1 | 12/2013 |
| WO | 2013191567 | A1 | 12/2013 |
| WO | 2014036152 | A1 | 3/2014 |
| WO | 2016094334 | A1 | 6/2016 |
| WO | 2017066498 | A1 | 4/2017 |
| WO | 2019126400 | A1 | 6/2019 |

OTHER PUBLICATIONS

Zhou et al., Engineering *Escherichia coli* for selective geraniol production with minimized endogenous dehydrogenation, J. Biotechnol. 169, 2014, 42-50. (Year: 2014).*

Park et al., Efficient production of retinol in Yarrowia lipolytica by increasing stability using antioxidant and detergent extraction, Metabolic Eng. 73, 2022, 26-37. (Year: 2022).*

Kopke et al., Clostridium ljungdahlii represents a microbial production platform based on syngas, Proc. Natl. Acad. Sci. USA 107, 2010, 13087-92. (Year: 2010).*

Yang et al., Bio-isoprene production using exogenous MVA pathway and isoprene synthase in *Escherichia coli*, Bioresource Technol. 104, 2012, 642-47. (Year: 2012).*

Ragsdale et al. (Acetogenesis and the Wood-Ljungdahl pathway of CO2 fixation, Biochimica et Biophysica Acta 1784, 2008. 1873-1898. (Year: 2008).*

Wan et al., Recent progress in engineering Clostridium autoethanogenum to synthesize the biochemicals and biocommodities, Synthetic Systems Biotechnol. 9, 2024, 19-25. (Year: 2024).*

International Search Report and Written Opinion issued in International Application No. PCT/NZ2013/000095, mailed Oct. 11, 2013, 18 pages.

International Search Report and Written Opinion issued in International Application No. PCT/US2022/075292, mailed Dec. 9, 2022, 14 pages.

Babel, Heiko et al., "Evolutionary Engineering of *E. coli* MG1655 for Tolerance Against Isoprenol", as available at https://doi.org/10.1186/s13068-020-01825-6, 2020, 13:183, 13 pages.

Chatzivasileiou et al., "Two-step pathway for isoprenoid synthesis", Department of Chemical Engineering, Massachusetts Institute of Technology, Cambridge, MA and Department of Chemical Engineering, University of Waterloo, Canada, Jan. 8, 2019, vol. 116, No. 2, pp. 506-511.

Chiba, Section 18: Diet Formulation and Common Feed Ingredients, Animal Nutrition Handbook, 3rd revision, pp. 575-633, 2014.

Hensirisak et. al. Scale-up of microbubble dispersion generator for aerobic fermentation; Applied Biochemistry and Biotechnology vol. 101, No. 3 / pp. 211-227. Oct. 2002.

Hungate, 1969, Methods in Microbiology, vol. 3B. Academic Press, New York: 117-132.

Sambrook et al, Molecular Cloning: A laboratory Manual, Cold Spring Harbour Laboratory Press, Cold Spring Harbour, 1989.

Wolfe, R.S., "Microbial Formation of Methane", Department of Microbiology, University of Illinois, 1971, Adv. Microb. Physiol., 6: pp. 107-146.

Cornish-Bowden, et al., "Irreversible reactions in metabolic simulations: how reversible is irreversible" Animating the Cellular Map ( J.-H.S. Hofmeyr, J.M. Rohwer & J.L. Snoep, eds), pp. 65-71. Stellenbosch University Press, Stellenbosch, South Africa. (Year: 2000).

Katsyv et al., "Overcoming energenic barriers in Acetogenic C1 Conversion", Frontiers in Bioengineering & Biotechnology, Dec. 2020, 621166.

Liu et al., "Improving the catalytic activity of isopentenyl phosphate kinase through protein coevolution analysis", Scientific Reports, 2016, 24117 (Year: 2016).

Ochoa et al., "Chapter V: Carboxylases and the Role of Biotin", Comprehensive Biochemistry 16, 1965, 210-249.

* cited by examiner

SEQUENCE LISTING

```
Sequence total quantity: 111
SEQ ID NO: 1            moltype = DNA  length = 1875
FEATURE                 Location/Qualifiers
source                  1..1875
                        mol_type = other DNA
                        organism = Clostridium autoethanogenum
SEQUENCE: 1
atgagtaatt tattagataa ttataaagat ataaatgacg taaagaagat gtcgttaaat   60
gataaaaaaa agctagctag agaaattaga aaattttaa tagacaaagt atctaagaca   120
ggaggtcatt tggcgtctaa cttaggggt gtggagctca ctttgagttt atttagtgta   180
tttgatctaa attatgataa acttatatgg gatgtgggac atcaggctta tgtgcataaa   240
atcctcacgg gaagaaagga taaatttgat actttaaggc aatttggagg attaagtgga   300
```

```
tttcctaaaa ggtgcgaaag tatatatgat tttttcgaaa cagggcatag tagtacttca    360
atatctgcag cacttggaat ggctagggct agagatttaa agcatgagaa atataatgtt    420
gttgcagtta taggagatgg agcacttact ggaggtatgg cactagaggc cctaaatgat    480
gtaggttata gaaaaactaa gcttataata atattaaatg ataatcaaat gtctatagga    540
aaaaatgtag gtggagtatc taaatatttA aataaactta gcgtggaccc taagtataat    600
aaatttaaag cggatgtaga agctaaatta aaaaagatac ctaatatagg aaaaggaatg    660
gcaaaatatc ttgaaaaggt aaaaaatgga ataaaacaaa tggtagttcc tggaatgttt    720
tttgaagata tgggaattaa atatttagga ccaatagatg gtcataatat aaaagaactt    780
acagacgtac tcgcttctgc aaaagacata caaggtccag ttattataca tataataact    840
aagaaaggaa aaggatatga atttgcagaa aaaatccag gtaaattcca tggaataggg    900
cctttta att gcgccaatgg tgaactggat gctggatctt caaatactta ttccaaggcc    960
tttgaaatg aaatggtaaa gctagcagaa aagacgata gaatagtggc tataactgca    1020
gccatgaggg atggaacagg tcttaaaagt tttctccgaa agtttcctga aaggttttt    1080
gatgtgggaa tagcagaaca gcatgctgta accctggcag ctggaatgcc acaggcaaat    1140
ttaaaacctg tatttgcagt ttactctact tttcttcaaa gagcttatga tcaacttatt    1200
catgatgtat gtatgcaaaa acttccagta gttttgctg tagataggc cggcattgta    1260
ggagaagatg gtgaaacaca tcagggaata tttgatttat cttacttaac ggaaatgcca    1320
catatgacgc ttatgtctcc taaatgtata gatgaacttc catatatgtt aaaatgggca    1380
ttaggccaga gtttttcctgt agctataagg tatccaaggg gaggagatag tgtatgtctc    1440
aatcccgtag aaaattttaa acttggaaag tgggactgta tttcaaatga aggcagtgta    1500
gcaataattg ctcagggtaa aatggtacaa aatgcagtgt tagcaggaaa aaacttaaa    1560
gaaaagggta tagatgtaag gattataagt gcatgtttta ttaagccgct ggacaaggaa    1620
atgttaaaca ggttagttga agaaagtgta actatcgtta ctgttgaaga caatgtaata    1680
agaggaggat taggatccta tattagaa tatgtaaata aattaaataa aaagtaaaa    1740
ataataaact tagggttgga tgataagttt gtacagcatg gaaaatccga tattttgtat    1800
aagctgtatg gtttggatcc taaaggtatc gtaaatagtg tacttgaagc agcagaggta    1860
agtcatatat tttaa                                                    1875

SEQ ID NO: 2          moltype = AA  length = 627
FEATURE               Location/Qualifiers
source                1..627
                      mol_type = protein
                      organism = Clostridium autoethanogenum
SEQUENCE: 2
MSNLLDNYKD INDVKKMSLN DKKKLAREIR KFLIDKVSKT GGHLASNLGV VELTLSLFSV    60
FDLNYDKLIW DVGHQAYVHK ILTGRKDKFD TLRQFGGLSG FPKRCESIYD FFETGHSSTS    120
ISAALGMARA RDLKHEKYNV VAVIGDGALT GGMALEALND VGYRKTKLII ILNDNQMSIG    180
KNVGGVSKYL NKLRVDPKYN KFKADVEAKL KKIPNIGKGM AKYELEKVKNG IKQMVVPGMF    240
FEDMGIKYLG PIDGHNIKEL TDVLASAKDI QGPVIIHIIT KKGKGYEFAE KNPGKFHGIG    300
PFNCANGELD AGSSNTYSKA FGNEMVKLAE KDDRIVAITA AMRDGTGLKS FSQKFPERFF    360
DVGIAEQHAV TLAAGMAQAN LKPVFAVYST FLQRAYDQLI HDVCMQKLPV VFAVDRAGIV    420
GEDGETHQGI FDLSYLTEMP HMTLMSPKCI DELPYMLKWA LGQSFPVAIR YPRGGDSVCL    480
NPVENFKLGK WDCISNEGSV AIIAQGKMVQ NAVLAGKKLK EKGIDVRIIS ACFIKPLDKE    540
MLNRLVEESV TIVTVEDNVI RGGLGSYILE YVNKLNKKVK IINLGFDDKF VQHGKSDILY    600
KLYGLDPKGI VNSVLEAAEV SHIFREF                                       627

SEQ ID NO: 3          moltype = DNA  length = 1158
FEATURE               Location/Qualifiers
source                1..1158
                      mol_type = other DNA
                      organism = Clostridium autoethanogenum
SEQUENCE: 3
atgaagagaa tttcaataat tggagccaca ggttctatag aacccaaac tcttgatgta    60
cttagaaaac aaaaaggaga ttttcagctt ataggtgtat ctgcaaatag tagtgtagat    120
aaacttttac atataatag tgaatttaac cccaaatgtc cggtgctaac cgaaaaagaa    180
tcttatttaa agataaaaga tattttgagt aataaaaaat caaatacaaa aatattttt    240
ggagtagatg gattaaatac tatagctagt cttcctgaag ttgatatggt tgtaacatct    300
gtagttggaa tgatagggct tgtaccaact ataaaagcaa ttaaagcgaa gaaagacata    360
gctttagcta ataaggagac attagttgta ggaggagcata tggttacaaa attatcgaaa    420
gaaaataata taaaaatatt tcctgtagat tcagagcata gtgctgttt tcaatgcctt    480
cagggaaata attttgacga agttgctaat ttgattttaa ccgcttcagg tggacctttt    540
aggggaaaaa caaagatca actctcaaaa gtaactgtaa aagaggcgtt gaatcatcca    600
aattggagta tgggaaaaaa gctcacaata gattctgcta ctcttatgaa taaggacttt    660
gaagttatag aagctcactt cttatttaac ttaccttata aaaataataaa ggttgtagtt    720
catccacaaa gtatagtaca ttctatggtg gaatatagg atggaagtgt tatggcacag    780
cttgccactg cagatatgag attacctata caatatgcac tgaattatcc gaaaagaag    840
gaagctgtaa tagataaatt ggactttat agcgtaggaa atttaagttt tgaaaagcct    900
gatacagata cattcagacc acttaaatta gcttatgaag cagggaggat aggaggcaca    960
atgccagcta tactaaattg tgcaaatgaa gaagcagtaa gttattcct tgctaataaa    1020
ataaatttt tggatatagg caacatatta aagagtgta tgaataaatt tacttcacaa    1080
agtacgtata ctctgatga tttacttgac ctagaaataa agttaagaa atatgtaaaa    1140
gataaattta tcaaataa                                                 1158

SEQ ID NO: 4          moltype = AA  length = 385
FEATURE               Location/Qualifiers
source                1..385
                      mol_type = protein
                      organism = Clostridium autoethanogenum
SEQUENCE: 4
```

```
MKRISIIGAT GSIGTQTLDV LRKQKGDFQL IGVSANSSVD KLLHIIDEFN PKYAVLTEKE     60
SYLKIKDIFS NKKSNTKILF GVDGLNTIAS LPEVDMVVTS VVGMIGLVPT IKAIKAKKDI    120
ALANKETLVV GGELVTKLSK ENNIKIFPVD SEHSAVFQCL QGNNFDEVAN LILTASGGPF    180
RGKTKDQLSK VTVKEALNHP NWSMGKKLTI DSATLMNKGL EVIEAHFLFN LPYENIKVVV    240
HPQSIVHSMV EYRDGSVMAQ LATADMRLPI QYALNYPKRK EAVIDKLDFY SVGNLSFEKP    300
DTDTFRPLKL AYEAGRIGGT MPAILNCANE EAVSLFLANK INFLDIGNIL EECMNKFTSQ    360
STYTLDDLLD LEIKVKKYVK DKFIK                                         385

SEQ ID NO: 5            moltype = DNA  length = 693
FEATURE                 Location/Qualifiers
source                  1..693
                        mol_type = other DNA
                        organism = Clostridium autoethanogenum
SEQUENCE: 5
atgaatggta attatgctat tattgtagct gccggcaagg gaaaaagaat gggaactact     60
attaataagc aatttattaa aattaagggt aagcctatat tatattattc cataagggca    120
ttttccataa atcctcttat agatggaatt atactggtat gtgcagaaac tgagatagaa    180
tattgtaaaa gagaagtagt agataaatat gggcttcaga aggtaattaa attagttgct    240
gggggtaaag aacgtcagga ttcggtattt aatggactag gagttttaga aaaagaaaac    300
tgtagtgttg ttctaattca cgatggggct agacctttg tcactagtaa aattattgat     360
gatgaataa aatattctaa taggtatggg gcttgtgctt gtggagttag gcctaaggat     420
acactaaaag ttagggaaga aagtggattt tcttcttcta cattagagag aaaaagttta    480
tttgcagttc aaactccgca gtgttttaaa tatgatttaa tttatgactg tcataaaaaa    540
ttaatgaatg aaaaaaatgt gtgttactga gatactatgg tagtagagcg ttatggaaat    600
aaggtttatt tgtatgaagg taactatgaa aacataaaag tgaccacacc agaagattta    660
aatatagctg aaagtatagt tgaaaaatat taa                                 693

SEQ ID NO: 6            moltype = AA  length = 230
FEATURE                 Location/Qualifiers
source                  1..230
                        mol_type = protein
                        organism = Clostridium autoethanogenum
SEQUENCE: 6
MNGNYAIIVA AGKGKRMGTT INKQFIKIKG KPILYYSIRA FSINPLIDGI ILVCAETEIE     60
YCKREVVDKY GLQKVIKLVA GGKERQDSVF NGLGVLEKEN CSVVLIHDGA RPFVTSKIID    120
DGIKYSNRYG ACACGVRPKD TLKVREESGF SSSTLERKSL FAVQTPQCFK YDLIYDCHKK    180
LMNEKMCVTD DTMVVERYGN KVYLEGNYE NIKVTTPEDL NIAESIVEKY               230

SEQ ID NO: 7            moltype = DNA  length = 798
FEATURE                 Location/Qualifiers
source                  1..798
                        mol_type = other DNA
                        organism = Clostridium autoethanogenum
SEQUENCE: 7
gtgggaaaaa gaaaagatgg gtatcatctt ttgaaaatga taatgcagaa atatagactta     60
tatgatgttt taaaaataga tgagatcaaa actggaaatac agatatgctc taataataga    120
tatattccct gtgacaggag aaaatttggtt tacagagcag caaaattatt tattgataaa    180
tataatataa agaatggaat tagtataaac ataggtaaaa atatacctgt atcagctgga    240
cttgctggtg gaagtgcgga tgctgcagct atactaaaga ctatgagaaa tatttatact    300
cctgaagtaa gtgataaaga attgagcgaa ttaggcttaa atataggggc agatgttcct    360
tattgtataa taggaggtac agccttgtgc gaggggatag gagagaaggt tacaccactc    420
atgccgttta gaaaccatat actcatatta attaaaccac cttttggagt gagcacagca    480
gaggtatata agagtttaga cataagtaaa ataaaaaggc atcctaatac agaaatttta    540
atagatgcgg ttaatgaatc aaaattggag atgctgagta aaaacatgaa aaatgttttg    600
gaaaatgtaa cttaaaaaaa tatcccgtg cttagaaaata taaaactga tttgatagat     660
tttggagcag ttggttcact tatgagtgga agcggtccaa gcatttttgc ttttttgat    720
gatatgctaa aagcacagaa atgttatgat aatatgaaaa ctaggtatag agaggtgttt    780
attacaagaa ccatttaa                                                  798

SEQ ID NO: 8            moltype = AA  length = 265
FEATURE                 Location/Qualifiers
source                  1..265
                        mol_type = protein
                        organism = Clostridium autoethanogenum
SEQUENCE: 8
MGKRKDGYHL LKMIMQNIDL YDVLKIDEIK TGIQICSNNR YIPCDRRNLV YRAAKLFIDK     60
YNIKNGISIN IGKNIPVSAG LAGGSADAAA ILKTMRNIYT PEVSDKELSE LGLNIGADVP    120
YCIIGGTALC EGIGEKVTPL MPFRNHILIL IKPPFGVSTA EVYKSLDISK IKRHPNTEIL    180
IDAVNESKLE MLSKNMKNVL ENVTLKKYPV LRKIKTDLID FGAVGSLMSG SGPSIFAFFD    240
DMLKAQKCYD NMKTRYREVF ITRTI                                         265

SEQ ID NO: 9            moltype = DNA  length = 480
FEATURE                 Location/Qualifiers
source                  1..480
                        mol_type = other DNA
                        organism = Clostridium autoethanogenum
SEQUENCE: 9
gtgaaaatcg ggcttggtta tgatgtccat aaattagttt ataatagacc tcttatttta     60
ggaggcgtaa atatcccttt tgaaaaaggt cttatgggac attcagatgc agatgtactt    120
```

```
cttcatgcaa taatggatag tctccttgga gccttgtgtc taggtgatat cggcaagcat    180
ttccctgata atgataataa atataagaac atatgtagtc ttaaattgct gtcacatgta    240
tcagctttga ttaatgaaaa aggatatact atagggaaca tagattctat tataatagcc    300
gaaaagccta aactttcttc atacatacaa gatatgaggg taaatatagc taaaactcta    360
aatgtaacta cagccgtaat aagtgtaaaa gccactacag aggaaggtct tggctttacc    420
ggcaaggag aaggcatagc cgctcaaagc atctgtttgt taacagctaa ttcaaaataa    480

SEQ ID NO: 10         moltype = AA  length = 159
FEATURE               Location/Qualifiers
source                1..159
                      mol_type = protein
                      organism = Clostridium autoethanogenum
SEQUENCE: 10
MKIGLGYDVH KLVYNRPLIL GGVNIPFEKG LMGHSDADVL LHAIMDSLLG ALCLGDIGKH     60
FPDNDNKYKN ICSLKLLSHV SALINEKGYT IGNIDSIIIA EKPKLSSYIQ DMRVNIAKTL    120
NVTTAVISVK ATTEEGLGFT GKGEGIAAQS ICLLTANSK                           159

SEQ ID NO: 11         moltype = DNA  length = 1051
FEATURE               Location/Qualifiers
source                1..1051
                      mol_type = other DNA
                      organism = Clostridium autoethanogenum
SEQUENCE: 11
ttgaatagag taaaaagaa aacagtaaag gtaggcaata tattttttagg tggagatttt     60
ccagtagccg tacaatctat gacaaatacg gatactaggg atgtagaagc cactacagct    120
cagatatttc agctaaaaga agcaggttgt gatatcgtca ggcttgtgcgt gcctgatgat    180
atagcttgca attccatgaa aaaaatcata gaaagagtag atattccact tgtagcagat    240
atacattttg attataagtt ggcgcttaaa tctatagaaa atgggatatc tgcacttaga    300
ataaatcctg gaaatattgg aagcatagaa agagtacgag aagtggcaag agcagcaaaa    360
gaagctaata ttccaattag aatagggggta aactctagca cattaaaaaa agatattta    420
aataaaatatg gtagagtttg ttcggatgca ctagtagaga gtgctctaga acatgtaaaa    480
attttggaaa acgtaggatt ttatgatata gttatatcca taaaatcttc aaatgtaaat    540
cagatgatag aaagttatag aaaaatatct gaaattgtag attatccact tcaccttgga    600
gtaacagaag caggaactat ttggcgagga actataaaat caagcatagg cataggtact    660
cttttgatgg aaggtatagg agacactata agagtatctc ttacaggaaa tccagtggaa    720
gaagtaagag tgggaaaaga aatattaaaa tcctgtggaa ttataaaaga aggtgtggaa    780
tttatatcat gtcccacctg tggtagaact gaaattgatt taattaaaat agctgagcaa    840
gtggaaaaa gactttttaaa tatgcataaa aacataaagg ttgctgttat gggatgtgta    900
gtaaatggac caggtgaggc tcgggaagca gatattggta tagcaggcgg caaaggtgaa    960
ggcattatat ttaaaaaagg aaaaatagta aaaaaggtaa gtgaagaaag tttagtagaa   1020
tcacttatag aagaaataga aaacatttga r                                  1051

SEQ ID NO: 12         moltype = AA  length = 349
FEATURE               Location/Qualifiers
source                1..349
                      mol_type = protein
                      organism = Clostridium autoethanogenum
SEQUENCE: 12
MNRVKKKTVK VGNIFLGGDF PVAVQSMTNT DTRDVEATTA QIFQLKEAGC DIVRCAVPDD     60
IACNSMKKII ERVDIPLVAD IHFDYKLALK SIENGISALR INPGNIGSIE RVREVARAAK    120
EANIPIRIGV NSGSLKKDIL NKYGRVCSDA LVESALEHVK ILENVGFYDI VISIKSSNVN    180
QMIESYRKIS EIVDYPLHLG VTEAGTIWRG TIKSSIGIGT LLMEGIGDTI RVSLTGNPVE    240
EVRVGKEILK SCGIIKEGVE FISCPTCGRT EIDLIKIAEQ VEKRLLNMHK NIKVAVMGCV    300
VNGPGEAREA DIGIAGGKGE GIIFKKGKIV KKVSEESLVE SLIEEIENI                349

SEQ ID NO: 13         moltype = DNA  length = 1923
FEATURE               Location/Qualifiers
source                1..1923
                      mol_type = other DNA
                      organism = Clostridium autoethanogenum
SEQUENCE: 13
gtgataaaat tgaacattat tttagcagac aaatccggat tttgctttgg agtaaaaaga     60
gctgtagacg aatctttaaa ggttcaaaaa aaatttaata aaaaaatata tactttaggt    120
ccttttgattc ataatagtga tgtagtaaat aaattaaaaa gaaaaggtat atatcctata    180
gaaatagata atatagataa tctaagggaa gatgatgtgg ttataatacg ttctcatggt    240
gttcccgaaa aatatttttt tactttaaaa aataaaaaaa taaacatagt aaatgcaact    300
tgcccatatg ttttaaatat acaaagaaaa gtacaagaat attataaatt agggtattct    360
atattaatag taggagataa aaatcatcct gaagtaattg gaataaatgg atggtgtgaa    420
aataaagctt taatatctaa agatggcacc aatttagaaa agttaccatc aaaactgtgt    480
atagtttctc aaactacaga aaaacaatct aactgggaaa aagtgcttag tatagtggct    540
aaaaattgta agaatttat tgctttttaat actatatgca gtgccacaga atttcgtcag    600
aaggcagcag cagatatttc taagaagta gatatgatgg tagtaatagg tggtaaaaac    660
agctctaata ctactaaact ttatgaaata tgtaaagata actgcaataa tactatttat    720
gttgaaaatt gggagaaa acctgatgat ataagtaatt gtaaataat taaactata    780
ggtgttacag caggagcttc aaccaccagat tggataataa aggaggcaat tttaaaaatg    840
agtgatgaca aaaatttaga actaaatgag caactatctt atatgacaa aatgataccc    900
caataatat taggtgaaaa aattaaggggt acagtaatat ctgtaaatcc aaaagaggtt    960
tttttaaata taggatataa atcagaaggt gtacttccaa aacgtgaaat aacaaaaaat   1020
gaaagtgaca acttagaaga attaattcat tgtgtggaatg aattatatgt taaagtaata   1080
```

-continued

```
agaagacaaa atgaagatgg atatgtggta ttatctaaga tagaattaga aagagaaaat   1140
gcttataaag aattaaagga agctaatgga aatagtcagg tattaaaggt tattgtaaaa   1200
gaagctgtaa atggaggtct tgttgccaat tacaaaggtg ctagggtatt tatacctgct   1260
tctcatgtag aattatatca tgtagatgat ctttcacaat atgtagataa agagcttgat   1320
gtaactataa ttgaatttaa agaagaaaag aaaggtacca gaatagtagc ttcaagaaga   1380
gacctttttga gaatgaaaag agaaaaaatg gaagaacaga cttggaatgt gcttgaaaaa   1440
gatactgtag tagatggtga agttagaaga ttgactgatt ttggcgcatt tgttgatgta   1500
caaggagttg acgggcttct acatgtatct gaactttcct ggggaagagt tggaaaacca   1560
agtgatgttt taaaaatcgg agatacgatt aaggtttata tcttagacat tgataaagaa   1620
aaaaagaagt tatctttatc tttaaaaaag ctcatggaag atccatggat caacgtagac   1680
ataaaatatc ctgttggcaa tgtagttctt ggtaaagtag ttaggtttgc aaatttttggt   1740
gcatttgttg aattagagcc aggtgtagat gcattagttc atatatcaca aataagccat   1800
aagagaatag ataaaccaga agatgtactt aaaataggtc aggaaataaa ggctaagatc   1860
cttgaagtaa acaaagatag cgaaaaaata gctttaagta aaagaagt agatgaaatc     1920
taa                                                                1923

SEQ ID NO: 14           moltype = AA  length = 640
FEATURE                 Location/Qualifiers
source                  1..640
                        mol_type = protein
                        organism = Clostridium autoethanogenum
SEQUENCE: 14
MIKLNIILAD KSGFCFGVKR AVDESLKVQK KFNKKIYTLG PLIHNSDVVN KLKEKGIYPI    60
EIDNIDNLRE DDVVIIRSHG VPEKIFFTLK NKKINIVNAT CPYVLNIQRK VQEYYKLGYS   120
ILIVGDKNHP EVIGINGWCE NKALISKDGT NLEKLPSKLC IVSQTTEKQS NWEKVLSIVA   180
KNCKEFIAFN TICSATEFRQ KAAADISKEV DMMVVIGGKN SSNTTKLYEI CKDNCNNTIY   240
VENSGEIPDD ISNCNKIKTI GVTAGASTPD WIIKEAILKM SDDKNLELNE QLSYMDKNDT   300
QIILGEKIKG TVISVNPKEV FLNIGYKSEG VLPKREITKN ESDNLEELIH CGDELYVKVI   360
RRQNEDGYVV LSKIELEREN AYKELKEANG NSQVLKVIVK EAVNGGLVAN YKGARVFIPA   420
SHVELYHVDD LSQYVDKELD VTIIEFKEEK KGTRIVASRR DLLRMEREKM EEQTWNVLEK   480
DTVVDGEVRR LTDFGAFVDV QGVDGLLHVS ELSWGRVGKP SDVLKIGDTI KVYILDIDKE   540
KKKLSLSLKK LMEDPWINVD IKYPVGNVVL GKVVRFANFG AFVELEPGVD ALVHISQISH   600
KRIDKPEDVL KIGQEIKAKI LEVNKDSEKI ALSIKEVDEI                         640

SEQ ID NO: 15           moltype = DNA  length = 882
FEATURE                 Location/Qualifiers
source                  1..882
                        mol_type = other DNA
                        organism = Clostridium autoethanogenum
SEQUENCE: 15
atggaaatta aagtgtgtaat tgaaacatta agagaggaat tgaataaata cctctatgac    60
tatatggagg gaaaaggatc tttataatag agagtatatg aagctatgca gtatagctta   120
gatgcaggag gaaagagaat aagacctcta ctatttcttt tgacatataa actttataag   180
acagattgca atgaggttat ggatatagca gcagctatag aaatgataca cacttattcc   240
ttaattcatg atgatttacc tgctatggac aatgatgatt taagaagggg caaacctaca   300
aatcataagg tatttggaga agctattgct gtacttgcgg gagatggact tttaaatgaa   360
gcaatgagtc tgatgtttag acactgtatt gggaaaaagg ataacgctat aagggcttgta   420
agcattattt ctgaaagtgc aggagctgat gggatggttg gcggacagac agtggatatt   480
ttaagtgaaa acactaagat acctatagat cagctctatt acatgcacag taaaaaacg    540
ggagcgctca taaaggatc tataatatct gcagcagtat atgcgggagc aagtaaagct   600
gaaatagata aattaagcta ttatggagaa aagttaggat tggcatttca aataaaggat   660
gatatattgg atttaacagg agatactgct ctttttaggta aaaagataaa aagtgatcta   720
aataataaca aaactacatt tataagtact tatggaataa ataatgcaa agaaatgtgc    780
aattcaatta caagtgaatg tataggagta ctgaatggga tgagtgtaga tacttcttat   840
ctaaaagatt taacatcatt tttattaaat agagaaagt ga                       882

SEQ ID NO: 16           moltype = AA  length = 293
FEATURE                 Location/Qualifiers
source                  1..293
                        mol_type = protein
                        organism = Clostridium autoethanogenum
SEQUENCE: 16
MEIKGVIETL REELNKYLYD YMEGKGSYNK RVYEAMQYSL DAGGKRIRPL LFLLTYKLYK    60
TDCNEVMDIA AAIEMIHTYS LIHDDLPAMD NDDLRRGKPT NHKVFGEAIA VLAGDGLLNE   120
AMSLMFRHCI GKKDNAIRAC SIISESAGAD GMVGGQTVDI LSENTKIPID QLYYMHSKKT   180
GALIKGSIIS AAVYAGASKA EIDKLSYYGE KLGLAFQIKD DILDLTGDTA LLGKKIKSDL   240
NNNKTTFIST YGINKCKEMC NSITSECIGV LNGMSVDTSY LKDLTSFLLN REK          293

SEQ ID NO: 17           moltype = DNA  length = 519
FEATURE                 Location/Qualifiers
source                  1..519
                        mol_type = other DNA
                        organism = Clostridium autoethanogenum
SEQUENCE: 17
atgaataaaa caaggaaaat ggttttttta agctttctaa caagtatggc tttagtcata    60
tacataaatg aaactcaagt tccggtttta tttcccggaa taaaattagg acttgcaaat   120
acaatttccc tagctgcact tatacttata ggatggaaag aagccttact aattatgttt   180
ttaaggacgt tctaggatc tatgtttggt gggacaatgt ctacctttat gttcagcata   240
gccggaggaa ttttaagtaa cattgttatg atccttctat acaaatattt taaaaattcc   300
```

```
ttaagtctat ggactataag catatgcggg gcaatatttc acaacatagg ccaactttta  360
gtagcttcta tagtaattca agattttagg atatacatat atctaccggt gctttttaatc  420
tctgctataa tcacaggata ctttataggt tggtgcgtga aattcctaac taataactta  480
tataaaattc ctatgtttaa agaattaaaa ataagtaa                          519

SEQ ID NO: 18            moltype = AA   length = 172
FEATURE                  Location/Qualifiers
source                   1..172
                         mol_type = protein
                         organism = Clostridium autoethanogenum
SEQUENCE: 18
MNKTRKMVFL SFLTSMALVI YIIETQVPVL FPGIKLGLAN TISLAALILI GWKEALLIMF   60
LRTLLGSMFG GTMSTFMFSI AGGILSNIVM ILLYKYFKNS LSLWTISICG AIFHNIGQLL  120
VASIVIQDFR IYIYLPVLLI SAIITGYFIG WCVKFLTNNL YKIPMFKELK NK          172

SEQ ID NO: 19            moltype = DNA   length = 825
FEATURE                  Location/Qualifiers
source                   1..825
                         mol_type = other DNA
                         organism = Clostridium autoethanogenum
SEQUENCE: 19
atgaacttcg atggaatttc aattccaata ataaaagaac ttaatcaact tgagttagag   60
ttaaaaaata ttgcatcaaa attagattct actgttacac aagatatttt tacctacttt  120
ttttcaattc caggtaaaag actaagacct acattaacat ttttatctgc aggtgctatt  180
agtagcgagc ttacttcatc tgcaaaacac aacttaattc agttgtcaat aagcttagag  240
cttattcaca gcgctagtct aattcatgat gatatcggtg atcttttagg ctactaagac  300
ggtcagaaaa ccttaaataa gacctttgga aataaaaatg cagtacttgc cggtgatgct  360
ttgtactcaa gggcctttac tattttctca gatactctgc caagagaatt tgcgcaggta  420
atgggcagag ttactgaatc aatgtctgta gctgaaatat taaatgctaa caatccctct  480
cccgatcgtg aaacctattt taaaatcatc ttaggaaaaa cagcatcttt catgagcgct  540
tgttgtaggc ttggtggcag catagcttat gccccttacg aagagtctaa tatgctttct  600
aaatacggtg aaaaccttgg tatggcatat caaatactgg atgattatat cgatgaggat  660
cccgttgcaa tgaaaaatgt aactattgaa gagggatttg aatttgcata atgccaaa   720
gcttctattg aaaaatttaaa agactcagca tacaacaaa gcttaataat gttagtagac  780
tatgtttttag attttttatag tcctaaggta gagaatacat tatag                825

SEQ ID NO: 20            moltype = AA   length = 274
FEATURE                  Location/Qualifiers
source                   1..274
                         mol_type = protein
                         organism = Clostridium autoethanogenum
SEQUENCE: 20
MNFDGISIPI IKELNQLELE LKNIASKLDS TVTQDIFTYF FSIPGKRLRP TLTFLSAGAI   60
SSELTSSAKH NLIQLSISLE LIHSASLIHD DIIGDLLRR GQKTLNKTFG NKIAVLAGDA   120
LYSRAFTIFS DTLPREFAQV MGRVTESMSV AEILNANNPS PDRETYFKII LGKTASFMSA  180
CCRLGGSIAY APYEESNMLS KYGENLGMAY QILDDYIDED PVAMKNVTIE EGFEFAYNAK  240
ASIENLKDSA YKQSLIMLVD YVLDFYSPKV ENTL                              274

SEQ ID NO: 21            moltype = DNA   length = 1797
FEATURE                  Location/Qualifiers
source                   1..1797
                         mol_type = other DNA
                         organism = Populus tremuloides
SEQUENCE: 21
catatggcaa cagaattatt atgtttacac agacctatat cacttactca caaacttttt   60
aggaatccat tacctaaagt tattcaagct cacccttta cattaaaact taggtgtagt   120
gtttctacag aaaatgtatc atttagtgag acagaaactg aaacaagaag atcagcaaat  180
tatgaaccaa attcttggga ttatgattat cttctttctt ctgatactga tgagtcaata  240
gaagtacata aagtaaggc taagaaatta gaagctgaag ttaggagaga aataaataat  300
gagaaggctg aatttcttac acttcttgaa cttattgata atgtacaaag acttggatta  360
ggatatagat ttgagtctga tataagaaga gcattagata gatttgtaag tagtggagga  420
tttgatggag ttactaaaac ttcattacat ggaacagcat tatcatttag gttattaagg  480
caacatggtt ttgaagtatc tcaagaagct tttagtggat ttaaagatca gaatggaaac  540
tttcttgaga atttaaagga agacataaaa gcaattcttt ctcttttatga agcatcattt  600
ttagcattag aagggtagaa tatattagat gaggctaaag tatttgcaat atctcatctt  660
aaagaactta gtgaagaaaa gattggtaaa gaattagctg aacaagttct acatgcttta  720
gaattaccat tacatagaag aacacaaaga ttagaagcag tttggtcaat agaagcatat  780
agaaagaaag aagacgcaaa tcaagtactt ttagaacttt caatacttga ctacaatatg  840
attcaaagtg tatatcagag ggatttaaga gaaacatcaa gatggtggaa aagagtagga  900
ttagcaacta aattacatttt tgctagagat aggcttattg aaagtttta ttgggctgtt  960
ggagttgctt tgaaccaca atattctgat tgcagaaata gtgtagcaaa gatgtttca  1020
tttgttacta taattgacga tatttacgat gtatatggaa ctttagatga acttgaactt  1080
tttactgatg cagttgaaag atgggatgta aatgctatta atgatcttcc tgattatatg  1140
aagttatgtt ttcttgcact ttacaatact attaacgaga tagcttacga taacttaaaa  1200
gataaaggtg agaacatact tcctattta acaaaagcat gggcagattt atgtaatgca  1260
tttcttcaag aagctaagtg gctttataat aaatcaacac ctacatttga tgattattt  1320
ggaaatgcat ggaaaagttc tagtggacct ttacagctta ttttttgctta ttttgctgta  1380
gtacagaaca ttaaaaagga agagattgag aatcttcaga aatatcatga cataatatca  1440
agacctagtc acatttttag gctttgtaat gatttagcat ctgcttcagc agaaatagca  1500
```

-continued

```
agaggtgaaa ctgctaattc tgtaagttgt tatatgagaa caaaaggtat atctgaagaa  1560
ttagctactg aaagtgttat gaatcttata gacgaaactt ggaagaaaat gaacaaagaa  1620
aaacttggtg gatctttatt tgcaaaacct tttgttgaga ctgctataaa tttagctaga  1680
cagtctcatt gcacatatca taatggtgat gcacatacta gtccagatga attaactagg  1740
aaaagagtac ttagtgtaat aactgaacca atattaccat ttgaaagata agaattc     1797
```

```
SEQ ID NO: 22           moltype = DNA  length = 617
FEATURE                 Location/Qualifiers
source                  1..617
                        mol_type = other DNA
                        organism = Clostridium autoethanogenum
SEQUENCE: 22
ggttaatgtt aaaaatttat agtataactt taaaaaactg tcttaaaaag ttgttatata   60
aaaaatgttg acaattaaac agctatttag tgcaaaacaa ccataaaaat ttaaaaaata  120
ccataaaatta cttgaaaaat agttgataat aatgtagagt tataaacaaa ggtgaaaagc  180
attacttgta ttctttttta tatattatta taaattaaaa tgaagctgta ttagaaaaaa  240
tacacacctg taatataaaa ttttaaatta attttttaatt ttttcaaaat gtattttaca  300
tgtttagaat tttgatgtat attaaaatag tagaatacat aagtactta atttaattaa  360
agatagttaa gtacttttca atgtgctttt ttagatgttt aatacaaatc tttaattgta  420
aaagaaatgc tgtactattt actgtactag tgacgggatt aaactgtatt aattataaat  480
aaaaaataag tacagttgtt taaaattata ttttgtatta aatctaatag tacgatgtaa  540
gttattttat actattgcta gtttaataaa aagatttaat tatatacttg aaaaggagag  600
gaattttat gcgtaaa                                                   617
```

```
SEQ ID NO: 23           moltype = DNA  length = 30
FEATURE                 Location/Qualifiers
misc_feature            1..30
                        note = oligonucleotide Ppfor-NotI-F
source                  1..30
                        mol_type = other DNA
                        organism = synthetic construct
SEQUENCE: 23
aagcggccgc aaaatagttg ataataatgc                                    30
```

```
SEQ ID NO: 24           moltype = DNA  length = 30
FEATURE                 Location/Qualifiers
misc_feature            1..30
                        note = oligonucleotide Ppfor-NdeI-R
source                  1..30
                        mol_type = other DNA
                        organism = synthetic construct
SEQUENCE: 24
tacgcatatg aattcctctc cttttcaagc                                    30
```

```
SEQ ID NO: 25           moltype = DNA  length = 5345
FEATURE                 Location/Qualifiers
misc_feature            1..5345
                        note = plasmid pMTL 85146-ispS
source                  1..5345
                        mol_type = other DNA
                        organism = synthetic construct
SEQUENCE: 25
aattcgagct cggtacccgg ggatcctcta gagtcgacgt cacgcgtcca tggagatctc   60
gaggcctgca gacatgcaag cttggcactg gccgtcgttt tacaacgtcg tgactgggaa  120
aaccctggcg ttacccaact taatcgcctt gcagcacatc cccctttcgc cagctggcgt  180
aatagcgaag aggcccgcac cgatcgccct tcccaacagt tgcgcagcct gaatggcgaa  240
tggcgctagc ataaaaataa gaagcctgca tttgcaggct tcttattttt atggcgcgcc  300
gcattcactt cttttctata taatatgag cgaagcgaat aagcgtcgga aaagcagcaa  360
aaagtttcct ttttgctgtt ggagcatggg ggttcagggg gtgcagtatt tgacgtcaat  420
gccgagcgaa agcgagccga agggtagcat ttacgttaga taaccccctg atatgctccg  480
acgctttata tagaaaagaa gattcaacta ggtaaaatct taatatagg tgagatgata  540
aggtttataa ggaatttgtt tgttctaatt tttcactcat tttgttctaa tttctttaa  600
caaatgttct ttttttttta gaacagttat gatatagtta gaatagttta aataaggag  660
tgagaaaaag atgaaagaaa gatatggaac agtctataaa ggctctcaga ggctcataga  720
cgaagaaagt ggagaagtca tagaggtaga caagttatac cgtaaacaaa cgtctggtaa  780
cttcgtaaag gcatatatag tgcaattaat aagtatgtta gatatgattg gcggaaaaaa  840
acttaaaatc gttaactata tcctagataa tgtccactta agtaacaata caatgatagc  900
tacaacaaga gaaatagcaa aagctacagg aacaagtcta caaacagtaa taacaacact  960
taaaatctta gaagaaggaa atattataaa aagaaaaact ggagtattaa tgttaaaccc  1020
tgaactacta atgagaggcg acgaccaaaa acaaaaatac ctcttactcg aatttggaa  1080
ctttgagcaa gaggcaaatg aaatagattg acctcccaat aacaccacgt agttattggg  1140
aggtcaatct atgaaatgcg attaagggcc ggccagtggg caagtgaaa aattcacaaa  1200
aatgtggtat aatatctttg ttcattagag cgataaactt gaatttgaga gggaacttag  1260
atggtatttg aaaaaaattga taaaaatagt tggaacagaa aagagtattt tgaccactac  1320
tttgcaagtg taccttgtac ctacagcatg accgttaaag tggatatcac acaaataaag  1380
gaaaagggaa tgaactata tcctgcaatg ctttattata ttgcaatgat gtaaaccgc  1440
cattcagagt ttaggacggc aatcaatcaa gatggtgaat tggggatata tgatgagatg  1500
ataccaagct atacaaatat tcacaatgat actgaaacat tttccagcct ttggactgag  1560
tgtaagtctg actttaaatc atttttagca gattatgaaa gtgatacgca acggtatgga  1620
```

```
aacaatcata gaatggaagg aaagccaaat gctccggaaa acattttttaa tgtatctatg   1680
ataccgtggt caaccttcga tggctttaat ctgaatttgc agaaaggata tgattatttg   1740
attcctatttt ttactatggg gaaatattat aaagaagata acaaaattat acttcctttg   1800
gcaattcaag ttcatcacgc agtatgtgac ggatttcaca tttgccgttt tgtaaacgaa   1860
ttgcaggaat tgataaatag ttaacttcag gtttgtcttg aactaaaaac aagtatttaa   1920
gcaaaaacat cgtagaaata cggtgttttt tgttaccccta agtttaaaact cctttttgat   1980
aatctcatga ccaaaatccc ttaacgtgag ttttcgttcc actgagcgtc agaccccgta   2040
gaaaagatca aaggatcttc ttgagatcct tttttttctgc gcgtaatctg ctgcttgcaa   2100
acaaaaaaac caccgctacc agcggtggtt tgtttgccgg atcaagagct accaactctt   2160
tttccgaagg taactggctt cagcagagcg cagataccaa atactgttct tctagtgtag   2220
ccgtagttag gccaccactt caagaactct gtagcaccgc ctacatacct cgctctgcta   2280
atcctgttac cagtggctgc tgccagtggc gataagtcgt gtcttaccgg gttggactca   2340
agacgatagt taccggataa ggcgcagcgg tcgggctgaa cggggggttc gtgcacacag   2400
cccagcttgg agcgaacgac ctacaccgaa ctgagatacc tacagcgtga gctatgagaa   2460
agcgccacgc ttcccgaagg gagaaaggcg gacaggtatc cggtaagcgg cagggtcgga   2520
acaggagagc gcacgaggga gcttccaggg ggaaacgcct ggtatcttta tagtcctgtc   2580
gggtttcgcc acctctgact tgagcgtcga ttttttgtgat gctcgtcagg ggggcggagc   2640
ctatggaaaa acgccagcaa cgcggccttt ttacggttcc tggccttttg ctggccttt    2700
gctcacatgt tctttcctgc gttatcccct gattctgtgg ataaccgtat taccgccttt   2760
gagtgagctg ataccgctcg ccgcagccga acgaccgagc gcagcgagtc agtgagcgag   2820
gaagcggaag agcgcccaat acgcagggcc cctgcagga taaaaaaatt gtagataaat   2880
tttataaaat agttttatct acaatttttt tatcaggaaa cagctatgac cgcggccgcg   2940
gttaatgtta aaaattttata gtataacttt aaaaaactgt cttaaaaagt tgttatataa   3000
aaaatgttga caattaaaca gctatttagt gcaaacaac cataaaaatt taaaaaatac   3060
cataaattac ttgaaaaata gttgataata atgtagagtt ataaacaaag gtgaaaagca   3120
ttacttgtat tctttttttat atattattat aaattaaaat gaagctgtat tagaaaaaat   3180
acacacctgt aatataaaat tttaaattaa ttttttaattt tttcaaaatg tattttttacat   3240
gtttagaatt ttgatgtata ttaaaatagt agaatacata agatacttaa tttaattaaa   3300
gatagttaag tacttttcaa tgtgcttttt tagatgttta atacaaatct ttaattgtaa   3360
aagaaatgct gtactattta ctgtactagt gacggggatta aactgtatta attataaata   3420
aaaaataagt acagttgttt aaaattatat tttgtattaa atctaatagt acgatgtaag   3480
ttatttttata ctattgctag tttaataaaa agatttaatt atatacttga aaaggagagg   3540
aatttttatg cgtcatatgg caacagaatt attatgttta cacagaccta tatcacttac   3600
tcacaaactt tttaggaatc cattacctaa agttattcaa gctacacctt taacattaaa   3660
acttaggtgt agtgtttcta cagaaaatgt atcatttagt gagacagaaa ctgaaacaag   3720
aagatcagca aattatgaac caaattcttg ggattatgat tatcttcttt cttctgatac   3780
tgatgagtca atagaagtac ataaagtaa ggctaagaaa ttagaagctg aagttaggag   3840
agaaataaat aatgagaagg ctgaatttct tacacttctt gaacttattg ataatgtaca   3900
aagacttgga ttaggatata gatttgagtc tgatataaga agagccattag atagatttgt   3960
aagtagtgga ggatttgatg gagttactaa aacttcatta catgaacag cattatcatt   4020
taggttatta aggcaacatg gttttgaagt atctcaagaa gcttttagtg gatttaaaga   4080
tcagaatgga aactttcttg agaatttaaa ggaagcata aaagcaattc tttctcttta   4140
tgaagcatca tttttagcat tagaaggtga gaatatatta gatgaggcta aagtatttgt   4200
aatatctcat cttaaagaac ttagtgaaga aaagattggt aaagaattag ctgaacaagt   4260
ttcacatgct ttagaattac cattacatag aagaacacaa agattagaag cagtttggtc   4320
aatagaagca tatagaaaga aagaagacgc aaatcaagta cttttagaac ttgcaatact   4380
tgactacaat atgattcaaa gtgtatatca gagggattta agagaaacat caagatggtg   4440
gagaagagta ggattagcaa ctaaattaca ttttgctaga gataggctta ttgaaagttt   4500
ttattgggct gttggagttg cttttgaacc acaatattct gattgcagaa atagtgtagc   4560
aaagatgttt tcatttgtta ctataattga cgatatttac gatgtatatg gaactttaga   4620
tgaacttgaa cttttttactg atgcagttga aagatggat gtaaatgcta ttaatgatct   4680
tcctgattat atgaagttat gttttcttgc actttacaat actattaacg agatagctta   4740
cgataactta aaagataaag gtgagaacat acttccttat ttaacaaaag catgggcaga   4800
tttatgtaat gcatttcttc aagaagctaa gtggcttttat aataaatcaa cacctacatt   4860
tgatgattat tttggaaatg catggaaaag ttctagtgga cctttacagc ttatttttg   4920
ttattttgct gtagtacaga acattaaaaa ggaagagatt gagaatcttc agaaaatca   4980
tgacataata tcaagaccta gtcacatttt taggctttgt aatgatttag catctgcttc   5040
agcagaaata gcaagaggtg aaactgctaa ttctgtaagt tgtttatatga gaacaaaagg   5100
tatatctgaa gaattagcta ctgaaagtgt tatgaatctt atagacgaa cttggaagaa   5160
aatgaacaaa gaaaaacttg gtggatcttt atttgcaaaa cctttttgttg agactgtat   5220
aaatttagct agacagtctc attgcacata tcataatggt gatgcacata ctagtccaga   5280
tgaattaact aggaaaagag tacttagtgt aataactgaa ccaatattac catttgaaag   5340
ataag                                                              5345

SEQ ID NO: 26          moltype = DNA    length = 26
FEATURE                Location/Qualifiers
misc_feature           1..26
                       note = Oligonucleotide Idi-Cbei-SacI-F
source                 1..26
                       mol_type = other DNA
                       organism = synthetic construct
SEQUENCE: 26
gtgagctcga aagggggaaat taaatg                                       26

SEQ ID NO: 27          moltype = DNA    length = 27
FEATURE                Location/Qualifiers
misc_feature           1..27
                       note = Oligonucleotide Idi-Cbei-KpnI-R
source                 1..27
```

```
                         mol_type = other DNA
                         organism = synthetic construct
SEQUENCE: 27
atggtacccc aaatctttat ttagacg                                            27

SEQ ID NO: 28            moltype = DNA   length = 5905
FEATURE                  Location/Qualifiers
misc_feature             1..5905
                         note = plasmid pMTL85246-ispS-idi
source                   1..5905
                         mol_type = other DNA
                         organism = synthetic construct
SEQUENCE: 28
ccggggatcc tctagagtcg acgtcacgcg tccatggaga tctcgaggcc tgcagacatg     60
caagcttggc actggccgtc gttttacaac gtcgtgactg ggaaaaccct ggcgttaccc    120
aacttaatcg ccttgcagca catccccctt tcgccagctg gcgtaatagc gaagaggccc    180
gcaccgatcg cccttcccaa cagttgcgca gcctgaatgg cgaatggcgc tagcataaaa    240
ataagaagcc tgcatttgca ggcttcttat ttttatggcg cgccgcattc acttcttttc    300
tatataaata tgagcgaagc gaataagcgt cggaaaagca gcaaaagtt tccttttttgc    360
tgttggagca tgggggttca ggggtgcag tatctgacgt caatgccgag cgaaagcgag    420
ccgaagggta gcatttacgt tagataaccc cctgatatgc tccgacgctt tatatagaaa    480
agaagattca actaggtaaa atcttaatat aggttgagat gataaggttt ataaggaatt    540
tgtttgttct aattttttca c tcattttgtt ctaatttctt ttaacaaatg ttcttttttt    600
tttagaacag ttatgatata gttagaatag tttaaaataa ggagtgagaa aaagatgaaa    660
gaaagatatg gaacagtcta taaggctctc cagaggctca tagacgaaga agtggagaaa    720
gtcatagagg tagacaagtt ataccgtaaa caaacgtctg gtaacttcgt aaaggcatat    780
atagtgcaat taataagtat gttagatatg attggcggaa aaaaacttaa aatcgttaac    840
tatatcctag ataatgtcca cttagtaac aatacaatga tagctacaac aagagaaata    900
gcaaaagcta caggaacaag tctacaaaca gtaataacaa cacttaaaat cttagaagaa    960
ggaaatatta taaaaagaaa aactggagta ttaatgttaa accctgaact actaatgaga   1020
ggcgacgacc aaaaacaaaa atacctctta ctcgaatttg gaactttga gcaagaggca   1080
aatgaaatag attgacctcc caataacacc acgtagttat tgggaggtca atctatgaaa   1140
tgcgattaag ggccggccag tgggcaagtt gaaaaattca caaaaatgtg gtataatatc   1200
tttgttcatt agagcgataa acttgaattt gagagggaaa tatgatggta tttgaaaaaa   1260
ttgataaaaa tagttggaac agaaaagagt attttgacca ctactttgca agtgtacctt   1320
gtacctacag catgaccgtt aaagtgggata tcacacaaat aaaggaaaag ggaatgaaac   1380
tatatcctgc aatgctttat tatattgcaa tgattgtaaa ccgccattca gagtttagga   1440
cggcaatcaa tcaagatggt gaattgggga tatgatgga gatgatacca agctacaca   1500
tatttcacaa tgatactgaa acatttttcca gcctttggca tgagtgtaag tctgacttta   1560
aatcattttt agcagattat gaaagtgata cgcaacgtga tggaaacaat catagaatgg   1620
aaggaaagcc aaatgctccg gaaacatttt taatgtatc tatgatccg tggtcaacct   1680
tcgatggctt aatctgaat ttgcagaaag gatatgatta tttgattcct atttttacta   1740
tggggaaaata ttataaagaa gataacaaaa ttatacttcc ttttggcaatt caagttcatc   1800
acgcagtatg tgacggattt cacatttgcc gttttgtaaa cgaattgcag gaattgataa   1860
atagttaact tcaggtttgt ctgtaactaa aaacaagtat ttaagcaaaa acatcgtaga   1920
aatacgtgt tttttgttac cctaagttta aactcctttt tgataatctc atgaccaaaa   1980
tccttaacg tgagtttccg ttccactgag cgtcagaccc cgtagaaaag atcaaaggat   2040
cttcttgaga tcctttttt ctgcgcgtaa tctgctgctt gcaaacaaaa aaaccaccgc   2100
taccagcggt ggtttgtttg ccggatcaag agctaccaac tctttttccg aaggtaactg   2160
gcttcagcag agcgcagata ccaaatactg ttcttctagt gtagccgtag ttaggccacc   2220
acttcaagaa ctctgtagca ccgcctacat acctcgctct gctaatcctg ttaccagtgg   2280
ctgctgccag tggcgataag tcgtgtctta ccgggttgga ctcaagacga tagttaccgg   2340
ataaggcgca gcggtcgggc tgaacggggg gttcgtgcac acagcccagc ttggagcgaa   2400
cgacctacac cgaactgaga tacctacagc gtgagctatg agaaagcgcc acgcttcccg   2460
aagggagaaa ggcggacagg tatccggtaa gcggcaggt cggaacagga gcgcacga   2520
gggagcttcc agggggaaac gcctggtatc tttatagtcc tgtcgggttt cgccacctct   2580
gacttgagcg tcgatttttg tgatgctcgt caggggggcg gagcctatgg aaaaacgcca   2640
gcaacgcggc ctttttacgg ttcctggcct tttgctggcc ttttgctcac atgttctttc   2700
ctgcgttatc ccctgattct gtggataacc gtattaccgc ctttgagtga gctgataccg   2760
ctcgccgcag ccgaacgacc gagcgcagcg agtcagtgag cgaggaagcg gaagagcgcc   2820
caatacgcag ggcccctgc aggataaaaa aattgtagat aaatttata aaatagtttt   2880
atctacaatt ttttttatcag gaaacagcta tgaccgcggc gcggttaat gttaaaaatt   2940
tatagtataa ctttaaaaaa ctgtcttaaa aagttgttat ataaaaaatg ttgacaatta   3000
aacagctatt tagtgcaaaa caaccataaa aatttaaaaa ataccataaa ttacttgaaa   3060
aatagttgat aataatgtag agttataaac aaaggtgaaa agcattactt gtattctttt   3120
ttatatatta ttataaatta aaatgaagct gtattagaaa aaatacacac ctgtaatata   3180
aaattttaaa ttaattttta atttttttcaa atgtatttt acatgtttag aattttgatg   3240
tatattaaaa tagtagaata cataagatac ttaatttaat taaagatagt taagtacttt   3300
tcaatgtgct tttttagatg tttaataaa atctttaatt gtaaaagaaa tgctgtacta   3360
tttactgtac tagtgacggg attaaactgt attaattata aataaaaaat aagtacagtt   3420
gtttaaaatt atattttgta ttaaatctaa tagtacgatg taagttattt tatactattg   3480
ctagtttaat aaaaagattt aattatatac ttgaaaagga gggaatttt tatgcgtcat   3540
atggcaacag aattattatg tttacacaga cctatatcac ttactcacaa acttttttagg   3600
aatccattac ctaaagttat tcaagctaca cctttaacat taaacttag gtgtagtgtt   3660
tctacagaaa atgtatcatt tagtgagaca gaaactgaaa caagaagatc agcaaattat   3720
gaaccaaatt cttgggatta tgattatctt ctttcttctg atactgatga gtcaatagaa   3780
gtacataaag ataaggctaa gaaattgaa gctgaagtta ggagagaaat aaataatgag   3840
aaggctgaat tcttacact tcttgaactt attgataatg tacaaagact tggattagga   3900
tatagatttg agtctgatat aagaagagca ttagatagat ttgtaagtag tggaggattt   3960
```

-continued

```
gatggagtta ctaaaacttc attacatgga acagcattat catttaggtt attaaggcaa    4020
catggttttg aagtatctca agaagctttt agtggattta aagatcagaa tggaaacttt    4080
cttgagaatt taaaggaaga cataaaagca attctttctc tttatgaagc atcatttta     4140
gcattagaag gtgagaatat attagatgag ctaaagtat ttgcaatatc tcatcttaaa     4200
gaacttagtg aagaaaagat tggtaaagaa ttagctgaac aagtttcaca tgctttagaa    4260
ttaccattac atagaagaac acaaagatta gaagcagttt ggtcaataga agcatataga   4320
aagaaagaag acgcaaatca agtactttta gaacttgcaa tacttgacta caatatgatt    4380
caaagtgtat atcagaggga tttaagagaa acatcaagat ggtggagaag agtaggatta    4440
gcaactaaat tacatttgc tagagatagg cttattgaaa gttttattg ggctgttga      4500
gttgcttttg aaccacaata ttctgattgc agaaatagtg tagcaaagat gttttcattt    4560
gttactataa ttgacgatat ttcgatgta tatggaactt tagatgaact tgaactttt     4620
actgatgcag ttgaaagatg ggatgtaaat gctattaatg atcttcctga ttatatgaag    4680
ttatgttttc ttgcacttta caatactatt aacgagatag cttacgataa cttaaaagat    4740
aaaggtgaga acatactcc ttatttaaca aaagcatggg cagattttat taatgcattt    4800
cttcaagaag ctaagtggct ttataataaa tcaacaccta catttgatga ttattttgga    4860
aatgcatgga aaagttctag tggacccta cagcttattt ttgcttattt tgctgtagta    4920
cagaacatta aaaaggaaga gattgagaat cttcagaaat atcatgacat aatatcaaga    4980
cctagtcaca tttttaggct ttgtaatgat ttagcatctg cttcagcaga aatagcaaga    5040
ggtgaaactg ctaattctgt aagttgttat atgagaacaa aaggtatatc tgaagaatta    5100
gctactgaaa gtgttatgaa tcttatagac gaaacttgga agaaaatgaa caaagaaaaa   5160
cttggtggat ctttatttgc aaaacctttt gttgagactg ctataaattt agctagacag    5220
tctcattgca catatcataa tggtgatgca cataactagtc gatgaatt aactaggaaa    5280
agagtactta gtgtaataac tgaaccaata ttaccatttg aaagataaga attcgagctc    5340
gaaaggggaa attaaatggc agaatatata atagctgtag atgaatttga taacgaaata    5400
ggttcaattg aaaaaaatgga ggctcaccgt aaaggaacat tacatagagc tttttctata   5460
ttagtattta attctaaaaa tcaattgtta ttacagaaaa gaaatgtaaa aaaatatcat    5520
tcgcctggtc tctggacaaa tacgtgctgt agtcatccaa gatacggtga agtttacat    5580
gatgcgattt atagaaggct taaggaagaa atggggttta catgtgaact tgaagaagta    5640
tttagttta tttataaagt aaaacttgaa gataatcttt ttgaaaatga atatgatcat    5700
gtattcattg ggaaatatga tggagaaata atttgtaaaca aagatgaagt agatgatttt    5760
aagtgggttg atattaatga ggttaagaag gatattatag aaaggccaga agcatacact    5820
tattggttca agtatttagt taataaggca gaaaacaaaa tatttaaata agtaagaatt    5880
tcgtctaaat aaagatttgg ggtac                                         5905
```

```
SEQ ID NO: 29          moltype = DNA   length = 29
FEATURE                Location/Qualifiers
misc_feature           1..29
                       note = Oligonucleotide Dxs-SalI-F
source                 1..29
                       mol_type = other DNA
                       organism = synthetic construct
SEQUENCE: 29
gcagtcgact ttattaaagg gatagataa                                      29

SEQ ID NO: 30          moltype = DNA   length = 31
FEATURE                Location/Qualifiers
misc_feature           1..31
                       note = Oligonucleotide Dxs-XhoI-R
source                 1..31
                       mol_type = other DNA
                       organism = synthetic construct
SEQUENCE: 30
tgctcgagtt aaaatatatg acttacctct g                                   31

SEQ ID NO: 31          moltype = DNA   length = 7784
FEATURE                Location/Qualifiers
misc_feature           1..7784
                       note = plasmid pMTL85246-ispS-idi-dxs
source                 1..7784
                       mol_type = other DNA
                       organism = synthetic construct
SEQUENCE: 31
tcgaggcctg cagacatgca agcttggcac tggccgtcgt tttacaacgt cgtgactggg    60
aaaaccctgg cgttacccaa cttaatcgcc ttgcagcaca tccccctttc gccagctggc    120
gtaatagcga agaggcccgc accgatcgcc cttcccaaca gttgcgcagc ctgaatggcg    180
aatggcgcta gcataaaaat aagaagcctg catttgcagg cttcttattt ttatggcgcg    240
ccgcattcac ttcttttcta tataaatatg agcgaagcga taagcgtcg gaaaagcagc     300
aaaagttttc cttttgctg ttggagcatg ggggttcagg gggtgcagta tctgacgtca    360
atgccgagcg aaagcgagcc gaagggtagc atttacgtta gataaccccc tgatatgcct    420
cgacgcttta tatagaaaag aagattcaac taggtaaaat cttaatatag gttgagatga    480
taaggtttat aaggaaattg tttgttctaa tttttcactc attttgttct aatttctttt    540
aacaaatgtt cttttttttt tagaacagtt atgatatagt tagaatagtt taaaataagg    600
agtgagaaaa agatgaaaga agatatgga acagtctata aaggctctca gaggctcata    660
gacgaactaa ggtgagaagt cataggagta gacaagttat accgtaaaca aactgtcggt    720
aacttcgtaa aggcatatat agtgcaatta ataagtatgt tagatatgat tggcggaaaa    780
aaacttaaaa tcgttaacta tatcctagat aatgtccact taagtaacaa tacaatgata    840
gctacaacaa gagaaatagc aaaagctaca ggaacaagtc tacaaacagt aataacaaca    900
cttaaaatct tagaagaagg aaatattata aaaagaaaaa ctggagtatt aatgttaaac    960
cctgaactac taatgagagg cgacgaccaa aaacaaaaat acctcttact cgaatttggg    1020
```

```
aactttgagc aagaggcaaa tgaaatagat tgacctccca ataacaccac gtagttattg   1080
ggaggtcaat ctatgaaatg cgattaaggg ccggccagtg ggcaagttga aaaattcaca   1140
aaaatgtggt ataatatctt tgttcattag agcgataaac ttgaatttga gagggaactt   1200
agatggtatt tgaaaaaatt gataaaaata gttggaacag aaaagagtat tttgaccact   1260
actttgcaag tgtaccttgt acctacagca tgaccgttaa agtggatatc acacaaataa   1320
aggaaaaggg aatgaaacta tatcctgcaa tgctttatta tattgcaatg attgtaaacc   1380
gccattcaga gttaggacg gcaatcaatc aagatggtga attggggata tatgatgaga    1440
tgataccaag ctatacaata tttcacaatg atactgaaac attttccagc ctttggactg   1500
agtgtaagtc tgactttaaa tcattttttag cagattatga aagtgatacg caacggtatg   1560
gaaacaatca tagaatggaa ggaaagccaa atgctccgga aaacattttt aatgtatcta   1620
tgataccgtg gtcaaccttc gatggcttta atctgaattt gcagaaagga tatgattatt   1680
tgattcctat ttttactatg gggaaatatt ataagaaga taacaaaatt atacttcctt    1740
tggcaattca agttcatcac gcagtatgtg acggatttca catttgccgt tttgtaaacg   1800
aattgcagga attgataaat agttaacttc aggtttgtct gtaactaaaa acaagtattt   1860
aagcaaaaac atcgtagaaa tacggtgttt tttgttaccc taagtttaaa ctccttttttg  1920
ataatctcat gaccaaaatc ccttaacgtg agttttcgtt ccactgagcg tcagaccccg   1980
tagaaaagat caaaggatct tcttgagatc cttttttttct gcgcgtaatc tgctgcttgc   2040
aaacaaaaaa accaccgcta ccagcggtgg tttgtttgcc ggatcaagag ctaccaactc   2100
tttttccgaa ggtaactggc ttcagcagag cgcagatacc aaatactgtt cttctagtgt   2160
agccgtagtt aggccaccac ttcaagaact ctgtagcacc gcctacatac ctcgctctgc   2220
taatcctgtt accagtggct gctgccagtg gcgataagtc gtgtcttacc gggttggact   2280
caagacgata gttaccggat aaggcgcagc ggtcgggctg aacggggggt tcgtgcacac   2340
agcccagctt ggagcgaacg acctacaccg aactgagata cctacagcgt gagctatgag   2400
aaaagcgcca cgcttcccga agggagaaagg cggacaggta tccggtaagc ggcagggtcg   2460
gaacaggaga gcgcacgagg gagcttccag ggggaaacgc ctggtatctt tatagtcctg   2520
tcgggtttcg ccacctctga cttgagcgtc gatttttgtg atgctcgtca ggggggcgga   2580
gcctatggaa aaacgccagc aacgcggcct ttttacggtt cctggccttt tgctggcctt   2640
ttgctcacat gttctttcct gcgttatccc ctgattctgt ggataaccgt attaccgcct   2700
ttgagtgagc tgataccgct cgccgcagcc gaacgaccga cgcagcgag tcagtgagcg    2760
aggaagcgga agagcgccca atacgcaggg cccctgcga gataaaaaaa ttgtagataa   2820
attttataaa atagttttat ctacaatttt tttatcagga aacagctatg accgcggccg   2880
cggttaatgt taaaaattta tagtataact ttaaaaaact gtcttaaaaa gttgttatat   2940
aaaaaatgtt gacaattaaa cagctattta gtgcaaaaca accataaaaa tttaaaaaat   3000
accataaatt acttgaaaaa tagttgataa taatgtagag ttataaacaa aggtgaaaag   3060
cattacttgt attctttttt atatattatt ataaattaaa atgaagctgt attagaaaaa   3120
atacacacct gtaatataaa atttaaatt aattttaat tttttcaaaa tgtattttac     3180
atgtttagaa ttttgatgta tattaaaata gtagaataca aagtactt aatttaatta    3240
aagatagtta agtactttc aatgtgcttt tttagatgtt taatacaaat ctttaattgt    3300
aaaagaaatg ctgtactatt tactgtacta gtgacgggat taaactgtat taattataaa   3360
taaaaaataa gtacgttgt ttaaaattat attttgtatt aaatctaata gtacgatgta    3420
agttatttta tactattgct agtttaataa aaagatttaa ttatatactt gaaaaggaga   3480
ggaattttta tgcgtcatat ggcaacgaaa ttattatgtt tacacagacc tatatctactt  3540
actcacaaac tttttaggaa tccattaccct aaagttattca aagctaacc tttaacatta   3600
aaacttaggt gtagtgtttc tacagaaaat gtatcattta gtgagacaga aactgaaaca   3660
agaagatcag caaattatga accaaattct ggggattatg attatcttct ttcttctgat   3720
actgatgagt caatagaagt acataaagat aaggctaaga aattagaagc tgaagttagg   3780
agagaaataa ataatgagaa ggctgaattat cttacacttc ttgaacttat tgataatgta   3840
caaagacttg gattaggata tagatttgag tctgatataa gaagagcatt agatagattt   3900
gtaagtagtg gaggatttga tggagttact aaaaacttcat tacatggaac agcattatca   3960
tttaggttat taaggcaaca tggttttgaa gtatctcaag aagcttttag tggatttaaa   4020
gatcagaatg gaaactttct tgagaattta aaggaagaca taaaagcaat tctttctctt   4080
tatgaagcat cattttttagc attagaaggt gagaatatat tagatgaggc taaagtattt   4140
gcaatatctc atcttaaaga acttagtgaa gaaaagattg gtaaagaatt agctgaacaa   4200
gtttcacatg ctttagaatt accattacat agaagaacac aaagattaga agcagtttgg   4260
tcaatagaag catatagaaa gaaagaagac gcaaatcaag tacttttttaga acttgcaata  4320
cttgactaca atatgattca aagtgtatat cagagggatt taagagaaac atcaagatgg   4380
tggagaagag taggattagc aactaaatta cattttgcta gagataggct tattgaaagt   4440
ttttattggg ctgttggagt tgcttttgaa ccacaatatt ctgattgcag aaatagtgta   4500
gcaaagatgt tttcatttgt tactataatt gacgatattt acgatgtata tggaacttta   4560
gatgaacttg aactttttac tgatgcagtt gaaagatggg atgtaaatgc tattaatgat   4620
cttcctgatt atatgaagtt atgtttttctt gcacttaca atactattaa cgagatagct   4680
tacgataact aaaagataa aggtgagaac atacttcctt atttaacaaa agcatgggca   4740
gatttatgta atgcatttct tcaagaagct aagtggcttt ataataaatc aacacctaca   4800
tttgatgatt attttggaaa tgcatggaaa agttctagtg gacctttaca gcttatttt    4860
gcttatttg ctgtagtaca gaacattaaa aaggaagaga ttgagaatct tcagaaatat    4920
catgacataa tatcaagacc tagtcacatt tttaggcttt gtaatgattt agcatctgct   4980
tcagcagaaa tagcaagagg tgaaactgct aattctgtaa gttgttatat gagaacaaaa   5040
ggtatatctg aagaattagc tactgaaagt gttatgaatc ttatagacga aacttggaag   5100
aaaatgaaca aagaaaaact tggtgatcct ttatttgcaa aaccttttgt tgagactgct   5160
ataaatttag ctagacagtc tcattgcaca tatcataatg gtgatgcaca tactagtcca   5220
gatgaattaa ctaggaaaag agtacttagt gtaataactg aaccaatatt accatttgaa   5280
agataagaat tcgagctcga aaggggaaat taaatggcag aatatataat agctgtagat   5340
gaatttgata acgaaatagg ttcaattgaa aaaatggagg ctcaccgtaa aggaacatta   5400
catagacttt tttctatatt agtatttaat tctaaaaatc aattgttatt acagaaaaga   5460
aatgtaaaaa aatatcattc gcctggtctc tggacaaaata cgtgctgtag tcatccaaga   5520
tacggtgaaa gttacatga tgcgatttat agaaggctta aggaagaaat gggttttaca     5580
tgtgaacttg aagaagtatt tagttttatt tataaagtaa aacttgaaga taatcttttt   5640
gaaaatgaat atgatcatgt attcattggg aaatatgatg gagaaataat tgtaaacaaa   5700
gatgaagtag atgattttaa gtgggttgat attaatgagg ttaagaagga tattatagaa   5760
```

```
aggccagaag catacactta ttggttcaag tatttagtta ataaggcaga aacaaaata    5820
tttaaataag taagaatttc gtctaaataa agatttgggg tacccgggga tcctctagag    5880
tcgactttat taaagggata gataaggatg agtaatttat tagataatta taaagatata    5940
aatgacgtaa agaagatgtc gttaaatgat aaaaaaagc tagctagaga aattagaaaa    6000
tttttaatag acaaagtatc taagacagga ggtcatttga cgtctaactt aggggttgtg    6060
gagctcactt tgagtttatt tagtgtattt gatctaaatt atgataaact tatatgggat    6120
gtgggacatc aggcttatgt gcataaaatc ctcacgggaa gaaaggataa atttgatact    6180
ttaaggcaat ttggaggatt aagtggattt cctaaaaggt gcgaaagtat atatgatttt    6240
ttcgaaacag ggcatagtag tacttcaata tctgcagcac ttggaatggc tagggctaga    6300
gatttaaagc atgagaaata taatgttgtt gcagttatag gagatggaac acttactgga    6360
ggtatggcac tagaggccct aaatgatgta ggttatagaa aaactaagct tataataata    6420
ttaaatgata atcaaatgtc tataggaaaa aatgtaggtg gagtatctaa atatttaaat    6480
aaacttagag tggaccctaa gtataataaa tttaaagcgg atgtagaagc taaattaaaa    6540
aagataccta atataggaaa aggaatggca aaatatcttg aaaaggtaaa aaatggaaata    6600
aaacaaatgg tagttcctgg aatgtttttt gaagatatgg gaattaaaata tttaggacca    6660
atagatggtc ataatataaa agaacttaca gacgtactcg cttctgcaaa agacatacaa    6720
ggtccagtta ttatacatat aataactaag aaaggaaaag gatatgaatt tgcaagaaaa    6780
aaatccaggt aaattccatg gaatagggcc ttttaattgc gccaatggtg aactggatgc    6840
tggatcttca aatacttatt ccaaggcctt tggaaatgaa atggtaaagc tagcagaaaa    6900
agacgataga atagtggcta taactgcagc catgagggat ggaacaggtc ttaaaagttt    6960
ttctcaaaag tttcctgaaa ggttttttga tgtgggaata gcagaacagc atgctgtaac    7020
cctgcagct ggaatggcac aggcaaattt aaaacctgta tttgcagttt actctacttt    7080
tcttcaaaga gcttatgatc aacttattca tgatgtatgt atgcaaaaac ttccagtagt    7140
ttttgctgta gataggccg gcattgtagg agaagatggt gaaacacatc agggaatatt    7200
tgatttatct tacttaacgg aaatgccaca tatgacgctt atgtctccta aatgtataga    7260
tgaacttcca tatatgttaa aatgggcatt aggccagcat tttcctgtag ctataaggta    7320
tccaagggga ggagatagtg tatgtctcaa tcccgtagaa aatttaaac ttggaaagtg    7380
ggactgtatt tcaaatgaag gcagtgtagc aataattgct cagggtaaaa tggtacaaaa    7440
tgcagtgtta gcaggaaaaa aacttaaaga aaagggtata gatgtaagga ttataagtgc    7500
atgttttatt aagccgctgg acaaggaaat gttaaacagg ttagttgaag aaagtgtaa    7560
tatcgttact gttgaagaca atgtaataag aggaggatta ggatcctata tattagaata    7620
tgtaaataaa ttaaataaaa aagtaaaaat aataaactta gggtttgatg ataagtttgt    7680
acagcatgga aaatccgata tttttgtataa gctgtatggt ttggatccta aaggtatcgt    7740
aaatagtgta cttgaagcag cagaggtaag tcatatattt taac                    7784

SEQ ID NO: 32          moltype = DNA  length = 17
FEATURE                Location/Qualifiers
misc_feature           1..17
                       note = Oligonucleotide M13R
source                 1..17
                       mol_type = other DNA
                       organism = synthetic construct
SEQUENCE: 32
caggaaacag ctatgac                                                   17

SEQ ID NO: 33          moltype = DNA  length = 20
FEATURE                Location/Qualifiers
misc_feature           1..20
                       note = Oligonucleotides Isoprene-seq1
source                 1..20
                       mol_type = other DNA
                       organism = synthetic construct
SEQUENCE: 33
gttattcaag ctacaccttt                                                20

SEQ ID NO: 34          moltype = DNA  length = 20
FEATURE                Location/Qualifiers
misc_feature           1..20
                       note = Oligonucleotide Isoprene-seq2
source                 1..20
                       mol_type = other DNA
                       organism = synthetic construct
SEQUENCE: 34
gattggtaaa gaattagctg                                                20

SEQ ID NO: 35          moltype = DNA  length = 18
FEATURE                Location/Qualifiers
misc_feature           1..18
                       note = Oligonucleotide Isoprene-seq3
source                 1..18
                       mol_type = other DNA
                       organism = synthetic construct
SEQUENCE: 35
tcaagaagct aagtggct                                                  18

SEQ ID NO: 36          moltype = DNA  length = 17
FEATURE                Location/Qualifiers
misc_feature           1..17
                       note = Oligonucleotide Isoprene-seq4
```

| | | |
|---|---|---|
| source | 1..17<br>mol_type = other DNA<br>organism = synthetic construct | |
| SEQUENCE: 36 | | |
| ctcaccgtaa aggaaca | | 17 |
| | | |
| SEQ ID NO: 37<br>FEATURE<br>misc_feature | moltype = DNA   length = 20<br>Location/Qualifiers<br>1..20<br>note = Oligonucleotide Isoprene-seq5 | |
| source | 1..20<br>mol_type = other DNA<br>organism = synthetic construct | |
| SEQUENCE: 37 | | |
| gctagctaga gaaattagaa | | 20 |
| | | |
| SEQ ID NO: 38<br>FEATURE<br>misc_feature | moltype = DNA   length = 20<br>Location/Qualifiers<br>1..20<br>note = Oligonucleotide Isoprene-seq6 | |
| source | 1..20<br>mol_type = other DNA<br>organism = synthetic construct | |
| SEQUENCE: 38 | | |
| ggaatggcaa aatatcttga | | 20 |
| | | |
| SEQ ID NO: 39<br>FEATURE<br>misc_feature | moltype = DNA   length = 20<br>Location/Qualifiers<br>1..20<br>note = Oligonucleotide Isoprene-seq7 | |
| source | 1..20<br>mol_type = other DNA<br>organism = synthetic construct | |
| SEQUENCE: 39 | | |
| gaaacacatc agggaatatt | | 20 |
| | | |
| SEQ ID NO: 40<br>FEATURE<br>source | moltype = DNA   length = 1179<br>Location/Qualifiers<br>1..1179<br>mol_type = other DNA<br>organism = Clostridium acetobutylicum | |
| SEQUENCE: 40 | | |
| atgaaagagg ttgttattgc atcagctgtt agaactgcaa taggatctta tggaaaagt | | 60 |
| cttaaagatg taccagcagt agacttaggt gcaactgcaa taaggaagc agtaaagaaa | | 120 |
| gcaggtataa aacctgaaga tgttaatgaa gttatttag aaacgtatt acaagctgga | | 180 |
| cttggacaga atccagctag acaggcatca ttcaaagcag gattaccagt agagatacct | | 240 |
| gctatgacta ttaataaagt ttgtggttca ggattaagaa cagtttctt agctgctcaa | | 300 |
| attataaaag ctggtgacgc agatgtaata atagcaggtg gtatggaaaa tatgtcaaga | | 360 |
| gcaccatacc ttgctaataa tgctagatgg ggttatagaa tgggaaacgc taaatttgta | | 420 |
| gacgaaaatga taactgatgg actttgggat gcatttaacg attatcacat gggaattact | | 480 |
| gctgaaaata tagctgagag atggaatata agtagagaag aacaagatga gtttgcactt | | 540 |
| gcatctcaga aaaaggcaga agaagctatt aaatcaggac aatttaaaga tgaaattgtt | | 600 |
| ccagtagtaa ttaaaggtag aaaaggtgaa acagttgtag acactgatga acatcctaga | | 660 |
| tttggatcta caatagaagg tttagctaaa ttaaagcctg cttttaagaa agacggaaca | | 720 |
| gtaactgctg gaaacgcatc aggttttaaat gattgtgcaa ctgttttagt tattatgtct | | 780 |
| gctgaaaagg caaaggaatt aggtgttaaa ccacttgcta agatagttag ttatggttca | | 840 |
| gcaggtgtag atcctgctat tatgggatat ggacctttt atgctacaaa ggcagctatt | | 900 |
| gaaaaggctg gttggacagt tgatgaactt gatcttatag agtcaaatga ggcatttgca | | 960 |
| gcacaaagtc ttgctgttgc taaggatctt aaattcgata tgaataaagt aaatgtaaac | | 1020 |
| ggtggtgcta tagcacttgg tcatccaata ggtgctagtg gtgctagaat tttagttaca | | 1080 |
| ttagttcatg caatgcaaaa agagagacgct aaaaagggac ttgcaacttt atgcataggt | | 1140 |
| ggtggtcaag gaacagcaat acttcttgaa aaatgttaa | | 1179 |
| | | |
| SEQ ID NO: 41<br>FEATURE<br>source | moltype = DNA   length = 1140<br>Location/Qualifiers<br>1..1140<br>mol_type = other DNA<br>organism = Staphylococcus aureus<br>sub_species = subsp. aureus | |
| SEQUENCE: 41 | | |
| atgaatcagg ctgttatagt tgctgcaaag agaactgcat ttggaaaata tggtggtact | | 60 |
| ttaaaacacc ttgaaccaga acaattactt aagccattat ttcagcactt taagaaaaaa | | 120 |
| tatcctgaag ttatatctaa aatagatgat gtagttttag gaaacgtagt tggaaatggt | | 180 |
| ggtaatattg ctagaaaagc acttcttgaa gcaggattaa aagatagtat accaggtgta | | 240 |
| actatagaca gacaatgcgg atctggatta gaatcagtac aatacgcatg tagaatgata | | 300 |
| caagcaggtg ctgaaaagt ttatattgca ggtggtgttg aatctacatc aagagcacct | | 360 |
| tggaaaataa agagaccaca ttctgttat gaaactgcat taccagagtt ctatgaagga | | 420 |
| gcatcattcg cacctgaaat gtcagatcca agtatgatac aaggtgctga gaatgtagct | | 480 |
| aaaatgtatg atgttagtag agaacttcaa gatgagttgt cataccagatc acatcaactt | | 540 |

```
acagctgaaa atgtaaagaa tggaaatatt tcacaagaaa ttcttccaat aacagtaaag   600
ggtgaaatat tcaatactga tgaaagttta aatctcata ttccaaaga taatttcggt    660
agatttaaac ctgtaataaa aggtggtact gtaacagctg ctaatagttg tatgaagaac   720
gatggtgcag tattattact tattatggaa aaggatatgg cttatgaact tggatttgag   780
catggattat tatttaaaga cggtgtaact gtaggtgtag atagtaactt tccaggaata   840
ggacctgttc ctgctatatc aaatcttta aagagaaacc aacttacaat agaaaatatt    900
gaagtaattg agataaatga agcattttct gctcaggtag ttgcttgtca gcaagctctt   960
aatataagta atactcagtt aaacatttgg ggtggtgcat tagcaagtgg tcatcctat   1020
ggtgcatcag gtgcacagtt agttacaaga ttatttata tgttcgataa agagacaatg   1080
attgcttcta tgggaatagg tggtggttta ggaaatgcag ctcttttac tagattttaa   1140

SEQ ID NO: 42            moltype = DNA   length = 1167
FEATURE                  Location/Qualifiers
source                   1..1167
                         mol_type = other DNA
                         organism = Staphylococcus aureus
                         sub_species = subsp. aureus
SEQUENCE: 42
atgactatag gaattgacaa aataaactt tacgtaccaa atattatgt agatatggca     60
aaattagcag aagcaagaca gtagaccca aataaattc ttattggaat aggacagact    120
gaaatggcag ttagtccagt aaaccaagat atagtatcaa tgggtgctaa tgctgctaaa   180
gatataataa ctgatgaaga caaaaagaaa ataggaatgg taatagtagc aactgagtca   240
gcagtagatg cagcaaaggc agcagcagta cagattcata atttattagg tattcaacca   300
tttgcaagat gtttcgaaat gaagaagca tgttatgctg ctactcctgc aattcagtta   360
gctaaggatt atttagctac aagaccaaat gagaaagttt tagttatagc tacagataca   420
gctagatatg gacttaattc aggtggtgaa cctactcaag gtgctggtgc tgttgctatg   480
gttatagctc ataatcctag tatacttgca ttaaatgaag acgctgttgc ttatacagaa   540
gatgtttatg atttctggag accaacagga cataagtatc cattagtaga tggtgcttta   600
tcaaagacg catatattag atcttttcaa caatcttgga atgaatatgc taagagacaa    660
ggaaagagtt tagctgattt tgctagtctt gctttcatg ttccttttac taaaatgggt    720
aaaaaggctt tagaatctat aatagataac gcagatgaaa caactcaaga gagattaaga   780
tctggatatg aagatgcagt tgattacaat agatatgttg gaaatatata cacaggaagt   840
cttatctttt ctcttataag tcttcttgaa aatagagatt tacaggctgg tgaaactatt   900
ggattatttt catacggatc aggttctgtt ggtgaatttt attcagctac acttgtagaa   960
ggatataaag atcaccttga tcaggcagca cacaaagcac ttttaaacaa tagaactgaa  1020
gtatcagtag atgcatacga aacatttttc aagagatttg atgatgtaga atttgatgaa  1080
gagcaggatg cagttcatga agatagacat atattctatc tttcaaacat agagaataat  1140
gtaagagaat atcatagacc tgaataa                                      1167

SEQ ID NO: 43            moltype = DNA   length = 1278
FEATURE                  Location/Qualifiers
source                   1..1278
                         mol_type = other DNA
                         organism = Staphylococcus aureus
                         sub_species = subsp. aureus
SEQUENCE: 43
atgcaatcat tagacaaaaa tttcagacat ttatcaagac aacaaaagtt acaacaatta    60
gttgataaac agtggctttc agaagatcag tttgatattt tacttaatca tcctcttata   120
gatgaagaag ttgctaatag tcttatagaa aatgtaattg cacagggtgc attaccagtt   180
ggacttcttc ctaatataat agttgatgat aaggcttatg ttgtaccaat gatggttgaa   240
gaacctagtg ttgttgcagc tgcatccttat ggtgctaata tagaaatca gacaggtagt   300
tttaaaactg tatcatcaga aagaataatg attggacaga tagtatttga tggtgtagat   360
gacactgaaa aattaagtgc agatattaaa gcattagaaa aacaaatac taagattgca   420
gatgaagcat atcctagtat aaaagcaaga ggtggtggtt atcaaagaat agcaatagat   480
acatttccag agcaacaact tttaagtctt aaggtatttg tagatacaaa agatgctatg   540
ggtgctaata tgcttaatac tatacttgag gcaataactg cattccttaa aaatgaatct   600
cctcaatcag atattaat gtctatactt tcaaaccatg caactgctag tgtagtaaaa    660
gtacaaggtg agatagatgt aaaagatctt gctagaggtg aaagaacagg tgaagaagta   720
gctaagagaa tggaaagagc ttctgtatta gctcaggttg atatcatag agctgcaaca   780
cataacaaag gtgttatgaa tggaatacat gctgttgttt tagctacagg aaatgatact   840
agaggtctga agcatctgc acatgcatac gcatcaagag acggacaata tagaggtata   900
gcaacttgga gatatgatca gaagagacaa agacttattg gaactattga agttccaatg   960
acacttgcta tagtaggtgg tggtactaaa gtattaccaa tagctaaggc atcattagag  1020
ttattaaatg ttgattctgc acaagaactt ggacacgtat ttgtcgtgt tggattacga  1080
caaaactttg ctgcttgtag agcacttgtt tctgaaggta ttcaacaagg acacatgtca  1140
ttacaatata aagtttagc aatagtagta ggtgcaaaag gtgacgagat agcacaagta   1200
gcagaagctc ttaaacagga accaagagct aatacacagg ttgctgaaag aattttacag  1260
gaaattagac agcaataa                                                1278

SEQ ID NO: 44            moltype = DNA   length = 552
FEATURE                  Location/Qualifiers
source                   1..552
                         mol_type = other DNA
                         organism = Clostridium autoethanogenum
SEQUENCE: 44
agatagtcat aatagttcca gaatagttca atttagaaat tagactaaac ttcaaaatgt    60
ttgttaaata tataccaatc tagtatagat attttttaaa tactggactt aaacagtagt   120
aatttgccta aaaaatttt tcaattttt ttaaaaaatc cttttcaagt tgtacattgt    180
tatggtaata tgtaattgaa gaagttatgt agtaatattg taaacgtttc ttgatttttt   240
```

```
tacatccatg tagtgcttaa aaaaccaaaa tatgtcacat gcacttgtat atttcaaata    300
acaatattta ttttctcgtt aaattcacaa ataatttatt aataatatca ataaccaaga    360
ttatacttaa atggatgttt atttttttaac acttttatag taaatatatt tattttatgt    420
agtaaaaagg ttataattat aattgtattt attacaatta attaaaataa aaaatagggt    480
tttaggtaaa attaagttat tttaagaagt aattacaata aaaattgaag ttatttcttt    540
aaggaggaaa tt                                                        552

SEQ ID NO: 45           moltype = DNA   length = 386
FEATURE                 Location/Qualifiers
source                  1..386
                        mol_type = other DNA
                        organism = Clostridium autoethanogenum
SEQUENCE: 45
gttataaattt tcaatttca ttctttttaa aggagattag catacatttt atcataatta    60
tacagacaat atagtaatat atgatgttaa aaatatcaata tatggttaaa aatctgtata   120
ttttttccca tttaattat ttgtactata atattcact gagtgtattg catatttaaa     180
aaatatttgg tacaattagt tagttaaata aattctaaat tgtaaattat cagaatcctt    240
attaaggaaa tacatagatt taaggagaaa tcataaaag gtgtaatata aactggctaa    300
aattgagcaa aaattgagca attaagactt tttgattgta tctttttata tatttaaggt    360
atataatctt atttatattg ggggaa                                         386

SEQ ID NO: 46           moltype = DNA   length = 21
FEATURE                 Location/Qualifiers
misc_feature            1..21
                        note = oligonucleotide pUC57-F
source                  1..21
                        mol_type = other DNA
                        organism = synthetic construct
SEQUENCE: 46
agcagattgt actgagagtg c                                              21

SEQ ID NO: 47           moltype = DNA   length = 21
FEATURE                 Location/Qualifiers
misc_feature            1..21
                        note = oligonucleotide pUC57-R
source                  1..21
                        mol_type = other DNA
                        organism = synthetic construct
SEQUENCE: 47
acagctatga ccatgattac g                                              21

SEQ ID NO: 48           moltype = DNA   length = 3552
FEATURE                 Location/Qualifiers
misc_feature            1..3552
                        note = plasmid pMTL 85245
source                  1..3552
                        mol_type = other DNA
                        organism = synthetic construct
SEQUENCE: 48
aaactccttt ttgataatct catgaccaaa atcccttaac gtgagttttc gttccactga    60
gcgtcagacc ccgtagaaaa gatcaaagga tcttcttgag atcctttttt tctgcgcgta   120
atctgctgct tgcaaacaaa aaaaccaccg ctaccagcgg tggtttgttt gccggatcaa   180
gagctaccaa ctcttttcc gaaggtaact ggcttcagca gagcgcagat accaaatact    240
gttcttctag tgtagccgta gttaggccac cacttcaaga actctgtagc accgcctaca   300
tacctcgctc tgctaatcct gttaccagtg gctgctgcca gtggcgataa gtcgtgtctt   360
accgggttgg actcaagacg atagttaccg gataaggcgc agcggtcggg ctgaacgggg   420
ggttcgtgca cacagcccag cttggagcga acgacctaca ccgaactgag atacctacag   480
cgtgagctat gagaaagcgc cacgcttccc gaagggagaa aggcggacag gtatccggta   540
agcggcaggg tcggaacagg agagcgcacg agggagcttc caggggggaaa cgcctggtat   600
ctttatagtc ctgtcgggtt tcgccacctc tgacttgagc gtcgattttt gtgatgctcg   660
tcagggggc ggagccatg gaaaacgcc agcaacgcgg ccttttacg gttcctggcc       720
ttttgctggc cttttgctca catgttcttt cctgcgttat cccctgattc tgtggataac   780
cgtattaccg cctttgagtg agctgatacc gctcgccgca gccgaacgac cgagcgcagc   840
gagtcagtga gcgaggaagc ggaagagcgc ccaatacgca aaccgcctctg caggataaaa   900
aaattgtaga taaattttat aaaatagttt tatctacaat tttttttatca ggaaacagct   960
atgaccgcgg ccgcaatatg atatttatgt ccattgtgaa aggattata ttcaactatt    1020
attccagtta cgtccataga aaattttcctt tctaaaatat tttattccat gtcaagaact   1080
ctgttttattt cattaaagaa ctataagtac aagtataag gcatttgaaa aaataggcta    1140
tgtatattgat tgattattta tttaaaatg cctaagtgaa atatatacat attattacaa    1200
taaaataagt attagtgtag gatttttaaa tagagtatct attttcagat taaattttttg   1260
attattgat ttacattata taattgaag taaagtatg actagcaaaa ttttttgata       1320
cttttaattg tgaatttct tatcaaagt tatattttgg aataattttt attgaaaat       1380
acaactaaaa aggattataa gataagtgtg tgtaattttg tgttaaattt aaagggagga   1440
aatgaacatg aaaataatgg tgaccatgat tacgaattcg agctcggtac ccggggatcc   1500
tctagagtcg acgtcacgcg tccatggaga tctcgaggcc tgcagacatg caagcttggc   1560
actggccgtc gttttacaac gtcgtgactg ggaaaaccct ggcgttaccc aacttaatcg   1620
ccttgcagca catccccctt tcgccagctg gcgtaatagc gaagaggccc gcaccgatcg   1680
cccttcccaa cagttgcgca gcctgaatgg cgaatgcgc tagcataaaaa ataagaagcc   1740
tgcatttgca ggcttcttat ttttatggcg cgccgcattc acttctttc tatataaaata   1800
```

```
tgagcgaagc gaataagcgt cggaaaagca gcaaaaagtt tccttttttgc tgttggagca  1860
tgggggttca gggggtgcag tatctgacgt caatgccgag cgaaagcgag ccgaagggta  1920
gcatttacgt tagataaccc cctgatatgc tccgacgctt tatatagaaa agaagattca  1980
actaggtaaa atcttaatat aggttgagat gataaggttt ataaggaatt tgtttgttct  2040
aattttttcac tcattttgtt ctaatttctt ttaacaaatg ttcttttttt tttagaacag  2100
ttatgatata gttagaatag tttaaaataa ggagtgagaa aaagatgaaa gaaagatatg  2160
gaacagtcta taaaggctct cagaggctca tagacgaaga aagtggagaa gtcatagagg  2220
tagacaagtt ataccgtaaa caaacgtctg gtaacttcgt aaaggcatat atagtgcaat  2280
taataagtat gttagatatg attggcggaa aaaaacttaa aatcgttaac tatatcctag  2340
ataatgtcca cttaagtaac aatacaatga tagctacaac aagagaaata gcaaaagcta  2400
caggaacaag tctacaaaca gtaataacaa cacttaaaat cttagaagaa ggaaatatta  2460
taaaagaaa aactggagta ttaatgttaa accctgaact actaatgaga ggcgacgacc  2520
aaaaacaaaa atacctctta ctcgaatttg ggaactttga gcaagaggca aatgaaatag  2580
attgacctcc caataacacc acgtagttat tgggaggtca atctatgaaa tgcgattaag  2640
ggccggccga agcaaactta agagtgtgtt gatagtgcag tatcttaaaa ttttgtataa  2700
taggaattga agttaaatta gatgctaaaa atttgtaatt aagaaggagt gattacatga  2760
acaaaaatat aaaatattct caaaactttt taacgagtga aaaagtactc aaccaaataa  2820
taaaacaatt gaatttaaaa gaaaccgata ccgtttacga agttaaacg ggtaaagggc  2880
atttaacgac gaaactggct aaaataagta aacaggtaac gtctattgaa ttagacagtc  2940
atctattcaa cttatcgtca gaaaaattaa aactgaatac tcgtgtcact ttaattcacc  3000
aagatattct acagtttcaa ttccctaaca acagaggta taaaattgtt gggagtattc  3060
cttaccattt aagcacacaa ttattaaaa aagtggtttt tgaaagccat ccgtctgaca  3120
tctatctgat tgttgaagaa ggattctaca agcgtacctt ggatattcac cgaacactag  3180
ggttgctctt gcacactcaa gtctcgattc agcaattgct taagctgcca gcggaatgct  3240
ttcatcctaa accaaaagta aacagtgtct taataaaact tacccgccat accacagatg  3300
ttccagataa atattggaag ctatatacgt actttgtttc aaaatgggtc aatcgagaat  3360
atcgtcaact gtttactaaa aatcagtttc atcaagcaat gaaacacgcc aaagtaaaca  3420
atttaagtac cgttacttat gagcaagtat tgtctatttt taatagttat ctattattta  3480
acgggaggaa ataattctat gagtcgcttt tgtaaatttg gaaagttaca cgttactaaa  3540
gggaatgtgt tt                                                      3552
```

| SEQ ID NO: 49 | moltype = DNA  length = 4186 |
|---|---|
| FEATURE | Location/Qualifiers |
| misc_feature | 1..4186 |
| | note = plasmid pMTL 83145 |
| source | 1..4186 |
| | mol_type = other DNA |
| | organism = synthetic construct |

SEQUENCE: 49
```
aaactccttt ttgataatct catgaccaaa atccccttaac gtgagttttc gttccactga    60
gcgtcagacc ccgtagaaaa gatcaaagga tcttcttgag atcctttttt tctgcgcgta   120
atctgctgct tgcaaacaaa aaaaccaccg ctaccagcgg tggtttgttt gccggatcaa   180
gagctaccaa ctctttttcc gaaggtaact ggcttcagca gagcgcagat accaaatact   240
gttcttctag tgtagccgta gttaggccac cacttcaaga actctgtagc accgcctaca   300
tacctcgctc tgctaatcct gttaccagtg gctgctgcca gtggcgataa gtcgtgtctt   360
accgggttgg actcaagacg atagttaccg gataaggcgc agcggtcggg ctgaacgggg   420
ggttcgtgca cacagcccag cttggagcga acgacctaca ccgaactgag atacctacag   480
cgtgagctat gagaaagcgc cacgcttccc gaagggagaa aggcggacag gtatccggta   540
agcggcaggg tcggaacagg agagcgcacg agggagcttc caggggggaaa cgcctggtat   600
ctttatagtc ctgtcgggtt tcgccacctc tgacttgagc gtcgattttt gtgatgctcg   660
tcaggggggc ggagcctatg gaaaaacgcc agcaacgcgg cctttttacg gttcctggcc   720
ttttgctggc cttttgctca catgttcttt cctgcgttat cccctgattc tgtggataac   780
cgtattaccg cctttgagtg agctgatacc gctcgccgca gccgaacgac cgagcgcagc   840
gagtcagtga gcgaggaagc ggaagagcgc ccaatacgca gggcccctg caggataaaa   900
aaattgtaga taaattttat aaaatagttt tatctacaat tttttttatca ggaaacagct   960
atgaccgcgg ccgcaatatg atatttatgt ccattgtgaa agggattata ttcaactatt  1020
attccagtta cgttcataga attttccctt tctaaaatat tttattccat gtcaagaact  1080
ctgtttattt cattaaagaa ctataagtac aaagtataag gcatttgaaa aaataggcta  1140
gtatattgat tgattattta ttttaaaatg cctaagtgaa atatatacat attataacaa  1200
taaaataagt attagtgtag gattttaaa tagagtatct attttcagat taaattttg  1260
attatttgat ttacattata taatattgag taaagtattg actagcaaaa ttttttgata  1320
ctttaatttg tgaatttct tatcaaaagt tatattttg aataattttt attgaaaaat  1380
acaactaaaa aggattatag tataagtgtg tgtaattttg tgttaaattt aaagggagga  1440
aatgaacatg aaacatatgg tgaccatgat tacgaattcg ccggtac ccgggggatcc  1500
tctagagtcg acgtcacgcg tccatggaga tctcgaggcc tgcagacatg caagcttggc  1560
actggccgtc gttttacaac gtcgtgactg ggaaaaccct ggcgttaccc aacttaatcg  1620
ccttgcagca catcccccctt tcgccagctg gcgtaatagc gaagaggccc gcaccgatcg  1680
cccttcccaa cagttgcgca gcctgaatgg cgaatggcgc tagcataaaa ataagaagcc  1740
tgcatttgca ggcttctat cgccgccatt atttttttga acaattgaca  1800
attcatttct tatttttat taagtgatag tcaaaaggca taacagtgct gaatagaaag  1860
aaatttacag aaaagaaat tatagaattt agtatgatta attatactca tttatgaatg  1920
tttaattgaa tacaaaaaaa aatacttgtt atgtattcaa ttacgggtta aaatatagac  1980
aagttgaaaa atttaataaa aaaataagtc ctcagctctt atatattaag ctaccaactt  2040
agtatataag acaaaactta aatgtgctac caacacatca agccgttaga gaactctatc  2100
tatagcaata tttcaaatgt accgacatac aagagaaaca ttaactatat atattcaatt  2160
tatgagatta tcttaacaga tataaatgta aattgcaata agtaagattt agaagtttat  2220
agccttttgtg tattggaagc agtacgcaaa ggcttttttta tttgataaaa attagaagta  2280
tatttatttt tcataatta atttatgaaa atgaaagggg gtgagcaaag tgacagagga  2340
aagcagtatc ttatcaaata acaaggtatt agcaatatca ttattgactt tagcagtaaa  2400
```

```
cattatgact tttatagtgc ttgtagctaa gtagtacgaa aggggagct ttaaaaagct  2460
ccttggaata catagaattc ataaattaat ttatgaaaag aagggcgtat atgaaaactt  2520
gtaaaaattg caaagagttt attaaagata ctgaaatatg caaatacat tcgttgatga  2580
ttcatgataa aacagtagca acctattgca gtaaatacaa tgagtcaaga tgtttacata  2640
aagggaaagt ccaatgtatt aattgttcaa agatgaaccg atatggatgg tgtgccataa  2700
aaatgagatg ttttacagag gaagaacaga aaaaagaacg tacatggcatt aaatattatg  2760
caaggagctt taaaaaagct catgtaaaga agagtaaaaa gaaaaataa tttatttatt  2820
aatttaatat tgagagtgcc gacacagtat gcactaaaaa atatatctgt ggtgtagtga  2880
gccgatacaa aaggatagtc actcgcattt tcataataca tcttatgtta tgattatgtg  2940
tcggtgggac ttcacgacga aaacccacaa taaaaaaaga gttcggggta gggttaagca  3000
tagttgaggc aactaaacaa tcaagctagg atatgcagta gcagaccgta aggtcgttgt  3060
ttaggtgtgt tgtaatacat acgctattaa gatgtaaaaa tacggatacc aatgaaggga  3120
aaagtataat ttttggatgt agtttgtttg ttcatctatg ggcaaactac gtccaaagcc  3180
gtttccaaat ctgctaaaaa gtatatcctt tctaaaatca aagtcaagta tgaaatcata  3240
aataaagttt aattttgaag ttattatgat attatgtttt tctattaaaa taaattaagt  3300
atatagaata gtttaataat agtatatact taatgtgata agtgtctgac agtgtcacag  3360
aaaggatgat tgttatggat tataagcggc cggccagtgg gcaagttgaa aaattcacaa  3420
aaatgtggta taatatcttt gttcattaga gcgataaact tgaatttgag agggaactta  3480
gatggtattt gaaaaaattg ataaaaatag ttggaacaga aaagagtatt ttgaccacta  3540
ctttgcaagt gtaccttgta cctacagcat gaccgttaaa gtggatatca cacaaataaa  3600
ggaaaaggga atgaaactat atcctgcaat gcttttattat attgcaatga ttgtaaaccg  3660
ccattcagag tttaggacgg caatcaatca agatggtgaa ttggggatat atgatgaagt  3720
gataccaagc tatacaatat ttcacaatga tactgaaaca ttttccagcc tttggactga  3780
gtgtaagtct gactttaaat cattttttagc agattatgaa agtgatacgc aacggtatgg  3840
aaacaatcat agaatggaag gaaagccaaa tgctccggaa acatttttta atgtatctat  3900
gataccgtcg tcaaccttcg atggcttaa tctgaatttc cagaaaggat atgattattt  3960
gattcctatt tttactatgg ggaaatatta taagaagat aacaaaatta tacttccttt  4020
ggcaattcaa gttcatcacg cagtatgtga cggattcac atttgccgtt ttgtaaacga  4080
attgcaggaa ttgataaata gttaacttca ggtttgtctg taactaaaaa caagtattta  4140
agcaaaaaca tcgtagaaat acggtgtttt ttgttaccct aagttt        4186

SEQ ID NO: 50           moltype = DNA   length = 9827
FEATURE                 Location/Qualifiers
misc_feature            1..9827
                        note = plasmid pMTL8215-Pptaack-thlA-HMGS-Patp-HMGR
source                  1..9827
                        mol_type = other DNA
                        organism = synthetic construct
SEQUENCE: 50
cctgcaggat aaaaaaattg tagataaatt ttataaaata gttttatcta caatttttttt  60
atcaggaaac agctatgacc gcggccgcag atagtcataa tagttccaga atagttcaat  120
ttagaaatta gactaaactt caaaatgttt gttaaatata taccaatcta gtatagatat  180
tttttaaata ctggacttaa acagtagtaa tttgcctaaa aaattttttc aatttttttt  240
aaaaaatcct ttttcaagttg tacattgtta tggtaatatg taattgaaga agttatgtag  300
taatattgta aacgtttctt gatttttttta catccatgta gtgcttaaaa aaccaaaata  360
tgtcacatgc acttgtatat ttcaaataac aatatttatt ttctcgttaa attcacaaat  420
aatttattaa taatatcaat aaccaagatt atacttagta ttttttaaacac  480
tttttatagta aatatattta ttttatgtag taaaaaggtt ataattataa ttgtatttat  540
tacaattaat taaaataaaa aataggggttt taggtaaaat taagttatttt taagaagtaa  600
ttacaataaa aattgaagtt atttctttaa ggaggaaatt catatgaaag aggttgttat  660
tgcatcagct gttagaactg caataggatc ttatggaaaa agtcttaaag atgtaccagc  720
agtagactta ggtgcaactg caataaagga agcagtaaag aaagcaggta taaacctga  780
agatgttaat gaagttattt taggaaacgt attacaagct ggacttggac agaatccagc  840
tagacaggca tcattcaaag caggattacc agtagagata cctgctatga ctattaataa  900
agtttgtggt tcaggattaa gaacagtttt cttagctcgt caaattataa aagctggtga  960
cgcagatgta ataatagcag gtggtatgga aaatatgtca agagcaccat accttgctaa  1020
taatgctaga tggggttata gaatgggaaa cgctaaattt gtagacgaaa tgataactga  1080
tggactttgg gatgcattta acgattatca catgggaatt actgctgaaa atagcctga  1140
gagatggaat ataagtagag aagaacaaga tgagtttgca cttgcatctc agaaaaaaagc  1200
agaagaagct attaaatcag gacaattaa agatgaaatt gttccagtag taattaaagg  1260
tagaaaaggt gaaacagttg tagacactga tgaacatcct agatttggat ctacaatag  1320
aggtttagct aaattaaagc tgcttttaa gaaagacgga acagtaactg ctggaaacgc  1380
atcaggttta aatgattgtg cagctgtttt agtattatg tctgctgaaa aggcaaagga  1440
attaggtgtt aaaccacttg ctaagatagt tagtatggt tcagcaggtg tagatccttc  1500
tattatggga tatgaccctt tttatgctac aaaggcagct attgaaaagg ctggttggac  1560
agttgatgaa cttgatctta tagagtcaaa tgaggcattt gcagcacaaa gtcttgctgt  1620
tgctaaggat cttaaattcg atatgaataa agtaaatgta aacggtggtg ctatagcact  1680
tggtcatcca ataggtgcta gtggtgctag aatttttagt acattagttc atgcaatgca  1740
aaagagagac gctaaaaagg gacttgcaac tttatgcata ggtggtgtc aaggaacagc  1800
aatacttctt gaaaaatgtt aagaattcga ggctttact aaaaacaata aaaacaggag  1860
gaaataatat gactatagga attgacaaaa taaactttta cgtaccaaaa tattatgtag  1920
atatggcaaa attagcagaa gcaagacaag tagcccaaa taaatttctt attggaatag  1980
gacagactga aatggcagtt agtccagtaa accaagatat agtatcaatg ggtgctaatg  2040
ctgctaaaga tataataact gatgaagaca aaaaagaatt aggtagtgcaa  2100
ctgagtcagc agtagatgca gcaaaggcag cagcagtaca gattcataat ttattaggta  2160
ttcaaccatt tgcaagatgt ttcgaaatga aagaagcatg ttatgctgct actcctgcaa  2220
ttcagttagc taaggattat ttagctcaaa gaccaaatga aaagttttta gttatagcta  2280
cagatacagc tagatatgga cttaattcag gtggtgaacc tactcaaggt gctggtgctg  2340
ttgctatggt tatagctcat aatcctagta tacttgcatt aaatgaagac gctgttgctt  2400
```

```
atacagaaga tgtttatgat ttctggagac caacaggaca taagtatcca ttagtagatg   2460
gtgctttatc aaaagacgca tatattagat cttttcaaca atcttggaat gaatatgcta   2520
agagacaagg aaagagttta gctgattttg ctagtctttg ctttcatgtt cctttttacta  2580
aaatgggtaa aaaggcttta gaatctataa tagataacgc agatgaaaca actcaagaga   2640
gattaagatc tggatatgaa gatgcagttg attacaatag atatgttgga aatatataca   2700
caggaagtct ttatctttct cttataagtc ttcttgaaaa tagagattta caggctggtg   2760
aaactattgg attattttca tacgatcag gttctgttgg tgaattttat tcagctacac    2820
ttgtagaaga atataaagat caccttgatc aggcagcaca caaagcactt ttaaacaata   2880
gaactgaagt atcagtagat gcatacgaaa cattttttcaga tgagatttgat gatgtagaat 2940
ttgatgaaga gcaggatgca gttcatgaag atagacatat attctatctt tcaaacatag   3000
agaataatgt aagagaatat catagacctg aataagagct cgttataatt ttcaatttttc  3060
attcttttta aaggagatta gcatacattt tatcataatt atacagacaa tatagtaata   3120
tatgatgtta aaatatcaat atatggttaa aaatctgtat atttttttccc attttaatta  3180
tttgtactat aatattacac tgagtgtatt gcatattttaa aaaatatttg gtacaattag  3240
ttagttaaat aaattctaaa ttgtaaatta tcagaatcct tattaaggaa atacatagat   3300
ttaaggagaa atcataaaaa ggtgtaatat aaactggcta aaattgagca aaaattgagc   3360
aattaagact ttttgattgt atcttttttat atatttaagg tatataatct tatttatatt  3420
gggggaaggt accatgcaat cattagacaa aaatttcaga catttatcaa gacaacaaaa   3480
gttacaacaa ttagttgata aacagtggct ttcagaagat cagtttgata ttttacttaa   3540
tcatcctctt atagatgaag aagttgctaa tagtcttata gaaaatgtaa ttgcacaggg   3600
tgcattacca gttggacttc ttcctaatat aatagttgat gataaggctt atgttgtacc   3660
aatgatggtt gaagaaccta gtgttgttgc agctgcatct tatggtgcta aattagtaaa   3720
tcagacaggt ggatttaaaa ctgtatcatc agaaagaata atgattggac agatagtatt   3780
tgatggtgta gatgacactg aaaaattaag tgcagatatt aaagcattag aaaaacaaat   3840
acataagatt gcagatgaag catatcctag tataaaagca agaggtggtg ttatcaaag   3900
aatagcaata gatacatttc cagagcaaca acttttaagt cttaaggtat ttgtagatac   3960
aaaagatgct atgggtgcta atatgcttaa tactatactt gaggcaataa ctgcattcct   4020
taaaaatgaa tctcctcaat cagatatatt aatgtctata ctttcaaacc atgcaactgc   4080
tagtgtagta aaagtacaag gtgagataga tgtaaaagat cttgctagag gtgaaagaac   4140
aggtgaagaa gtagctaaga gaatggaaag agcttctgta ttagctcagg ttgatattca   4200
tagagctgca acacataaca aaggtgttat gaatgaata catgctgttg ttttagctac    4260
aggaaatgat actagaggtg ctgaagcatc tgcacatgca tacgcatcaa gagacggaca   4320
atatagaggt atagcaactt ggagatatga tcagaagaga caaagactta ttggaactat   4380
tgaagttcca atgacacttg ctatagtagg tggtggtaat aaagtattac caatagctaa   4440
ggcatcatta gagttattaa atgttgattc tgcacaagaa cttggacacg tagttgctgc   4500
tgttggatta gcacaaaact ttgctgcttg tagagcactt gtttctgaag gtattcaaca   4560
aggacacatg tcattacaat ataaaagttt agcaatagta gtaggtgcaa aaggtgacga   4620
gatagcacaa gtagcagaag ctcttaaaca ggaaccaaga gctaatacac aggttgctga   4680
aagaattta caggaaatta gacagcaata atctagagtc gacgtcacgc gtccatggag   4740
atctcgaggc ctgcagacat gcaagcttgg cactggccgt cgttttacaa cgtcgtgact   4800
gggaaaaccc tggcgttacc caacttaatc gccttgcagc acatccccct ttcgccagct   4860
ggcgtaatag cgaagaggcc cgcaccgatc gcccttccca cagttgcgc agcctgaatg    4920
gcgaatggcg ctagcataaa aataagaagc ctgcatttgc aggcttctta ttttttatgg   4980
gcgccgttct gaatcctag ctaatggttc aacaggtaac tatgacgaag atagcaccct    5040
ggataagtct gtaatggatt ctaaggcatt taatgaagac gtgtatataa aatgtgctaa   5100
tgaaaaagaa aatgcgttaa aagagcctaa aatgagttca aatggttttg aaattgattg   5160
gtagtttaat ttaatatatt tttttctattg gctatctcga tacctatag atcttctgtt    5220
cacttttgtt tttgaaatat aaaaaggggc ttttttagccc cttttttttta aaactccgga  5280
ggagtttctt cattcttgat actatacgta actattttcg atttgacttc attgtcaatt   5340
aagctagtaa aatcaatggt taaaaacaa aaaacttgca ttttttctacc tagtaattta    5400
taattttaag tgtcgagttt aaaagtataa tttaccagga aaggagcagg ttttttaaaa   5460
aggaaaaatt tttcctttta aaattctatt tcgttatatg actaattata atcaaaaaaa   5520
tgaaaataaa caagaggtaa aaactgcttt agagaaatgt actgataaaa aagaaaaaa    5580
tcctagattt acgtcataca tagcacccttt aactactaag aaaaatattg aaaggacttc   5640
cacttgtgga gattatttgt ttatgttgag tgatgcagac ttagaacatt ttaaattaca   5700
taaaggtaat ttttgcggta atagattttg tccaatgtgt agttggcgac ttgcttgtaa   5760
ggatagttta gaaatatcta ttcttatgga gcatttaaga aaagaagaaa ataaagagtt   5820
tatattttta actcttacaa ctccaaatgt aaaaagttat gatcttaatt attctattaa   5880
acaatataat aaatctttta aaaaattaat ggagcgtaag ggagttaagg atataactaa   5940
aggttatata agaaaattag aagtaactta ccaaaaggaa aaatacataa caaaggatt    6000
atggaaaata aaaaaagatt attatcaaaa aaaaggactt gaaattggtg atttagaacc   6060
taattttgat acttataatc ctcatttca tgtagttatt gcagtaata aaagttatt      6120
tacagataaa aattattata taaatcgaga aagatggttg gaattatgga gtttgctac    6180
taaggatgat tctataactc aagttgatgt tagaaaagca aaaattaatg tagaaaga     6240
ggttacgaa cttgcgaaat attcagctaa agacactgat tatttaatat cgaggccagt    6300
atttgaaatt ttttataaag cattaaaagg caagcaggta ttagttttta gtggatttt    6360
taaagatgca cacaaattgt acaagcaagg aaaacttgat gtttataaaa agaaagtgaa    6420
aattaaatat gtctatatag tttattataa ttggtgcaaa aacaatatg aaaaactag     6480
aataagggaa cttacggaga atgaaaaaga agaattaaat caagatttta tagatgaaat   6540
agaaatagat taaagtgtaa ctatactta tatatatatg attaaaaaaa taaaaaacaa    6600
cagcctatta ggttgttgtt ttttattttc tttattaatt ttttaatttt ttagtttta    6660
gttcttttt aaaataagtt tcagcctctt ttcaatattt ttaaagaa ggagtatttg      6720
catgaattgc cttttttcta acagacttag gaaatttt aacagtatct tcttgcgccg     6780
gtgattttgg aacttcataa cttactaatt ataattctttt ttaattgtaa              6840
cagttgcaaa agaagctgaa cctgttcctt caactagtta atcatcttca atataatatt   6900
cttgacctat atagtataa tatatttta ttatttttt ctttttttct gaatctatta      6960
ttttataatc ataaaagtt ttaccaccaa aagaaggttg tactccttct ggtccaacat    7020
atttttttac tatatatcct aaataatttt tgggaactgg tgttgtaatt tgattaatcg   7080
aacaaccagt tatacttaaa ggaattataa ctataaaaat atataggatt atcttttttaa  7140
```

```
atttcattat tggcctcctt tttattaaat ttatgttacc ataaaaagga cataacggga  7200
atatgtagaa tatttttaat gtagacaaaa ttttacataa atataaagaa aggaagtgtt  7260
tgtttaaatt ttatagcaaa ctatcaaaaa ttagggggat aaaaatttat gaaaaaaagg  7320
ttttcgatgt tattttttatg tttaacttta atagtttgtg gtttatttac aaattcggcc  7380
ggccagtggg caagttgaaa aattcacaaa aatgtggata aatatctttg ttcattagag  7440
cgataaactt gaatttgaga gggaacttag atggtatttg aaaaaattga taaaaatagt  7500
tggaacagaa aagagtattt tgaccactac tttgcaagtg taccttgtac ctacagcatg  7560
accgttaaag tggatatcac acaaataaag gaaaagggaa tgaaactata tcctgcaatg  7620
ctttattata ttgcaatgat tgtaaaccgc cattcagagt ttaggacggc aatcaatcaa  7680
gatggtgaat tggggatata tgatgagatg ataccaagct atacaatatt tcacaatgat  7740
actgaaacat tttccagcct ttggactgag tgtaagtctg actttaaatc attttttagca  7800
gattatgaaa gtgatacgca acggtatgga aacaatcata gaatgggaagg aaagccaaat  7860
gctccggaaa acattttttaa tgtatctatg ataccgtggt caaccttcga tggctttaat  7920
ctgaatttgc agaaaggata tgattatttg attcctattt ttactatgg gaaatattat  7980
aaagaagata acaaaattat acttcctttg gcaattcaag ttcatcacgc agtatgtgac  8040
ggatttcaca tttgccgttt tgtaaacgaa ttgcaggaat tgataaaatag ttaacttcag  8100
gtttgtctgt aactaaaaac aagtatttaa gcaaaaacat cgtagaaata cggtgttttt  8160
tgttacccta agtttaaact cctttttgat aatctcataa ccaaaatccc ttaacgtgag  8220
ttttcgttcc actgagcgtc agaccccgta gaaaagatca aaggatcttc ttgagatcct  8280
tttttttctgc gcgtaatctg ctgcttgcaa acaaaaaaac caccgctacc agcggtggtt  8340
tgtttgccgg atcaagagct accaactctt tttccgaagg taactggctt cagcagagcg  8400
cagataccaa atactgttct tctagtgtag ccgtagttag gccaccactt caagaactct  8460
gtagcaccgc ctacatacct cgctctgcta atcctgttac cagtggctgc tgccagtggc  8520
gataagtcgt gtcttaccgg gttggactca agacgatagt taccggataa ggcgcagcgg  8580
tcgggctgaa cggggggttc gtgcacacag cccagcttgg agcgaacgac ctacaccgaa  8640
ctgagatacc tacagcgtga gctatgagaa agcgccacgc ttcccgaagg gagaaaggcg  8700
gacaggtatc cggtaagcgg cagggtcgga acaggagagc gcacgaggg gcttccaggg  8760
ggaaacgcct ggtatcttta tagtcctgtc gggtttcgcc acctctgact tgagcgtcga  8820
ttttttgtgat gctcgtcagg ggggcggagc ctatggaaaa acgccagcaa cgcggccttt  8880
ttacggttcc tggcctttttg ctggcctttt gctcacatgt tctttcctgc gttatcccct  8940
gattctgtgg ataaccgtat taccgccttt gagtgagctg ataccgctcg ccgcagccga  9000
acgaccgagc gcagcgagtc agtgagcgag gaagcggaag agcgcccaat acgcagggcc  9060
ccctgcttcg gggtcattat agcgatttttt tcggtatatc catcctttttt cgcacgatat  9120
acaggatttt gccaaagggt tcgtgtagac tttccttggt gtatccaacg gcgtcagccg  9180
ggcaggatag gtgaagtagg cccacccgcg agcgggtgtt ccttcttcac tgtccctttat  9240
tcgcacctgg cggtgctcaa cgggaatcct gctctgcgag gctggccggc taccgccggc  9300
gtaacagatg agggcaagcg gatggctgat gaaaccaagc caaccaggaa gggcagccca  9360
cctatcaagg tgtactgcct tccagacgaa cgaagagcga ttgaggaaaa ggcggcggcg  9420
gccggcatga gcctgtcggc ctacctgctg gccgtcgctg agggctacaa aatcacgggc  9480
gtcgtggact atgagcacgt ccgcgagctg gcccgcatca atggcgacct gggccgcctg  9540
ggcggcctgc tgaaactctg gctcaccgac gacccgcgca cggcgcggtt cggtgatgcc  9600
acgatcctcg ccctgctggc gaagatcgaa gagaagcagg acgagcttgg caaggtcatg  9660
atgggcgtgg tccgcccgag ggcagagcca tgacttttttt agccgctaaa acggccgggg  9720
ggtgcgcgtg attgccaagc acgtccccat gcgctccatc aagaagagcg acttcgcgga  9780
gctggtgaag tacatcaccg acgagcaagg caagaccgat cgggccc              9827

SEQ ID NO: 51          moltype = DNA   length = 843
FEATURE                Location/Qualifiers
source                 1..843
                       mol_type = other DNA
                       organism = Staphylococcus aureus
                       sub_species = subsp. aureus
SEQUENCE: 51
atgatagctg ttccatttaa cgctggaaaa ataaagtttt taattgaggc attagaatct  60
ggaaattatt catcaataaa atcagatgta tatgacggaa tgttatatga tgcaccagat  120
caccttaaat cattagtaaa cagatttgta gaacttaata atataactga gccattagca  180
gtaactatac agacaaatct tcctccttca agaggtcttg gatctagtgc agctgttgct  240
gttgcttttg taagagcaag ttatgatttc ttaggaaaaa gtttaactaa agaagagctt  300
atagaaaagg ctaattgggc tgaacaaata gctcatgaga agccatctgg aatagataca  360
caaacaatag tatctggaaa gcctgtttgg tttcaaaagg gacatgcaga aacacttaaa  420
actctttcac ttgatggata catggtagta attgatacag tgttaaagg aagtacaaga  480
caggctgtag aagatgttca taaactttgc gaagatcctc aatatatgag tcacgtaaaa  540
cacataggaa aacttgtact tagagcatct gatgttattg aacatcataa ctttgaagca  600
cttgctgtat tattcaatga atgtcatgct gatttaaagg ctcttacagt aagtcatgac  660
aaaatagaac agttaatgaa gataggaaaa gaaaatggtg ctatagctgg taaattaact  720
ggtgctggta gaggtggttc aatgttatta cttgcaaaag acttaccaac tgcaaagaat  780
atagttaaag cagtagagaa agctggtgca gcacatactt ggattgaaaa tttaggtggt  840
taa                                                                843

SEQ ID NO: 52          moltype = DNA   length = 1077
FEATURE                Location/Qualifiers
source                 1..1077
                       mol_type = other DNA
                       organism = Staphylococcus aureus
                       sub_species = subsp. aureus
SEQUENCE: 52
atgatacaag taaaggcacc aggaaaatta tatatagcag gtgaatacgc tgttacagaa  60
ccaggatata aatctgttct tatagctctt gatagatttg ttacagctac tattgaggaa  120
gctgatcaat acaaaggaac aatacattca aaggcattac atcacaatcc agtaactttt  180
```

```
agtagagatg aagattctat tgttatatca gacccacacg cagcaaaaca acttaattat  240
gtagtaactg ctatagaaat atttgagcaa tatgcaaaat catgtgacat agcaatgaag  300
cattttcatt taactataga ttctaactta gatgatagta atggacataa gtatggactt  360
ggatcttctg ctgctgtttt agtttcagta attaaagtac ttaacgaatt ttatgatatg  420
aaacttccaa acctttatat atataagtta gcagtaattg ctaatatgaa attacagagt  480
ttatcttcat gcggtgatat agcagtaagt gtttattcag gttggttagc ttattctaca  540
tttgaccatg aatgggtaaa acaccagata gaagatacaa cagttgaaga agtacttatt  600
aaaaattggc ctggattaca catagagcca cttcaagctc ctgaaaatat ggaagttctt  660
ataggttgga caggtagtcc agctagtagt ccctcatttg tttctgaagt taaaagactt  720
aagtcagatc cttcatttta cggtgatttc ttagaagatt cacatagatg tgtgaaaaaa  780
ttaattcatg cattcaaaac taataatatt aagggtgttc agaaaatggt aagacagaat  840
agaactatta tacaaagaat ggataaggaa gcaacagttg atatagagac tgagaagtta  900
aaatatttat gtgatattgc tgaaaaatat catggtgcaa gtaaaacttc aggtgctggt  960
ggtggtgatt gcggaataac tataataaat aaggatgtag acaaagagaa aatatatgat  1020
gaatggacta aacatggaat aaaagcctct taagtttaata tttatcatgg acaataa    1077

SEQ ID NO: 53          moltype = DNA  length = 984
FEATURE                Location/Qualifiers
source                 1..984
                       mol_type = other DNA
                       organism = Staphylococcus aureus
                       sub_species = subsp. aureus
SEQUENCE: 53
atgataaaat ctggaaaagc aagagcacac actaatatag cacttataaa atattggggt  60
aagaaagatg aggcattaat aataccaatg aataactcaa tatcagtaac tttagaaaag  120
ttttatactg aaacaaaagt tacatttaac gatcagctta ctcaagatca attttggctt  180
aatggtgaaa aagtttctgg aaaagaatta gaaaagattt caagtatat ggatattgtt  240
agaaatagag ctggaataga ttggtatgct gagatagaat ctgataattt tgttcctaca  300
gctgctggtc ttgctagttc tgctagtgct tatgcagcat tagctgctgc atgtaaccaa  360
gcacttgatt tacagttaag tgataaagac ttaagtagat tggatcagga  420
tcagcatcaa gatcaatata cggtggtttt gcagaatggg aaaaaggata taatgacgaa  480
acttcttatg ctgttccatt agaaagtaat cactttgaag atgatcttgc tatgattttt  540
gtagtaataa accaacattc taaaaaggtt ccttcaagat atggaatgtc tcttacaaga  600
aatacaagta gattctatca atattggtta gaccatattg atgaagatct tgcaggagca  660
aaggcagcaa tacaagataa ggattttaag agattaggtg aagttattga agagaatgta  720
cttagaatgc atgctacaaa tcttggatca actccacctt ttacttactt agtacaagag  780
tcatacgatg taatgcatt agtacatgag tgtagagaag caggatatcc atgctatttc  840
actatggatg ctggacctaa tgtaaaaata cttgtagaga agaaaaacaa acaacagata  900
atagataaac ttttaactca gttcgataat aatcagataa tagatagtga tattatagct  960
acaggtattg aaattataga ataa                                        984

SEQ ID NO: 54          moltype = DNA  length = 516
FEATURE                Location/Qualifiers
source                 1..516
                       mol_type = other DNA
                       organism = Clostridium beijerinckii
SEQUENCE: 54
atggcagagt atataatagc agtagatgag ttcgataacg aaataggatc aatagaaaag  60
atggaagctc atagaaaagg aacacttcat agagcattca gtattttagt ttttaactca  120
aagaatcaac ttttattaca gaaaagaaat gtaaagaaat atcactctcc aggattatgg  180
acaaacactt gttgtagtca cccaagatat ggtgaatctc ttcatgatgc tatatacaga  240
agattaaaag aagagatggg atttacttgc gaacttgaag aagtattctc attcatatat  300
aaggtaaaac ttgaagataa tttatttgag aatgaatatg accatgtatt tattggtaaa  360
tatgatggtg agataattgt taataaagat gaagttgatg atttttaaatg ggtagacatt  420
aatgaagtta aaaaggacat aatagaaaga cctgaggcat atacttactg gtttaagtat  480
cttgtaaata aagctgaaaa taagatattt aaataa                             516

SEQ ID NO: 55          moltype = DNA  length = 120
FEATURE                Location/Qualifiers
source                 1..120
                       mol_type = other DNA
                       organism = Clostridium autoethanogenum
SEQUENCE: 55
atatcgatac agataaaaaa atatataata cagaagaaaa aattataaat ttgtggtata  60
atataaagta tagtaattta agtttaaacc tcgtgaaaac gctaacaaat aataggaggt  120

SEQ ID NO: 56          moltype = DNA  length = 900
FEATURE                Location/Qualifiers
source                 1..900
                       mol_type = other DNA
                       organism = Escherichia coli
SEQUENCE: 56
atggatttcc cacaacaatt agaagcatgt gtaaaacagg ctaatcaggc acttagtaga  60
tttattgctc ctcttccttt tcaaaataca ccagtagtag aaactatgca atacggtgca  120
cttttaggtg gtaaaagatt aagaccattc ttagtatatg ctacaggaca tatgtttggt  180
gtatcaacta atacttttaga cgctccagct gctgctgttg aatgtattca tgcatattct  240
ttaatacatg atgacttacc agcaatggat gacgatgatt taagaagagg tttacctaca  300
tgtcatgtta aatttggtga agctaatgca atttttagcag gtgacgcttt acaaactta  360
gcttttctta ctttcagat gcagacatg cctgaagttt cagatagaga tagaatttct  420
```

```
atgatatcag agcttgcatc tgcatcagga atagctggaa tgtgcggtgg tcaagcactt    480
gatttagatg cagaaggtaa acacgtacca cttgatgcat tagagagaat tcatagacat    540
aaaacaggtg ctcttataag agcagcagta agattaggtg ctttaagtgc tggtgacaag    600
ggtagaagag cacttccagt acttgataag tatgcagaaa gtataggatt agcttttcaa    660
gttcaagatg acatacttga cgttgttggt gatactgtca ctttaggaaa aagacagggt    720
gcagatcagc aattaggaaa atctacatac cctgctttac ttggattaga acaggctaga    780
aagaaagcaa gagacttaat agatgacgca agacaaagtc ttaaacagtt agctgaacaa    840
tcacttgaca caagtgcact tgaagcactt gcagattata ttatacagag aaacaagtaa    900

SEQ ID NO: 57          moltype = DNA  length = 975
FEATURE                Location/Qualifiers
source                 1..975
                       mol_type = other DNA
                       organism = Malus x domestica
SEQUENCE: 57
atggaattta gagtacattt acaggcagac aacgaacaga aaatatttca aaatcaaatg     60
aaaccagagc cagaagcatc atatcttata aatcaaagaa gaagtgctaa ttataaacca    120
aacatttgga aaaacgattt tcttgatcag tctttaatat caaaatatga tggtgatgaa    180
tatagaaaac tttcagaaaa gttaatagaa gaagtaaaga tatacatatc agcagagact    240
atggatttag ttgctaaatt agaacttata gattctgtta gaaaacttgg acttgctaat    300
cttttttgaga agaaataaa ggaagcatta gacagtatag cagcaataga atcagataat    360
ttaggaacta gagacgcatc ttatggaaca gctcttcatt ttaagattct tagacagcat    420
ggatataagg taagtcaaga tatatttggt agatttatgg atgagaaagg aacattagaa    480
aatcatcact ttgcacactt aaaaggaatg ttagaattat ttgaggcaag taatcttgga    540
tttgaaggtg aagacatatt agatgaagct aaagcatctc ttacacttgc tcttagagat    600
tcaggacata tttgttatcc agactcaaac ttaagtagag atgtagttca tagtttagaa    660
ttacctagtc atagaagagt tcaatggttc gatgtaaaat ggcagattaa tgcatacgaa    720
aaagatattt gtagagtaaa tgcaacttta ttagagttag caaagttaaa ttttaatgtt    780
gttcaagctc agcttcagaa gaatcttaga gaagctagta gatggtgggc taatcttggt    840
ttcgcagata atttaaagtt tgctagagat agacttgtag agtgttttc atgcgcagta    900
ggtgtagcat ttgaaccaga gcattcatct tttagaaat gtttaactaa ggtaattaat    960
cttgttctta ttata                                                   975

SEQ ID NO: 58          moltype = DNA  length = 13817
FEATURE                Location/Qualifiers
misc_feature           1..13817
                       note =
                       pMTL8314-Pptaack-thlA-HMGS-Patp-HMGR-Prnf-MK-PMK-PMD-Pfor-i
                       di-ispS
source                 1..13817
                       mol_type = other DNA
                       organism = synthetic construct
SEQUENCE: 58
aaactccttt ttgataatct catgaccaaa atccttaac gtgagttttc gttccactga     60
gcgtcagacc ccgtagaaaa gatcaaagga tcttcttgag atccttttt tctgcgcgta    120
atctgctgct tgcaaacaaa aaaaccaccg ctaccagcgg tggtttgttt gccggatcaa    180
gagctaccaa ctctttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggaaa cgcctggtat    600
ctttatagtc ctgtcgggtt tcgccacctc tgacttgagc gtcgattttt gtgatgctcg    660
tcaggggggc ggagcctatg gaaaaacgcc agcaacgcgg cctttttac gttcctggcc    720
tttttgctgg cttttgctca catgttcttt cctgcgttat cccctgattc tgtggataac    780
cgtattaccg cctttgagtg agctgatacc gctcgccgca gccgaacgac cgagcgcagc    840
gagtcagtga gcgaggaagc ggaagagcgc ccaatacgca gggccccctg caggataaaa    900
aaattgtaga taaattttat aaaatagttt tatctacaat tttttatca ggaaacagct    960
atgaccgcgg ccgcagatag tcataatagt tccagaatag ttcaatttag aaattagact   1020
aaacttcaaa atgtttgtta aatatatacc aatctagtat agatatttt taaatactgg   1080
acttaaacag tagtaatttg cctaaaaaat tttttcaatt tttttaaaa atccttttc   1140
aagttgtaca ttgttatggt aatatgtaat tgaagaagtt atgtagtaat attgtaaacg   1200
tttcttgatt tttttacatc catgtagtgc ttaaaaaacc aaaatatgtc acatgccttt   1260
gtatatttca aataacaata tttattttct cgttaaattc acaaataatt tattaataat   1320
atcaataacc aagattatac ttaaatggat gtttatttt taacttttt atagtaaata   1380
tatttatttt atgtagtaaa aaggttataa ttataattgt atttattaca attaattaaa   1440
ataaaaaata gggtttttagg taaaattaag ttattttaag aagtaattac aataaaaatt   1500
gaagttatttt cttttaaggag gaaattcata tgaaagaggt tgttattgca tcagctgtta   1560
gaactgcaat aggatcttat ggaaaaagtc ttaaagatgt accagcagta gacttaggtg   1620
caactgcaat aaaggaagca gtaaagaaag caggtataaa acctgaagat gttaatgaag   1680
ttattttagg aaacgtatta caagctggac ttggacagaa tccagctaga caggcatcat   1740
tcaaagcagg attaccagta gagatacctg ctatgactat taataaagtt tgtggttcag   1800
gattaagaac agttttctta gctgctcaaa ttataaacag tggtgacgca gataatatta   1860
tagcaggtgg tatggaaaat atgtcaagag caccatacct tgctaataat ctgactgggg   1920
gttataaat gggaaacgct aaatttgtag acgaaatgat aactgatgga ctttgggatg   1980
catttaacga ttatcacatg ggaattactg ctgaaaatat agctgagaga tggaatataa   2040
gtagagaaga acaagatgag tttgcacttg catctcagaa aaggcagaa gaagctatta   2100
aatcaggaca atttaaagat gaaattgttc cagtagtaat taaaggtaga aaaggtgaaa   2160
```

-continued

```
cagttgtaga cactgatgaa catcctagat ttggatctac aatagaaggt ttagctaaat  2220
taaagcctgc ttttaagaaa gacgaacag taactgctgg aaacgcatca ggtttaaatg   2280
attgtgcagc tgttttagtt attatgtctg ctgaaaaggc aaaggaatta ggtgttaaac  2340
cacttgctaa gatagttagt tatggttcag caggtgtaga tcctgctatt atgggatatg  2400
gaccttttta tgctacaaag gcagctattg aaaaggctgg ttggacagtt gatgaacttg  2460
atcttataga gtcaaatgag gcatttgcag cacaaagtct tgctgttgct aaggatctta  2520
aattcgatat gaataaagta aatgtaaacg gtggtgctat agcacttggt catccaatag  2580
gtgctagtgg tgctagaatt ttagttacat tagttcatgc aatgcaaaag agagacgcta  2640
aaaagggact tgcaacttta tgcataggtg gtggtcaagg aacagcaata cttcttgaaa  2700
aatgttaaga attcgaggct tttactaaaa acaataaaaa caggaggaaa taatatgact  2760
ataggaattg acaaaataaa cttttacgta ccaaatatt atgtagatat ggcaaaatta   2820
gcagaagcaa gacaagtaga cccaaataaa tttcttattg gaataggaca gactgaaatg  2880
gcagttagtc cagtaaacca agatatagta tcaatgggtg ctaatgctgc taaagatata  2940
ataactgatg aagacaaaaa gaaaatagga atggtaaata tagcaactga gtcagcagta  3000
gatgcagcaa aggcagcagc agtacagatt cataatttat taggtattca accatttgca  3060
agatgtttcg aaatgaaaga agcatgttat gctgctactc ctgcaattca gttagctaag  3120
gattatttag ctacaagacc aaatgagaaa gttttagtta tagctacaga tacagctaga  3180
tatggactta attcaggtgg tgaacctact caaggtgctg gtgctgttgc tgtagtttta  3240
gctcataatc ctagtatact tgcattaaat gaagacgctg ttgcttatac agaagatgtt  3300
tatgatttct ggagaccaac aggacataag tatccattag tagatggtgc tttatcaaaa  3360
gacgcatata ttagatcttt tcaacaatct tggaatgaat atgctaagag acaaggaaag  3420
agtttagctg attttgctag tctttgcttt catgttcctt ttactaaaat gggtaaaaag  3480
gctttagaat ctataataga taacgcagat gaaacaactc aagagagatt aagatctgga  3540
tatgaagatg cagttgatta caatagatat gttggaaata tatacacagg aagtctttat  3600
cttttctctta taagtcttct tgaaaataga gatttacagg ctggtgaaac tattggatta  3660
ttttcatacg gatcaggttc tgttggtgaa ttttattcag ctacacttgt agaaggatat  3720
aaagatcacc ttgatcaggc agcacacaaa gcacttttaa acaatagaac tgaagtatca  3780
gtagatgcat acgaaacatt tttcaagaga tttgatgatg tagaatttga tgaagagcag  3840
gatgcagttc atgaagatag acatatattc tatctttcaa acatagagaa taatgtaaga  3900
gaatatcata gacctgaata agagctcgtt ataattttca attttcattc ttttttaaagg  3960
agattagcat acatttttatc ataattatac agacaatata gtaatatatg atgttaaaat  4020
atcaatatat ggttaaaaat ctgtatattt tttcccattt taattatttg tactataata  4080
ttacactgag tgtattgcat attttaaaaaa tatttggtac aattagttag ttaaataaat  4140
tctaaattgt aaattatcag aatccttatt aaggaaatac atagatttaa ggagaaatca  4200
taaaaggtg taatataaac tggctaaaat tgagcaaaaa ttgagcaatt aagacttttt   4260
gattgtatct ttttatatat ttaaggtata taatcttatt tatattgggg gaaggtacca  4320
tgcaatcatt agacaaaaat ttcagacatt tatcaagaca acaaaagtta caacaattag  4380
ttgataaaca gtggctttca gaagatcagt ttgatatttt acttaatcat cctcttatag  4440
atgaagaagt tgctaatagt cttataagaa atgtaattgc acagggtgca ttaccagttg  4500
gacttcttcc taatataata gttgatgata aggcttatgt tgtaccaatg atggttgaag  4560
aacctagtgt tgttgcagct gcatcttatg gtgctaaatt agtaaatcag acaggtggat  4620
ttaaaactgt atcatcagaa agaataatga ttggacagat agtatttgat ggtgtagatg  4680
acactgaaaa attaagtgca gatattaaag cattagaaaa aacaattataa aattattaaa  4740
atgaagcata tcctagtata aaagcaagag gtggtggtta tcaaagaata gcaatagata  4800
catttccaga gcaacaactt ttaagtctta aggtatttgt agatacaaaa gatgctatgg  4860
gtgctaatat gcttaatact atacttgagg caataactgc attccttaaa aatgaatctc  4920
ctcaatcaga tatattaatg tctatacttt caaaccatgc aactgctagt gtagtaaaag  4980
tacaaggtga gatagatgta aaagatcttg ctagaggtga aagaacaggt gaagaagtag  5040
ctaagagaat ggaaagagct tctgtattag ctcaggttga tattcataga gctgcaacac  5100
ataacaaagg tgttatgaat ggaatacatg ctgttgtttt agctacagga aatgatacta  5160
gaggtgctga agcatctgca catgcatacg catcaagaga cggacaatat agaggtatag  5220
caacttggag atatgatcag aagagacaaa gacttattgg aactattgaa gttccaatga  5280
cacttgctat agtaggtggt ggtactaaag tattaccaat agctaaggca tcattagagt  5340
tattaaatgt tgattctgca caagaacttg gacacgtagt tgctgctgtt ggattagcac  5400
aaaacttgc tgcttgtaga gcacttgttt ctgaaggtat tcaacaagga cacatgtcat  5460
tacaatataa aagtttagca atagtagtag gtgcaaaagt tgacgagata gcacaagtag  5520
cagaagctct taaacaggaa ccaagagcta atacacaggt tgctgaaaga attttacagg  5580
aaattagaca gcaataatct agaatatcga tacagataaa aaatatata atacagaaga  5640
aaaaattata aatttgtggt ataataaa gtatagtaat ttaagtttaa acctcgtgaa    5700
aacgctaaca aataatagga ggtcaattga tgatagctgt tccatttaac gctgaaaaa   5760
taaaagttttt aattgaggca ttagaatctg gaaattattc atcaataaaa tcagatgtat  5820
atgacgaat gttatatgat gcaccagatc accttaaatc attagtaaac agatttgtag   5880
aacttaataa tataactgag ccattagcag taactataca gacaaatctt cctccttcaa   5940
gaggtcttgg atctagtgca gctgttgctg ttgcttttgt aagagcaagt tatgatttct  6000
taggaaaaag tttaactaaa gaagagctta tagaaaaggc taattgggct gaacaaatag   6060
ctcatggaaa gccatctgga atagatacac aaacaatagt atctgaaaag cctgtttggt   6120
ttcaaaaggg acatgcagaa acacttaaaa ctctttcact tgatggatac atggtagtaa   6180
ttgatacagg tgttaaagga agtacaagag aggctgtcat aaactttgcg              6240
aagatcctca atatatgagt cacgtaaaac acataggaaa acttgtatct agacgcatcg   6300
atgttattga acatcataac tttgaagcac ttgctgatat attcaatgaa tgtcatgctg   6360
atttaaaggc tcttacagta agtcatgaca aaatagaaca gttaatgaag ataggaaaag   6420
aaaatggtgc tatagctggt aaattaactg gtgctgtag aggtggttca atgttattac    6480
ttgcaaaaga cttaccaact gcaaagaata tagttaaagc agtagagaaa gctggtgcag   6540
cacatacttg gattgaaaat ttaggtggtt aagtcgacaa agacactaaa aaattataaa   6600
agtaaaggag gacattaaat gatacaagta aaggcaccag gaaaattata tatagcaggt   6660
gaatacgctg ttacagaacc aggatataaa tctgttctta gctcttgat tagatttgtt     6720
acagctacta ttgaggaagc tgatcaatac aaaggaacaa tacattcaaa ggcattacat   6780
cacaatccga taacttttag tagagatgaa gattctattg ttatatcaga cccacacgca   6840
gcaaaacaac ttaattatgt agtaactgct atagaaatat ttgagcaata tgcaaaatca   6900
```

```
tgtgacatag caatgaagca tttttcattta actatagatt ctaacttaga tgatagtaat    6960
ggacataagt atggacttgg atcttctgct gctgttttag tttcagtaat taaagtactt    7020
aacgaattt atgatatgaa actttcaaac ctttatatat ataagttagc agtaattgct    7080
aatatgaat tacagagttt atcttcatgc ggtgatatag cagtaagtgt ttattcaggt    7140
tggttagctt attctacatt tgaccatgaa tgggtaaaac accagataga agatacaaca    7200
gttgaagaag tacttattaa aaattggcct ggattacaca tagagccact tcaagctcct    7260
gaaaatatgg aagttcttat aggttggaca ggtagtccag ctagtagtcc tcattttgtt    7320
tctgaagtta aaagacttaa gtcagatcct tcattttacg gtgatttctt agaagattca    7380
catagatgtg tagaaaaatt aattcatgca ttcaaaacta ataatattaa gggtgttcag    7440
aaaatggtaa gacagaatag aactattata caaagaatgg ataaggaagc aacagttgat    7500
atagagactg agaagttaaa atattttatgt gatattgctg aaaaatatca tggtgcaagt    7560
aaaacttcag gtgctggtgg tgtgattgc ggaataacta taaataataa ggatgtagac    7620
aaagagaaaa tatatgatga atggactaaa catggaataa agcctcttaa gtttaatatt    7680
tatcatggac aataaccatg gtcaataatc ttacaataaa taaaagaaag gaggcaaaaa    7740
tatgataaaa tctggaaaag caagagcaca cactaatata gcacttataa aatattgggg    7800
taagaaagat gaggcattaa taataccaat gaataactca atatcagtaa ctttagaaaa    7860
gttttatact gaaacaaaag ttacatttaa cgatcagctt actcaagatc aattttggct    7920
taatggtgaa aaagtttctg gaaaagaatt agaaaagatt tcaaagtata tggatattgt    7980
tagaaaataga gctggaataa attggtatgc tgagatagaa tctgataatt ttgttcctac    8040
agctgctggt cttgctagtt ctgctagtgc ttatgcagca ttagctgctg catgtaacca    8100
agcacttgat ttacagttaa gtgataaaga cttaagtaga ttagctagaa ttggatcagg    8160
atcagcatca agatcaatat acggtgtttt tgcagagtgg gaaaaaggat ataatgacga    8220
aacttcttat gctgttccat tagaaagtaa tcactttgaa gatgatcttg ctatgatttt    8280
tgtagtaata aaccaacatt ctaaaaaggt tccttcaaga tatggaatgt ctcttacaag    8340
aaatacaagt agattctatc aatattggtt agaccatatt gatgaagatc ttgcagaagc    8400
aaaggcagca atacaagata aggattttaa gagattgtc aagttattg aagagaattg    8460
acttagaatg catgctacaa atcttggatc aactccacct tttacttact tagtacaaga    8520
gtcatacgat gtaatggcat tagtacatga gtgtagagaa gcaggatatc catgctatt    8580
cactatggat gctggaccta atgtaaaaat acttgtagag aagaaaaaca aacaacagat    8640
aatagataaa cttttaactc agttcgataa taatcagata atagagtg atattatagc    8700
tacaggtatt gaaattatag aataaactag ttgtatatta aaatagtaga atacataaga    8760
tacttaattt aattaaagat agttaagtac ttttcaatgt gcttttttag atgttaata    8820
caaatcttta attgtaaaag aaatgctgta ctatttactg ttctagtgac gggattaaac    8880
tgtattaatt ataataaaa ataagtaca gttgtttaaa attattt gtattaatc    8940
taatagtacg atgtaagtta ttttatacta ttgctagttt aataaaaga tttaattata    9000
tacttgaaaa ggagaggaac tcgagatggc agagtatata atagcagtag atgagttcga    9060
taacgaaata ggatcaatag aaaagatgga agctcataga aaaggaacac ttcatagagc    9120
attcagtatt ttagttttta actcaaagaa tcaactttta ttacagaaaa gaaatgtaaa    9180
gaaatatcac tctccaggat tatggacaaa cacttgttgt agtcacccaa gatatggtga    9240
atctcttcat gatgctatat acagaagatt aaaagaagag atgggattta cttgcgaact    9300
tgaagaagta ttctcattca tatataaggt aaaacttgaa gataatttat ttgagaatga    9360
atatgaccat gtatttattg gtaaaatga tggtgagata attgttaata aagatgaagt    9420
tgatgatttt aaatgggtag acattaatga agttaaaag gacataatga aaagacctga    9480
ggcatatact tactggttta agtatcttgt aaataaagct gaaaataaga tatttaaata    9540
aaccggtggg aggaaatgaa catggcaaca gaattattat gtttacacag acctatatca    9600
cttactcaca aactttttag gaatccatta cctaaagtta ttcaagctac acctttaaca    9660
ttaaaactta ggtgtagtgt ttctacagaa aatgtatcat ttagtgagac agaaactgaa    9720
acaagaagat cagcaaatta tgaaccaaat tctgggatt atgattatct tctttcttct    9780
gatactgatg agtcaataga agtacataaa gataaggcta agaaattaga agctgaagtt    9840
aggagagaaa taaataatga gaaggctgaa tttcttacac ttcttgaact tattgataat    9900
gtacaaagac ttggattagg atatagattt gagtctgata taagaagagc attagataga    9960
tttgtaagta gtggaggatt tgatggagtt actaaaactt cattcatgg aacagcatta   10020
tcatttaggt tattaaggca acatggtttt gaagtatctc aagaagcttt tagtggattt   10080
aaagatcaga atggaaactt tcttgagaat ttaaaggaag acataaaagc aattctttct   10140
ctttatgaag catcatttt agcattagaa ggtgagaata tattagatga ggctaaagta   10200
tttgcaatat ctcatcttaa agaacttagt gaagaaaaga ttggtaaaga attagctgaa   10260
caagtttcac atgctttaga attaccatta catagaagaa cacaaagatt agaagcagtt   10320
tggtcaatag aagcatatag aaagaaagaa gacgcaaatc aagtacttt agaacttgca   10380
atacttgact acaatatgat tcaaagtgta tatcagaggg attaagaga aacatcaaga   10440
tggtggagaa gagtaggatt agcaactaaa ttacattttg ctagagatag gcttattgaa   10500
agttttatt gggctgttgg agttgctttt gaaccacaat attctgattg cagaaaatagt   10560
gtagcaaaga tgttttcatt tgttactata attgacgata tttacgatgt atatggaact   10620
ttagatgaac ttgaactttt tactgatgca gttgaaagat gggatgtaaa tgctattaat   10680
gatcttcctg attatatgaa gttatgtttt acaatactat taacgagata   10740
gcttacgata acttaaaaga taaaggtgag aacatacttc cttatttaac aaaagcatgg   10800
gcagatttat gtaatgcatt tcttcaagaa gctaagtggc tttataataa atcaacacct   10860
acatttgatg attattttgg aaatgcatgg aaaagttcta gtggaccttt acagcttatt   10920
tttgcttatt ttgctgtagt acagaacatt aaaaaggaag agattgagaa tcttcagaaa   10980
tatcatgaca taatatcaag acctagtcac attttagcc tttgtaatga tttagcatct   11040
gcttcagcag aaaatagcaag aggtgaaact gctaattctg taagtttgtta tatgagaaca   11100
aaaggtatat ctgaagaatt agctactgaa agtgttatga atcttataga cgaaacttgg   11160
aagaaatga acaagaaaa acttggtgga tcttttattg caaaccttt tgttgagact   11220
gctataattt tagctagaca gtctcattgc acatatcata atggtgatgc acatactagt   11280
ccagatgaat taactaggaa aagagtactt agtgataata ctgaaccaat attaccattt   11340
gaaagataag ctagcataaa aataagaagc ctgcatttgc aggcttctta tttttatggc   11400
gcgccgccat tatttttttg aacaattgac aattcatttc ttatttttta ttaagtgata   11460
gtcaaaaggc ataacagtgc tgaatagaaa gaattaca gaaaagaaaa ttatagaatt   11520
tagtatgatt aattatactc atttatgaat gtttaattga atacaaaaaa aaatacttgt   11580
tatgtattca attacggttt aaatatagta caagttgaaa aatttaataa aaaaataagt   11640
```

```
cctcagctct tatatattaa gctaccaact tagtatataa gccaaaactt aaatgtgcta   11700
ccaacacatc aagccgttag agaactctat ctatagcaat atttcaaatg taccgcacata  11760
caagagaaac attaactata tatattcaat ttatgagatt atcttaacag atataaatgt   11820
aaattgcaat aagtaagatt tagaagttta tagcctttgt gtattggaag cagtacgcaa   11880
aggctttttt atttgataaa aattagaagt atatttattt tttcataatt aatttatgaa   11940
aatgaaaggg ggtgagcaaa gtgacagagg aaagcagtat cttatcaaat aacaaggtat   12000
tagcaatatc attattgact ttagcagtaa acattatgac ttttatagtg cttgtagcta   12060
agtagtacga aaggggggagc tttaaaaagc tccttggaat acatagaatt cataaattaa  12120
tttatgaaaa gaagggcgta tatgaaaact tgtaaaaatt gcaaagagtt tattaaagat   12180
actgaaaatat gcaaaataca ttcgttgatg attcatgata aaacagtagc aacctattgc  12240
agtaaaataca atgagtcaag atgtttacat aaagggaaag tccaatgtat taattgttca  12300
aagatgaacc gatatggatg gtgtgccata aaaatgagat gttttacaga ggaagaacag   12360
aaaaaagaac gtacatgcat taaatattat gcaaggagct ttaaaaaagc tcatgtaaag  12420
aagagtaaaa agaaaaaata attttatttat taatttaata ttgagagtgc cgacacagta  12480
tgcactaaaa aatatatctg tggtgtagtg agccgataca aaaggatagt cactcgcatt   12540
ttcataatac atcttatgtt atgattatgt gtcggtggga cttcacgacg aaaacccaca   12600
ataaaaaaag agttcgggt agggttaagc atagttgagg caactaaaca atcaagctag    12660
gatatgcagt agcagaccgt aaggtcgttg tttaggtgtg ttgtaataca tacgctatta   12720
agatgtaaaa atacgatac caatgaaggg aaaagtataa ttttttggatg tagtttgttt   12780
gttcatctat gggcaaacta cgtccaaagc cgtttccaaa tctgctaaaa agtatatcct   12840
ttctaaaatc aaagtcaagt atgaaatcat aaataaagtt taattttgaa gttattatga   12900
tattatgttt ttctattaaa ataaattaag tatataagat agttaataa tagtatatac    12960
ttaatgtgat aagtgtctga cagtgtcaca gaaaggatga ttgttatgga ttataagcgg   13020
ccggccagtg ggcaagttga aaaattcaca aaaatgtggt ataatatctt tgttcattag   13080
agcgataaac ttgaatttga gagggaactt agatggtatt tgaaaaaatt gataaaaata   13140
gttggaacag aaaagagtat tttgaccact actttgcaag tgtaccttgt acctacagca   13200
tgaccgttaa agtggatatc acacaaataa aggaaaggg aatgaaacta tatcctgcaa    13260
tgctttatta tattgcaatg attgtaaacc gccattcaga gtttaggacg gcaatcaatc   13320
aagatggtga attggggata tatgatgaga tgataccaag ctatacaata tttcacaatg   13380
atactgaaac attttccagc cttttggactg agtgtaagtc tgactttaaa tcattttag   13440
cagattatga aagtgatacg caacggtatg gaaacaatca tagaatggaa ggaaagccaa   13500
atgctccgga aaacatttt aatgtatcta tgataccgtg gtcaaccttc gatggcttta   13560
atctgaattt gcagaaagga tatgattatt tgattcctat tttactatg gggaaatatt    13620
ataaagaaga taacaaaatt atacttcctt tggcaattca agttcatcac gcagtatgtg   13680
acggatttca catttgccgt tttgtaaacg aattgcagga attgataaat agttaacttc   13740
aggtttgtct gtaactaaaa acaagtattt aagcaaaaac atcgtagaaa tacggtgttt   13800
tttgttaccc taagttt                                                 13817

SEQ ID NO: 59          moltype = DNA   length = 14709
FEATURE                Location/Qualifiers
misc_feature           1..14709
                       note =
                       plasmidpMTL8314-Pptaack-thlA-HMGS-Patp-HMGR-Prnf-MK-PMK-PMD
                       -Pfor-idi-ispA-FS
source                 1..14709
                       mol_type = other DNA
                       organism = synthetic construct
SEQUENCE: 59
aaactcctttt ttgataatct catgaccaaa atcccttaac gtgagttttc gttccactga   60
gcgtcagacc ccgtagaaaa gatcaaagga tcttcttgag atcctttttt tctgcgcgta   120
atctgctgct tgcaaacaaa aaaaccaccg ctaccagcgg tggtttgttt gccggatcaa   180
gagctaccaa ctctttttcc gaaggtaact ggcttcagca gagcgcagat accaaatact   240
gttcttctag tgtagccgta gttaggccac cacttcaaga actctgtagc accgcctaca   300
tacctcgctc tgctaatcct gttaccagtg gctgctgcca gtggcgataa gtcgtgtctt   360
accgggttgg actcaagacg atagttaccg gataaggcgc agcggtcggg ctgaacgggg   420
ggttcgtgca cacagcccag cttggagcga acgacctaca ccgaactgag atacctacag   480
cgtgagctat gagaaagcgc cacgcttccc gaagggagaa aggcggacag gtatccggta   540
agcggcaggt cggaacagga gagcgcacg agggagcttc caggggggaaa cgcctggtat   600
ctttatagtc ctgtcgggtt tcgccacctc tgacttgagc gtcgattttt gtgatgctcg   660
tcagggggggc ggagcctatg gaaaaacgcc agcaacgcgg ccttttttacg gttcctggcc   720
ttttgctggc cttttgctca catgttcttt cctgcgttat cccctgattc tgtggataac   780
cgtattaccg cctttgagtg agctgatacc gctcgccgca gccgaacgac cgagcgcagc   840
gagtcagtga gcgaggaagc ggaagagcgc ccaatacgca gggcccctg caggataaaa   900
aaattgtaga taattttat aaaatagttt tatctacaat tttttatca ggaaacagct   960
atgaccgcgg ccgcagatag tcataatagt tccagaatag ttcaatttag aaattagact  1020
aaacttcaaa atgtttgtta aatatatacc aatctagtat agatattttt taaatactgg  1080
acttaaacag tagtaatttg cctaaaaaat ttttcaatt tttttaaaa aatccttttc    1140
aagttgtaca ttgttatggt aatatgtaat tgaagaagtt atgtagtaat attgtaaacg  1200
tttcttgatt tttttacatc catgtagtgc ttaaaaaacc aaaatatgtc acatgcactt  1260
gtatatttca aataacaata tttatttct cgttaaattc acaaataatt tattaataat   1320
atcaataacc aagattatac ttaaatggat gtttattttt taacactttt atagtaaata  1380
tatttatttt atgtagtaaa aaggtatataa ttataattgt atttattaca attaattaaa  1440
ataaaaaata gggttttagg taaaattaag ttatttaag aagtaattac aataaaaatt   1500
gaagtttattt ctttaaggag gaaattcata tgaaagaggt tgttattgca tcagcagtta  1560
gaactgcaat aggatcttat ggaaaaagtc ttaaagatgt accagcagta gacttaggtg  1620
caactgcaat aaaggaagca gtaaaagaag caggtataaa acctgaagat gttaatgaag  1680
ttatttttgg aaacgtatta caagctggac ttggacagaa tccagctaga caggcatcat  1740
tcaaagcagg attaccagta gagatacctg ctatgactat taataaagtt tgtggttcag  1800
gattaagaac agtttctttt agctgctcaaa ttataaaagc tggtgacgca gatgtaataa  1860
```

```
tagcaggtgg tatggaaaat atgtcaagag caccatacct tgctaataat gctagatggg   1920
gttatagaat gggaaacgct aaatttgtag acgaaatgat aactgatgga ctttgggatg   1980
catttaacga ttatcacatg ggaattactg ctgaaaatat agctgagaga tggaatataa   2040
gtagagaaga acaagatgag tttgcacttg catctcagaa aaaggcagaa gaagctatta   2100
aatcaggaca atttaaagat gaaattgttc cagtagtaat taaaggtaga aaaggtgaaa   2160
cagttgtaga cactgatgaa catcctagat ttggatctac aatagaaggt ttagctaaat   2220
taaagcctgc ttttaagaaa gacggaacag taactgctgg aaacgcatca ggtttaaatg   2280
attgtgcagc tgttttagtt attatgtctg ctgaaaaggc aaaggaatta ggtgttaaac   2340
cacttgctaa gatagttagt tatggttcag caggtgtaga tcctgctatt atgggatatg   2400
gaccttttta tgctacaaag gcagctattg aaaaggctgg ttggacagtt gatgaacttg   2460
atcttataga gtcaaatgag gcatttgcag cacaaagtct tgctgttgct aaggatctta   2520
aattcgatat gaataaagta aatgtaaacg gtggtgctat agcacttggt catccaatag   2580
gtgctagtgg tgctagaatt ttagttacat tagttcatgc aatgcaaaag agagacgcta   2640
aaaagggact tgcaacttta tgcataggtg gtggtcaagg aacagcaata cttcttgaaa   2700
aatgttaaga attcgaggct tttactaaaa acaataaaaa caggaggaaa taatatgact   2760
ataggaattg acaaaataaa cttttacgta ccaaaatatt atgtagatat ggcaaaatta   2820
gcagaagcaa gacaagtaga cccaaataaa tttcttattg gaataggaca gactgaaatg   2880
gcagttagtc cagtaaaacca agatatagta tcaatggctg ctaatgctgc taaagatata   2940
ataactgatg aagacaaaaa gaaaatagga atggtaatag tagcaactga gtcagcagta   3000
gatgcagcaa aggcagcagc agtacagatt cataatttat taggtattca accatttgca   3060
agatgtttcg aaatgaaaga agcatgttat gctgctactc ctgcaattca gttagctaag   3120
gattatttag ctacaagacc aaatgagaaa gttttagtta tagctacaga tacagctaga   3180
tatggactta attcaggtgg tgaacctact caaggtgctg gtgctgttgc tatggttata   3240
gctcataatc ctagtatact tgcattaaat gaagacgctg ttgcttatac agaagatgtt   3300
tatgatttct ggagaccaac aggacataag tatccattag tagatggtgc tttatcaaaa   3360
gacgcatata ttagatcttt tcaacaatct tggaatgaat atctaagag acaaggaaag   3420
agtttagctg attttgctag tctttgcttt catgttcctt ttactaaaat gggtaaaaag   3480
gctttagaat ctataatgga taacgcagat gaaacaactc aagagagatt aagatctgga   3540
tatgaagatg cagttgatta caatagatat gttggaaata tatacacagg aagtctttat   3600
ctttctctta taagtcttct tgaaaataga gatttacgag ctggtgaaac tattggatta   3660
ttttcatacg gatcaggttc tgttggtgaa ttttattcag ctacacttgt agaaggatat   3720
aaagatcacc ttgatcaggc agcacacaaa gcacttttaa acaatagaac tgaagtatca   3780
gtagatgcat acgaaacatt tttcaagaga tttgatgatg tagaatttga tgaagagcag   3840
gatgcagttc atgaagatag acatatattc tatctttcaa acataagaa taatgtaaga   3900
gaatatcata gacctgaata agagctcgtt ataattttca attttcattc tttttaaagg   3960
agattagcat acatttttatc ataattatac agacaatata gtaatatatg atgttaaaat   4020
atcaatatat ggttaaaaat ctgtatattt tttcccattt taattatttg tactataata   4080
ttacactgag tgtattgcat atttaaaaaa tatttggtac aattagttag ttaaataaat   4140
tctaaattgt aaattatcag aatccttatt aaggaaatac atagatttaa gggaaaatca   4200
taaaaaggtg taatataaac tggctaaaat tgagcaaaaa ttgagcaatt aagacttttt   4260
gattgtatct ttttatatat ttaaggtata taatcttatt tatattgggg gaaggtacca   4320
tgcaatcatt agacaaaaat ttcagacatt tatcaagaca acaaaagtta caacaattag   4380
ttgataaaca gtggctttca gaagatcagt tgtatatttt acttaatcat cctcttatag   4440
atgaagaagt tgctaatagt cttatagaaa atgtaattgc acagggtgca ttaccagttg   4500
gacttcttcc taatataata gttgatgata aggcttatgt tgtaccaatg atggttgaag   4560
aacctagtgt tgttgcagct gcatcttatg gtgctaaatt agtaaatcag acaggtggat   4620
ttaaaactgt atcatcagaa agaataatga ttggacagat agtattttgat ggtgtagatg   4680
acactgaaaa attaagtgca gatattaaag cattagaaaa acaaatacat aagattgcag   4740
atgaagcata tcctagtata aaagcaagag gtggtggtta tcaaagaata gcaatagata   4800
catttccaga gcaacaactt ttaagtctta aggtatttgt agatacaaaa gatgctatgg   4860
gtgctaatat gcttaatact atacttgagg caataactgc attccttaaa aatgaatctc   4920
ctcaatcaga tatattaatg tctatacttt caaaccatgc aactgctagt gtagtaaaag   4980
tacaaggtga gatagatgta aaagatcttg ctagaggtga agaacaggt gaagaagtag   5040
ctaagagaat ggaaagagct tctgtattag ctcaggttga tattcataga gctgcaacac   5100
ataacaaagg tgttatgaat ggaatacatg ctgttgtttt agctacagga aatgatacta   5160
gaggtgctga agcatctgca catgcatacg catcaagaga cggacaatat agaggtatag   5220
caacttggag atatgatcag aagagacaaa gacttattgg aactattgaa gttccaatga   5280
cacttgctat agtaggtggt ggtactaaag tattaccaat agctaaggca tcattagagt   5340
tattaaatgt tgattctgca caagaacttg gacacgtagt tgctgctgtt ggattagcac   5400
aaaactttgc tgcttgtaga gcacttgttt ctgaaggtat tcaacaagga cacatgtcat   5460
tacaatataa aagtttagca atagtagtag gtgcaaaagg tgacgagata gcacaagtag   5520
cagaagctct taacaggaa ccaagagcta atacacaggt tgctgaaaga attttacagg   5580
aaattagaca gcaataatct agaatatcga tacagataaa aaaatatata atacagaaga   5640
aaaaattata aatttgtggt ataatataaa gtatagtaat ttaagtttaa acctcgtaga   5700
aacgctaaca aataatagga ggtcaattga tgatagctgt tccattttaac gctggaaaaa   5760
taaaagtttt aattgaggca ttagaatctg gaaattattc atcaataaaa tcagatgtat   5820
atgacggaat gttatgtgat gcaccagatc accttaaatc attagtaaac agattttgtag   5880
aacttaataa tataactgag ccattagcag taactataca gacaaatctt cctccttcaa   5940
gaggtcttgg atctagtgca gctgttgctg ttgcttttgt aagagcaagt tatgatttct   6000
taggaaaaag tttaactaaa gaagagctta gaaaaggc taattgggct gaacaaatag   6060
ctcatgaaa gccatctgga atagatacac aaacaatagt atctgaaag cctgtttggt   6120
ttcaaaaggg acatgcagaa acacttaaaa ctctttcact tgatggatac atggtagtaa   6180
ttgatacagg tgttaaagga agtacaagac aggctgtaga agatgttcat aaactttgcg   6240
aagatcctca atatatgagt cacgtaaaac acataggaca acttgtactt agagcatctg   6300
atgttattga acatcataac tttgaagcac ttgctgatat attcaatgaa tgtcatgctg   6360
atttaaaggc tcttacagta agtcatgaca aaatagaaca gttaatgaag ataggaaaag   6420
aaaatggtgc tatagctggt aaattaactg gtgctgtag aggtggttca atgttattac   6480
ttgcaaaaga cttaccaact gcaaagaata tagttaaagc agtagagaaa gctggtcag   6540
cacatacttg gattgaaaat ttaggtggtt aagtcgacaa agacactaaa aaattataaa   6600
```

```
agtaaaggag gacattaaat gatacaagta aaggcaccag gaaaattata tatagcaggt   6660
gaatacgctg ttacagaacc aggatataaa tctgttctta tagctcttga tagatttgtt   6720
acagctacta ttgaggaagc tgatcaatac aaaggaacaa tacattcaaa ggcattacat   6780
cacaatccga taacttttag tagagatgaa gattctattg ttatatcaga cccacacgca   6840
gcaaaacaac ttaattatgt agtaactgct atagaaaatt ttgagcaata tgcaaaatca   6900
tgtgacatag caatgaagca ttttcattta actatagatt ctaacttaga tgatagtaat   6960
ggacataagt atggacttgg atcttctgct gctgttttag tttcagtaat taaagtactt   7020
aacgaatttt atgatatgaa actttcaaac ctttatatat ataagttagc agtaattgct   7080
aatatgaaat tacagagttt atcttcatgc ggtgtatag cagtaagtgt ttattcaggt    7140
tggttagctt attctacatt tgaccatgaa tgggtaaaac accagataga agatacaaca   7200
gttgaagaag tacttattaa aaattggcct ggattacaca tagagccact tcaagctcct   7260
gaaaatatgg aagttcttat aggttggaca ggtagtccag ctagtagtcc tcattttgtt   7320
tctgaagtta aaagacttaa gtcagatcct tcatttacg gtgatttctt agaagattca    7380
catagatgtg tagaaaaatt aattcatgca ttcaaaacta ataatattaa gggtgttcag   7440
aaaatggtaa gacagaatag aactattata caaagaatgg ataaggaagc aacagttgat   7500
atagagactg agaagttaaa atatttatgt gatattgctg aaaaatatca tggtgcaagt   7560
aaaacttcag gtgctggtgg tggtgattgc ggaataacta taataaataa ggatgtagac   7620
aaagagaaaa tatatgatga atggactaaa catggaataa agcctcttaa gtttaatatt   7680
tatcatggac aataaccatg gtcaataatc ttacaataaa taaaagaaag gaggcaaaaa   7740
tatgataaaa tctggaaaag caagagcaca cactaatata gcacttataa aatattgggg   7800
taagaaagat gaggcattaa taataccaat gaataactca atatcagtaa ctttagaaaa   7860
gttttatact gaaacaaaag ttacatttaa cgatcagctt actcaagatc aatttttggct  7920
taatggtgaa aaagtttctg gaaaagaatt agaaaagatt tcaaagtata tggatattgt   7980
tagaaaataga gctggaatag attggtatgc tgagatagaa tctgataatt ttgttcctac    8040
agctgctggt cttgctagtt ctgctagtgc ttatgcagca ttagctgctg catgtaacca   8100
agcacttgat ttacagttaa gtgataaaga cttaagtaga ttagctgaag ttggatcagg   8160
atcagcatca agatcaatat acggtggttt tgcagaatgg gaaaaaggat ataatgacga   8220
aacttcttat gctgttccat tagaaagtaa tcactttgaa gatgatcttg ctatgatttt    8280
tgtagtaata aaccaacatt ctaaaaaggt tccttcaaga tatggaatgt ctcttacaag   8340
aaatacaagt agattctatc aatattggtt agaccatatt gatgaagatc ttgcagaagc   8400
aaaggcagca atacaagata aggattttaa gagattaggt gaagttattg aagagaatgg   8460
acttagaatg catgctacaa atcttggatc aactccacct tttacttact tagtacaaga   8520
gtcatacgat gtaatggcat tagtacatga gtgtagagaa gcaggatatc catgctattt   8580
cactatggat gctggaccta atgtaaaaat acttgtagag aagaaaaaca acaacagat    8640
aatagataaa cttttaactc agttcgataa taatcagata atagatagtg atattatagc   8700
tacaggtatt gaaattatag aataaactag ttgtatatta aaatagtaga atacataaga   8760
tacttaatttt aattaaagat agtaagtac ttttcaatgt gcttttttag atgtttaata    8820
caaatcttta attgtaaaag aaatgctgta ctatttactg ttcatgtgac gggattaaac   8880
tgtattaatt ataaataaaa aataagtaca gttgtttaaa attatatttt gtattaatc    8940
taatagtacg atgtaagtta ttttatacta ttgctagttt aataaaaaga tttaattata   9000
tacttgaaaa ggagaggaac tcgagatggc agagtatata atagcagtag atgagttcga   9060
taacgaaata ggatcaatag aaaagatgga agctcataga aaaggaacac ttcatagagc   9120
attcagtatt ttagttttta actcaaagaa tcaacttttta ttacagaaaa gaaatgtaaa   9180
gaaatatcac tctccaggat tatggacaaa cacttgttgt agtcacccaa gatatggtga   9240
atctcttcat gatgctatat acagaagatt aaaagaagag atgggattta cttgcgaact   9300
tgaagaagta ttctcattca tatataaggt aaaacttgaa gataattttat ttgagaatga   9360
atatgaccat gtatttattg gtaaaatatga tggtgagata ttgttaata aagatgaagt    9420
tgatgatttt aaatgggtag acattaatga agttaaaaag gacataatag aaagacctga   9480
ggcatatact tactggttta gtatcttgt aaataaaagct gaaaataaga tatttaaata    9540
aaccggtcag taacgaatag aattagaaaa acaaaggagg caagacaatg gatttcccac   9600
aacaattaga agcatgtgta aaacaggcta atcaggcaat tagtagattt attgctcatc   9660
ttccttttca aaatacacca gtagtagaaa ctatgcaata cggtgcactt ttaggtggta   9720
aaagattaag accattctta gtatatgcta caggacacat gtttggtgta tcaactaata   9780
ctttagacgc tccagctgct gctgttgaat gtattcatgc ttattcttta atacatgatg   9840
acttaccagc aatggatgac gatgatttaa gaagaggttt acctaacatgt catgttaaat   9900
ttggtgaagc taatgcaatt ttagcaggtg acgctttaca aacttagct ttttctatac    9960
tttcagatgc agacatgcct gaagtttcag atagagatag aatttctatg atatcagagc  10020
ttgcatctgc atcaggaata gctggaatgt gcggtggtca agcacttgat ttagatgcag  10080
aagttaaaca cgtaccactt gatgctttag agagaataca tagacataaa acaggtgctc  10140
ttataagagc agcagtaaga ttaggtgctt taagtgctgg tgacaagggt agaagagcac  10200
ttccagtact tgataagtat gcagaaagta taggattagc ttttcaagtt caagatgaca  10260
tacttgacgt tgttggtgat actgctactt taggaaaaag acagggtgca gatcagcaat  10320
taggaaaatc tacataccct gctttacttg gattagaaca ggctagaaag aaagcaagag  10380
acttaataga tgacgcaaga caaagtctta aacagttagc tgaacaatca cttgacacaa  10440
gtgcacttga agcacttgca gattatatta tacagaaaa caagtaaaag cttttaaagg   10500
agggggaaaaa atggaattta gagtacatt acaggcagac aacgaacaga aaatatttca  10560
aaatcaaatg aaaccagagc cagaagcatc atatcttata aatcaaagaa gaagtgctaa  10620
ttataaaacca acatttggga aaaacagattt tcttgatcag tcttttaatat caaaatatga  10680
tggtgatgaa tatagaaaac ttttcagaaa a gttaatgaa gaagtaaaga tatacatatc  10740
agcagagact atggatttag ttgctaaatt agaacttata gattctgtta gaaaacttgg  10800
acttgctaat ctttttgaga aagaaataaa ggaagcatta gacagtatag cagcaataga  10860
atcagataat ttaggaacta gagacgatct ttatggaaca gctcttcatt ttaagattct  10920
tagacagcat ggatataagg taagtcaaga tatatttggt agatttatgg atgagaaagg  10980
aacattaaga aatcatcact ttgcacactt aaaaggaatg ttagaattat ttgaggcaag  11040
taatcttgga tttgaaggtg aagacatatt agatgaagct aaagcatctc ttacacttgc  11100
tcttagagat tcaggacata tttgttatcc agactcaaac ttaagtagag atgtagttca  11160
tagtttagaa ttacctagtc atagaagagt tcaatggttc gatgtaaaat ggcagattaa  11220
tgcatacgaa aaagatattt gtagagtaaa tgcaacttta ttagagttag caagttaaa   11280
ttttaatgtt gttcaagctc agcttcagaa gaatcttaga gaagctagta gatggtgggc  11340
```

```
taatcttggt tccgcagata atttaaagtt tgctagagat agacttgtag agtgtttttc  11400
atgcgcagta ggtgtagcat ttgaaccaga gcattcatct tttagaatat gtttaactaa  11460
ggtaattaat cttgttctta ttatagatga tgtatacgat atatatggat ctgaagaaga  11520
gttaaaacat tttacaaatg ctgttgatag atgggacagt agagaaacag aacagcttcc  11580
tgaatgcatg aaaatgtgtt ttcaagtatt atataacact acttgcgaaa tagcaagaga  11640
gatagaagaa gaaaacggtt ggaatcaagt attacctcaa cttactaagg tttgggctga  11700
tttttgtaag gctctttttag ttgaagcaga gtggtacaat aaatcacata ttccaacatt  11760
agaagaatat cttagaaacg gatgtatatc aagtagtgta tctgtacttt tagttcactc  11820
tttcttttca ataactcatg aaggtacaaa agaaatggct gatttcttac ataaaaatga  11880
agatctttta tacaacataa gtcttatagt aagattaaac aatgatttag gtacatcagc  11940
tgctgaacag gaaagaggtg attctccttc ttctatagtt tgctatatga gagaagttaa  12000
tgcttctgaa gagactgcaa gaaagaatat aaagggaatg attgataatg cttggaaaaa  12060
ggttaatgga aaatgtttca caactaacca agttccattt ctttcatcat tcatgaataa  12120
tgcaactaac atggcaagag tagcacactc attatataaa gacggtgatg gttttggtga  12180
tcaagaaaaa ggacctagaa cacatattct tagtttatta ttccaacctt tagtaaatta  12240
agctagcata aaaataagaa gcctgcattt gcaggcttct tatttttatg gcgcgccgcc  12300
attatttttt tgaacaattg acaattcatt tcttatttt tattaagtga tagtcaaaag  12360
gcataacagt gctgaataga aagaaattta cagaaaagaa aattatagaa tttagtatga  12420
ttaattatac tcatttatga atgtttaatt gaatacaaaa aaaatactt gttatgtatt  12480
caattacggg ttaaaatata gacaagttga aaaatttaat aaaaaaataa gtcctcagct  12540
cttatatatt aagctaccaa cttagtatat aagccaaaac ttaaatgtgc taccaacaca  12600
tcaagccgtt agagaactct atctatagca atatttcaaa tgtaccgaca tacaagagaa  12660
acattaacta tatatattca atttatgaga ttatcttaac agatataaat gtaaattgca  12720
ataagtaaga tttagaagtt tatagccttt gtgtattgga agcagtacgc aaaggctttt  12780
ttatttgata aaaattagaa gtatatttat ttttttcataa ttaatttatg aaaatgaaag  12840
ggggtgagca aagtgacaga ggaaaagcagt atcttatcca ataacaaggt attagcaata  12900
tcattattga cttttagcagt aaacattatg acttttatag tgcttgtagc taagtagtac  12960
gaaagggggga gctttaaaaa gctccttgga atacatagaa ttcataaatt aatttatgaa  13020
aagaagggcg tatatgaaaa cttgtaaaaa ttgcaaagag tttattaaag atactgaaat  13080
atgcaaaata cattcgttga tgattcatga taaaacgata gcaacctatt gcagtaaata  13140
caatgagtca agatgtttac ataaagggaa agtccaatgt attaattgtt caaagatgaa  13200
ccgatatgga tggtgtgcca taaaaatgag atgtttttaca gaggaagaac agaaaaaaga  13260
acgtacatgc attaaaatatt atgcaaggag ctttaaaaaa gctcatgtaa agaagagtaa  13320
aaagaaaaaa taatttattt attaatttaa tattgagagt gccgacacag tatgcactaa  13380
aaaatatatc tgtggtgtag tgagccgata caaaaggata gtcactcgca ttttcataat  13440
acatcttatg ttatgattat gtgtcggtgg gacttcacga cgaaaaccca caataaaaaa  13500
agagttcggg gtagggttaa gcatagttga ggcaactaaa caatcaagct aggatatgca  13560
gtagcagacc gtaaggtcgt tgtttaggtg tgttgtaata catacgctat taagatgtaa  13620
aaatacggat accaatgaag ggaaaagtat aattttttgt tgtagtttgt ttgttcatct  13680
atgggcaaac tacgtccaaa gccgtttcca aatctgctaa aaagtatatc ctttctaaaa  13740
tcaaagtcaa gtatgaaatc ataaataaag tttaattttg aagttattat gatattatgt  13800
ttttctatta aaataaatta agtatataga atagtttaat aatagtatat acttaatgtg  13860
ataagtgtct gacagtgtca cagaaaggat gattgttatg gattataagc ggccggccag  13920
tgggcaagtt gaaaaattca caaaaatgtg gtataatatc tttgttcatt agagcgataa  13980
acttgaattt gagagggaac ttagatggta tttgaaaaaa ttgataaaaa tagttggaac  14040
agaaaagagt attttgacca ctactttgca agtgtacctt gtacctacag catgaccgtt  14100
aaagtggata tcacacaaat aaaggaaaag ggaatgaaac tatatcctgc aatgctttat  14160
tatattgcaa tgattgtaaa ccgccattca gagtttagga cggcaatcaa tcaagatggt  14220
gaattgggga tatatgatga gatgatacca agctatacaa tatttcacaa tgatactgaa  14280
acattttcca gcctttggac tgagtgtaag tctgacttta aatcatttt agcagattat  14340
gaaagtgata cgcaacggta tggaaacaat catgaatgt aaggaaagcc aaatgctccg  14400
gaaaacattt ttaatgtatc tatgataccg tggtcaacct tcgatggctt taatctgaat  14460
ttgcagaaag gatatgatta tttgattcct atttttacta tggggaaata ttataaagaa  14520
gataacaaaa ttatacttcc tttggcaatt caagttcatc acgcagtatg tgacggattt  14580
cacattttgcc gttttgtaaa cgaattgcag gaattgataa atagttaact tcaggtttgt  14640
ctgtaactaa aaacaagtat ttaagcaaaa acatcgtaga aatacggtgt ttttttgttac  14700
cctaagttt                                                           14709

SEQ ID NO: 60         moltype = AA  length = 601
FEATURE               Location/Qualifiers
REGION                1..601
                      note = hybrid Type II methyltransferase
source                1..601
                      mol_type = protein
                      organism = synthetic construct
SEQUENCE: 60
MFPCNAYIEY GDKNMNSFIE DVEQIYNFIK KNIDVEEKMH FIETYKQKSN MKKEISFSEE   60
YYKQKIMNGK NGVVYTPPEM AAFMVKNLIN VNDVIGNPPI KIIDPSCGSG NLICKCFLYL  120
NRIFIKNIEV INSKNNLNLK LEDISYHIVR NNLFGFDIDE TAIKVLKIDL FLISNQFSEK  180
NFQVKDFLVE NIDRKYDVFI GNPPYIGHKS VDSSYSYVLR KIYGSIYRDK GDISYCFFQK  240
SLKCLKEGGK LVFVTSRYFC ESCSGKELRK FLIENTSIYK IIDFYGIRPF KRVGIDPMII  300
FLVRTKNWNN NIEIIRPNKI EKNEKNKFLD SLFLDKSEKC KKFSISQKSI NNDGWVFVDE  360
VEKNIIDKIK EKSKFILKDI CHSCQGIITG CDRAFIVDRD IINSRKIELR LIKPWIKSSH  420
IRKNEVIKGE KFIIYSNLIE NETECPNAIK YIEQYKKRLM ERRECKKGTR KWYELQWGRK  480
PEIFEEKKIV FPYKSCDNRF ALDKGSYFSA DIYSLVLKKN VPFTYEILLN ILNSPLYEFY  540
FKTFAKKLGE NLYEYYPNNL MKLCIPSIDF GGENNIEKKL YDFFGLTDKE IEIVEKIKDN  600
C                                                                  601

SEQ ID NO: 61         moltype = DNA  length = 419
```

```
FEATURE                 Location/Qualifiers
source                  1..419
                        mol_type = other DNA
                        organism = Clostridium autoethanogenum
SEQUENCE: 61
agaaattttc ctttctaaaa tattttattc catgtcaaga actctgttta tttcattaaa   60
gaactataag tacaaagtat aaggcatttg aaaaaatagg ctagtatatt gattgattat  120
ttatttaaa  atgcctaagt gaaatatata catattataa caataaaata agtattagtg  180
taggatttt  aaatagagta tctatttca gattaaattt ttgattattt gatttacatt   240
atataatatt gagtaaagta ttgactagca aaattttttg atactttaat ttgtgaaatt  300
tcttatcaaa agttatattt ttgaataatt tttattgaaa aatacaacta aaaaggatta  360
tagtataagt gtgtgtaatt ttgtgttaaa tttaaaggga ggaaatgaac atgaaattg   419

SEQ ID NO: 62           moltype = DNA  length = 567
FEATURE                 Location/Qualifiers
source                  1..567
                        mol_type = other DNA
                        organism = Clostridium autoethanogenum
SEQUENCE: 62
ctcctaattt tgaaatctaa tatatctatt aaatcatatt ttcatatgta aataaataag   60
tttttatgca attttgaaaa aggtatttgc ataaaacggc ttgaaatcaa tagttaacgc  120
aatagttatt cttttagcat acattaagtc aacaaaatta gcatgtaata attatgaata  180
attattacat atattcaata ttatattaaa aaaaatactt tgtttaagt  ataaagtaaa  240
aaaataggca taaatgtaac aaaaactgtt aattttttgt gtcaataatt tttgttatat  300
tattttaatt aaatttttca catgtataat taaaagtaag atagatattc taatgtactt  360
acttaggtag aaaaacatgt atacaaaatt aaaaaactaa tataacacat agtatcaata  420
ttgaaggtaa tactgttcaa tatcgataca gataaaaaaa atatataata cagaagaaaa  480
aattataaat ttgtggtata atataaagta tagtaattta agtttaaacc tcgtgaaaac  540
gctaacaaat aataggaggt gtattat                                       567

SEQ ID NO: 63           moltype = DNA  length = 1806
FEATURE                 Location/Qualifiers
misc_feature            1..1806
                        note = hybrid Type II methyltransferase
source                  1..1806
                        mol_type = other DNA
                        organism = synthetic construct
SEQUENCE: 63
atgtttccgt gcaatgccta tatcgaatat ggtgataaaa atatgaacag ctttatcgaa   60
gatgtggaac agatctacaa cttcattaaa aagaacattg atgtggaaga aaagatgcat  120
ttcattgaaa cctataaaca gaaaagcaac atgaagaaag agattagctt tagcgaagaa  180
tactataaac agaagattat gaacggcaaa aatggcgttg tgtacacccc gccggaaatg  240
gcggccttta tggttaaaaa tctgatcaac gttaacgata gcatgtaata tccgttatt   300
aaaatcattg acccgagctg cggtagcggc aatctgattt gcaaatgttt tctgtatctg  360
aatcgcatct ttattaagaa cattgaggtg attaacagca aaaataacct gaatctgaaa  420
ctggaagaca tcagctacca catcgttcgc aacaatctgt ttggcttcga tattgacgaa  480
accgcgatca aagtgctgaa aattgatctg ttttctgatca gcaaccaatt tagcgagaaa  540
aatttccagg ttaaagactt tctggtggaa aatattgatc gcaaatatga cgtgttcatt  600
ggtaatccgc cgtatatcgg tcacaaaagc gtggacagca gctacagcta cgtgctgcgc  660
aaaatctacg gcagcatcta ccgcgacaaa ggcgatatca gctattgttt ctttcagaag  720
agcctgaaat gtctgaagga aggtgggcaaa ctggtgtttg tgaccagccg ctacttctcg  780
gagagctgca gcggtaaaga actgcgtaaa ttcctgatcg aaaacacgag catttacaag  840
atcattgatt tttacggcat ccgcccgttc aaacgcgtgg gtatcgatcc gatgattatt  900
tttctggttc gtacgaagaa ctggaacaat aacattgaaa ttattcgccc gaacaagatt  960
gaaaagaacg aaaagaacaa attcctggat agcctgttcc tggacaaaag cgaaaagtgt 1020
aaaaagttta gcattagcca gaaaagcatt aataacgatg gctgggtttt cgtggacgaa 1080
gtggagaaaa acattatcga caaatcaaa gagaaagca agttcattct gaaagatatt 1140
tgccatagct gtcaaggcat tatcaccggt tgtgatcgcg cctttattgt ggaccgtgat 1200
atcatcaata gccgtaaagat cgaactgcgt ctgattaaca cgtggattaa aagcagccat 1260
atccgtaaga atgaagttat taagggcgaa aaattcatca tctatagcaa cctgattgag 1320
aatgaaaccg agtgtccgaa tgcgattaaa tatatcgaac agtacaagaa acgtctgatg 1380
gagcgccgcg aatgcaaaaa gggcacgcgt aagtggtatg aactgcaatg gggccgtaaa 1440
ccggaaatct tcgaagaaaa gaaaattgtt tcccgtata aaagctgtga caatcgtttt 1500
gcactggata agggtagcta ttttagcgca gacatttata gcctggttct gaagaaaaat 1560
gtgccgttca cctatgagat cctgctgaat atcctgaata gccgctgta cgagttttac 1620
tttaagacct tcgcgaaaaa gctgggcgag aatctgtacg agtactatcc gaacaacctg 1680
atgaagctgt gcatcccgag catcgatttc ggcggtgaga acaatattga gaaaagctg 1740
tatgatttct ttggtctgac ggataaagaa attgagattg tggagaagat caaagataac 1800
tgctaa                                                             1806

SEQ ID NO: 64           moltype = DNA  length = 4709
FEATURE                 Location/Qualifiers
misc_feature            1..4709
                        note = designed methylation plasmid
source                  1..4709
                        mol_type = other DNA
                        organism = synthetic construct
SEQUENCE: 64
gtttgccacc tgacgtctaa gaaaaggaat attcagcaat ttgcccgtgc cgaagaaagg   60
```

```
cccacccgtg aaggtgagcc agtgagttga ttgctacgta attagttagt tagcccttag    120
tgactcgtaa tacgactcac tatagggctc gaggcggccg cgcaacgcaa ttaatgtgag    180
ttagctcact cattaggcac cccaggcttt acactttatg cttccggctc gtatgttgtg    240
tggaattgtg agcggataac aatttcacac aggaaacaca tatgtttccg tgcaatgcct    300
atatcgaata tggtgataaa aatatgaaca gctttatcga agatgtggaa cagatctaca    360
acttcattaa aaagaacatt gatgtgaaag aaaagatgca tttcattgaa acctataaac    420
agaaaagcaa catgaagaaa gagattagct ttagcgaaga atactataaa cagaagatta    480
tgaacgcaa aaatgcgtt gtgtacaccc cgccggaaat ggcggccttt atggttaaaa     540
atctgatcaa cgttaacgat gttattggca atccgtttat taaaatcatt gacccgagct    600
gcggtagcgg caatctgatt tgcaaatgtt ttctgtatct gaatcgcatc tttattaaga    660
acattgaggt gattaacagc aaaaataacc tgaatctgaa actggaagac atcagctacc    720
acatcgttcg caacaatctg tttggcttcg atattgacga aaccgcgatc aaagtgctga    780
aaattgatct gtttctgatc agcaaccaat ttagcgagaa aaatttccag gttaaagact    840
ttctgtgtgga aaatattgat cgcaaatatg acgtgttcat tggtaatccg ccgtatatcg    900
gtcacaaaag cgtggacagc agctacagct acgtgctgcg caaaatctac ggcagcatct    960
accgcgacaa aggcgatatc agctattgtt tctttcagaa gagcctgaaa tgtctgaagg   1020
aaggtggcaa actggtgttt gtgaccagcc gctacttctg cgagagctgc agcggtaaag   1080
aactgcgtaa attcctgatc gaaaacacga gcatttacaa gatcattgat tttacgggca   1140
tccgcccgtt caaacgcgtg ggtatcgatc cgatgattat ttttctggtt cgtacgaaga   1200
actgaacaa taacattgaa attattcgcc cgaacaagat tgaaaagaac gaaaagaaca   1260
aattcctgga tagcctgttc ctggacaaaa gcgaaaagtg taaaaagttt agcattagcc    1320
agaaaagcat taataacgat ggctgggttt tcgtggacga agtggagaaa aacattatcg   1380
acaaaatcaa agagaaaagc aagttcattc tgaaagatat ttgccatagc tgtcaaggca    1440
ttatcaccgg ttgtgatcgc gcctttattg tggaccgtga tatcatcaat agccgtaaga   1500
tcgaactgcg tctgattaaa ccgtggatta aaagcagcca tatccgtaag aatgaagtta   1560
ttaaggcga aaaattcatc atctatagca acctgattga gaatgaaaac gagtgtccga    1620
atgcgattaa atatatcgaa cagtacaaga aacgtctgat ggagcgccgc gaatgcaaaa   1680
agggcacgcg taagtggtat gaactgcaat ggggccgtaa accggaaatc ttcgaagaaa   1740
agaaaattgt tttcccgtat aaaagctgtg acaatcgttt tgcactggat aagggtagct    1800
attttagcgc agacatttat agcctggttc tgaagaaaaa tgtgccgttc acctatgaga   1860
tcctgctgaa tatcctgaat agcccgctgt acgagttta ctttaagacc ttcgcgaaaa    1920
agctgggcga aatctgtac gagtactatc cgaacaacct gatgaagctg tgcatcccga    1980
gcatcgattt cggcggtgag aacaatattg agaaaaagct gtatgatttc tttggtctga   2040
cggataaaga aattgagatt gtggagaaga tcaaagataa ctgctaagaa ttcgatatca   2100
cccgggaact agtctgcagc cctttagtga gggttaattg gagtcactaa gggttagtta    2160
gttagattag cagaaagtca aaagcctccg accggaggct tttgactaaa acttcccttg   2220
gggttatcat tggggctcac tcaaaggcgg taatcagata aaaaaaatcc ttagctttcg    2280
ctaaggatga tttctgctag agatggaata gactggatgg aggcggataa agttgcagga    2340
ccacttctgc gctcggccct tccggctggc tggtttattg ctgataaatc tggagccggt    2400
gagcgtgggt ctcgcggtat cattgcagca ctggggccag atggtaagcc ctcccgtatc    2460
gtagttatct acacgacggg gagtcaggca actatgatg aacgaaatag acagatcgct    2520
gagataggtg cctcactgat taagcattgg taactgtcag accaagttta ctcatatata    2580
ctttagattg atttaaaact tcattttaa tttaaaagga tctaggtgaa gatcctttt    2640
gataatctca tgaccaaaat cccttaacgt gagttttcgt tccactgagc gtcagacccc    2700
ttaataagat gatcttcttg agatcgtttt ggtctgcgcg taatctcttg ctctgaaaac    2760
gaaaaaaccg ccttgcaggg cggttttttcg aaggttctct gagctaccaa ctctttgaac    2820
cgaggtaact ggcttggagg agcgcagtca ccaaaacttg tcctttcagt ttagccttaa    2880
ccggcgcatg acttcaagac taactcctct aaatcaatta ccagtggctg ctgccagtgg   2940
tgcttttgca tgtcttttccg ggttggactc aagacgatag ttaccggata aggcgcagcg   3000
gtcggactga acgggggtt cgtgcataca gtccagcttg gagcgaactg cctacccgga    3060
actgagtgtc aggcgtggaa tgagacaaac gcggccataa cagcggaatg acaccggtaa    3120
accgaaaggc aggaacagga gagcgcacga gggagccgcc aggggaaacg cctggtatct    3180
ttatagtcct gtcgggtttc gccaccactg atttgagcgt cagatttcgt gatgcttgtc    3240
agggggggcgg agcctatgga aaaacggctt tgccgcggcc ctctcacttc cctgttaagt    3300
atcttcctgg catcttccag gaaatctccg ccccgttcgt aagccatttc cgctcgccgc    3360
agtcgaacga ccgagcgtag cgagtcagtg agcgaggaag cggaatatat cctgtatcac    3420
atattctgct gacgcaccgg tgcagccttt tttctcctgc cacatgaagc acttcactga    3480
caccctcatc agtgccaaca tagtaagcca gtatacactc cgctagcgct gaggtctgcc    3540
tcgtgaagaa ggtgttgctg actcatacca ggcctgaatc gccccatcat ccagccagaa    3600
agtgagggag ccacggttga tgagagcttt gttgtaggtg gaccagttgg tgattttgaa   3660
cttttgcttt gccacggaac ggtctgcgtt gtcgggaaga tgcgtgatct gatccttcaa   3720
ctcagcaaaa gttcgattta ttcaacaaag ccacgttgtg tctcaaaatc tctgatgtta   3780
cattgcacaa gataaaaata tatcatcatg aacaataaaa ctgtctgctt acataaacag    3840
taatacaagg ggtgtttact agaggttgat cgggcacgta aggttcca acttcacca     3900
taatgaaata agatcactac cgggcgtatt ttttgagtta tcgagatttt caggagctaa    3960
ggaagctaaa atggagaaaa aaatcacggg atataccacc gttgatatat cccaatggca    4020
tcgtaaagaa cattttgagg catttcagtc agttgctcaa tgtacctata accagaccgt    4080
tcagctggat attacggcct ttttaaagac cgtaaagaaa aataagcaca agttttatcc   4140
ggcctttatt cacattcttg cccgcctgat gaacgctcca ccggagtttc gtatggcat    4200
gaaagacggt gagctggtga tctgggatag tgttcaccct tgttacaccg ttttccatga   4260
gcaaactgaa acgttttcgt ccctctggag tgaataccac gacgatttcc ggcagtttct    4320
ccacatatat tcgcaagatg tggcgtgtta cggtgaaaac ctggcctatt ccctaaagg    4380
gtttattgag aaatatgttt ttgtctcagc caatccctgg gtgagtttca ccagttttga   4440
tttaaacgtg gccaatatgg acaacttctt cgcccccgtt ttcaccgatgg caaatatta    4500
tacgcaaggc gacaaggtgc tgatgccgct ggcgatccga gttcatcatg ccgtttgtga   4560
tggcttccat gtcggccgca tgcttaatga attacaacag tactgtgatg agtggcaggg   4620
cggggcgtaa taatactagc tccggcaaaa aaacgggcaa ggtgtcacca ccctgccctt    4680
tttctttaaa accgaaaaga ttacttcgc                                     4709
```

```
SEQ ID NO: 65               moltype = DNA  length = 18
FEATURE                     Location/Qualifiers
misc_feature                1..18
                            note = Oligonucleotide colE1-F
source                      1..18
                            mol_type = other DNA
                            organism = synthetic construct
SEQUENCE: 65
cgtcagaccc cgtagaaa                                                         18

SEQ ID NO: 66               moltype = DNA  length = 18
FEATURE                     Location/Qualifiers
misc_feature                1..18
                            note = Oligonucleotide colE1-R
source                      1..18
                            mol_type = other DNA
                            organism = synthetic construct
SEQUENCE: 66
ctctcctgtt ccgaccct                                                         18

SEQ ID NO: 67               moltype = DNA  length = 37
FEATURE                     Location/Qualifiers
misc_feature                1..37
                            note = Oligonucleotide fD1
source                      1..37
                            mol_type = other DNA
                            organism = synthetic construct
SEQUENCE: 67
ccgaattcgt cgacaacaga gtttgatcct ggctcag                                    37

SEQ ID NO: 68               moltype = DNA  length = 37
FEATURE                     Location/Qualifiers
misc_feature                1..37
                            note = Oligonucleotide Rp2
source                      1..37
                            mol_type = other DNA
                            organism = synthetic construct
SEQUENCE: 68
cccgggatcc aagcttacgg ctaccttgtt acgactt                                    37

SEQ ID NO: 69               moltype = DNA  length = 25
FEATURE                     Location/Qualifiers
misc_feature                1..25
                            note = Oligonucleotide ispS-F
source                      1..25
                            mol_type = other DNA
                            organism = synthetic construct
SEQUENCE: 69
aggctgaatt tcttacactt cttga                                                 25

SEQ ID NO: 70               moltype = DNA  length = 25
FEATURE                     Location/Qualifiers
misc_feature                1..25
                            note = Oligonucleotide ispS-R
source                      1..25
                            mol_type = other DNA
                            organism = synthetic construct
SEQUENCE: 70
gtaactccat caaatcctcc actac                                                 25

SEQ ID NO: 71               moltype = DNA  length = 25
FEATURE                     Location/Qualifiers
misc_feature                1..25
                            note = Oligonucleotide idi-F
source                      1..25
                            mol_type = other DNA
                            organism = synthetic construct
SEQUENCE: 71
atacgtgctg tagtcatcca agata                                                 25

SEQ ID NO: 72               moltype = DNA  length = 25
FEATURE                     Location/Qualifiers
misc_feature                1..25
                            note = Oligonucleotide idiR
source                      1..25
                            mol_type = other DNA
                            organism = synthetic construct
SEQUENCE: 72
tcttcaagtt cacatgtaaa accca                                                 25
```

```
SEQ ID NO: 73            moltype = DNA  length = 25
FEATURE                  Location/Qualifiers
misc_feature             1..25
                         note = oligonucleotide dxs-F
source                   1..25
                         mol_type = other DNA
                         organism = synthetic construct
SEQUENCE: 73
acaaagtatc taagacagga ggtca                                       25

SEQ ID NO: 74            moltype = DNA  length = 25
FEATURE                  Location/Qualifiers
misc_feature             1..25
                         note = oligonucleotide dxs-R
source                   1..25
                         mol_type = other DNA
                         organism = synthetic construct
SEQUENCE: 74
gatgtcccac atcccatata agttt                                       25

SEQ ID NO: 75            moltype = DNA  length = 6018
FEATURE                  Location/Qualifiers
misc_feature             1..6018
                         note = plasmid pMTL85246-IspS-Idi
source                   1..6018
                         mol_type = other DNA
                         organism = synthetic construct
SEQUENCE: 75
ccggggatcc tctagagtcg acgtcacgcg tccatggaga tctcgaggcc tgcagacatg    60
caagcttggc actggccgtc gttttacaac gtcgtgactg ggaaaaccct ggcgttaccc   120
aacttaatcg ccttgcagca catccccctt tcgccagctg gcgtaatagc gaagaggccc   180
gcaccgatcg cccttcccaa cagttgcgca gcctgaatgg cgaatggcgc tagcataaaa   240
ataagaagcc tgcatttgca ggcttcttat ttttatggcg cgccgcattc acttcttttc   300
tatataaata tgagcgaagc gaataagcgt cggaaaagca gcaaaaagtt tccttttttgc  360
tgttggagca tgggggttca ggggggtgcag tatctgacgt caatgccgag cgaaagcgag   420
ccgaagggta gcatttacgt tagataaccc cctgatatgc tccgacgctt tatatagaaa   480
agaagattca actaggtaaa atcttaatat aggttgagat gataaggttt ataaggaatt   540
tgtttgttct aattttttcac tcatttttgtt ctaattttct taacaaatg ttcttttttt    600
tttagaacag ttatgatata gttagaatag tttaaaataa ggagtgagaa aaagatgaaa   660
gaaagatatg gaacagtcta taaaggctct cagaggctca tagacgaaga agtggagaa    720
gtcatagagg tagacaagtt ataccgtaaa caaacgtctg gtaacttcgt aaaggcatat   780
atagtcgaat taataagtat gttagatatg attggcgaaa aaaaacttaa aatcgttaac    840
tatatcctag ataatgtcca cttaagtaac aatacaatga tagctacaac aagagaaata    900
gcaaaagcta caggaacaag tctacaaaca gtaataacaa cacttaaaat cttagaagaa    960
ggaaatatta taaaaagaaa aactggagta ttaatgttaa accctgaact actaatgaga   1020
ggcgacgacc aaaaacaaaa ataccctctta ctcgaatttg caagaggca                1080
aatgaaatag attgacctcc caataacacc acgtagttat tgggaggtca atctatgaaa   1140
tgcgattaag ggccggccga agcaaactta agagtgtgtt gatagtgcag tatcttaaaa   1200
tttttgtataa taggaattga agttaaatta gatgctaaaa atttgtaatt aagaaggagt   1260
gattacatga acaaaaatat aaaatattct caaaacttttt taacgagtga aaaagtactc   1320
aaccaaataa taaaacaatt gaatttaaaa gaaaccgata ccgtttacga aattggaaca   1380
ggtaaagggc atttaacgac gaaactggct aaaaataagta aacaggtaac gtctattgaa   1440
ttagacagtc atcattccaa cttatcgtca gaaaaattaa aactgaatac tcgtgtcact   1500
ttaattcacc aagatattct acagtttcaa ttccctaaca aacagaggta taaaattgtt   1560
gggagtattc cttaccattt aagcacacaa attattaaaa aagtggtttt tgaaaagccat   1620
gcgtctgaca tctatctgat tgttgaagaa ggattctaca agcgtacctt ggatattcac   1680
cgaacactag ggttgctctt gcacactcaa gtctcgattc agcaattgct taagctgcca   1740
gcggaatgct ttcatcctaa accaaaagta aacagtgtct taataaaact taccccgccat   1800
accacagatg ttccagataa atattggaag ctatatacgt actttgtttc aaaatggggtc   1860
aatcgagaat atcgtcaact gtttactaaa aatcagtttc atcaagcaat gaaacacgcc   1920
aaagtaaaca atttaagtac cgttacttat gagcaagtat tgtctatttt taatagttat   1980
ctattattta acgggaggaa ataattctat gagtcgcttt gtgtaaattttg gaaagttaca   2040
cgttactaaa gggaatgtgt ttaaactcct ttttgataat ctcatgacca aatccccttaa    2100
acgtgagttt tcgttccact gagcgtcaga ccccgtagaa aagatcaaag gatcttcttg    2160
agatcctttt tttctgcgcg taatctgctg cttgcaaaca aaaaaaccac cgctaccagc   2220
ggtggtttgt ttgccggatc aagagctacc aactcttttt ccgaaggtaa ctggcttcag    2280
cagagcgcag ataccaaata ctgttcttct agtgtagccg tagttaggcc accaccttcaa   2340
gaactctgta gcaccgccta catacctcgc tctgctaatc ctgttaccag tggctgctgc    2400
cagtggcgat aagtcgtgtc ttaccgggtt ggactcaaga cgatagttac cggataaggc    2460
gcagcggtcg ggctgaacgg ggggttcgtg cacacagccc agcttggagc gaacgaccta    2520
caccgaactg agatacctac agcgtgagct atgagaaagc gccacgcttc ccgaagggag    2580
aaaggcggac aggtatccgg taagcggcag ggtcgggaaca ggagagcgca cgaggagct    2640
tccagggga aacgcctggt atctttatag tcctgtcggg tttcgccacc tctgacttga    2700
gcgtcgattt ttgtgatgct cgtcaggggg gcggagccta tggaaaaacg ccagcaacgc   2760
ggcctttta cggttcctgg ccttttgctg gccttttgct cacatgttct ttcctgcgtt    2820
atcccctgat tctgtggata accgtattac cgcctttgag tgagctgata ccgctcgccg    2880
cagccgaacg accgagcgca gcgagtcagt gagcgaggaa gcggaagagc gcccaatacg    2940
cagggccccc tgcaggataa aaaaattgta gataaattttt ataaaatagt tttatctaca   3000
```

```
atttttttat caggaaacag ctatgaccgc ggccgcggtt aatgttaaaa atttatagta  3060
taactttaaa aaactgtctt aaaaagttgt tatataaaaa atgttgacaa ttaaacagct  3120
atttagtgca aaacaaccat aaaaatttaa aaaataccat aaattacttg aaaaatagtt  3180
gataataatg tagagttata aacaaggtg aaaagcatta cttgtattct ttttatata  3240
ttattataaa ttaaaatgaa gctgtattag aaaaaataca cacctgtaat ataaaatttt  3300
aaattaattt ttaatttttt caaaatgtat tttacatgtt tagaaatttg atgtatatta  3360
aaatagtaga atacataaga tacttaattt aattaaagat agttaagtac ttttcaatgt  3420
gcttttttag atgtttaata caaatcttta attgtaaaag aaatgctgta ctatttactg  3480
tactagtgac gggattaaac tgtattaatt ataaataaaa aataagtaca gttgtttaaa  3540
attatatttt gtattaaatc taatagtacg atgtaagtta ttttatacta ttgctagttt  3600
aataaaaaga tttaattata tacttgaaaa ggagaggaat ttttatgcgt catatggcaa  3660
cagaattatt atgtttacac agacctatat cacttactca caaacttttt aggaatccat  3720
tacctaaagt tattcaagct acaccttaa cattaaaact taggtgtagt gtttctacag  3780
aaaatgtatc atttagtgag acagaaactg aaacaagaag atcagcaaat tatgaaccaa  3840
attcttggga ttatgattat cttctttctt ctgatactga tgagtcaata gaagtacata  3900
aagataaggc taagaaatta gaagctgaag ttaggagaga aataaataat gagaaggctg  3960
aatttcttac acttcttgaa cttattgata atgtacaaag acttggatta ggatatagat  4020
tgagtctga tataagaaga gcattagata gatttgtaag tagtggagga tttgatggag  4080
ttactaaaac ttcattacat ggaacagcat tatcatttag gttattaagg caacatggtt  4140
ttgaagtatc tcaagaagct tttagtggat ttaaagatca gaatgaaaac tttcttgaga  4200
atttaaagga agacataaaa gcaattcttt ctctttatga agcatcattt ttagcattag  4260
aaggtgagaa tatattagat gaggctaaag tatttgcaat atctcatctt aaagaactta  4320
gtgaagaaaa gattggtaaa gaattagctg aacaagtttc acatgcttta gaattaccat  4380
tacatagaag aacacaaaga ttagaagcag tttggtcaat agaagcatat agaaagaaag  4440
aagacgcaaa tcaagtactt ttagaacttg caatacttga ctacaatatg attcaaagtg  4500
tatatcagag ggatttaaga gaaacatcaa gatggtggaa aagagtagga ttagcaacta  4560
aattacattt tgctagagat aggcttattg aaagttttta ttgggctgtt ggagttgctt  4620
ttgaaccaca atattctgat tgcagaaata gtgtagcaaa gatgttttca tttgttacta  4680
taattgacga tatttacgat gtatatgaaa ctttagtga acttgaactt tttactgatg  4740
cagttgaaag atgggatgta aatgctatta atgatcttcc tgattatatg aagttatgtt  4800
ttcttgcact ttacaatact attaacgaga tagcttacga taacttaaaa gataaaggtg  4860
agaacatact tccttattta acaaaagcat gggcagattt atgtaatgca tttcttcaag  4920
aagctaagtg gctttataat aaatcaacac ctacatttga tgattattt ggaaatgcat  4980
ggaaaagttc tagtggacct ttacagctta tttttgctta tttgctgtta gtacagaaca  5040
ttaaaaaggga agagattgag aatcttcaga aatatcatga cataatatca agacctagtc  5100
acatttttag gctttgtaat gatttagcat ctgcttcagc agaaatagca agaggtgaaa  5160
ctgctaattc tgtaagttgt tatatgagaa caaaaggtat atctgaagaa ttagctactg  5220
aaagtgttat gaatctctata gacgaaactt ggaagaaaat gaacaaagaa aaacttggtg  5280
gatctttatt tgcaaaacct tttgttgaga ctgctataa tttagctaga cagtctcatt  5340
gcacatatca taatggtgat gcacatacta gtccagatga attaactagg aaaagagtac  5400
ttagtgtaat aactgaacca atattaccat tgaaagata agaattcgag ctcgaaaggg  5460
gaaattaaat ggcagaatat ataatagctg tagatgaatt tgataacgaa ataggttcaa  5520
ttgaaaaaat ggaggctcac cgtaaaggaa cattacatag agcttttct atattagtat  5580
ttaattctaa aaatcaattg ttattacaga aaagaaatgt aaaaaaatat cattcgcctg  5640
gtctctggac aaaatacgtgc tgtagtcatc caagatacgg tgaaagttta catgatgcga  5700
tttatagaag gcttaaggaa gaaatgggtt ttacatgtga acttgaagaa gtatttagtt  5760
ttatttataa agtaaaactt gaagatatc tttttgaaaa tgaatatgat catgtattca  5820
ttgggaaata tgatgagaa ataattgtaa acaaagatga agtagatgat tttaagtggg  5880
ttgatattaa tgaggttaag aaggatatta tagaaaggcc agaagcatac acttattggt  5940
tcaagtatttt agttaataag gcagaaaaca aaatatttaa ataagtaaga atttcgtcta  6000
aataaagatt tggggtac                                                 6018
```

```
SEQ ID NO: 76          moltype = DNA   length = 6909
FEATURE                Location/Qualifiers
misc_feature           1..6909
                       note = plasmid pMTL 82151-Patp-HMGR
source                 1..6909
                       mol_type = other DNA
                       organism = synthetic construct
SEQUENCE: 76
cctgcaggat aaaaaaattg tagataaatt ttataaaata gttttatcta caatttttt   60
atcaggaaac agctatgacc gcggccgctg tatccatatg accatgatta cgaattcgag  120
ctcgttataa ttttcaattt tcattctttt taaaggagat tagcatacat tttatcataa  180
ttatacagac aatatagtaa tatatgatgt taaaatatca atatatggtt ataaaatttt  240
atatttttc ccattttaat tatttgtact ataatattac actgagtgta ttgcatatttt  300
aaaaaatatt tggtacaatt agttagttaa ataaattcta aattgtaaat tatcagaatc  360
cttattaagg aaatacatag atttaaggag aaatcataaa aaggtgtaat ataaactggc  420
taaaattgag caaaaattga gcaattaaga cttttttgatt gtatcttttt atatattaa  480
ggtatataat cttatttata ttgggggaag gtaccatgga atcattagac aaaaaatttca  540
gacatttatc aagacaacaa aagttacaac aattagttga taaacagtgg ctttcagaag  600
atcagtttga tattttactt aatcatccct ttatagatga agaagttgct aatagtctta  660
tagaaaatgt aattgcacag ggtgcattac cagttggact tcttcctaat ataatagttg  720
atgataaggc ttatgttgta ccaatgatgg ttgaagaacc tagtgttgtt gcagctgcat  780
gctgtaaagt ccttatgata aatcagacag ttggatttca actatctatc tcagaaagaa  840
taatgattgg acagatagta tttgatggtg tagatgacac tgaaaaatta agtgcagata  900
ttaaagcatt agaaaaacaa atacataaga ttgcagtga agcatatcct gtataaaag   960
caagaggtgg tggttatcaa agaatagcaa tagatacatt tccagagcaa caactttaa  1020
gtcttaaggt atttgtagat acaaaagatg ctatgggtgc taatatgctt aatactatac  1080
ttgaggcaat aactgcattc ctaaaaaatg aatctcctca atcagatata ttaatgtcta  1140
```

```
tactttcaaa ccatgcaact gctagtgtag taaaagtaca aggtgagata gatgtaaaag  1200
atcttgctag aggtgaaaga acaggtgaag aagtagctaa gagaatggaa agagcttctg  1260
tattagctca ggttgatatt catagagctg caacacataa caaaggtgtt atgaatggaa  1320
tacatgctgt tgtttagct acaggaaatg atactagagg tgctgaagca tctgcacatg  1380
catacgcatc aagagacgga caatatagag gtatagcaac ttggagatat gatcagaaga  1440
gacaaagact tattggaact attgaagttc caatgacact tgctatagta ggtggtggta  1500
ctaaagtatt accaatagct aaggcatcat tagagttatt aaatgttgat tctgcacaag  1560
aacttggaca cgtagttgct gctgttggat tagcacaaaa ctttgctgct tgtagagcac  1620
ttgtttctga aggtattcaa caaggacaca tgtcattaca atataaaagt ttagcaatag  1680
tagtaggtgc aaaaggtgac gagatagcac aagtagcaga agctcttaaa caggaaccaa  1740
gagctaatac acaggttgct gaaagaattt tacaggaaat tagacagcaa taatctagag  1800
tcgacgtcac gcgtccatgg agatctcgag gcctgcagac atgcaagctt ggcactggcc  1860
gtcgttttac aacgtcgtga ctgggaaaac cctggcgtta cccaacttaa tcgccttgca  1920
gcacatcccc ctttcgccag ctggcgtaat agcgaagagg cccgcaccga tcgcccttcc  1980
caacagttgc gcagcctgaa tggcgaatgg cgctagcata aaaataagaa gcctgcattt  2040
gcaggcttct tattttatg gcgcgccgtt ctgaatcctt agctaatggt tcaacaggta  2100
actatgacga agatagcacc ctggataagt ctgtaatgga ttctaaggca tttaatgaag  2160
acgtgtatat aaaatgtgct aatgaaaaag aaaatgcgtt aaagagcct aaaatgagtt  2220
caaatggttt tgaaattgat tggtagttta atttaatata ttttttctat tggctatctc  2280
gatacctata gaatcttctg ttcacttttg tttttgaaat ataaaagggg cttttttagc  2340
ccctttttt taaaactccg gaggagtttc ttcattcttg atactatacg taactatttt  2400
cgatttgact tcattgtcaa ttaagctagt aaaatcaatg gttaaaaaac aaaaaacttg  2460
catttttcta cctagtaatt tataattta agtgtcgagt ttaaaagtat aatttaccag  2520
gaaaggagca agtttttaa taaggaaaaa tttttccttt taaaattcta tttcgttata  2580
tgactaatta taatcaaaaa aatgaaaata acaagaggg aaaaactgct ttagagaaat  2640
gtactagtaa aaaagaaaa aatcctagat ttacgtcata catgcacct ttaactacta  2700
agaaaaatat tgaaaggact tccacttgtg gagattattt gtttatgttg agtgatgcag  2760
acttagaaca ttttaaatta cataaaggta atttttgcgg taatagattt tgtccaatgt  2820
gtagttggcg acttgcttgt aaggatagtt tagaaatatc tattcttatg gagcatttaa  2880
gaaaagaaga aaataaagag tttataatttt taactcttac aactccaaat gtaaaaagtt  2940
atgatcttaa ttattctatt aaacaatata ataaatcttt taaaaaatta atggagcgta  3000
aggaagttaa ggatataact aaaggttata taagaaaatt agaagtaact taccaaaagg  3060
aaaaatacat aacaaaggat ttatggaaaa taaaaaaga ttattatcaa aaaaaaggac  3120
ttgaaattgg tgatttagaa cctaattttg atacttataa tcctcatttt catgtagtta  3180
ttgcagttaa taaagttat tttacagata aaaattatta tataaatcga gaaagatggt  3240
tggaattatg gaagtttgct actaaggatg attctataac tcaagttgat gttagaaaag  3300
caaaaattaa tgattataaa gaggtttacg aacttgcgaa atattcagct aaagacactg  3360
attatttaat atcgaggcca gtatttgaaa tttttttaaa agcattaaaa ggcaagcagg  3420
tattagtttt tagtggattt tttaaagatg cacacaaatt gtacaagcaa ggaaaacttg  3480
atgttttata aaagaaagat gaaattaaat atgtctatat agtttattat aattggtgca  3540
aaaaacaata tgaaaaaact agaataaggg aacttacgga agatgaaaa gaagaattaa  3600
atcaagattt aatagatgaa atagaaatag attaaagtgt aactatactt tatatatata  3660
tgattaaaaa aataaaaaac aacagcctat taggttgttg ttttttattt tcttttattaa  3720
tttttttaat ttttagtttt tagttctttt ttaaaataag tttcagcctc ttttcaata  3780
tttttaaag aaggagtatt tgcatgaatt gccttttttc taacagactt aggaaatatt  3840
ttaacagtat cttcttgcgc cggtgatttt ggaacttcat aacttactaa tttataatta  3900
ttattttctt ttttaattgt aacagttgca aagaagctg aacctgttcc ttcaactagt  3960
ttatcatctt caatataata ttcttgacct atatagtata aatatatttt tattatatttt  4020
ttactttttt ctgaatctat tattttataa tcataaaaag ttttaccacc aaaagaaggt  4080
tgtactcctt ctggtccaac atattttttt actatattat ctaaataatt tttgggaact  4140
ggtgttgtaa tttgattaat cgaacaacca gttatactta aaggaattat aactataaaa  4200
atatataggga ttatcttttt aaatttcatt attggcctcc tttttattaa atttatgtta  4260
ccataaaaag gacataacgg gaatatgtag aatattttta atgtagacaa aattttcat  4320
aaatataaag aaaggaagtg tttgtttaaa ttttatagca aactatcaaa aattagggg  4380
ataaaattt atgaaaaaaa ggttttcgat gttattttta tgtttaactt taatagtttg  4440
tggtttattt acaaattcgg ccggccagtg ggcaagttga aaattcaca aaatgtggt  4500
ataatatctt tgttcattag agcgataaac ttgaatttga gagggaactt agatggtatt  4560
tgaaaaaatt gataaaaata gttggaacag aaaagagtat tttgaccact actttgcaag  4620
tgtaccttgt acctacagca tgaccgttaa agtggatatc acacaaataa aggaaaaggg  4680
aatgaaacta tatcctgcaa tgctttatta tattgcaatg attgtaaacc gccattcaga  4740
gtttaggacg gcaatcaatc aagatggtga attggggata tatgatgaga tgataccaag  4800
ctatacaata tttcacaatg atactgaaac attttccagc ctttgggactg agtgtaagtc  4860
tgactttaaa tcattttag cagattatga aagtgatacg caacggtatg gaaacaatca  4920
tagaatggaa ggaaagccaa atgctccgga caaacatttt aatgtatcta tgataccgtg  4980
gtcaaccttc gatggcttta atctgaattt gcagaaagga tatgattatt tgattcctat  5040
ttttactatg gggaaatatt ataaagaaga taacaaaatt atacttcctt tggcaattca  5100
agttcatcac gcagtatgtg acggatttca catttgccgt tttgtaaacg aattgcagga  5160
attgataaat agttaacttc aggtttgtct gtaactaaaa acaagtattt aagcaaaaac  5220
atcgtagaaa tacggtgttt tttgttaccc taagtttaaa ctccttttg ataatctcat  5280
gaccaaaatc ccttaacgtg agttttcgtt ccactgagcg tcagacccccg tagaaaagat  5340
caaaggatct tcttgagatc cttttttttct gcgcgtaatc tgctgcttgc aaacaaaaaa  5400
accaccgcta ccagcggtgg tttgtttgcc ggatcaagag ctaccaactc ttttttccgaa  5460
ggtaactggc ttcagcagag cgcagatacc aaatactgtt cttctagtgt agccgtagtt  5520
aggccaccac ttcaagaact ctgtagcacc gcctacatac ctcgctctgc taatcctgtt  5580
accagtggct gctgccagtg gcgataagtc gtgtcttacc gggttggact caagacgata  5640
gttaccggat aaggcgcagc ggtcgggctg aacggggggt tcgtgcacac agcccagctt  5700
ggagcgaacg acctacaccg aactgagata cctacagcgt gagctatgag aaagcgccac  5760
gcttcccgaa gggagaaagg cggacaggta tccggtaagc ggcagggtcg gaacaggaga  5820
gcgcacgagg gagcttccag ggggaaacgc ctggtatctt tatagtcctg tcgggtttcg  5880
```

```
ccacctctga cttgagcgtc gattttgtg atgctcgtca ggggggcgga gcctatggaa    5940
aaacgccagc aacgcggcct ttttacggtt cctggccttt tgctggcctt ttgctcacat    6000
gttctttcct gcgttatccc ctgattctgt ggataaccgt attaccgcct ttgagtgagc    6060
tgataccgct cgccgcagcc gaacgaccga gcgcagcgag tcagtgagcg aggaagcgga    6120
agagcgccca atacgcaggg ccccctgctt cgggtcatt atagcgattt tttcggtata    6180
tccatccttt ttcgcacgat atacaggatt ttgccaaagg gttcgtgtag actttccttg    6240
gtgtatccaa cggcgtcagc cgggcaggat aggtgaagta ggcccacccg cgagcgggtg    6300
ttccttcttc actgtccctt attcgcacct ggcggtgctc aacgggaatc ctgctctgcg    6360
aggctggccg gctaccgccg gcgtaacaga tgagggcaag cggatggctg atgaaaccan    6420
gccaaccagg aagggcagcc cacctatcaa ggtgtactgc cttccagacg aacgaagagc    6480
gattgaggaa aaggcggcgg cggccggcat gagcctgtcg gcctacctgc tggccgtcgg    6540
ccagggctac aaaatcacgg gcgtcgtgga ctatgagcac gtccgcgagc tggcccgcat    6600
caatggcgac ctgggccgcc tgggcggcct gctgaaactc tggctcaccg acgacccgcg    6660
cacggcgcgg ttcggtgatg ccacgatcct cgccctgctg gcgaagatcg aagagaagca    6720
ggacgagctt ggcaaggtca tgatgggcgt ggtccgcccg agggcagagc catgactttt    6780
ttagccgcta aaacgccgg ggggtgcgcg tgattgccaa gcacgtcccc atgcgctcca    6840
tcaagaagag cgacttcgcg gagctggtga agtacatcac cgacgagcaa ggcaagaccg    6900
atcgggccc                                                            6909

SEQ ID NO: 77           moltype = DNA   length = 31
FEATURE                 Location/Qualifiers
misc_feature            1..31
                        note = oligonucleotide EcoRI-HMGS_F
source                  1..31
                        mol_type = other DNA
                        organism = synthetic construct
SEQUENCE: 77
agccgtgaat tcgaggcttt tactaaaaac a                                   31

SEQ ID NO: 78           moltype = DNA   length = 32
FEATURE                 Location/Qualifiers
misc_feature            1..32
                        note = oligonucleotide EcoRI-HMGS_R
source                  1..32
                        mol_type = other DNA
                        organism = synthetic construct
SEQUENCE: 78
aggcgtctag atgttcgtct ctacaaataa tt                                  32

SEQ ID NO: 79           moltype = DNA   length = 8116
FEATURE                 Location/Qualifiers
misc_feature            1..8116
                        note = plasmid pMTL 82151-HMGS-Patp-HMGR
source                  1..8116
                        mol_type = other DNA
                        organism = synthetic construct
SEQUENCE: 79
cctgcaggat aaaaaaattg tagataaatt ttataaaata gttttatcta caatttttttt    60
atcaggaaac agctatgacc gcggccgctg tatccatatg accatgatta cgaattcgag    120
gcttttacta aaaacaataa aacaggagg aaataatatg actataggaa ttgacaaaat    180
aaacttttac gtaccaaaat attatgtaga tatggcaaaa ttagcagaag caagacaagt    240
agacccaaat aaatttctta ttggaatagg acagactgaa atggcagtta gtccagtaaa    300
ccaagatata gtatcaatgg gtgctaatgc tgctaaagat ataataactg atgaagacaa    360
aaagaaaata ggaatggtaa tagtagcaac tgagtcagca gtagatgcag caaaggcagc    420
agcagtacag attcataatt tattaggtat tcaaccattt gcaagatgtt tcgaaatgaa    480
agaagcatgt tatgctgcta ctcctgcaat tcagttagct aaggattatt tagctacaag    540
accaaatgag aaagttttag ttatagctac agatacagct gatatggact taattcagg    600
tggtgaacct actcaaggtg ctggtgctgt tgctatggtt atagctcata atcctagtat    660
acttgcatta aatgaagacg ctgttgctta tacagaagat gtttatgatt tctgagacc    720
aacaggacat aagtatccat tagtagatgg tgctttatca aaagacgcat atattgatc    780
ttttcaacaa tcttggaatg aatatgctaa gagacaagga aagagtttag ctgattttgc    840
tagtctttgc tttcatgttc cttttactaa aatgggtaaa aaggctttag aatctataat    900
agataacgca gatgaaacaa ctcaagagag attaagatct ggatatgaag atgcagttga    960
ttacaataga tatgttggaa atatatacac aggaagtctt atctttctc ttataatct    1020
tcttgaaaat agagatttac aggctggtga aactattgga ttatttttcat acggatcagg    1080
ttctgttggt gaatttttatt cagctacact tgtagaagga tataagatc accttgatca    1140
ggcagcacac aaagcacttt taaacaatag aactgaagta tcagtagatg catacgaaac    1200
atttttcaag agatttgatg atgtagaatt tgatgaagag caggatgcag ttcatgaaga    1260
tagacatata ttctatcttt caaacatgga gaataatatc agagaatatc atagacctga    1320
ataagagctc gttataattt tcaattttca ttctttttaa aggagattag catacatttt    1380
atcataatta tacagacaat atagtaatat atgatgttaa aatatcaata tatggttaaa    1440
aatctgtata tttttccca tttaattat ttgtactata atattacact gagtgtattg    1500
catatttaaa aaatattgg tacaattagt tagttaaata aattctaaat tgtaaattat    1560
cagaatcctt attaaggaaa tacatagatt taaggagaaa tcataaaaag gtgtaatata    1620
aactggctaa aattgagcaa aaattgagca attaagactt tttgattgta tcttttata    1680
tatttaaggt ataataatctt atttatattg ggggaaggta ccatgcaatc attagacaaa    1740
aatttcagac atttatcaag acaacaaaag ttacaacaat tagttgataa acagtggctt    1800
tcagaagatc agtttgatat tttacttaat catcctctta tagatgaaga agttgctaat    1860
agtcttatag aaaaatgtaat tgcacagggt gcattaccag ttggacttct tcctaatata    1920
```

```
atagttgatg ataaggctta tgttgtacca atgatggttg aagaacctag tgttgttgca   1980
gctgcatctt atggtgctaa attagtaaat cagacaggtg gatttaaaac tgtatcatca   2040
gaaagaataa tgattggaca gatagtattt gatggtgtag atgacactga aaaattaagt   2100
gcagatatta aagcattaga aaaacaaata cataagattt cagatgaagc atatcctagt   2160
ataaaagcaa gaggtggtgg ttatcaaaga atagcaataa atacatttcc agagcaacaa   2220
cttttaagtc ttaaggtatt tgtagataca aaagatgcta tgggtgctaa tatgcttaat   2280
actatacttg aggcaataac tgcattcctt aaaaatgaat ctcctcaatc agatatatta   2340
atgtctatac tttcaaacca tgcaactgct agtgtagtaa aagtacaagg tgagatagat   2400
gtaaaagatc ttgctagagg tgaaagaaca ggtgaagaa tagctaaagg aatggaaaga   2460
gcttctgtat tagctcaggt tgatattcat agagctgcaa cacataacaa aggtgttatg   2520
aatgaaatac atgctgttgt tttagctaca ggaaatgata ctagaggtgc tgaagcatct   2580
gcacatgcat acgcatcaag agacggacaa tatagaggta tagcaacttg gagatatgat   2640
cagaagagac aaagacttat tggaactatt gaagttccaa tgcacttgc tatagtaggt   2700
ggtggtacta aagtattacc aatagctaag gcatcattca agttattaaa tgttgattct   2760
gcacaagaac ttggacacgt agttgctgct gttggattag cacaaaactt tgctgcttgt   2820
agagcacttg tttctgaagg tattcaacaa ggacacatgt cattacaata taaaagttta   2880
gcaatagtag taggtgcaaa aggtgacgag atagcacaag tagcagaagc tcttaaacag   2940
gaaccaagag ctaatacaca ggttgctgaa agaattttaa aggaaattag acagcaataa   3000
tctagagtcg acgtcacgcg tccatggaga tctcgaggcc tgcagacatg caagcttggc   3060
actgccgtc gttttacaac gtcgtgactg ggaaaaccct ggcgttaccc aacttaatcg   3120
ccttgcagca catcccccctt tcgccagctg gcgtaatagc gaagaggccc gcaccgatcg   3180
cccttcccaa cagttgcgca gcctgaatgg cgaatggcgc tagcataaaa ataagaagcc   3240
tgcatttgca ggcttcttat ttttatggcg cgccgttctg aatccttagc taatggttca   3300
acaggtaact atgacgaaga tagcaccctg gataagtctg taatggattc taaggcattt   3360
aatgaagacg tgtatataaa atgtgctaat gaaaagaaa atgcgttaaa agagcctaaa   3420
atgagttcaa atggtttta aattgattgg tagtttaatt taatatattt tttctattgg   3480
ctatctcgat acctatagaa tcttctgttc acttttgttt ttgaaatata aaaaggggct   3540
ttttagcccc tttttttttaa aactccggag gagtttcttc attcttgata ctatacgtaa   3600
ctattttcga tttgacttca ttgtcaatta agctagtaaa atcaatggtt aaaaaacaaa   3660
aaacttgcat ttttctacct agtaatttat aattttaagt gtcgagttta aagtataat   3720
ttaccaggaa aggagcaagt ttttttaataa ggaaaaattt ttcctttttaa aattctattt   3780
cgttatatga ctaattataa tcaaaaaaat gaaaataaac aagaggtaaa aactgcttta   3840
gagaaatgta ctgataaaaa aagaaaaaat cctagattta cgtcatacat agcacccttta   3900
actactaaga aaaatattga aaggacttcc acttgtggag attatttgtt tatgttgagt   3960
gatgcagact tagaacattt taaattacat aaaggtaatt tttgcggtaa tagattttgt   4020
ccaatgtgta gttggcgact tgcttgtaag gatagtttag aaatatctat tcttatggag   4080
catttaagaa aagaagaaaa taaagagttt atattttaa ctcttacaac tccaaatgta   4140
aaaagttatg atcttaatta ttctattaaa caatataata aatcttttaa aaaattaatg   4200
gagcgtaagg aagttaagga tataactaaa ggttatataa gaaaattaga agtaacttac   4260
caaaaggaaa aatacataac aaaggattta tggaaaataa aaaaagatta ttatcaaaaa   4320
aaaggacttg aaattggtga tttagaacct aattttgata cttataatcc tcatttttcat   4380
gtagttattg cagttaataa aagttattt acagataaaa attattatat aaatcgaaaa   4440
agatggttgg aattatggaa gtttgctact aaggatgatt ctataactca agttgatgtt   4500
agaaaagcaa aaattaatga ttataaagag gtttacgaac ttgcgaaata ttcagctaaa   4560
gacactgatt atttaatatc gaggccagta tttgaaattt tttataaagc attaaaaggc   4620
aagcaggtat tagttttttag tggattttttt aaagatgcac acaaattgta caagcaagga   4680
aaacttgatg tttataaaaa gaaagatgaa tctctatagt ttattataat   4740
tggtgcaaaa aacaatatga aaaaactaga ataagggaac ttacggaaga tgaaaaagaa   4800
gaattaaatc aagatttaat agatgaaata gaaatagatt aaagtgtaac tatactttat   4860
atatatatga ttaaaaaaat aaaaaacaac agcctattag gttgttgttt tttattttct   4920
ttattaattt tttaaattttt tagtttttag ttcttttttt aaataagttt cagcctcttt   4980
ttcaatatttt ttttaaagaag gagtatttgc atgaattgcc tttttttctaa cagacttagg   5040
aaatatttta acagtatctt cttgcgccgg tgatttggga acttcataac ttactaattt   5100
ataattatta ttttctttttt taattgtaac agttgcaaaa aagctgaac ctgttccttc   5160
aactagttta tcatcttcaa tataatattc ttgacctata tagtataat atattttttat   5220
tatattttta ctttttttctg aatctattat tttataatca taaaagttt taccaccaaa   5280
agaaggttgt actccttctg gtccaacata ttttttttact atattatcta aataattttt   5340
gggaactggt gttgtaattt gattaatcga acaaccagtt atacttaaag gaattataac   5400
tataaaaata tataggatta tcttttttaaa tttcattatt ggcctccttt ttattaaatt   5460
tatgttacca taaaaggac ataacgggaa tatgtagaat atttttaatg tagacaaaat   5520
tttacataaa tataaagaaa ggaagtgttt gtttaaattt tatagcaaac tatcaaaaat   5580
tagggggata aaaattatg aaaaaaaggt tttcgatgtt attttttatgt ttaacttttaa   5640
tagtttgtgg tttattttaca aattcggccg gccagtgggc aagttgaaaa attcacaaaa   5700
atgtggtata atatctttgt tcattagagc gataaacttt aatttgagag ggaacttaga   5760
tggtatttga aaaaattgat aaaaatagtt ggaacagaaa agagtatttt gaccactact   5820
ttgcaagtgt accttgtacc tacagcatga ccgttaaagt ggatatcaca caaatataaagg   5880
aaaagggaat gaaactatat cctgcaatgc tttattattat tgcaatgatt gtaaaccgcc   5940
attcagagtt taggacggca atcaatcaag atggtgaatt ggggatatat gatgagatga   6000
taccagcta tacaatattt cacaatgata ctgaaacatt ttccagcctt tggactgagt   6060
gtaagtctga ctttaaatca ttttttagcag attatgaaag tgatacgcaa cggtatggaa   6120
acaatcatag aatggaagga aagccaaatg ctccggaaaa catttttaat gtatctatga   6180
taccgtggtc aaccttcgat ggctttaatc tgaatttgca gaaggatat gattatttga   6240
ttcctatttt tactatgggg aaatattata agaagataa caaattata cttcctttgg   6300
caattcaagt tcatcacgca gtatgtgacg gatttcacat ttgcgttttt gtaaacgaat   6360
tgcaggaatt gataaatagt taacttcagg tttgtctgta actaaaaaca agtattaag   6420
caaaaacatc gtagaaatac ggtgtttttt gttaccctaa gtttaaactc cttttttgata   6480
atctcatgac caaaatccct taacgtgagt tttcgttcca ctgagcgtca gaccccgtag   6540
aaaagatcaa aggatcttct tgagatcctt ttttctgcg cgtaatctgc tgcttgcaaa   6600
caaaaaaacc accgctacca gcggtggttt gtttgccgga tcaagagcta ccaactcttt   6660
```

-continued

```
ttccgaaggt aactggcttc agcagagcgc agataccaaa tactgttctt ctagtgtagc    6720
cgtagttagg ccaccacttc aagaactctg tagcaccgcc tacatacctc gctctgctaa    6780
tcctgttacc agtggctgct gccagtggcg ataagtcgtg tcttaccggg ttggactcaa    6840
gacgatagtt accggataag gcgcagcggt cgggctgaac gggggggttcg tgcacacagc    6900
ccagcttgga gcgaacgacc tacaccgaac tgagatacct acagcgtgag ctatgagaaa    6960
gcgccacgct tcccgaaggg agaaaggcgg acaggtatcc ggtaagcggc agggtcggaa    7020
caggagagcg cacgagggag cttccagggg gaaacgcctg gtatctttat agtcctgtcg    7080
ggtttcgcca cctctgactt gagcgtcgat ttttgtgatg ctcgtcaggg gggcggagcc    7140
tatggaaaaa cgccagcaac gcggcctttt tacggttcct ggccttttgc tggccttttg    7200
ctcacatgtt ctttcctgcg ttatccctg attctgtgga taaccgtatt accgcctttg    7260
agtgagctga taccgctcgc cgcagccgaa cgaccgagcg cagcgagtca gtgagcgagg    7320
aagcggaaga gcgcccaata cgcagggccc cctgcttcgg ggtcattata gcgattttt    7380
cggtatatcc atcctttttc gcacgatata caggattttg ccaaagggtt cgtgtagact    7440
ttccttggtg tatccaacgg cgtcagccgg gcaggatagg tgaagtaggc ccacccgcga    7500
gcgggtgttc cttcttcact gtcccttatt cgcacctggc ggtgctcaac gggaatcctg    7560
ctctgcgagg ctggccggct accgccgcg taacagatga gggcaagcgg atggctgatg    7620
aaaccaagcc aaccaggaag gcagcccac ctatcaaggt gtactgcctt ccagacgaac    7680
gaagagcgat tgaggaaaag gcggcggcgg ccggcatgaa cctgtcggcc tacctgctgg    7740
ccgtcggcca gggctacaaa atcacggcgc tcgtggacta tgagcacgtc cgcgagctgg    7800
cccgcatcaa tggcgacctg gccgcctggg cggcctgct gaaactctgg ctcaccgacg    7860
acccgcgcac ggcgcggttc ggtgatgcca cgatcctcgc cctgctggcg aagatcgaag    7920
agaagcagga cgagcttggc aaggtcatga tgggcgcat ccgcccgagg gcagagccat    7980
gactttttta gccgctaaaa cggccggggg gtgcgcgtga ttgccaagca cgtcccatg    8040
cgctccatca agaagagcga cttcgcggag ctggtgaagt acatcaccga cgagcaaggc    8100
aagaccgatc gggccc                                                   8116

SEQ ID NO: 80            moltype = DNA    length = 55
FEATURE                  Location/Qualifiers
misc_feature             1..55
                         note = Oligonucleotide NotI-XbaI-Prnf-MK_F
source                   1..55
                         mol_type = other DNA
                         organism = synthetic construct
SEQUENCE: 80
atgcgcggcc gctaggtcta gaatatcgat acagataaaa aaatatataa tacag          55

SEQ ID NO: 81            moltype = DNA    length = 27
FEATURE                  Location/Qualifiers
misc_feature             1..27
                         note = Oligonucleotide SalI-Prnf-MK_R
source                   1..27
                         mol_type = other DNA
                         organism = synthetic construct
SEQUENCE: 81
tggttctgta acagcgtatt cacctgc                                         27

SEQ ID NO: 82            moltype = DNA    length = 4633
FEATURE                  Location/Qualifiers
misc_feature             1..4633
                         note = plasmid pMTL8314-Prnf-MK
source                   1..4633
                         mol_type = other DNA
                         organism = synthetic construct
SEQUENCE: 82
aaactccttt ttgataatct catgaccaaa atcccttaac gtgagttttc gttccactga      60
gcgtcagacc ccgtagaaaa gatcaaagga tcttcttgag atccttttt tctgcgcgta     120
atctgctgct tgcaaacaaa aaaaccaccg ctaccagcgg tggtttgttt gccggatcaa    180
gagctaccaa ctcttttcc gaaggtaact ggcttcagca gagcgcagat accaaatact    240
gttcttctag tgtagccgta gttaggccac cacttcaaga actctgtagc accgcctaca    300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccggta    540
agcggcaggg tcggaacagg agagcgcacg agggagcttc caggggaaa cgcctggtat    600
ctttatagtc ctgtcgggtt tcgccacctc tgacttgagc gtcgattttt gtgatgctct    660
tcagggggc ggagcctatg gaaaaacgcc agcaacgcgg ccttttacg ttcctggcc     720
ttttgctggc cttttgctca catgttcttt cctgcgttat cccctgattc tgtggataac    780
cgtattaccg cctttgagtg agctgatacc gctcgccgca gccgaacgac cgagcgcagc    840
gagtcagtga ggaagcgga ggaagagcgc ccaatacgca gggcccctg caggataaaa    900
aaattgtaga taaattttat aaaatagttt tatctacaat ttttttatca ggaaacagct    960
atgaccgcgg ccgctaggtc tagaatatcg atacagataa aaaaatatat aatacagaag   1020
aaaaaattat aaatttgtgg tataatataa agtatagtaa tttaagttta aacctcgtga   1080
aaacgctaac aaataatagg aggtcaattg atgatagctg ttcatttaa cgctggaaaa   1140
ataaaagttt taattggagc atcatagaat ctggaatatt atcaataaa atcagatgta   1200
tatgacggaa tgttatatga tgcaccagat cacctaaat cattagtaaa cagatttgta   1260
gaacttaata atataactga gccattagca gtaactatac agacaaatct tcctccttca   1320
agaggtcttg gatctagtgc agctgttgct gttgcttttg taagagcaag ttatgatttc   1380
ttaggaaaaa gtttaactaa agaagagctt ataagaaagg ctaattgggc tgaacaaata   1440
gctcatggaa agccatctgg aatagataca caaacaatag tatctggaaa gcctgttggg   1500
```

-continued

```
tttcaaaagg gacatgcaga aacacttaaa actctttcac ttgatggata catggtagta 1560
attgatacag gtgttaaagg aagtacaaga caggctgtag aagatgttca taaactttgc 1620
gaagatcctc aatatatgag tcacgtaaaa cacataggaa aacttgtact tagagcatct 1680
gatgttattg aacatcataa ctttgaagca cttgctgata tattcaatga atgtcatgct 1740
gatttaaagg ctcttacagt aagtcatgac aaaataaac agttaatgaa gataggaaaa 1800
gaaaatggtg ctatagctgg taaattaact ggtgctggta gaggtggttc aatgttatta 1860
cttgcaaaag acttaccaac tgcaaagaat atagttaaag cagtagagaa agctggtgca 1920
gcacatactt ggattgaaaa tttaggtggt taagtcgacg tcacgcgtcc atggagatct 1980
cgaggcctgc agacatgcaa gcttggcact ggccgtcgtt ttacaacgtc gtgactggga 2040
aaaccctggc gttacccaac ttaatcgcct tgcagcacat ccccctttcg ccagctggcg 2100
taatagcgaa gaggcccgca ccgatcgccc ttcccaacag ttgcgcagcc tgaatggcga 2160
atggcgctag cataaaaata agaagcctgc atttgcaggc ttcttatttt tatggcgcgc 2220
cgccattatt ttttgaaca attgacaatt catttcttat tttttattaa gtgatagtca 2280
aaaggcataa cagtgctgaa tagaaagaaa tttacagaaa agaaaattat agaatttagt 2340
atgattaatt atactcattt atgaatgttt aattgaatac aaaaaaaaat acttgttatg 2400
tattcaatta cgggttaaaa tatagacaag ttgaaaaatt taataaaaaa ataagtcctc 2460
agctcttata tattaagcta ccaacttagt atataagcca aaacttaaat gtgctaccaa 2520
cacatcaagc cgttagagaa ctctatctat agcaatattt caaatgtacc gacatacaag 2580
agaaacatta actatatata ttcaatttat gagattatct taacagatat aaatgtaaat 2640
tgcaataagt aagatttaga agtttatagc ctttgtgtat tggaagcagt acgcaaaggc 2700
ttttttattt gataaaaatt agaagtatat ttatttttc ataattaatt tatgaaaatg 2760
aaagggggtg agcaaagtga cagaggaaag cagtatctta tcaaataaca aggtattagc 2820
aatatcatta ttgactttag cagtaaacat tatgactttt atagtgcttg tagctaagta 2880
gtacgaaagg gggagcttta aaagctcct tggaatacat agaattcata aattaattta 2940
tgaaagaag ggcgtatatg aaaacttgta aaaattgcaa agagttatt aaagatactg 3000
aaatatgcaa aatacattcg ttgatgattc atgataaaac agtagcaacc tattgcagta 3060
aatacaatga gtcaagatgt ttacataaag ggaaagtcca atgtattaat tgttcaaaga 3120
tgaaccgata tggatggtgt gccataaaaa tgagatgttt tacagaggaa aacagaaaa 3180
aagaacgtac atgcattaaa tattatgcaa ggagctttaa aaaagctcat gtaaagaaga 3240
gtaaaaagaa aaaataattt atttattaat ttaattattga ggtgccgac acagtatgca 3300
ctaaaaaata tatctgtggt gtagtgagc gatacaaaag gatagtcact cgcattttca 3360
taatacatct tatgttatga ttatgtgtcg gtgggacttc acgacgaaaa cccacaataa 3420
aaaaagagtt cggggtaggg ttaagcatag ttgaggcaac taaacaatca agctaggata 3480
tgcagtagca gaccgtaagg tcgttgttta ggtgtgttgt aatacatacg ctattaagat 3540
gtaaaaatac ggataccaat gaagggaaaa gtataatttt tggatgtagt tgtttgttc 3600
atctatgggc aaactacgtc caaagccgtt tccaaatctg ctaaaagta tatccttct 3660
aaaatcaaag tcaagtatga aatcataaat aaagttaat tttgaagtta ttatgatatt 3720
atgtttttct attaaaataa attaagtata tagaatagtt taataatagt atatacttaa 3780
tgtgataagt gtctgacagt gtcacagaaa ggatgattgt tatggattat aagcggccgg 3840
ccagtgggca agttgaaaaa ttcacaaaaa tgtggtataa tatctttgtt cattagagcg 3900
ataaacttga atttgagagg gaacttagat ggtatttgaa aaaattgata aaaatagttg 3960
gaacagaaaa gagtattttg accactactt tgcaagtgta ccttgtacct acagcatgac 4020
cgttaaagtg gatatcacac aaataaagga aaagggatta aaactatatc ctgcaatgct 4080
ttattatatt gcaatgattg taaaccgcca ttcagagtttt aggacggcaa tcaatcaaga 4140
tggtgaattg gggatatatg atgagatgat accaagctat acaatatttc acaatgatac 4200
tgaaacattt tccagccttt ggactgagtg taagtctgac tttaaatcat ttttagcaga 4260
ttatgaaagt gatacgcaac ggtatggaaa caatcataga atggaaggaa agccaaatgc 4320
tccgaaaac atttttaatg tatctatgat accgtggtca accttcgatg gctttaatct 4380
gaatttgcag aaaggatatg attatttgat tcctatttt actatgggga aatattataa 4440
agaagataac aaaattatac ttcctttggc aattcaagtt catcacgcag tatgtgacgg 4500
atttcacatt tgccgttttg taaacgaatt gcaggaattg ataaatagtt aacttcaggt 4560
ttgtctgtaa ctaaaaacaa gtatttaagc aaaaacatcg tagaaatacg gtgttttttg 4620
ttaccctaag ttt                                                   4633
```

| SEQ ID NO: 83 | moltype = DNA length = 6753 |
|---|---|
| FEATURE | Location/Qualifiers |
| misc_feature | 1..6753 |
| | note = plasmid pMTL 8314-Prnf-MK-PMK-PMD |
| source | 1..6753 |
| | mol_type = other DNA |
| | organism = synthetic construct |

SEQUENCE: 83

```
aaaactccttt tgataatct catgaccaaa atcccttaac gtgagttttc gttccactga   60
gcgtcagacc ccgtagaaaa gatcaaagga tcttcttgag atccttttt tctgcgcgta  120
atctgctgct tgcaaacaaa aaaccaccgc taccagcgg tggtttgttt gccggatcaa  180
gagctaccaa ctctttttcc gaaggtaact ggcttcagca gagcgcagat accaaatact  240
gttcttctag tgtagccgta gttaggccac cacttcaaga actctgtagc accgcctaca  300
tacctcgctc tgctaatcct gttaccagtg gctgctgcca gtggcgataa gtcgtgtctt  360
accgggttgg actcaagacg atagttaccg gataaggcgc agcggtcggg ctgaacgggg  420
ggttcgtgca cacagcccag cttggagcga acgacctaca ccgaactgag atacctacag  480
cgtgagctat gagaaagcgc cacgcttccc gaagggagaa aggcggacag gtatccggta  540
agcggcaggt tcgaacaggg agagcgcacg agggagcttc caggggggaaa cgcctggtat  600
ctttatagtc ctgtcgggtt tcgccacctc tgacttgagc gtcgattttt gtgatgctcg  660
tcaggggggc ggagcctatg gaaaaacgcc agcaacgcgg cctttttacg gttcctggcc  720
ttttgctggc cttttgctca catgttcttt cctgcgttat cccctgattc tgtggataac  780
cgtattaccg cctttgagtg agctgatacc gctcgccgca gccgaacgac cgagcgcagc  840
gagtcagtga gcgaggaagc ggaagagcgc ccaatacgca gggccccctg caggataaaa  900
aaattgtaga taaatttat aaaatagttt tatctacaat ttttttatca ggaaacagct  960
atgaccgcgg ccgctaggtc tagaatatcg atacagataa aaaaatatat aatacagaag 1020
```

```
aaaaaattat aaatttgtgg tataatataa agtatagtaa tttaagttta aacctcgtga   1080
aaacgctaac aaataatagg aggtcaattg atgatagctg ttccatttaa cgctggaaaa   1140
ataaaagttt taattgaggc attagaatct ggaaattatt catcaataaa atcagatgta   1200
tatgacggaa tgttatatga tgcaccagat caccttaaat cattagtaaa cagatttgta   1260
gaacttaata atataactga gccattagca gtaactaaca agacaaatct tcctccttca   1320
agaggtcttg gatctagtgc agctgttgct gttgcttttg taagagcaag ttatgatttc   1380
ttaggaaaaa gtttaactaa agaagagctt atagaaaagg ctaattgggc tgaacaaata   1440
gctcatggaa agccatctgg aatagataca caaacaatag tatctggaaa gcctgtttgg   1500
tttcaaaagg gacatgcaga aacacttaaa actctttcac ttgatggata catggtagta   1560
attgatacag gtgttaaagg aagtacaaga caggctgtag aagatgttca taaacttttgc  1620
gaagatcctc aatatatgag tcacgtaaaa cacataggaa aacttgtact tagagcatct   1680
gatgttattg aacatcataa ctttgaagca cttgctgata tattcaatga atgtcatgct   1740
gatttaaagg ctcttacagt aagtcatgac aaaatagaac agttaatgaa gataggaaaa   1800
gaaaatggtg ctatagctgg taaattaact ggtgctggta gaggtggttc aatgttatta   1860
cttgcaaaag acttaccaac tgcaaagaat atagttaaag cagtagagaa agctggtgca   1920
gcacatactt ggattgaaaa tttaggtggt taagtcgaca aagacactaa aaaattataa   1980
aagtaaagga ggacattaaa tgatacaagt aaaggcacca ggaaaattat atatagcagg   2040
tgaatacgct gttacagaac caggatataa atctgttctt atagctcttg atagatttgt   2100
tacagctact attgaggaag ctgatcaata caaaggaaca atacattcaa aggcattaca   2160
tcacaatccca gtaacttttta gtagagatga agattctatt gttatatcag cccacacgc   2220
agcaaaacaa cttaattatg tagtaactgc tatagaaata tttgagcaat atgcaaaatc   2280
atgtgacata gcaatgaagc attttcattt aactatagat tctaacttag atgatagtaa   2340
tggacataag tatggacttg gatcttctgc tgctgttttta gtttcagtaa ttaaagtact   2400
taacgaattt tatgatatga aactttcaaa ccttttatata tataagttag cagtaattgc   2460
taatatgaaa ttacagagtt tatcttcatg cggtgatata gcagtaagtg tttattcagg   2520
ttggttagct tattctacat ttgaccatga atgggtaaaa caccagatag aagatacaac   2580
agttgaagaa gtacttatta aaaattggcc tggattacac atagagccac ttcaagctcc   2640
tgaaaatatg gaagttctta taggttggac aggtagtcca gctagtagtc ctcattttgt   2700
ttctgaagtt aaaagactta agtcagatcc ttcattttac ggtgatttct tagaagattc   2760
acatagatgt gtagaaaaat taattcatgc attcaaaact aataatatta agggtgttca   2820
gaaaatggta agacagaata gaactattat acaagaatg gataaggaag caacagttga   2880
tatagagact gagaagttaa aatatttatg tgatattgct gaaaaatatc atggtgcaag   2940
taaaacttca ggtgctggtg gtggtgattg cggaataact ataataaaata aggatgtaga   3000
caaagagaaa atatatgatg aatggactaa acatggaaata aagcctctta agtttaaat   3060
ttatcatgga caataaccat ggtcaataat cttacaataa ataaaagaaa ggaggcaaaa   3120
atatgataaa atctggaaaa gcaagagcac acactaatat agcacttata aaatattggg   3180
gtaagaaaga tgaggcatta ataataccaa tgaataactc aatatcagta actttagaaa   3240
agttttatac tgaaacaaaa gttacattta acgatcagct tactcaagat caattttggc   3300
ttaatggtga aaaagtttct ggaaaagaat taagaaaat ttcaaagtat atggatattg   3360
ttagaaaatag agctggaata gattggtatg ctgagataga atctgataat tttgttccta   3420
cagctgctgg tcttgctagt tctgctagtg cttatgcagc attagctgct gcatgtaacc   3480
aagcacttga tttacagtta agtgataaag acttaagtag attagctaga attggatcag   3540
gatcagcatc aagatcaata tacggtcggtt ttgcagaatg ggaaaaagga tataatgacg   3600
aaacttctta tgctgttcca ttagaaagta atcactttga agatgatctt gctatgattt   3660
ttgtagtaat aaaccaacat tctaaaaagg ttccttcaag atatgaaatg tctcttacaa   3720
gaaatacaag tagattctat caatattggt tagaccatat tgatgaagat cttgcagaag   3780
caaaggcagc aatacaagat aaggatttta agagattaga tgaagttatt gaagagaatg   3840
gacttagaat gcatgctaca aatcttggat caactccacc ttttacttac ttagtacaag   3900
agtcatacga tgtaatggca ttagtacatg agtgtagaga agcaggatat ccatgctatt   3960
tcactatgga tgctggacct aatgtaaaaa tacttgtaga gaagaaaaac aaacaacaga   4020
taataagataa acttttaact cagttcgata ataatcagat aatagatagt gatattatag   4080
ctacaggtat tgaaattata gaataaaacta gttccgctaa gcttggcact ggccgtcgtt   4140
ttacaacgtc gtgactggga aaaccctggc gttacccaac ttaatcgcct tgcagcacat   4200
ccccctttttcg ccagctggcg taatagcgaa gaggcccgca ccgatcgccc ttcccaacag   4260
ttgcgcagcc tgaatggcga atggcgctag cataaaaata agaagcctgc atttgcaggc   4320
ttcttatttt tatggcgcgc cgccattatt ttttttgaaca attgacaatt catttctat   4380
tttttattaa gtgatagtca aaaggcataa cagtgctgaa tagaaagaaa tttacagaaa   4440
agaaaattat agaatttagt atgattaatt atactcattt atgaatgttt aattgaatac   4500
aaaaaaaaat acttgttatg tattcaatta cgggttaaaa tatagacaag ttgaaaaatt   4560
taataaaaaa ataagtcctc agctcttata tattaagcta ccaacttagt atataagcca   4620
aaacttaaat gtgctaccaa cacatcaagc cgttagagaa ctctatctat agcaatattt   4680
caaatgtacc gacatacaag agaaacatta actatatata ttcaatttat gagattatct   4740
taacagatat aaatgtaaat tgcaataagt aagatttaga agtttatagc ctttgtgtat   4800
tggaagcagt acgcaaaggc tttttttattt gataaaaatt agaagtatat ttatttttc   4860
ataattaatt tatgaaaatg aaaggggtg agcaaagtga cagaggaaag cagtatctta   4920
tcaaataaca aggtattagc aatatcatta ttgactttag cagtaaacat tatgactttt   4980
atagtgcttg tagctaagta gtacgaaagg gggagcttta aaaagctcct tggaatacat   5040
agaattcata aattaattta tgaaaagaag ggcgtatatg aaaacttgta aaaattgcaa   5100
agagtttatt aaagatactg aaatatgcaa aatacattcg ttgatgattc atgataaaac   5160
agtagcaacc tattgcagta aatacaatga gtcaagatgt ttacataaag ggaagtcca   5220
atgtattaat tgttcaaaga tgaaccgata tggatggtgt gccataaaaa tgagatgttt   5280
tacagaggaa gaacagaaaa aagaacgtac atgcattaaa tattatgcaa ggagctttaa   5340
aaagctcat gtaaagaaga gtaaaagaa aaaataattt atttattaat ttaatattga   5400
gagtgccgac acagtatgca ctaaaaaata tatctgtggt gtagtgagcc gatacaaaag   5460
gatagtcact cgcatttttca taatacatct tatgttatga ttatgtgtcg gtgggacttc   5520
acgacgaaaa cccacaataa aaaaagagtt cggggtaggg ttaagcatag ttgaggcaac   5580
taaacaatca agctaggata tgcagtagca gaccgtaagg tcgttgttta ggtgtgttgt   5640
aatacatacg ctattaagat gtaaaaatac ggataccaat gaagggaaaa gtataatttt   5700
tggatgtagt ttgtttgttc atctatgggc aaactacgtc caaagccgtt tccaaatctg   5760
```

-continued

```
ctaaaaagta tatcctttct aaaatcaaag tcaagtatga aatcataaat aaagtttaat 5820
tttgaagtta ttatgatatt atgttttct  attaaaataa attaagtata tagaatagtt 5880
taataatagt atatacttaa tgtgataagt gtctgacagt gtcacagaaa ggatgattgt 5940
tatgattat  aagcggccgg ccagtgggca agttgaaaaa ttcacaaaaa tgtggtataa 6000
tatctttgtt cattagagcg ataaacttga atttgagagg gaacttagat ggtatttgaa 6060
aaaattgata aaaatagttg gaacagaaaa gagtattttg accactactt tgcaagtgta 6120
ccttgtacct acagcatgac cgttaaagtg gatatcacac aaataaagga aagggaatg  6180
aaactatatc ctgcaatgct ttattatatt gcaatgattg taaaccgcca ttcagagttt 6240
aggacggcaa tcaatcaaga tggtgaattg gggatatatg atgagatgat accaagctat 6300
acaatatttc acaatgatac tgaaacattt tccagccttt ggactgagtg taagtctgac 6360
tttaaatcat ttttagcaga ttatgaaagt gatacgcaac ggtatggaaa caatcataga 6420
atggaaggaa agccaaatgc tccggaaaac attttaatg  tatctatgat accgtggtca 6480
accttcgatg gctttaatct gaatttgcag aaaggatatg attatttgat tcctattttt 6540
actatgggga aatattataa agaagataac aaaattatac ttcctttggc aattcaagtt 6600
catcacgcag tatgtgacgg atttcacatt tgccgttttg taaacgaatt gcaggaattg 6660
ataaatagtt aacttcaggt ttgtctgtaa ctaaaaacaa gtatttaagc aaaaacatcg 6720
tagaaatacg gtgttttttg ttaccctaag ttt                              6753
```

SEQ ID NO: 84        moltype = DNA   length = 9198
FEATURE              Location/Qualifiers
misc_feature       1..9198
                       note = plasmid pMTL8314-Prnf-MK-PMK-PMD-Pfor-idi-ispS
source                1..9198
                       mol_type = other DNA
                       organism = synthetic construct
SEQUENCE: 84

```
aaactccttt ttgataatct catgaccaaa atcccttaac gtgagttttc gttccactga 60
gcgtcagacc ccgtagaaaa gatcaaagga tcttcttgag atccttttt  tctgcgcgta 120
atctgctgct tgcaaacaaa aaaaccaccg ctaccagcgg tggtttgttt gccggatcaa 180
gagctaccaa ctctttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcggaacagg agagcgcacg agggagcttc caggggaaa  cgcctggtat 600
ctttatagtc ctgtcgggtt tcgccacctc tgacttgagc gtcgattttt gtgatgctcg 660
tcaggggggc ggagcctatg gaaaaacgcc agcaacgcgg cctttttacg gttcctggcc 720
ttttgctgg  cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggcccctg  caggataaaa 900
aaattgtaga taaattttat aaaatagttt tatctacaat ttttttatca ggaaacagct 960
atgaccgcgg ccgctaggtc tagaatatcg atacagataa aaaaatatat aatacagaaa 1020
aaaaaattat aaatttgtgg tataatataa agtatagtaa tttaagttta aacctcgtga 1080
aaacgctaac aaataatagg aggtcaattg atgatagctg ttccatttaa cgctggaaaa 1140
ataaaagttt taattgaggc attagaatct ggaaattatt catcaataaa atcagatgta 1200
tatgacggaa tgttatatga tgcaccagat caccttaaca cattagtaaa cagatttgta 1260
gaacttaata atataactga gccattagca gtaactatac agacaaatct tcctccttca 1320
agaggtctg  gatcagtgc  agctgttgct gttgcttttg taagagcaag ttatgatttc 1380
ttaggaaaaa gtttaactaa agaagagctt atagaaaagg ctaattgggc tgaacaaata 1440
gctcatggaa agccatctgg aatagataca caaacaatag tatctggaaa gcctgttttg 1500
tttcaaaagg gacatgcaga aacacttaaa actctttcac ttgatggata catggtagta 1560
attgatacag gtgttaaagg aagtacaaga caggctgtag aagatgttca taactttgc  1620
gaagatcctc aatatatgag tcacgtaaaa cacataggaa aacttgtact tagagcatct 1680
gatgttattg aacatcataa cttttgaagct cttgctgata tattcaatga atgtcatgct 1740
gatttaaagg ctcttacagt aagtcatgac aaaaatagaa agttaatgaa gataggaaaa 1800
gaaaatggtg ctatagctgg taaattaact ggtgctggta gaggtggttc aatgttatta 1860
cttgcaaaag acttaccaac tgcaagaat  atagttaaag cagtagaaaa agctggtgca 1920
gcacatactt ggattgaaaa tttaggtggt taagtcgaca aagacactaa aaattataa  1980
agtaaaagga ggacattaaa tgatacaagt aaaggcacca ggaaaattat atatagcagg 2040
tgaatacgct gttacagaac caggatataa atctgttctt atagctcttg atagatttgt 2100
tacagctact attgaggaag ctgatcaata caaaggaaca atacattcaa aggcattaca 2160
tcacaatcca gtaactttta gtagagatga agattctatt gttatatcag acccacacgc 2220
agcaaaacaa cttaattatg tagtaactgc tatagaaata tttgagcaat atgcaaaatc 2280
atgtgacata gcaatgaagc atttttcattt aactatagat tctaacttag atagtaa    2340
tggacataag tatggacttg gatcttctgc tgctgtttta gttcagtaa  ttaaagtact 2400
taacgaattt tatgatatga aactttcaaa cctttatata tataagttag cagtaattgc 2460
taatatgaaa ttcagagtt  tatcttcatg cggtgatata gcagtaagtg tttattcagg 2520
ttggttagct tattctacat ttgaccatga atgggtaaaa caccagatag aagatacaac 2580
agttgaagaa gtacttatta aaaattggcc tggattacac atagagccac ttcaagctcc 2640
tgaaaatatg aagttctta  taggttggac aggtagtcca gctagtagtc ctcattttgt 2700
ttctgaagtt aaaagactta agtcagatcc ttcattttac ggtgatttct agaagattc  2760
acatagagtg gtagaaaaat taattcatgc attcaaaact aataatatta agggtgttca 2820
gaaaagcggta agacagaata gaactattat acaaagaatg ataaggaag caacagttga 2880
tatagagact gagaagttaa aatatttatg tgatattgct gaaaaatatc atggtgcaag 2940
taaaacttca ggtgctggtg gtggtgattg cggaataact ataataaaata aggatgtaga 3000
caaagagaaa atatatgatg aatggactaa acatggaata aagccttcta agtttaatat 3060
ttatcatgga caataaccat ggtcaataat cttacaataa ataaaagaaa ggaggcaaaa 3120
atgatataaa atctggaaaa gcaagagcac acactaatat agcacttata aaatattggg 3180
```

```
gtaagaaaga tgaggcatta ataataccaa tgaataactc aatatcagta acttttagaaa   3240
agttttatac tgaaacaaaa gttacattta acgatcagct tactcaagat caattttggc   3300
ttaatggtga aaaagtttct ggaaaagaat tagaaaagat ttcaaagtat atggatattg   3360
ttagaaatag agctggaata gattggtatg ctgagataga atctgataat tttgttccta   3420
cagctgctgg tcttgctagt tctgctagtg cttatgcagc attagctgct gcatgtaacc   3480
aagcacttga tttacagtta agtgataaag acttaagtag attagctaga attggatcag   3540
gatcagcatc aagatcaata tacggtggtt ttgcagaatg ggaaaaagga tataatgacg   3600
aaacttctta tgctgttcca ttagaaagta atcactttga agatgatctt gctatgattt   3660
ttgtagtaat aaaccaacat tctaaaaagg ttccttcaag atatggaatg tctcttacaa   3720
gaaatacaag tagattctat caatattggt tagaccatat tgatgaagat cttgcagaag   3780
caaaggcagc aatacaagat aaggatttta agagattagg tgaagttatt gaagagaatg   3840
gacttagaat gcatgctaca aatcttggat caactccacc ttttacttac ttagtacaag   3900
agtcatacga tgtaatggca ttagtacatg agtgtagaga agcaggatat ccatgctatt   3960
tcactatgga tgctggacct aatgtaaaaa tacttgtaga gaagaaaaac aaacaacaga   4020
taatagataa acttttaact cagttcgata ataatcagat aatagatagt gatattatag   4080
ctacaggtat tgaaattata gaataaaacta gttgtatatt aaaatagtag aatacataag   4140
atacttaatt taattaaaga tagttaagta cttttcaatg tgcttttttta gatgtttaat   4200
acaaatcttt aattgtaaaa gaaatgctgt actatttact gttctagtga cgggattaaa   4260
ctgtattaat tataaataaa aaataagtac agttgtttaa aattatatttt tgtattaaat   4320
ctaatagtac gatgtaagtt attttatact attgctagtt taataaaaag atttaattat   4380
atacttgaaa aggagaggaa ctcgagatgg cagagtatat aatagcagta gatgagttcg   4440
ataacgaaat aggatcaata gaaaagatgg aagctcatag aaaaggaaca cttcatagag   4500
cattcagtat tttagttttt aactcaaaga atcaactttt attacagaaa agaaatgtaa   4560
agaaatatca ctctccagga ttatggacaa acacttgttg tagtcaccca agatatggtg   4620
aatctcttca tgatgctata tacagaagat taaaagaaga gatgggattt acttgcgaac   4680
ttgaagaagt attctcattc atatataagg taaaacttta agataatttta tttgagaatg   4740
aatatgacca tgtatttatt ggtaaatatg atggtgagat aattgttaat aaagatgaag   4800
ttgatgattt taaatgggta gacattaatg aagttaaaaa ggacataata gaaagacctg   4860
aggcatatac ttactggttt aagtatcttg taaataaagc tgaaaataag atatttaaat   4920
aaaccggtgg gaggaaatga acatggcaac agaattatta tgtttacaca gacctatatc   4980
acttactcac aaactttta ggaatccatt acctaaagtt attcaagcta cacctttaac   5040
attaaaactt aggtgtagtg tttctacaga aaatgtatca tttagtgaga cagaaactga   5100
aacaagaaga tcagcaaatt atgaaccaaa ttcttgggat tatgattatc ttctttcttc   5160
tgatactgat gagtcaatag aagtacataa agataaggct aagaaattag aagctgaagt   5220
taggagagaa ataaataatg agaaggctga atttcttaca cttcttgaac ttattgataa   5280
tgtacaaaga cttggattag gatatagatt tgagtctgat ataagaagag cattagatag   5340
atttgtaagt agtggaggat ttgatggagt tactaaaact tcattacatg gaacagcatt   5400
atcatttagg ttattaaggc aacatggttt tgaagtatct caagaagctt ttagtggatt   5460
taaagatcag aatggaaact ttcttgaaaa tttaaaggaa gacataaaag caattcttcc   5520
tctttatgaa gcatcatttt tagcattaga aggtgagaat atattagatg aggctaaagt   5580
attttgcaata tctcatctta agaaacttag tgaagaaaag attggtaaag aattagctga   5640
acaagtttca catgctttag aattaccatt acatagaaga acacaaagat tagaagcagt   5700
ttggtcaata gaagcatata gaaagaaaga agacgcaaat tagtacttct tagaacttgc   5760
aatacttgac tacaatatga ttcaaagtgt atatcagagg gatttaagag aaacatcaag   5820
atggtggaga agagtaggat tagcaactaa attacatttt gctagagata ggcttattga   5880
aagttttttat tgggctgttg gagttgcttt tgaaccacaa tattctgatt gcagaaatag   5940
tgtagcaaag atgttttcat ttgttactat aattgacgat atttacgatg tatatggaac   6000
tttagatgaa cttgaacttt ttactgatgc agttgaaaga tgggatgtaa atgctattaa   6060
tgatcttcct gattatatga agttatgttt tcttgcactt tacaatacta ttaacgagat   6120
agcttacgat aacttaaaag ataaaggtga gaacatactt ccttatttaa caaaagcatg   6180
ggcagttta tgtaatgcat ttcttcaaga agctaagtgg ctttataata aatcaacacc   6240
tacatttgat gattattttg gaaatgcatg gaaagttct agtggacctt tacagcttat   6300
ttttgcttat tttgctgtag tacagaacat taaaaaggaa gagattgaga atcttcagaa   6360
atatcatgac ataatatcaa gacctagtca cattttagg ctttgtaatg atttagcatc   6420
tgcttcagca gaaatagcaa gaggtgaaac tgctaattcc gtaagttgtt atatgagaac   6480
aaaaggtata tctgaagaat tagctactga aagtgttatg aatcttatag acgaaacttg   6540
gaagaaaatg aacaaagaaa aacttggtgg atctttattt gcaaaacctt tgttgagac    6600
tgctataaat ttagctagac agtctcattg cacatatcat aatggtgatg cacatactag   6660
tccagatgaa ttaactagga aaagatact tagtgtaata actgaaccaa tattaccatt   6720
tgaaagataa gctagcataa aaataagaag cctgcatttg caggcttctt attttatgg    6780
cgcgccgcca ttattttttt gaacaattga caattcattt cttatttttt attaagtgat   6840
agtcaaaagg cataacagtg ctgaatagaa agaaatttac agaaagaaa attatagaat    6900
ttagtatgat taattatact catttatgaa tgtttaattg aatacaaaaa aaaatacttg   6960
ttatgtattc aattacgggt taaaatatag acaagttgaa aatttaata aaaaaataag    7020
tcctcagctc ttatatatta agctaccaac ttagtatata agccaaaact taaatgtgct   7080
accaacacat caagccgtta gagaactcta tctatagcaa tatttcaaat gtaccgacat   7140
acaagagaaa cattaactat atatattcaa tttatgagat tatcttaaca gatataaatg   7200
taaattgcaa taagtaagat ttagaagttt atagcctttg tgtattggaa gcatacgca    7260
aaggctttt tatttgtaaa aaattagaag tatatttatt tttcataat taatttatga    7320
aaatgaaagg gggtgagcaa agtgacagag aaagcagta tcttatcaaa taacaaagta    7380
ttagcaatat cattattgac tttagcagta aacattatga cttttatagt gcttgtagct   7440
aagtagtacg aaaggggag ctttaaaaag ctccttggaa tacatagaat tcataaatta    7500
atttatgaaa agaagggcgt atatgaaaac ttgtaaaaat tgcaaagagt ttattaaaga   7560
tactgaaata tgcaaaatac attcgttgat gattcatgat aaaacagtag caacctattg   7620
cagtaaaatac aatgagtcaa gatgtttaca taaagggaaa gtccaatgta ttaattgttc   7680
aaagatgaac cgatatggat ggtgtgccat aaaaatgaga tgtttacag aggaagaaca    7740
gaaaaagaa cgtacatgca ttaaatatta tgcaaggagc tttaaaaaag ctcatgtaaa    7800
gaagagtaaa aagaaaaaat aatttattta ttaatttaat attgagagtg ccgacacagt   7860
atgcactaaa aaatatatct gtggtgtagt gagccgatac aaaaggatag tcactcgcat   7920
```

```
tttcataata catcttatgt tatgattatg tgtcggtggg acttcacgac gaaaacccac 7980
aataaaaaaa gagttcgggg tagggttaag catagttgag gcaactaaac aatcaagcta 8040
ggatatgcag tagcagaccg taaggtcgtt gtttaggtgt gttgtaatac atacgctatt 8100
aagatgtaaa aatacggata ccaatgaagg gaaaagtata atttttggat gtagtttgtt 8160
tgttcatcta tgggcaaact acgtccaaag ccgtttccaa atctgctaaa aagtatatcc 8220
tttctaaaat caaagtcaag tatgaaatca taaataaagt ttaattttga agttattatg 8280
atattatgtt tttctattaa aataaattaa gtatatagaa tagtttaata atagtatata 8340
cttaatgtga taagtgtctg acagtgtcac agaaaggatg attgttatgg attataagcg 8400
gccggccagt gggcaagttg aaaaattcac aaaaatgtgg tataatatct ttgttcatta 8460
gagcgataaa cttgaatttg agagggaact tagatggtat ttgaaaaaat tgataaaaat 8520
agttggaaca gaaaagagta tttttgaccac tactttgcaa gtgtaccttg tacctacagc 8580
atgaccgtta aagtggatat cacacaaata aaggaaaagg gaatgaaact atatcctgca 8640
atgctttatt atattgcaat gattgtaaac cgccattcag agtttaggac ggcaatcaat 8700
caagatggtg aattgggat atatgatgag atgatacaat gctatacaat atttcacaat 8760
gatactgaaa cattttccag cctttggact gagtgtaagt ctgactttaa atcattttta 8820
gcagattatg aaagtgatac gcaacggtat ggaaacaatc atagaatgga aggaaagcca 8880
aatgctccgg aaaacatttt taatgtatct atgataccgt ggtcaacctt cgatggcttt 8940
aatctgaatt tgcagaaagg atatgattat ttgattccta ttttttactat gggaaatat 9000
tataaagaag ataacaaaat tatacttcct ttggcaattc aagttcatca cgcagtatgt 9060
gacggatttc acatttgccg tttttgtaaac gaattgcagg aattgataaa tagttaactt 9120
caggtttgtc tgtaactaaa aacaagtatt taagcaaaaa catcgtagaa atacggtgtt 9180
ttttgttacc ctaagtttt                                              9198

SEQ ID NO: 85           moltype = DNA  length = 6841
FEATURE                 Location/Qualifiers
misc_feature            1..6841
                        note = plasmid pMTL83245-Pfor-FS-idi
source                  1..6841
                        mol_type = other DNA
                        organism = synthetic construct
SEQUENCE: 85
aaactcctttt ttgataatct catgaccaaa atccctttaac gtgagttttc gttccactga  60
gcgtcagacc ccgtagaaaa gatcaaagga tcttcttgag atccttttttt tctgcgcgta 120
atctgctgct tgcaaacaaa aaaaccaccg ctaccagcgg tggtttgttt gccggatcaa 180
gagctaccaa ctcttttttcc gaaggtaact ggcttcagca gagcgcagat accaaatact 240
gttcttctag tgtagccgta gttaggccac cacttcaaga actctgtagc accgcctaca 300
tacctcgctc tgctaatcct gttaccagtg gctgctgcca gtggcgataa gtcgtgtctt 360
accgggttgg actcaagacg atagttaccg gataaggcgc agcggtcggg ctgaacgggg 420
ggttcgtgca cacagcccag cttggagcga acgacctaca ccgaactgag atacctacag 480
cgtgagctat gagaaagcgc cacgcttccc gaagggagaa aggcggacag gtatccggta 540
agcggcaggg tcgaacagg agagcgcacg agggagcttc caggggggaaa cgcctggtat 600
ctttatagtc ctgtcgggtt tcgccacctc tgacttgagc gtcgattttt gtgatgctcg 660
tcaggggggc ggagcctatg gaaaaacgcc agcaacgcgg ccttttttacg gttcctggcc 720
ttttgctggc cttttgctca catgttcttt cctgcgttat cccctgattc tgtggataac 780
cgtattaccg cctttgagtg agctgatacc gctcgccgca gccgaacgac cgagcgcagc 840
gagtcagtga gcgaggaagc ggaagagcgc ccaatacgca gggcccctg caggataaaa 900
aaattgtaga taattttat aaaatagttt tatctacaat tttttatca gggaaacagct 960
atgaccgcgg ccgcaatatg atatttatgt ccattgtgaa agggattata ttcaactatt 1020
attccagtta cgttcataga aattttcctt tctaaaatat tttattccat gtcaagaact 1080
ctgtttattt cattaaagaa ctataagtac aaagtataag gcatttgaaa aaataggcta 1140
gtatattgat tgattattta tttaaaatg cctaagtgaa atatatacat attataaacaa 1200
taaaataagt attagtgtag gatttttaaa tagagtatct attttcagat taaatttttg 1260
attatttgat ttacattata taatattgag taaagtattg actagcaaaa tttttttgata 1320
cttaatttg tgaatttct tatcaaagt tatatttttg aataattttt attgaaaaat 1380
acaactaaaa aggattatag tataagtgtg tgtaattttg tgttaaattt aaagggagga 1440
aatgaacatg aaacatatgg tgaccatgat tacgaattcg agctcggtac ccggggatcc 1500
tctagttgta tattaaaata gtagaataca taagatactt aatttaatta aagatagtta 1560
agtacttttc aatgtgcttt tttagatgtt taatacaaat ctttaattgt aaaagaaatg 1620
ctgtactatt tactgttcta gtgacgggat taaactgtat taattataaa taaaaaataa 1680
gtacagttgt ttaaaattat atttgtatt aaatctaata gtacgatgta agttatttta 1740
tactattgct agtttaataa aaagatttaa ttatatactt gaaaaggaga ggaactcgag 1800
atggaattta gagtacattt acaggcagac aacgaacaga aaatatttca aaatcaaatg 1860
aaaccagagc cagaagcatc atatcttata aatcaaagaa gaagtgctaa ttataaacca 1920
aacatttgga aaaacgattt tcttgatcag tcttttaaat caaaatatga tggtgatgaa 1980
tatagaaaac tttcagaaaa gttaataga gaagtaaaga tatacatatc agcagagact 2040
atggatttag ttgctaaatt agaacttata gattctgtta gaaaacttgg acttgctaat 2100
cttttttgaga agaaataaa ggaagcatta gacagtatag cagcaataga atcagataat 2160
ttaggaacta gagacgatct ttatggaaca gctcttcatt ttaagattct tagacagcat 2220
ggatataagg taagtcaaga tatattggt agatttatgt atgagaaagg aacattagaa 2280
aatcatcact ttgcacactt aaaaggaatg ttagaattat ttgaggcaag taatcttgga 2340
tttgaaggtg aagacatatt agatgaagct aaagcatctc ttacacttgc tcttagagat 2400
tcaggacata tttgttatcc agactcaaac ttaagtagag atgtagttca tagtttagaa 2460
ttacctagtc atagaagagt tcaatggttc gatgtaaaat ggcagattaa tgcatacgaa 2520
aaagatattt gtagagtaaa tgcaaccttta ttaagttgag caaagtttaa ttttaatgtt 2580
gttcaagctc agcttcagaa gaatcttaga gaagctagta gatggtgggc taatcttggt 2640
ttcgcagata atttaaagtt tgctagagat agacttgtag agtgttttc atgcgcagta 2700
ggtgtagcat ttgaaccaga gcattcatct tttagaatat gttaactaa ggtaattaat 2760
cttgttctta ttatagatga tgtatacgat atatatggat ctgaagaaga gttaaaacat 2820
tttacaaaatg ctgttgatag atgggacagt agagaaacag aacagcttcc tgaatgcatg 2880
```

```
aaaatgtgtt ttcaagtatt atataacact acttgcgaaa tagcaagaga gatagaagaa   2940
gaaaacggtt ggaatcaagt attacctcaa cttactaagg tttgggctga tttttgtaag   3000
gctcttttag ttgaagcaga gtggtacaat aaatcacata ttccaacatt agaagaatat   3060
cttagaaacg gatgtatatc aagtagtgta tctgtacttt tagttcactc tttcttttca   3120
ataactcatg aaggtacaaa agaaatggct gatttcttac ataaaaatga agatcttttta  3180
tacaacataa gtcttatagt aagattaaac aatgatttag gtacatcagc tgctgaacag   3240
gaaagaggtg attctccttc ttctatagtt tgctatatga gagaagttaa tgcttctgaa   3300
gagactgcaa gaaagaatat aaagggaatg attgataatg cttggaaaaa ggttaatgga   3360
aaatgtttca caactaacca agttccattt ctttcatcat tcatgaataa tgcaactaac   3420
atggcaagag tagcacactc attatataaa gacggtgatg gttttggtga tcaagaaaaa   3480
ggacctagaa cacatattct tagtttatta ttccaacctt tagtaaatta actgcagggt   3540
tcaaaacata gattaaaaaa ttaaaggagg ggaaaaatg gcagagtata taatagcagt   3600
agatgagttc gataacgaaa taggatcaat agaaaagatg gaagctcata gaaaaggaac   3660
acttcataga gcattcagta tttttagtttt taactcaaag aatcaactt tattacagaa   3720
aagaaatgta aagaaatatc actctccagg attatggaca aacacttgtt gtagtcaccc   3780
aagatatggt gaatctcttc atgatgctat atacagaaga ttaaaagaag agatgggatt   3840
tacttgcgaa cttgaagaag tattctcatt catatataag gtaaaacttg aagataattt   3900
atttgagaat gaatatgacc atgtatttat tggtaaatat gatggtgaga taattgttaa   3960
taaagatgaa gttgatgatt ttaaatgggg agacattaat gaagttaaaa aggacataat   4020
agaaagacct gaggcatata cttactggtt taagtatctt gtaaataaag ctgaaaataa   4080
gatatttaaa taaaagcttg gcactggccg tcgttttaca acgtcgtgac tgggaaaacc   4140
ctggcgttac ccaacttaat cgccttgcag cacatccccc tttcgccagc tggcgtaata   4200
gcgaagaggc ccgcaccgat cgcccttccc aacagttgcg cagcctgaat ggcgaatggc   4260
gctagcataa aaataagaag cctgcatttg caggcttctt atttttatgg cgcgccgcca   4320
ttatttttttt gaacaattga caattcattt cttattttttt attaagtgat agtcaaaagg  4380
cataacagtg ctgaatagaa agaaatttac agaaaagaaa attatagaat ttagtatgat   4440
taattatact catttatgaa tgtttaattg aatacaaaaa aaaatacttg ttatgtattc   4500
aattacgggt taaatatag acaagttgaa aaatttaata aaaaaataag tcctcagctc   4560
ttatatatta agctaccaac ttagtatata agccaaaact taaatgtgct accaacacat   4620
caagccgtta gagaactcta tctatagcaa tatttcaaat gtaccgacat acaagagaaa   4680
cattaactat atatattcaa tttatgagat tatcttaaca gatataaatg taaattgcaa   4740
taagtaagat ttagaagttt atagcctttg tgtattggaa gcagtacgca aaggcttttt   4800
tatttgataa aaattagaag tatatttatt ttttcataat taatttatga aaatgaaagg   4860
gggtgagcaa agtgacagag gaaagcagta tcttatcaaa taacaaggta ttagcaatat   4920
cattattgac tttagcagta aacattatga ctttttatagt gcttgtagct aagtagtacg   4980
aaaggggggag ctttaaaaag ctccttggaa tacatagaat tcataaatta atttatgaaa  5040
agaagggcgt atatgaaaac ttgtaaaaat tgcaaagagt ttattaaaga tactgaaata   5100
tgcaaaatac attcgttgat gattcatgat aaaacagtag caacctattg cagtaaatac   5160
aatgagtcaa gatgtttaca taaaggggaaa gtccaatgta ttaattgttc aaagatgaac  5220
cgatatggat ggtgtgccat aaaaatgaga tgtttttacag aggaagaaca gaaaaaagaa   5280
cgtacatgca ttaaatatta tgcaaggagc tttaaaaaag ctcatgtaaa gaagagtaaa   5340
aagaaaaaat aatttattta ttaattttaat attgagagtc cgacacagt atgcactaaa   5400
aaatatatct gtggtgtagt gagccgatac aaaaggatag tcactcgcat tttcataata   5460
catcttatgt tatgattatg tgtcggtggg acttcacgac gaaaacccac aataaaaaaa   5520
gagttcgggg tagggttaag catagttgag gcaactaaac aatcaagcta ggatatgcag   5580
tagcagaccg taaggtcgtt gtttaggtgt gttgtaatac atacgctatt aagatgtaaa   5640
aatacggata ccaatgaagg gaaaagtata attttttggat gtagtttgtt tgttcatcta   5700
tgggcaaact acgtccaaag ccgtttccaa atctgctaaa aagtatatcc tttctaaaat   5760
caaagtcaag tatgaaatca taaataaagt ttaaattttga agtattatg atatttatgtt   5820
tttctattaa aataaattaa gtatatagaa tagtttaata atagtatata cttaatgtga   5880
taagtgtctg acagtgtcac agaaaggatg attgttaatg attataagcg gccggccgaa   5940
gcaaacttaa gagtgtgttg atagtgcagt atcttaaaat tttgtataat aggaattgaa   6000
gttaaattag atgctaaaaa tttgtaatta agaaggagtg attacatgaa caaaaatata   6060
aaatattctc aaaacttttt aacgagtgaa aaagtactca accaaataat aaaacaattg   6120
aatttaaaag aaaccgatac cgtttacgaa attggaacag gtaaagggca tttaacgacg   6180
aaactggcta aaataagtaa acaggtaacg tctattgaat tagacagtca tctattcaac   6240
ttatcgtcag aaaaattaaa actgaatact cgtgtcactt taattcacca agatattcta   6300
cagtttcaat tccctaacaa acagaggtat aaaattgttg ggagtattcc ttaccattta   6360
agcacacaaa ttattaaaaa agtggttttt gaaagccatg cgtctgacat ctatctgatt   6420
gttgaagaag gattctacaa gcgtaccttg gatattcacc gaacactagg gttgctcttg   6480
cacactcaag tctcgattca gcaattgctt aagctgccag cggaatgctt tcatcctaaa   6540
ccaaaagtaa acagtgtctt aataaaactt acccgcccata ccacagatgt tccagataaa  6600
tattggaagc tatatacgta ctttgtttca aaatgggtca atcgagaata tcgtcaactg   6660
tttactaaaa atcagtttca tcaagcaatg aaacacgcca aagtaaacaa tttaagtacc   6720
gttacttatg agcaagtatt gtctattttt aataagttatc tattatttaa cgggaggaaa   6780
taattctatg agtcgctttt gtaaatttgg aaagttacac gttactaaag ggaatgtgtt   6840
t                                                                   6841

SEQ ID NO: 86           moltype = DNA   length = 36
FEATURE                 Location/Qualifiers
misc_feature            1..36
                        note = Oligonucleotide idi_F2
source                  1..36
                        mol_type = other DNA
                        organism = synthetic construct
SEQUENCE: 86
aggcactcga gatggcagag tatataatag cagtag                             36

SEQ ID NO: 87           moltype = DNA   length = 47
```

```
FEATURE                Location/Qualifiers
misc_feature           1..47
                       note = Oligonucleotide idi_R2
source                 1..47
                       mol_type = other DNA
                       organism = synthetic construct
SEQUENCE: 87
aggcgcaagc ttggcgcacc ggtttattta aatatcttat tttcagc          47

SEQ ID NO: 88          moltype = DNA  length = 5075
FEATURE                Location/Qualifiers
misc_feature           1..5075
                       note = plasmid pMTL83245-Pfor-idi
source                 1..5075
                       mol_type = other DNA
                       organism = synthetic construct
SEQUENCE: 88
aaactccttt ttgataatct catgaccaaa atcccttaac gtgagttttc gttccactga    60
gcgtcagacc ccgtagaaaa gatcaaagga tcttcttgag atcctttttt tctgcgcgta   120
atctgctgct tgcaaacaaa aaaaccaccg ctaccagcgg tggtttgttt gccggatcaa   180
gagctaccaa ctctttttcc gaaggtaact ggcttcagca gagcgcagat accaaatact   240
gttcttctag tgtagccgta gttaggccac cacttcaaga actctgtagc accgcctaca   300
tacctcgctc tgctaatcct gttaccagtg gctgctgcca gtggcgataa gtcgtgtctt   360
accgggttgg actcaagacg atagttaccg gataaggcgc agcggtcggg ctgaacgggg   420
ggttcgtgca cacagcccag cttggagcga acgacctaca ccgaactgag atacctacag   480
cgtgagctat gagaaagcgc cacgcttccc gaagggagaa aggcggacag gtatccggta   540
agcggcaggg tcggaacagg agagcgcacg agggagcttc caggggggaaa cgcctgtat    600
ctttatagtc ctgtcgggtt tcgccacctc tgacttgagc gtcgatttt gtgatgctcg   660
tcagggggc ggagcctatg gaaaaacgcc agcaacgcgg ccttttacg gttcctggcc   720
ttttgctgc cttttgctca catgttcttt cctgcgttat cccctgattc tgtggataac   780
cgtattaccg cctttgagtg agctgatacc gctcgccgca gccgaacgac cgagcgcagc   840
gagtcagtga gcgaggaagc ggaagagcgc ccaatacgca gggcccctg caggataaaa   900
aaattgtaga taaatttttat aaaatagttt tatctacaat tttttatca ggaaacagct   960
atgaccgcgg ccgcaatatg atatttatgt ccattggatta ttcaactatt  1020
attccagta cgttcataga aattttcctt tctaaaatat tttattccat gtcaagaact  1080
ctgttttattt cattaaagaa ctataagtac aaagtataag gcatttgaaa aaataggcta  1140
gtatattgat tgattattta ttttaaaatg cctaagtgaa atatatacat attataacaa  1200
taaaataagt attagtgtag gatttttaaa tagagtatct attttcagat taaattttg    1260
attattgat ttacattata taatattgag taaagtattg actagcaaaa ttttttgata  1320
ctttaatttg tgaaatttct tatcaaaagt tatattttg aataattttt attgaaaaat  1380
acaactaaaa aggattatag tataagtgtg tgtaattttg tgttaaattt aaagggagga  1440
aatgaacatg aaacatatgg tgaccatgat tacgaattgc agctcggtac ccggggatcc  1500
tctagttgta tattaaaaata gtagaataca taagatactt aatttaattaa agatagtta  1560
agtacttttc aatgtgcttt tttagatgtt taatacaaat cttttaattgt aaaagaatg    1620
ctgtactatt tactgttcta gtgacgggat taaactgtat taattataaaa taaaaataa   1680
gtacagttgt ttaaaattat attttgtatt aaatctaata gtacgatgta agttattta    1740
tactattgct agtttaataa aaagatttaa ttatatactt gaaaaggaga ggaactcgag  1800
atggcagagt atataatagc agtagatgag ttcgataacg aaataggatc aatagaaaag  1860
atggaagctc atagaaaagg aacacttcat agagcattca gtattttagt ttttaactca  1920
aagaatcaac ttttattaca gaaaagaat gtaaagaaat atcactctcc aggattatgg  1980
acaaacactt gttgtagtca cccaagatat ggtgaatctc ttcatgatgc tatatacaga  2040
agattaaaag aagagatggg atttacttgc gaacttgaag aagtattctc attcatatat  2100
aaggtaaaac ttgaagataa tttatttgag aatgaatatg accatgtatt tattggtaaa  2160
tatgatggtg agataattgt taataaagat gaagttgatg attttaaatg ggtagacatt  2220
aatgaagtta aaaaggacat aatagaaaga cctgaggcat atacttactg gtttaagtat  2280
cttgtaaata aagctgaaaa taagatattt aaataaaccg gtgcgccaag cttggcactg  2340
gccgtcgttt tacaacgtcg tgactgggaa aaccctggcg ttacccaact taatcgcctt  2400
gcagcacatc ccccttttcgc cagctggcgt aatagcgaag aggcccgcac cgatcgccct  2460
tcccaacagt tgcgcagcct gaatggcgaa tggcgctagc ataaaaataa gaagcctgca  2520
tttgcaggct tcttattttt atggcgcgcc gccattattt ttttgaacaa ttgacaattc  2580
atttcttatt ttttattaag tgatagtcaa aaggcataac agtgctgaat agaaagaaat  2640
ttacagaaaa gaaaattata gaatttagta tgattaatta tactcattta tgaatgtttta  2700
attgaataca aaaaaaaata cttgttatgt attcaattac gggtaaaaat atagacaagt  2760
tgaaaatttt aataaaaaaa taagtcctca gctcttataa ttaagctac caacttagta  2820
tataagccaa aacttaaatg tgctaccaac acatcaagcc gttagagaac tctatctata  2880
gcaatatttc aaatgtaccg acatacaaga gaaacattaa ctatatatat tcaatttatg  2940
agattatctt aacagatata aatgtaaatt gcaataagta agatttagaa gtttatagcc  3000
tttgtgtatt ggaagcagta cgcaaaggct tttttatttg ataaaaatta gaagtatatt  3060
tattttttca taattaattt atgaaaatga aaggggtga gcaaagtgac agaggaaagc  3120
agtatcttat caaataacaa ggtattagca atatcattat tgactttagc agtaaacatt  3180
atgactttta tagtcttgt agctaagtag tacgaaaggg ggagcttaa aaagctcctt  3240
ggaatacata gaattcataa attaattttat gaaagaagg gcgtatatga aaacttgtaa  3300
aaattgcaaa gagtttatta aagatactga aaatatgcaaa atacattcgt tgatgattca  3360
tgataaaaca gtagcaacct attgcagtaa atcaagtgtt tactaaaagg tacataaagg  3420
gaaagtccaa tgtattaatt gttcaaagat gaaccgatat ggatggtgtg ccataaaaat  3480
gagatgtttt acagaggaag aacagaaaaa agaacgtaca tgcattaaat attatgcaag  3540
gagctttaaa aaagctcatg taagaagag taaaagaaa aataattta ttattaatt   3600
taatattgag agtgccgaca cagtatgcac taaaaaatat atctgtggtg tagtgagccg  3660
atacaaaagg atagtcactc gcattttcat aatacatctt atgttatgat tatgtgtcgg  3720
```

```
tgggacttca cgacgaaaac ccacaataaa aaaagagttc ggggtagggt taagcatagt    3780
tgaggcaact aaaacaatcaa gctaggatat gcagtagcag accgtaaggt cgttgtttag   3840
gtgtgttgta atacatacgc tattaagatg taaaaatacg gataccaatg aagggaaaag   3900
tataattttt ggatgtagtt tgtttgttca tctatgggca aactacgtcc aaagccgttt   3960
ccaaatctgc taaaaagtat atcctttcta aaatcaaagt caagtatgaa atcataaata   4020
aagtttaatt ttgaagttat tatgatatta tgttttcta ttaaaataaa ttaagtatat    4080
agaatagttt aataatagta tatacttaat gtgataagtg tctgacagtg tcacagaaag   4140
gatgattgtt atggattata agcggccggc cgaagcaaac ttaagagtgt gttgatagtg   4200
cagtatctta aaattttgta taataggaat tgaagttaaa ttagatgcta aaaatttgta   4260
attaagaagg agtgattaca tgaacaaaaa tataaaatat tctcaaaact ttttaacgaa   4320
tgaaaaagta ctcaaccaaa taataaaaca attgaattta aaagaaaccg ataccgttta   4380
cgaaattgga acaggtaaag ggcatttaac gacgaaactg gctaaaataa gtaaacaggt   4440
aacgtctatt gaattagaca gtcatctatt caacttatcg tcagaaaaat taaaactgaa   4500
tactcgtgtc actttaattc accaagatat tctacagttt caattcccta acaaacagag   4560
gtataaaatt gttgggagta ttccttacca tttaagcaca caaattatta aaaaagtggt   4620
ttttgaaagc catgcgtctg acatctatct gattgttgaa gaaggattct acaagcgtac   4680
cttggatatt caccgaacac tagggttgct cttgcacact caagtctcga ttcagcaatt   4740
gcttaagctg ccagcggaat gctttcatcc taaaccaaaa gtaaacagtg tcttaataaa   4800
acttacccgc cataccacag atgttccaga taaatattgg aagctatata cgtactttgt   4860
ttcaaaatgg gtcaatcgag aatatcgtca actgttact aaaaatcagt ttcatcaagc    4920
aatgaaacac gccaaagtaa acaatttaag taccgttact tatgagcaag tatttgtctat  4980
tttaatagt tatctattat ttaacgggag gaaataattc tatgagtcgc ttttgtaaat    5040
ttggaaagtt acacgttact aaagggaatg tgttt                              5075

SEQ ID NO: 89         moltype = DNA   length = 6662
FEATURE              Location/Qualifiers
misc_feature         1..6662
                     note = plasmid pMTL83245-Pfor-idi-FS
source               1..6662
                     mol_type = other DNA
                     organism = synthetic construct
SEQUENCE: 89
aaactcctttt ttgataatct catgaccaaa atccctaac gtgagttttc gttccactga    60
gcgtcagacc ccgtagaaaa gatcaaagga tcttcttgag atcctttttt tctgcgcgta   120
atctgctgct tgcaaacaaa aaaaccaccg ctaccagcgg tggtttgttt gccggatcaa   180
gagctaccaa ctctttttcc gaaggtaact ggcttcagca gagcgcagat accaaatact   240
gttcttctag tgtagccgta gttaggccac cacttcaaga actctgtagc accgcctaca   300
tacctcgctc tgctaatcct gttaccagtg gctgctgcca gtggcgataa gtcgtgtctt   360
accgggttgg actcaagacg atagttaccg gataaggcgc agcggtcggg ctgaacgggg   420
ggttcgtgca cacagcccag cttggagcga acgacctaca ccgaactgag atacctacag   480
cgtgagctat gagaaagcgc cacgcttccc gaagggagaa aggcggacag gtatccggta   540
agcggcaggg tcggaacagg agagcgcacg agggagcttc caggggggaaa cgcctggtat  600
ctttatagtc ctgtcgggtt tcgccacctc tgacttgagc gtcgatttt gtgatgctcg    660
tcagggggggc ggagcctatg gaaaaacgcc agcaacgcgg cctttttacg gttcctggcc  720
ttttgctggc cttttgctca catgttcttt cctgcgttat cccctgattc tgtggataac   780
cgtattaccg cctttgagtg agctgatacc gctcgccgca gccgaacgac cgagcgcagc   840
gagtcagtga gcgaggaagc ggaagagcgc ccaatacgca aaccgcctct caggataaaa   900
aaattgtaga taaattttat aaaatagttt tatctacaat ttttttatca ggaaacagct   960
atgaccgcgg ccgcaaatatg atatttatgt ccattgtgaa agggattata ttcaactatt 1020
attccagtta cgttcataga aatttttcctt tctaaaatat tttattccat gtcaagaact 1080
ctgtttattt cattaaagaa ctataagtac aaagtataag gcatttgaaa aataggctta 1140
gtatattgat tgattattta ttttaaaatg cctaagtgaa atatatacat attataacaa 1200
taaaataagt attagtgtag gatttttaaa tagagtatct attttcagat taaattttg   1260
attatttgat ttacattata taatattgag taaagtattg actagcaaaa ttttttgata   1320
cttttaattg tgaaatttct tatcaaaagt tatattttta aataatttt attgaaaaat   1380
acaactaaaa aggattatag tataagtgtg tgtaattttg tgttaaattt aaagggagga   1440
aatgaacatg aaacatatgg tgaccatgat tacgaattcg agctcggtac ccggggatcc  1500
tctagttgta tattaaaata gtagaataca taagatactt aatttaatta aagatagtta  1560
agtactttc aatgtgcttt tttagatgtt taatacaaat cttaattgt aaaagaaatg    1620
ctgtactatt tactgttcta gtgacgggat taaactattt taattataaa taaaaataaa  1680
gtacagttgt ttaaaattat atttgtatt aaatctaata gtacgatgta agttatttta   1740
tactattgct agtttaataa aaagatttaa ttatatactt gaaaggaga ggaactcgag    1800
atggcagagt atataatagc agtagatgag ttcgataacg aaataggatc aatagaaaag  1860
atggaagctc atagaaaggg aacacttcat agacattcat agagcttcat gtatttttagt 1920
aagaatcaac ttttattaca gaaagaaat gtaaagaaat atcactctcc aggattatgg   1980
acaaacactt gttgtagtca cccaagatat ggtgaatctc ttcatgatgc tatatacaga  2040
agattaaaag aagagatggg atttacttgc gaacttgaag agtattctc attcatatat    2100
aagtaaaac ttgaagataa tttatttgag aatgaataag accatgtatt tattggtaaa   2160
tatgatggta agataattgt taataaagat gaagttgatg attttaaatg ggtagacatt  2220
aatgaagtta aaaggacat aatagaaaga cctgaggcat atacttactg gtttaagtat   2280
cttgtaaata aagctgaaaa taagatattt aaataaaccg gtgcgccaag cttttaaagg   2340
agggggaaaaa atgaatttta gagtacattt acaggcagac aacgaacaga aaatatttca  2400
aaatcaaatg aaaccagagc cagaagcatc atatcttata aatcaaagaa gaagtgctaa  2460
ttataaacca acatttggga aaaacgattt tcttgatcag tctttaatat caaaatatga  2520
tggtgatgaa tatagaaaac tttcagaaaa gttaatagaa gaagtaaaga tatacatatc 2580
agcagagact atggatttag ttgctaaatt agaacttata gattctgtta gaaaacttgg  2640
acttgctaat cttttgaga aagaaataaa ggaagcatta gacagtatag cagcaataga   2700
atcagataat ttaggaacta gagacgatct ttatggaaca gctcttcatt ttaagattct  2760
tagacagcat ggatataagg taagtcaaga tatatttggt agattatgg atgagaaagg   2820
```

```
aacattagaa aatcatcact ttgcacactt aaaaggaatg ttagaattat ttgaggcaag  2880
taatcttgga tttgaaggtg aagacatatt agatgaagct aaagcatctc ttacacttgc  2940
tcttagagat tcaggacata tttgttatcc agactcaaac ttaagtagag atgtagttca  3000
tagtttagaa ttacctagtc atagaagagt tcaatggttc gatgtaaaat ggcagattaa  3060
tgcatacgaa aaagatattt gtagataaa  tgcaacttta ttagagttag caaagttaaa  3120
ttttaatgtt gttcaagctc agcttcagaa gaatcttaga gaagctagta gatggtgggc  3180
taatcttggt ttcgcagata atttaaagtt tgctagagat agacttgtag agtgttttc   3240
atgcgcagta ggtgtagcat ttgaaccaga gcattcatct tttagaatat gtttaactaa  3300
ggtaattaat cttgttctta ttatagatga tgtatacgat atatatggat ctgaagaaga  3360
gttaaaacat tttacaaatg ctgttgatag atgggacagt agagaaacag aacagcttcc  3420
tgaatgcatg aaaatgtgtt ttcaagtatt atataacact acttgcgaaa tagcaagaga  3480
gatagaagaa gaaaacggtt ggaatcaagt attacctcaa cttactaagg tttgggctga  3540
tttttgtaag gctctttttag ttgaagcaga gtggtacaat aaatcacata ttccaacatt  3600
agaagaatat cttagaaacg gatgtatatc aagtagtgta tctgtacttt tagttcactc  3660
tttcttttca ataactcatg aaggtacaaa agaaatggct gatttcttac ataaaaatga  3720
agatctttta tacaacataa gtcttatagt aagattaaac aatgatttag gtacatcagc  3780
tgctgaacag gaaagaggtg attctccttc ttctatagtt tgctatatga gagaagttaa  3840
tgcttctgaa gagactgcaa gaaagaatat aaagggaatg attgatacgt cttggaaaaa  3900
ggttaatgga aaatgtttca caactaacca agttccattt ctttcatcat tcatgaataa  3960
tgcaactaac atggcaagag tagcacactc attatataaa gacggtgatg gttttggtga  4020
tcaagaaaaa ggacctagaa cacatattct tagtttatta ttccaacctt tagtaaatta  4080
agctagcata aaaataagaa gcctgcattt gcaggcttct tattttatg  gcgcgccgcc  4140
attatttttt tgaacaattg acaattcatt tcttatttt  tattaagtga tagtcaaaag  4200
gcataacagt gctgaataga aagaaattta cagaaaagaa aattatagaa tttagtatga  4260
ttaattatac tcatttatga atgtttaatt gaatacaaaa aaaaatactt gttatgtatt  4320
caattacggg ttaaaatata gacaagttga aaaatttaat aaaaaaataa gtcctcagct  4380
cttatatatt aagctaccaa cttagtatat aagccaaaac ttaaatgtgc taccaacaca  4440
tcaagccgtt agagaactct atctatagca atatttcaaa tgtaccgaca tacaagagaa  4500
acattaacta tatatattca atttatgaga ttatcttaac agatataaat gtaaattgca  4560
ataagtaaga tttagaagtt tatagccttt gtgtattgga agcagtacgc aaaggctttt  4620
ttatttgata aaaattgaaa gtatatttat tttttcataa ttaatttatg aaaatgaaag  4680
ggggtgagca aagtgacaga ggaaagcagt atcttatcaa ataacaaggt attagcaata  4740
tcattattga ctttagcagt aaacattatg acttttatag tgcttgtagc taagtagtac  4800
gaaaggggga gcttttaaaaa gctccttgga atacatagaa ttcataaatt aatttatgaa  4860
aagaagggcg tatatgaaaa cttgtaaaaa ttgcaaagag tttattaaag atactgaaat  4920
atgcaaaata cattcgttga tgattcatga taaaacagta gcaacctatt gcagtaaata  4980
caatgagtca agatgtttac ataaagggaa agtccaatgt attaattgtt caaagatgaa  5040
ccgatatgga tggtgtgcca taaaaatgag atgtttaca gaggaagaac agaaaaaaga  5100
acgtacatgc attaaatatt atgcaaggag cttttaaaaaa gctcatgtaa agaagagtaa  5160
aaagaaaaaa taatttattt attaatttaa tattgagagt gccgacacag tatgcactaa  5220
aaaatatatc tgtggtgtag tgagccgata caaaaggata gtcactcgca ttttcataat  5280
acatcttatg ttatgattat gtgtcggtgg gacttcacga cgaaacccca caataaaaaa  5340
agagttcggg gtaggggttaa gcatagttga ggcaactaaa caatcaagct aggatatgca  5400
gtagcagacc gtaaggtcgt tgtttaggtg tgttgtaata catacgctat taagatgaa   5460
aaatacggat accaatgaag ggaaaagtat aattttttgga tgtagtttgt ttgttcatct  5520
atgggcaaac tacgtccaaa gccgtttcca aatctgctaa aaagtatatc ctttctaaaa  5580
tcaaagtcaa gtatgaaatc ataaataaag tttaattttg aagttattat gatattatgt  5640
ttttctatta aaataaatta agtatataga atagtttaat aatagtatat acttaatgtg  5700
ataagtgtct gacagtgtca cagaaaggat gattgttatg gattataagc ggccggccga  5760
agcaaactta agagtgtgtt gatagtcag  tatcttaaaa ttttgtataa taggaattga  5820
agttaaatta gatgctaaaa attttgtaatt aagaaggagt gattacatga acaaaaatat  5880
aaaaatattct caaaactttt taacgagtga aaaagtactc aaccaaataa taaaacaatt  5940
gaatttaaaa gaaaccgata ccgtttacga aattggaaca ggtaaagggc atttaacgac  6000
gaaactggct aaaataagta acaggtaac  gtcattgaa ttagacagtc atctattcaa  6060
cttatcgtca gaaaaattaa aactgaatac tcgtgtcact ttaattcacc aagatattct  6120
acagtttcaa ttccctaaca aacagaggta taaaattgtt gggagtattc cttaccattt  6180
aagcacacaa attattaaaa aagtggtttt tgaaagccat gcgtctgaca tctatctgat  6240
tgttgaagaa ggattctaca agcgtacctt ggatattcac cgaacactag gttgctctt   6300
gcacactcaa gtctcgattc agcaattgct taagctgcca gcggaatgct ttcatcctaa  6360
accaaaagta aacagtgtct taataaaact tacccgccat accacagtta ttccagataa  6420
atattggaag ctatatacgt actttgtttc aaaatgggtc aatcgagaat atcgtcaact  6480
gtttactaaa aatcagtttc atcaagcaat gaaacacgcc aaagtaaaca atttaagtac  6540
cgttacttat gagcaagtat tgtctatttt taatagttat ctattattta acgggaggaa  6600
ataattctat gagtcgcttt tgtaaatttg gaaagttaca cgttactaaa gggaatgtgt  6660
tt                                                                 6662
```

SEQ ID NO: 90        moltype = DNA   length = 7077  
FEATURE             Location/Qualifiers  
misc_feature        1..7077  
                           note = plasmid pMTL83245-Pfor-idi-ispA-FS  
source              1..7077  
                           mol_type = other DNA  
                           organism = synthetic construct  
SEQUENCE: 90

```
aaactccttt tgataatct  catgaccaaa atcccttaac gtgagttttc gttccactga   60
gcgtcagacc ccgtagaaaa gatcaaagga tcttcttgag atcctttttt tctgcgcgta  120
atctgctgct tgcaaacaaa aaaaccaccg ctaccagcgg tggtttgttt gccggatcaa  180
gagctaccaa ctctttttcc gaaggtaact ggcttcagca gagcgcagat accaaatact  240
gttcttctag tgtagccgta gttaggccac cacttcaaga actctgtagc accgcctaca  300
```

```
tacctcgctc tgctaatcct gttaccagtg gctgctgcca gtggcgataa gtcgtgtctt  360
accgggttgg actcaagacg atagttaccg gataaggcgc agcggtcggg ctgaacgggg  420
ggttcgtgca cacagcccag cttggagcga acgacctaca ccgaactgag atacctacag  480
cgtgagctat gagaaagcgc cacgcttccc gaagggagaa aggcggacag gtatccgta   540
agcggcagga tcggaacagg agagcgcacg agggagcttc caggggggaaa cgcctggtat  600
ctttatagtc ctgtcgggtt tcgccacctc tgacttgagc gtcgattttt gtgatgctcg  660
tcaggggggc ggagcctatg gaaaaacgcc agcaacgcgg ccttttttacg gttcctggcc  720
ttttgctggc cttttgctca catgttcttt cctgcgttat ccctgattc  tgtggataac  780
cgtattaccg cctttgagtg agctgatacc gctcgccgca gccgaacgac cgagcgcagc  840
gagtcagtga gcgaggaagc ggaagagcgc ccaatacgca gggcccctg  caggataaaa  900
aaattgtaga taaattttat aaaatagttt tatctacaat ttttttatca ggaaacagct  960
atgaccgcgg ccgcaccgag actagttgta tattaaaata gtagaataca taagatactt 1020
aatttaatta aagatagtta agtacttttc aatgtgcttt tttagatgtt taatacaaat 1080
ctttaattgt aaaagaaatg ctgtactatt tactgttcta gtgacgggat taaactgtat 1140
taattataaa taaaaaataa gtacagttgt ttaaaattat atttttgtatt aaatctaata 1200
gtacgatgta agttattttta tactattgct agtttaataa aaagatttaa ttatatactt 1260
gaaaggagaa ggaactcgag atggcagagt atataatagc agtagatgag ttcgataacg 1320
aaataggatc aatagaaaag atggaagctc ataagaaaagg aacactttcat agagcattca 1380
gtattttagt ttttaactca aagaatcaac ttttattaca gaaaagaaat gtaaagaaat 1440
atcactctcc aggattatgg acaaacactt gttgtagtca cccaagatat ggtgaatctc 1500
ttcatgatgc tatatacaga agattaaaag aagagatggg atttacttgc gaacttgaag 1560
aagtattctc attcatatat aaggtaaaac ttatatttgag aatgaatatg 1620
accatgtatt tattggtaaa tatgatggtg agataattgt taataaagat gaagttgatg 1680
attttaaatg ggtagacatt aatgaagtta aaaaggacat aatagaaaga cctgaggcat 1740
atacttactg gtttaagtat cttgtaaata aagctgaaaa taagatattt aaataaaccg 1800
gtcagtaacg aatagaatta gaaaaacaaa ggaggcaaga caatggattt cccacaacaa 1860
ttagaagcat gtgtaaaaca ggctaatcag gcacttagta gatttattgc tcctcttcct 1920
tttcaaaata caccagtagt agaaactatg caatacggtg cacttttagg tggtaaaaga 1980
ttaagaccat tcttagtata tgctacagga cacatgtttg gtgtatcaac taatacttta 2040
gacgctccag ctgctgctgt tgaatgtatt catgcttatt ctttaataca tgatgactta 2100
ccagcaatgt atgacgatga tttaagaaga ggtttaccta catgtcatgt taaatttggt 2160
gaagctaatg caattttagc aggtgacgct ttacaaactt agcttttttc tatactttca 2220
gatgcagaca tgcctgaagt ttcagataga gatagaattt ctatgatatc agagcttgca 2280
tctgcatcag gaatagctgg aatgtgcggt ggtcaaggcac ttgatttaga tgcagaaggt 2340
aaacacgtac cacttgatgc tttagagaga atacatagac ataaaacagg tgctcttata 2400
agagcagcag taagattagg tgctttaagt gctggtgaca agggtagaag agcacttcca 2460
gtacttgata agtatgcaga aagtatagga ttagcttttc aagttcaaga tgacatactt 2520
gacgttgttg gtgatactgc tacttttagga aaaagacagg gtgcagatca gcaattagga 2580
aaatctacat accctgcttt acttggatta gaacaggcta gaaagaaagc aagagactta 2640
atagatgacg caagacaaag tcttaaacag ttagctgaac aatcacttga cacaagtgca 2700
cttgaagcac ttgcagatta tattatacag agaaacaagt aaaagctttt aaggagggg  2760
aaaaaatgga atttagagta catttacagg cagacaacga acagaaaata tttcaaaatc 2820
aaatgaaacc agagccagaa gcatcatatc ttataaatca aagaagaagt gctaattata 2880
aaccaaacat ttgaaaaaac gatttttcttg atcagtcttt aatatcaaaa tatgatggtg 2940
atgaatatag aaaactttca gaaaagttaa tagaagaagt aaagatatac atatcagcag 3000
agactatgga tttagttgct aaattagaac ttatagattc tgttagaaaa cttggacttg 3060
ctaatctttt tgagaaagaa ataaagagaa cattagacag tatgcagcag atagaatcag 3120
ataatttagg aactagagac gatctttatg gaacagctct tcattttaag attcttagac 3180
agcatggata taaggtaagt caagatatat ttggtagatt tatggatgag aaaggaacat 3240
tagaaaatca tcactttgca cacttaaaag gaatgttaga attatttgag gcaagtaatc 3300
ttggatttga aggtgaagac atattagta agctaaagc atctcttaca cttgctctta 3360
gagattcagg acatatttgt tatccagact caaacttaag tagagatgta gttcatagtt 3420
tagaattacc tagtcataga agagttcaat ggttcgatgt aaaatggcag attaatgcat 3480
acgaaaaaga tatttgtaga gtaaatgcaa ctttattaga gttagcaaag ttaaattta  3540
atgttgttca agctcagctt cagaagaatc ttagagaagc tagtagatgg tgggctaatc 3600
ttggtttcgc agataattta aagtttgcta gagatagact tgtagagtgt ttttcatgcg 3660
cagtaggtgt agcatttgaa ccagagcatt catctttag aatatgttta actaaggtaa 3720
ttaatccttg tcttattata gatgatgtat acgatatata tggatctgaa gaagagttaa 3780
aacatttttac aaatgctgtt gatagatggg acagtagaga aacagaacg cttcctgaat 3840
gcatgaaaat gtgttttcaa gtattatata acactacttg cgaaatagca agagagatag 3900
aagaagaaaa cggttggaat caagtattac ctcaacttac taaggttttgg gctgattttt 3960
gtaaggctct tttagttgaa gcagagtggt acaataaatc acatattcca acattagaag 4020
aatatcttag aaacggatgt atatcaagta gtgtatctgt acttttaagtt cactcttttct 4080
tttcaataac tcatgaaggt acaaaagaaa tggctgaattt cttacataaa aatgaagatc 4140
ttttttatacaa cataagtctt atagtaagat taaacaatga tttaggtacc tcagctgctg 4200
aacaggaaaa aggtgattct ccttcttcta gtttgctag atgagagaa gttaatgctt 4260
ctgaagagac tgcaagaaag aatataaagg gaatgattga taatgcttgg aaaaaggtta 4320
atggaaaatg tttcacaact aaccaagttc catttctttc atcattcatg aataatgcaa 4380
ctaacatggc aagagtagca cactcattat ataaagacgg tgatggtttt ggtgatcaag 4440
aaaaaggacc tagaacacat attcttagtt tattattcca acctttagta aattaagcta 4500
gcataaaaat aagaagcctg catttgcagg cttcttatttt ttatgcgcg ccgccattat 4560
tttttgaac aattgacaat tcatttcttaa tttttatta agtgatagtc aaaaggcata 4620
acagtgctga atagaaaagaa atttacagaa aagaaaatta tagaatttag tatgattaat 4680
tatactcatt tatgaatgtt taattgaata caaaaaaaaa tacttgttat gtattcaatt 4740
acgggttaaa atatagacaa gttgaaaat ttaataaaaa aataagtcct cagctcttat 4800
atattaagct accaacttag tatataagcc aaaacttaaa tgtgctacca acacatcaag 4860
ccgtatagaga actctatcta tagcaatatt tcaaatgtac cgacatacaa gagaaacatt 4920
aactatatat attcaatttta tgagattatc ttaacagata taaatgtaaa ttgcaataag 4980
taagatttag aagtttatag cctttgtgta ttggaagcag tacgcaaagg cttttttatt 5040
```

```
tgataaaaat tagaagtata tttattttt cataattaat ttatgaaaat gaaaggggt    5100
gagcaaagtg acagaggaaa gcagtatctt atcaaataac aaggtattag caatatcatt   5160
attgacttta gcagtaaaca ttatgacttt tatagtgctt gtagctaagt agtacgaaag   5220
ggggagcttt aaaaagctcc ttggaataca tagaattcat aaattaattt atgaaaagaa   5280
gggcgtatat gaaaacttgt aaaaattgca aagagtttat taaagatact gaaatatgca   5340
aaatacattc gttgatgatt catgataaaa cagtagcaac ctattgcagt aaatacaatg   5400
agtcaagatg tttacataaa gggaaagtcc aatgtattaa ttgttcaaag atgaaccgat   5460
atggatggtg tgccataaaa atgagatgtt ttacagagga agaacagaaa aaagaacgta   5520
catgcattaa atattatgca aggagcttta aaaaagctca tgtaaagaag agtaaaaaga   5580
aaaaataatt tatttattaa tttaatattg agagtgccga cacagtatgc actaaaaaat   5640
atatctgtgg tgtagtgagc cgatacaaaa ggatagtcac tcgcattttc ataatacatc   5700
ttatgttatg attatgtgtc ggtgggactt cacgacgaaa acccacaata aaaaaagagt   5760
tcggggtagg gttaagcata gttgaggcaa ctaaacaatc aagctaggat atgcagtagc   5820
agaccgtaag gtcgttgttt aggtgtgttg taatacataa gctattaaga tgtaaaaata   5880
cggataccaa tgaagggaaa agtataattt ttggatgtag tttgtttgtt catctatggg   5940
caaactacgt ccaaagccgt ttccaaatct gctaaaaagt atatcctttc taaaatcaaa   6000
gtcaagtatg aaatcataaa taagtttaa ttttgaagtt attatgatat tatgtttttc    6060
tattaaaata aattaagtat atagaatagt ttaataatag tatatactta atgtgataag   6120
tgtctgacag tgtcacagaa aggatgattg ttatggatta taagcggccg gccgaagcaa   6180
acttaagagt gtgttgatag tgcagtatct taaaattttg tataatagga attgaagtta   6240
aattagatgc taaaaatttg taattaagaa ggagtgatta catgaacaaa aatataaaat   6300
attctcaaaa cttttttaacg agtgaaaaag tactcaacca aataataaaa caattgaatt   6360
taaaagaaac cgataccgtt tacgaaattg gaacaggtaa agggcattta acgacgaaac   6420
tggctaaaat aagtaaacag gtaacgtcta ttgaattaga cagtcatcta ttcaacttat   6480
cgtcagaaaa attaaaactg aatactcgtg tcactttaat tcaccaagat attctacagt   6540
ttcaattccc taacaaacag aggtataaaa ttgttgggaa tattccttac cattaagca    6600
cacaaattat taaaaagtg gttttttgaaa gccatgcgtc tgacatctat ctgattgttg    6660
aagaaggatt ctacaagcgt accttggata ttcaccgaac actagggttg ctcttgcaca   6720
ctcaagtctc gattcagcaa ttgcttaagc tgccagcgga atgctttcat cctaaaccaa   6780
aagtaaacag tgtcttaata aaacttaccc gccataccac agtgttcca gataaatatt     6840
ggaagctata tacgtacttt gtttcaaaat gggtcaatcg agaatatcct caactgttta   6900
ctaaaaatca gtttcatcaa gcaatgaaac acgccaaagt aaacaattta agtaccgtta   6960
cttatgagca agtattgtct atttttaata gttatctatt atttaacggg aggaaataat   7020
tctatgagtc gcttttgtaa atttggaaag ttacacgtta ctaaagggaa tgtgttt       7077
```

SEQ ID NO: 91          moltype = DNA   length = 10090
FEATURE                Location/Qualifiers
misc_feature           1..10090
                       note = plasmid pMTL 8314-Prnf-MK-PMK-PMD-Pfor-idi-ispA-FS
source                 1..10090
                       mol_type = other DNA
                       organism = synthetic construct
SEQUENCE: 91

```
aaactccttt ttgataatct catgaccaaa atccctttaac gtgagttttc gttccactga   60
gcgtcagacc ccgtagaaaa gatcaaagga tcttcttgag atcctttttt tctgcgcgta   120
atctgctgct tgcaaacaaa aaaaccaccg ctaccagcgg tggtttgttt gccggatcaa   180
gagctaccaa ctctttttcc gaaggtaact ggcttcagca gagcgcagat accaaatact   240
gttcttctag tgtagccgta gttaggccac cacttcaaga actctgtagc accgcctaca   300
tacctcgctc tgctaatcct gttaccagtg gctgctgcca gtggcgataa gtcgtgtctt   360
accgggttgg actcaagacg atagttaccg gataaggcgc agcggtcggg ctgaacgggg   420
ggttcgtgca cacagcccag cttggagcga acgacctaca ccgaactgag atacctacag   480
cgtgagctat gagaaagcgc cacgcttccc gaagggagaa aggcggacag gtatccggta   540
agcggcaggg tcggaacagg agagcgcacg agggagcttc caggggggaaa cgcctggtat   600
ctttatagtc ctgtcgggtt tcgccacctc tgacttgagc gtcgatttt gtgatgctcg    660
tcagggggcg gagcctatg gaaaacgcc agcaacgcgg ccttttttacg gttcctggcc     720
ttttgctggc cttttgctca catgttcttt cctgcgttat cccctgattc tgtggataac    780
cgtattaccg cctttgagtg agctgatacc gctcgccgca gccgaacgac cgagcgcagc   840
gagtcagtga gcgaggaagc ggaagagcgc ccaatacgca gggccccctg caggataaaa   900
aaattgtaga taaatttttat aaaatagttt tatctacaat ttttttatca ggaaacagct   960
atgaccgcgg ccgctaggtc tagaatatcg atacagataa aaaaatatat aatacagaag  1020
aaaaaattat aaatttgtgg tataataaag agtatagtaa tttaagttta aacctcgtga  1080
aaacgctaac aaataatagg aggtcaattg atgatagctg ttccatttaa cgctggaaaa  1140
ataaaagttt taattgaggc attagaatct ggaaattatt catcaataaa atcagatgta  1200
tatgacggaa tgttatatga tgcaccagat caccttaaca cattagtaga cagatttgta  1260
gaacttaata atataactga gccattagca gtaactatac agacaaatct tcctccttca  1320
agaggtcttg gatctagtgc agctgttgct gttgcttttg taagagcaag ttatgatttc  1380
ttaggaaaaa gtttaactaa agaagagctt ataggaaagg ctaattgggc tgaacaaata  1440
gctcatggaa agccatctgg aatagataca caaacaatag tatctggaaa gcctgtttg   1500
tttcaaaagg gacatgcaga aacacttaaa actctcttcac ttgatggata catggtagta  1560
attgatacag gtgttaaagg aagtacaaga caggctgtag aagatgttca taaacttttgc  1620
gaagatcctc aatatatgag tcacgtaaaa cacataggaa aacttgtact tagagcatct  1680
gatgttattg aacatcataa ctttgaagca cttgctgata tattcaatga atgtcatgct  1740
gatttaaagg ctcttacagt aagtcatgac aaaatagaac agttaatgaa gataggaaaa  1800
gaagtgtg ctatagctgg taaattaact ggtgctggtg gtggttc aatgttatta         1860
cttgcaaaag acttaccaac tgcaagaat atagttaaag cagtagaa agctggtgca      1920
gcacatactt ggattgaaaa tttaggtggt taagtcgaca aagacactaa aaaattataa  1980
aagtaaagga ggacattaaa tgatacagt aaaggcacca ggaaaattat atatagcagg   2040
tgaatacgct gttacagaac caggatataa atctgttctt atagctctg atagatttgt   2100
tacagctact attgaggaag ctgatcaata caaaggaaca atacattcaa aggcattaca  2160
```

```
tcacaatcca gtaacttta gtagagatga agattctatt gttatatcag acccacacgc   2220
agcaaaacaa cttaattatg tagtaactgc tatagaaata tttgagcaat atgcaaaatc   2280
atgtgacata gcaatgaagc attttcattt aactatagat tctaacttag atgatagtaa   2340
tggacataag tatggacttg gatcttctgc tgctgtttta gtttcagtaa ttaaagtact   2400
taacgaattt tatgatatga aactttcaaa cctttatata tataagttag cagtaattgc   2460
taatatgaaa ttacagagtt tatcttcatg cggtgatata gcagtaagtg tttattcagg   2520
ttggttagct tattctacat ttgaccatga atgggtaaaa caccagatag aagatacaac   2580
agttgaagaa gtacttatta aaaattggcc tggattacac atagaccac ttcaagctcc   2640
tgaaaatatg gaagttctta taggttggac aggtagtca gctagtagtc ctcattttgt   2700
ttctgaagtt aaaagactta agtcagatcc ttcatttac ggtgatttct tagaagattc   2760
acatagatgt gtagaaaaat taattcatgc attcaaaact aataatatta agggtgttca   2820
gaaaatggta agacagaata gaactattat acaaagaatg gataaggaag caacagttga   2880
tatagagact gagaagttaa aatattatg tgatattgct gaaaaatatc atggtgcaag   2940
taaaacttca ggtgctggtg gtggtgattg cggaataact ataataaata aggatgtaga   3000
caaagagaaa atatatgatg aatggactaa acatggaata aagcctctta agtttaatat   3060
ttatcatgga caataaccat ggtcaataat cttacaataa ataaaagaaa ggaggcaaaa   3120
atatgataaa atctggaaaa gcaagagcac acactaatat agcacttata aaatattggg   3180
gtaagaaaga tgaggcatta ataataccaa tgaataactc aatatcagta actttagaaa   3240
agttttatac tgaaacaaaa gttacattta acgatcagct tactcaagat caattttggc   3300
ttaatggtga aaaagtttct ggaaaagaat tagaaaagat ttcaaagtat atggatattg   3360
ttagaaatag agctggaata gattggtatg ctgagataga atctgataat tttgttccta   3420
cagctgctgg tcttgctagt tctgctagtg cttatgcagc attagctgc tgcatgtaacc   3480
aagcacttga tttacagtta agtgataaag acttaagtag attagctaga attggatcag   3540
gatcagcatc aagatcaata tacggtggtt ttgcagaatg ggaaaaagga tataatgacg   3600
aaacttctta tgctgttcca ttagaaagta atcactttga agatgatctt gctatgattt   3660
ttgtagtaat aaaccaacta tctaaaaagg ttccttcaag atatggaatg tctccttacaa  3720
gaaatacaag tagattctat caatattggt tagaccatat tgatgaagaat cttgcagaag   3780
caaaggcagc aatacaagat aaggatttta agagattagg tgaagttatt gaagagaatg   3840
gacttagaat gcatgctaca aatcttggat caactccacc ttttacttac ttagtacaag   3900
agtcatacga tgtaatggca ttagtacatg agtgtagaga acaggatat ccatgctgt    3960
tcactatgga tgctggacct aatgtaaaaa tacttgtaga gaagaaaaac aaacaacaga   4020
taatagataa acttttaact cagttcgata taatcagat aatagatagt gatattatag   4080
ctacaggtat tgaaattata gaataaacta gttgtatatt aaaatagtag aatacataag   4140
atacttaatt taattaaaga tagttaagta cttttcaatg tgcttttta gatgtttaat   4200
acaaatcttt aattgtaaaa gaaatgctgt actatttact gttctagtga cgggattaaa   4260
ctgtattaat tataaataaa aaataagtac agttgtttaa aattatatt tgtattaaat   4320
ctaatagtac gatgtaagtt attttatact attgctagtt taataaaaag atttaattat   4380
atacttgaaa aggagaggaa ctcgagatgg cagagtatat aatagcagta gatgagttcg   4440
ataacgaaat aggatcaata gaaaagatgg aagctcatag aaaggaaca cttcatagag   4500
cattcagtat tttagttttt aactcaaaga atcaactttt attacagaaa agaaatgtaa   4560
agaaatatca ctctccagga ttatggacaa acacttgttg tagtcaccca agatatggtg   4620
aatctcttca tgatgctata tacagaagat taaagaaga gatgggattt acttgcgaac   4680
ttgaagaagt attctcattc atatataagg taaaacttga agataattta tttgagaatg   4740
aatatgacca tgtatttatt ggtaaatatg atggtgagat aattgttaat aaagatgaag   4800
ttgatgattt taaatgggta gacattaatg aagttaaaaa ggacataata gaaagacctg   4860
aggcatatac ttactggttt aagtatcttg taaataaagc tgaaataag atatttaaat   4920
aaaccggtca gtaacgaata gaattagaaa aacaaaggag caagacaat ggatttccca   4980
caacaattag aagcatgtgt aaaacaggct aatcaggcac ttagtagatt tattgctcct   5040
cttccttttc aaaatacacc agtagtagaa actatgcaat acggtgcact tttaggtggt   5100
aaaagattaa gaccattctt agtatatgct acaggacaca tgtttggtgt atcaactaat   5160
acttagacg ctccagctgc tgctgttgaa tgtattcatg cttattcttt aatacatgat   5220
gacttaccag caatggatga cgatgattta agaagaggtt tacctacatg tcatgttaaa   5280
tttggtgaag ctaatgcaat tttagcaggt gacgctttac aaactttagc ttttctata    5340
ctttcagatg cagacatgcc tgaagtttca gatagagata gaattctat gatatcagag   5400
cttgcatctg catcaggaat agctggaatg tgcggtgctc aagcacttga tttagatga    5460
gaaggtaaac acgtaccact tgatgcttta gagagaatac atagacataa aacaggtgct   5520
cttataagag cagcagtaag attaggtgct taagtgctg gtgacaaggg tagaagagca   5580
cttccagtac ttgataagta tgcagaaagt ataggattag ctttttcaagt tcaagatgac   5640
atacttgacg ttgttggtga tactgctact ttaggaaaaa gacagggtgc agatcagcaa   5700
ttaggaaaat ctacatcccc tgctttactt ggattagaac aggctagaaa gaaagcaaga   5760
gacttaatag atgacgcaag acaaagtctt aaacagttag ctgaacaatc acttgacaca   5820
agtgcacttg aagcacttgc agattatatt atacagagaa acaagtaaaa gcttttaaag   5880
gagggaaaa aatggaattt agagtacatt tacaggcaga caacgaacag aaaatatttc   5940
aaaatcaaat gaaaccagag ccagaagcat catatctcat aaatcaaaga agaagtgcta   6000
attataaacc aaacatttgg aaaaacgatt tccttgatca gtctttaata tcaaaatatg   6060
atggtgatga atatagaaaa cttcagaaa agttaataga agagtaaag atatacatat   6120
cagcagagac tatggattta gttgctaaat tagaacttat agattctgtt agaaaacttg   6180
gacttgctaa tcttttgag aaagaaataa aggaagcatt agacagtata gcagcaatag   6240
aatcagataa tttaggaact agagacgatc agctcttcat tttaagattc                6300
ttagacagca tggatataag gtaagtcaag atatatttgg tagatttatg gatgagaaag   6360
gaacattaga aaatcatcac tttgcacact aaaaggaat gttagaatta tttgaggcaa   6420
gtaatcttgg atttgaaggt gaagacatat tagatgaagc taaagcatct cttcacttg    6480
ctcttagaga ttcaggacat attttgttatc cagactcaaa cttaagtaga gatgtagttc   6540
atagtttaga attacctagt catagaagag ttcaatggtt gcatgtaaaa tggcagatta   6600
atgcatacga aaaagatatt tgtagagtaa atgcaacttt attagagtta gcaaagtaa    6660
attttaatgt tgttcaagct cagcttcaga agaatcttag agaagctagt agatggtggg   6720
ctaatcttgg tttcgcagat aatttaaagt tgctagaga tagacttgta gagtgttttt   6780
catgcgcagt aggtgtagca tttgaaccag agcattcatc ttttagaata tgtttaacta   6840
aggtaattaa tcttgttctt attatagatg atgtatacga tatatatgga tctgaagaag   6900
```

-continued

```
agttaaaaca ttttacaaat gctgttgata gatgggacag tagagaaaca gaacagcttc    6960
ctgaatgcat gaaaatgtgt tttcaagtat tatataacac tacttgcgaa atagcaagag    7020
agatagaaga agaaaacggt tggaatcaag tattacctca acttactaag gtttgggctg    7080
atttttgtaa ggctctttta gttgaagcag agtggtacaa taaatcacat attccaacat    7140
tagaagaata tcttagaaac ggatgtatat caagtagtgt atctgtactt ttagttcact    7200
cttctttttc aataactcat gaaggtacaa agaaatggc tgatttctta cataaaaatg    7260
aagatctttt atacaacata agtcttatag taagattaaa caatgattta ggtacatcag    7320
ctgctgaaca ggaaagaggt gattctcctt cttctatagt ttgctatatg agagaagtta    7380
atgcttctga agagactgca agaaagaata taaagggaat gattgataat gcttggaaaa    7440
aggttaatgg aaaatgtttc acaactaacc aagttccatt tctttcatca ttcatgaata    7500
atgcaactaa catggcaaga gtagcacact cattatataa agacggtgat ggttttggtg    7560
atcaagaaaa aggacctaga acacatattc ttagtttatt attccaacct ttagtaaatt    7620
aagctagcat aaaaataaga agcctgcatt tgcaggcttc ttatttttat ggcgcgccgc    7680
cattattttt ttgaacaatt gacaattcat ttcttatttt ttattaagtg atagtcaaaa    7740
ggcataacag tgctgaatag aaagaaattt acagaaaaga aaattataga atttagtatg    7800
attaattata ctcatttatg aatgtttaat tgaatacaaa aaaaaatact tgttatgtat    7860
tcaattacgg gttaaaatat agacaagttg aaaaatttaa taaaaaaata agtcctcagc    7920
tcttatatat taagctacca acttagtata taagccaaaa cttaaatgtg ctaccaacac    7980
atcaagccgt tagagaactc tatctatagc aatatttcaa atgtaccgac atacaagaga    8040
aacattaact atatatattc aatttatgag attatcttaa cagatataaa tgtaaattgc    8100
aataagtaag atttagaagt ttatagcctt tgtgtattgg aagcagtacg caaaggcttt    8160
tttatttgat aaaaattaga agtatattta ttttttcata attaatttat gaaaatgaaa    8220
gggggtgagc aaagtgacag aggaaagcag tatcttatca aataacaagg tattagcaat    8280
atcattattg actttagcag taaacattat gactttttata gtgcttgtag ctaagtagta    8340
cgaaggggg agctttaaaa agctccttgg aatacataga attcataaat taatttatga    8400
aaagaagggc gtatatgaaa acttgtaaaa attgcaaaga gtttattaaa gatactgaaa    8460
tatgcaaaat acattcgttg atgattcatg ataaaacagt agcaacctat tgcagtaaat    8520
acaatgagtc aagatgttta cataaaggga aagtccaatg tattaattgt tcaaagatga    8580
accgatatgg atggtgtgcc ataaaaatga gatgttttac agaggaagaa cagaaaaaag    8640
aacgtacatg cattaaatat tatgcaagga gctttaaaaa agtcatgta aagaagagta    8700
aaaagaaaaa ataattttatt tattaattta atattgagag tgccgacaca gtatgcacta    8760
aaaaatatat ctgtggtgta gtgagccgat acaaaaggat agtcactcgc attttcataa    8820
tacatcttat gttatgatta tgtgtcggtg ggacttcacg acgaaaaccc acaataaaaa    8880
aagagttcgg ggtagggtta agcatagttg aggcaactaa acaatcaagc taggatatgc    8940
agtagcagac cgtaaggtcg ttgtttaggt gtgttgtaat acatacgcta ttaagatgta    9000
aaaatacgga taccaatgaa gggaaaagta taatttttgg atgtagtttg tttgttcatc    9060
tatgggcaaa ctacgtccaa agccgtttcc aaatctgcta aaaagtatat cctttctaaa    9120
atcaaagtca agtatgaaat cataaataaa gtttaatttt gaagttatta tgatattatg    9180
tttttctatt aaaataaatt aagtatatag aatagtttaa taatagtata tacttaatgt    9240
gataagtgtc tgacagtgtc acagaaagga tgattgttat ggattataag cggccggcca    9300
gtgggcaagt tgaaaaattc acaaaaatgt ggtataatat ctttgttcat tagagcgata    9360
aacttgaatt tgagagggaa cttagatggt atttgaaaaa attgataaaa atagttggaa    9420
cagaaaagag tattttgacc actactttgc aagtgtacct tgtacctaca gcatgaccgt    9480
taaagtggat atcacacaaa taaggaaaa gggaatgcaaa ctatatcctg caatgcttta    9540
ttatattgca atgattgtaa accgccattc agagtttagg acggcaatca atcaagatgg    9600
tgaattgggg atatatgatg agatgatacc aagctataca atatttcaca atgatactga    9660
aacattttcc agcctttgga ctgagtgtaa gtctgacttt aaatcatttt tagcagatta    9720
tgaaagtgat acgcaacggt atggaaacaa tcatagaatg gaaggaaagc caaatgctcc    9780
ggaaaacatt tttaatgtat ctatgatacc gtggtcaacc ttcgatggct ttaatctgaa    9840
tttgcagaaa ggatatgatt atttgattcc tattttttact atggggaaat attataaaga    9900
agataacaaa attatacttc cttttggcaat tcaagttcat cacgcagtat gtgacgagtt    9960
tcacatttgc cgttttgtaa acgaattgca ggaattgata aatagttaac ttcaggtttg   10020
tctgtaacta aaaacaagta tttaagcaaa aacatcgtag aaatacggtg ttttttgtta   10080
ccctaagttt                                                          10090

SEQ ID NO: 92          moltype = DNA   length = 25
FEATURE                Location/Qualifiers
misc_feature           1..25
                       note = oligonucleotide repHF
source                 1..25
                       mol_type = other DNA
                       organism = synthetic construct
SEQUENCE: 92
aagaagggcg tatatgaaaa cttgt                                             25

SEQ ID NO: 93          moltype = DNA   length = 25
FEATURE                Location/Qualifiers
misc_feature           1..25
                       note = oligonucleotide catR
source                 1..25
                       mol_type = other DNA
                       organism = synthetic construct
SEQUENCE: 93
ttcgtttaca aaacggcaaa tgtga                                             25

SEQ ID NO: 94          moltype = DNA   length = 20
FEATURE                Location/Qualifiers
misc_feature           1..20
                       note = oligonucleotide MK-RTPCR-F
```

```
-continued source              1..20
                    mol_type = other DNA
                    organism = synthetic construct
SEQUENCE: 94
gtgctggtag aggtggttca                                              20

SEQ ID NO: 95       moltype = DNA   length = 20
FEATURE             Location/Qualifiers
misc_feature        1..20
                    note = oligonucleotide MK-RTPCR-R
source              1..20
                    mol_type = other DNA
                    organism = synthetic construct
SEQUENCE: 95
ccaagtatgt gctgcaccag                                              20

SEQ ID NO: 96       moltype = DNA   length = 20
FEATURE             Location/Qualifiers
misc_feature        1..20
                    note = oligonucleotide PMK-RTPCR-F
source              1..20
                    mol_type = other DNA
                    organism = synthetic construct
SEQUENCE: 96
atatcagacc cacacgcagc                                              20

SEQ ID NO: 97       moltype = DNA   length = 24
FEATURE             Location/Qualifiers
misc_feature        1..24
                    note = oligonucleotide PMK-RTPCR-R
source              1..24
                    mol_type = other DNA
                    organism = synthetic construct
SEQUENCE: 97
aatgcttcat tgctatgtca catg                                         24

SEQ ID NO: 98       moltype = DNA   length = 20
FEATURE             Location/Qualifiers
misc_feature        1..20
                    note = oligonucleotide PMD-RTPCR-F
source              1..20
                    mol_type = other DNA
                    organism = synthetic construct
SEQUENCE: 98
gcagaagcaa aggcagcaat                                              20

SEQ ID NO: 99       moltype = DNA   length = 23
FEATURE             Location/Qualifiers
misc_feature        1..23
                    note = oligonucleotide PMD-RTPCR-R
source              1..23
                    mol_type = other DNA
                    organism = synthetic construct
SEQUENCE: 99
ttgatccaag atttgtagca tgc                                          23

SEQ ID NO: 100      moltype = DNA   length = 24
FEATURE             Location/Qualifiers
misc_feature        1..24
                    note = oligonucleotide idi-RTPCR-F
source              1..24
                    mol_type = other DNA
                    organism = synthetic construct
SEQUENCE: 100
ggacaaacac ttgttgtagt cacc                                         24

SEQ ID NO: 101      moltype = DNA   length = 22
FEATURE             Location/Qualifiers
misc_feature        1..22
                    note = oligonucleotide idi-RTPCR-R
source              1..22
                    mol_type = other DNA
                    organism = synthetic construct
SEQUENCE: 101
tcaagttcgc aagtaaatcc ca                                           22

SEQ ID NO: 102      moltype = DNA   length = 20
FEATURE             Location/Qualifiers
misc_feature        1..20
```

| | | |
|---|---|---|
| | note = oligonucleotide ispA-RTPCR-F | |
| source | 1..20 | |
| | mol_type = other DNA | |
| | organism = synthetic construct | |
| SEQUENCE: 102 | | |
| accagcaatg gatgacgatg | | 20 |
| | | |
| SEQ ID NO: 103 | moltype = DNA  length = 21 | |
| FEATURE | Location/Qualifiers | |
| misc_feature | 1..21 | |
| | note = oligonucleotide ispA-RTPCR-R | |
| source | 1..21 | |
| | mol_type = other DNA | |
| | organism = synthetic construct | |
| SEQUENCE: 103 | | |
| agtttgtaaa gcgtcacctg c | | 21 |
| | | |
| SEQ ID NO: 104 | moltype = DNA  length = 20 | |
| FEATURE | Location/Qualifiers | |
| misc_feature | 1..20 | |
| | note = oligonucleotide FS-RTPCR-F | |
| source | 1..20 | |
| | mol_type = other DNA | |
| | organism = synthetic construct | |
| SEQUENCE: 104 | | |
| aagctagtag atggtgggct | | 20 |
| | | |
| SEQ ID NO: 105 | moltype = DNA  length = 20 | |
| FEATURE | Location/Qualifiers | |
| misc_feature | 1..20 | |
| | note = oligonucleotide FS-RTPCR-R | |
| source | 1..20 | |
| | mol_type = other DNA | |
| | organism = synthetic construct | |
| SEQUENCE: 105 | | |
| aatgctacac ctactgcgca | | 20 |
| | | |
| SEQ ID NO: 106 | moltype = DNA  length = 18 | |
| FEATURE | Location/Qualifiers | |
| misc_feature | 1..18 | |
| | note = oligonucleotide ermB-F | |
| source | 1..18 | |
| | mol_type = other DNA | |
| | organism = synthetic construct | |
| SEQUENCE: 106 | | |
| tttgtaatta agaaggag | | 18 |
| | | |
| SEQ ID NO: 107 | moltype = DNA  length = 18 | |
| FEATURE | Location/Qualifiers | |
| misc_feature | 1..18 | |
| | note = oligonucleotide ermB-R | |
| source | 1..18 | |
| | mol_type = other DNA | |
| | organism = synthetic construct | |
| SEQUENCE: 107 | | |
| gtagaatcct tcttcaac | | 18 |
| | | |
| SEQ ID NO: 108 | moltype = DNA  length = 20 | |
| FEATURE | Location/Qualifiers | |
| misc_feature | 1..20 | |
| | note = oligonucleotide GnK-F | |
| source | 1..20 | |
| | mol_type = other DNA | |
| | organism = synthetic construct | |
| SEQUENCE: 108 | | |
| tcaggacctt ctggaactgg | | 20 |
| | | |
| SEQ ID NO: 109 | moltype = DNA  length = 20 | |
| FEATURE | Location/Qualifiers | |
| misc_feature | 1..20 | |
| | note = oligonucleotide GnK-R | |
| source | 1..20 | |
| | mol_type = other DNA | |
| | organism = synthetic construct | |
| SEQUENCE: 109 | | |
| acctcccctt ttcttggaga | | 20 |
| | | |
| SEQ ID NO: 110 | moltype = DNA  length = 20 | |
| FEATURE | Location/Qualifiers | |

```
misc_feature           1..20
                       note = oligonucleotide FoT4L-F
source                 1..20
                       mol_type = other DNA
                       organism = synthetic construct
SEQUENCE: 110
caggtttcgg tgctgaccta                                                20

SEQ ID NO: 111         moltype = DNA  length = 20
FEATURE                Location/Qualifiers
misc_feature           1..20
                       note = oligonucleotide FoT4L-F
source                 1..20
                       mol_type = other DNA
                       organism = synthetic construct
SEQUENCE: 111
aactccgccg ttgtatttca                                                20
```

MICROBIAL FERMENTATION FOR THE PRODUCTION OF TERPENES

CROSS REFERENCE TO RELATED APPLICATIONS

This application is a continuation of U.S. patent application Ser. No. 17/095,064 filed Nov. 11, 2020, which is a continuation of U.S. patent application Ser. No. 15/867,306 filed Jan. 10, 2018 (U.S. Pat. No. 10,913,958 issued Feb. 9, 2021), which is a continuation of U.S. patent application Ser. No. 14/656,827 filed Mar. 13, 2015, which is a continuation of U.S. patent application Ser. No. 13/909,012 filed Jun. 3, 2013, which claims the benefit of U.S. Provisional Patent Application 61/654,412 filed Jun. 1, 2012, the entirety of which are incorporated herein by reference.

REFERENCE TO A SEQUENCE LISTING

The application contains a Sequence Listing which has been submitted electronically in ST.26 Sequence listing XML format and is hereby incorporated by reference in its entirety. Said ST.26 Sequence listing XML, created on Aug. 30, 2022, is named LT079US5-Sequences.xml and is 306,151 bytes in size.

FIELD OF THE INVENTION

The present invention relates to recombinant microorganisms and methods for the production of terpenes and/or precursors thereof by microbial fermentation of a substrate comprising CO.

BACKGROUND OF THE INVENTION

Terpenes are a diverse class of naturally occurring chemicals composed of five-carbon isoprene units. Terpene derivatives include terpenoids (also known as isoprenoids) which may be formed by oxidation or rearrangement of the carbon backbone or a number of functional group additions or rearrangements.

Examples of terpenes include: isoprene (C5 hemiterpene), farnesene (C15 Sesquiterpenes), artemisinin (C15 Sesquiterpenes), citral (C10 Monoterpenes), carotenoids (C40 Tetraterpenes), menthol (C10 Monoterpenes), Camphor (C10 Monoterpenes), and cannabinoids.

Terpenes are valuable commercial products used in a diverse number of industries. The highest tonnage uses of terpenes are as resins, solvents, fragrances and vitamins. For example, isoprene is used in the production of synthetic rubber (cis-1,4-polyisoprene) for example in the tyre industry; farnesene is used as an energy dense drop-in fuel used for transportation or as jet-fuel; artemisinin is used as a malaria drug; and citral, carotenoids, menthol, camphor, and cannabinoids are used in the manufacture of pharmaceuticals, butadiene, and as aromatic ingredients.

Terpenes may be produced from petrochemical sources and from terpene feed-stocks, such as turpentine. For example, isoprene is produced petrochemically as a by-product of naphtha or oil cracking in the production of ethylene. Many terpenes are also extracted in relatively small quantities from natural sources. However, these production methods are expensive, unsustainable and often cause environmental problems including contributing to climate change.

Due to the extremely flammable nature of isoprene, known methods of production require extensive safeguards to limit potential for fire and explosions.

It is an object of the invention to overcome one or more of the disadvantages of the prior art, or at least to provide the public with an alternative means for producing terpenes and other related products.

SUMMARY OF THE INVENTION

Microbial fermentation provides an alternative option for the production of terpenes. Terpenes are ubiquitous in nature, for example they are involved in bacterial cell wall biosynthesis, and they are produced by some trees (for example poplar) to protect leaves from UV light exposure. However, not all bacteria comprise the necessary cellular machinery to produce terpenes and/or their precursors as metabolic products. For example, carboxydotrophic acetogens, such as *C. autoethanogenum* or *C. ljungdahlii*, which are able to ferment substrates comprising carbon monoxide to produce products such as ethanol, are not known to produce and emit any terpenes and/or their precursors as metabolic products. In addition, most bacteria are not known to produce any terpenes which are of commercial value.

The invention generally provides, inter alia, methods for the production of one or more terpenes and/or precursors thereof by microbial fermentation of a substrate comprising CO, and recombinant microorganisms of use in such methods.

In a first aspect, the invention provides a carboxydotrophic acetogenic recombinant microorganism capable of producing one or more terpenes and/or precursors thereof and optionally one or more other products by fermentation of a substrate comprising CO.

In one particular embodiment, the microorganism is adapted to express one or more enzymes in the mevalonate (MVA) pathway not present in a parental microorganism from which the recombinant microorganism is derived (may be referred to herein as an exogenous enzyme). In another embodiment, the microorganism is adapted to over-express one or more enzymes in the mevalonate (MVA) pathway which are present in a parental microorganism from which the recombinant microorganism is derived (may be referred to herein as an endogenous enzyme).

In a further embodiment, the microorganism is adapted to:
a) express one or more exogenous enzymes in the mevalonate (MVA) pathway and/or overexpress one or more endogenous enzyme in the mevalonate (MVA) pathway; and
b) express one or more exogenous enzymes in the DXS pathway and/or overexpress one or more endogenous enzymes in the DXS pathway.

In one embodiment, the one or more enzymes from the mevalonate (MVA) pathway is selected from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a further embodiment, the one or more enzymes from the DXS pathway is selected from the group consisting of:
a) 1-deoxy-D-xylulose-5-phosphate synthase DXS (EC: 2.2.1.7), b) 1-deoxy-D-xylulose 5-phosphate reductoisomerase DXR (EC:1.1.1.267),
c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12),
f) 4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, one or more further exogenous or endogenous enzymes are expressed or over-expressed to result in the production of a terpene compound or a precursor thereof wherein the exogenous enzyme that is expressed, or the endogenous enzyme that is overexpressed, is selected from the group consisting of:
a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

In one embodiment, the parental microorganism is capable of fermenting a substrate comprising CO to produce Acetyl CoA, but not of converting Acetyl CoA to mevalonic acid or isopentenyl pyrophosphate (IPP) and the recombinant microorganism is adapted to express one or more enzymes involved in the mevalonate pathway.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

In one embodiment, the microorganism comprises one or more exogenous nucleic acids adapted to increase expression of one or more endogenous nucleic acids and which one or more endogenous nucleic acids encode one or more of the enzymes referred to herein before.

In one embodiment, the one or more exogenous nucleic acids adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster or Phosphotransacetylase/Acetate kinase operon promoters.

In one embodiment, the microorganism comprises one or more exogenous nucleic acids encoding and adapted to express one or more of the enzymes referred to hereinbefore. In one embodiment, the microorganisms comprise one or more exogenous nucleic acids encoding and adapted to express at least two of the enzymes. In other embodiments, the microorganism comprises one or more exogenous nucleic acids encoding and adapted to express at least three, at least four, at least five, at least six, at least seven, at least eight, at least nine or more of the enzymes.

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid.

In one particular embodiment, the parental microorganism is selected from the group of carboxydotrophic acetogenic bacteria. In certain embodiments the microorganism is selected from the group comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kivui*.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks one or more genes in the DXS pathway and/or the mevalonate (MVA) pathway. In one embodiment, the parental microorganism lacks one or more genes encoding an enzyme selected from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33),
g) 1-deoxy-D-xylulose-5-phosphate synthase DXS (EC: 2.2.1.7),
h) 1-deoxy-D-xylulose 5-phosphate reductoisomerase DXR (EC:1.1.1.267),
i) 2-C-methyl-D-erythritol 4-phosphate cytidylyltransferase IspD (EC:2.7.7.60),
j) 4-diphosphocytidyl-2-C-methyl-D-erythritol kinase IspE (EC:2.7.1.148),
k) 2-C-methyl-D-erythritol 2,4-cyclodiphosphate synthase IspF (EC:4.6.1.12),
l) 4-hydroxy-3-methylbut-2-en-1-yl diphosphate synthase IspG (EC:1.17.7.1),
m) 4-hydroxy-3-methylbut-2-enyl diphosphate reductase (EC:1.17.1.2), and
n) a functionally equivalent variant of any one thereof.

In a second aspect, the invention provides a nucleic acid encoding one or more enzymes which when expressed in a microorganism allows the microorganism to produce one or more terpenes and/or precursors thereof by fermentation of a substrate comprising CO.

In one embodiment, the nucleic acid encodes two or more enzymes which when expressed in a microorganism allows the microorganism to produce one or more terpenes and/or precursors thereof by fermentation of a substrate comprising CO. In one embodiment, a nucleic acid of the invention encodes at least three, at least four, at least five, at least six, at least seven, at least eight, at least nine or more of such enzymes.

In one embodiment, the nucleic acid encodes one or more enzymes in the mevalonate (MVA) pathway. In one embodiment, the one or more enzymes is chosen from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a particular embodiment, the nucleic acid encodes thiolase (which may be an acetyl CoA c-acetyltransferase), HMG-CoA synthase and HMG-CoA reductase, In a further embodiment, the nucleic acid encodes one or more enzymes in the mevalonate (MVA) pathway and one or more further nucleic acids in the DXS pathway. In one embodiment, the one or more enzymes from the DXS pathway is selected from the group consisting of:
  a) 1-deoxy-D-xylulose-5-phosphate synthase DXS (EC: 2.2.1.7),
  b) 1-deoxy-D-xylulose 5-phosphate reductoisomerase DXR (EC:1.1.1.267),
  c) 2-C-methyl-D-erythritol 4-phosphate cytidylyltransferase IspD (EC:2.7.7.60),
  d) 4-diphosphocytidyl-2-C-methyl-D-erythritol kinase IspE (EC:2.7.1.148),
  e) 2-C-methyl-D-erythritol 2,4-cyclodiphosphate synthase IspF (EC:4.6.1.12),
  f) 4-hydroxy-3-methylbut-2-en-1-yl diphosphate synthase IspG (EC:1.17.7.1),
  g) 4-hydroxy-3-methylbut-2-enyl diphosphate reductase (EC:1.17.1.2), and
  h) a functionally equivalent variant of any one thereof.

In a further embodiment, the nucleic acid encodes one or more further exogenous or endogenous enzymes are expressed or over-expressed to result in the production of a terpene compound or a precursor thereof wherein the exogenous nucleic acid that is expressed, or the endogenous enzyme that is overexpressed, encodes and enzyme selected from the group consisting of:
  a) geranyltranstransferase Fps (EC:2.5.1.10),
  b) heptaprenyl diphosphate synthase (EC:2.5.1.10),
  c) octaprenyl-diphosphate synthase (EC:2.5.1.90),
  d) isoprene synthase (EC 4.2.3.27),
  e) isopentenyl-diphosphate delta-isomerase (EC 5.3.3.2),
  f) farnesene synthase (EC 4.2.3.46/EC 4.2.3.47), and
  g) a functionally equivalent variant of any one thereof.

In one embodiment, the nucleic acid encoding thiolase (EC 2.3.1.9) has the sequence SEQ ID NO: 40 or is a functionally equivalent variant thereof.

In one embodiment, the nucleic acid encoding thiolase (EC 2.3.1.9) is acetyl CoA c-acetyl transferase that has the sequence SEQ ID NO: 41 or is a functionally equivalent variant thereof.

In one embodiment, the nucleic acid encoding HMG-CoA synthase (EC 2.3.3.10) has the sequence SEQ ID NO: 42 or is a functionally equivalent variant thereof.

In one embodiment, the nucleic acid encoding HMG-CoA reductase (EC 1.1.1.88) has the sequence SEQ ID NO: 43 or is a functionally equivalent variant thereof.

In one embodiment, the nucleic acid encoding Mevalonate kinase (EC 2.7.1.36) has the sequence SEQ ID NO: 51 or is a functionally equivalent variant thereof.

In one embodiment, the nucleic acid encoding Phosphomevalonate kinase (EC 2.7.4.2) has the sequence SEQ ID NO: 52 or is a functionally equivalent variant thereof.

In one embodiment, the nucleic acid encoding Mevalonate Diphosphate decarboxylase (EC 4.1.1.33) has the sequence SEQ ID NO: 53 or is a functionally equivalent variant thereof.

In one embodiment, the nucleic acid encoding 1-deoxy-D-xylulose-5-phosphate synthase DXS (EC:2.2.1.7) has the sequence SEQ ID NO: 1 or is a functionally equivalent variant thereof.

In one embodiment, the nucleic acid encoding 1-deoxy-D-xylulose 5-phosphate reductoisomerase DXR (EC: 1.1.1.267) has the sequence SEQ ID NO: 3 or is a functionally equivalent variant thereof.

In one embodiment, the nucleic acid encoding 2-C-methyl-D-erythritol 4-phosphate cytidylyltransferase IspD (EC:2.7.7.60) has the sequence SEQ ID NO: 5 or is a functionally equivalent variant thereof.

In one embodiment, the nucleic acid encoding 4-diphosphocytidyl-2-C-methyl-D-erythritol kinase IspE (EC: 2.7.1.148) has the sequence SEQ ID NO: 7 or is a functionally equivalent variant thereof.

In one embodiment, the nucleic acid encoding 2-C-methyl-D-erythritol 2,4-cyclodiphosphate synthase IspF (EC:4.6.1.12) has the sequence SEQ ID NO: 9 or is a functionally equivalent variant thereof.

In one embodiment, the nucleic acid encoding 4-hydroxy-3-methylbut-2-en-1-yl diphosphate synthase IspG (EC: 1.17.7.1) has the sequence SEQ ID NO: 11 or is a functionally equivalent variant thereof.

In one embodiment, the nucleic acid encoding 4-hydroxy-3-methylbut-2-enyl diphosphate reductase (EC:1.17.1.2) has the sequence SEQ ID NO: 13 or is a functionally equivalent variant thereof.

In one embodiment, the nucleic acid encoding geranyltranstransferase Fps has the sequence SEQ ID NO: 15, or it is a functionally equivalent variant thereof.

In one embodiment, the nucleic acid encoding heptaprenyl diphosphate synthase has the sequence SEQ ID NO: 17, or it is a functionally equivalent variant thereof.

In one embodiment, the nucleic acid encoding octaprenyl-diphosphate synthase (EC:2.5.1.90) wherein the octaprenyl-diphosphate synthase is polyprenyl synthetase is encoded by sequence SEQ ID NO: 19, or it is a functionally equivalent variant thereof.

In one embodiment, the nucleic acid encoding isoprene synthase (ispS) has the sequence SEQ ID NO: 21, or it is a functionally equivalent variant thereof.

In one embodiment, the nucleic acid encoding Isopentenyl-diphosphate delta-isomerase (idi) has the sequence SEQ ID NO: 54, or it is a functionally equivalent variant thereof.

In one embodiment, the nucleic acid encoding farnesene synthase has the sequence SEQ ID NO: 57, or it is a functionally equivalent variant thereof.

In one embodiment, the nucleic acid encodes the following enzymes:
  a) isoprene synthase;
  b) Isopentenyl-diphosphate delta-isomerase (idi); and
  c) 1-deoxy-D-xylulose-5-phosphate synthase DXS;
or functionally equivalent variants thereof.

In one embodiment, the nucleic acid encodes the following enzymes:
  a) Thiolase;
  b) HMG-CoA synthase;
  c) HMG-CoA reductase;
  d) Mevalonate kinase;
  e) Phosphomevalonate kinase;
  f) Mevalonate Diphosphate decarboxylase;
  g) Isopentenyl-diphosphate delta-isomerase (idi); and
  h) isoprene synthase;
or functionally equivalent variants thereof.

In one embodiment, the nucleic acid encodes the following enzymes:
  a) geranyltranstransferase Fps; and
  b) farnesene synthase
or functionally equivalent variants thereof.

In one embodiment, the nucleic acids of the invention further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum*.

In a third aspect, the invention provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the invention provides host organisms comprising any one or more of the nucleic acids of the second aspect or vectors or constructs of the third aspect.

In a fifth aspect, the invention provides a composition comprising an expression construct or vector as referred to in the third aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In a sixth aspect, the invention provides a method for the production of one or more terpenes and/or precursors thereof and optionally one or more other products by microbial fermentation comprising fermenting a substrate comprising CO using a recombinant microorganism of the first aspect of the invention.

In one embodiment the method comprises the steps of:
(a) providing a substrate comprising CO to a bioreactor containing a culture of one or more microorganisms of the first aspect of the invention; and
(b) anaerobically fermenting the culture in the bioreactor to produce at least one terpene and/or precursor thereof.

In one embodiment the method comprises the steps of:
(a) capturing CO-containing gas produced as a result of the industrial process;
(b) anaerobic fermentation of the CO-containing gas to produce at least one terpene and/or precursor thereof by a culture containing one or more microorganism of the first aspect of the invention.

In particular embodiments of the method aspects, the microorganism is maintained in an aqueous culture medium.

In particular embodiments of the method aspects, the fermentation of the substrate takes place in a bioreactor.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering a terpene and/or precursor thereof and optionally one or more other products from the fermentation broth.

In a seventh aspect, the invention provides one or more terpene and/or precursor thereof when produced by the method of the sixth aspect. In one embodiment, the one or more terpene and/or precursor thereof is chosen from the group consisting of mevalonic acid, IPP, dimethylallyl pyrophosphate (DMAPP), isoprene, geranyl pyrophosphate (GPP), farnesyl pyrophosphate (FPP) and farnesene.

In another aspect, the invention provides a method for the production of a microorganism of the first aspect of the invention comprising transforming a carboxydotrophic acetogenic parental microorganism by introduction of one or more nucleic acids such that the microorganism is capable of producing, or increasing the production of, one or more terpenes and/or precursors thereof and optionally one or more other products by fermentation of a substrate comprising CO, wherein the parental microorganism is not capable of producing, or produces at a lower level, the one or more terpene and/or precursor thereof by fermentation of a substrate comprising CO.

In one particular embodiment, a parental microorganism is transformed by introducing one or more exogenous nucleic acids adapted to express one or more enzymes in the mevalonate (MVA) pathway and optionally the DXS pathway. In another embodiment, a parental microorganism is transformed with one or more nucleic acids adapted to over-express one or more enzymes in the mevalonate (MVA) pathway and optionally the DXS pathway which are naturally present in the parental microorganism.

In certain embodiments, the one or more enzymes are as herein before described.

In one embodiment an isolated, genetically engineered, carboxydotrophic, acetogenic bacteria are provided which comprise an exogenous nucleic acid encoding an enzyme in a mevalonate pathway or in a DXS pathway or in a terpene biosynthesis pathway, whereby the bacteria express the enzyme. The enzyme is selected from the group consisting of:
a) thiolase (EC 2.3.1.9);
b) HMG-CoA synthase (EC 2.3.3.10);
c) HMG-CoA reductase (EC 1.1.1.88);
d) Mevalonate kinase (EC 2.7.1.36);
e) Phosphomevalonate kinase (EC 2.7.4.2);
f) Mevalonate Diphosphate decarboxylase (EC 4.1.1.33); 1-deoxy-D-xylulose-5-phosphate synthase DXS (EC: 2.2.1.7);
g) 1-deoxy-D-xylulose 5-phosphate reductoisomerase DXR (EC:1.1.1.267);
h) 2-C-methyl-D-erythritol 4-phosphate cytidylyltransferase IspD (EC:2.7.7.60);
i) 4-diphosphocytidyl-2-C-methyl-D-erythritol kinase IspE (EC:2.7.1.148);
j) 2-C-methyl-D-erythritol 2;4-cyclodiphosphate synthase IspF (EC:4.6.1.12);
k) 4-hydroxy-3-methylbut-2-en-1-yl diphosphate synthase IspG (EC:1.17.7.1);
l) 4-hydroxy-3-methylbut-2-enyl diphosphate reductase (EC:1.17.1.2); geranyltranstransferase Fps (EC: 2.5.1.10);
m) heptaprenyl diphosphate synthase (EC:2.5.1.10);
n) octaprenyl-diphosphate synthase (EC:2.5.1.90);
o) isoprene synthase (EC 4.2.3.27);
p) isopentenyl-diphosphate delta-isomerase (EC 5.3.3.2); and
q) farnesene synthase (EC 4.2.3.46/EC 4.2.3.47).

In some aspects the bacteria do not express the enzyme in the absence of said nucleic acid. In some aspects the bacteria which express the enzyme under anaerobic conditions.

One embodiment provides a plasmid which can replicate in a carboxydotrophic, acetogenic bacteria. The plasmid comprises a nucleic acid encoding an enzyme in a mevalonate pathway or in a DXS pathway or in a terpene biosynthesis pathway, whereby when the plasmid is in the bacteria, the enzyme is expressed by said bacteria. The enzyme is selected from the group consisting of:

a) thiolase (EC 2.3.1.9);
b) HMG-CoA synthase (EC 2.3.3.10);
c) HMG-CoA reductase (EC 1.1.1.88);
d) Mevalonate kinase (EC 2.7.1.36);
e) Phosphomevalonate kinase (EC 2.7.4.2);
f) Mevalonate Diphosphate decarboxylase (EC 4.1.1.33); 1-deoxy-D-xylulose-5-phosphate synthase DXS (EC: 2.2.1.7);
g) 1-deoxy-D-xylulose 5-phosphate reductoisomerase DXR (EC:1.1.1.267);
h) 2-C-methyl-D-erythritol 4-phosphate cytidylyltransferase IspD (EC:2.7.7.60);
i) 4-diphosphocytidyl-2-C-methyl-D-erythritol kinase IspE (EC:2.7.1.148);
j) 2-C-methyl-D-erythritol 2;4-cyclodiphosphate synthase IspF (EC:4.6.1.12);
k) 4-hydroxy-3-methylbut-2-en-1-yl diphosphate synthase IspG (EC:1.17.7.1);
l) 4-hydroxy-3-methylbut-2-enyl diphosphate reductase (EC:1.17.1.2); geranyltranstransferase Fps (EC: 2.5.1.10);
m) heptaprenyl diphosphate synthase (EC:2.5.1.10);
n) octaprenyl-diphosphate synthase (EC:2.5.1.90);
o) isoprene synthase (EC 4.2.3.27);
p) isopentenyl-diphosphate delta-isomerase (EC 5.3.3.2); and
q) farnesene synthase (EC 4.2.3.46/EC 4.2.3.47).

A process is provided in another embodiment for converting CO and/or $CO_2$ into isoprene. The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isoprene, and recovering the isoprene from the bioreactor. The carboxydotrophic acetogenic bacteria are genetically engineered to express an isoprene synthase.

Another embodiment provides an isolated, genetically engineered, carboxydotrophic, acetogenic bacteria which comprise a nucleic acid encoding an isoprene synthase. The bacteria express the isoprene synthase and the bacteria are able to convert dimethylallyldiphosphate to isoprene. In one aspect the isoprene synthase is a *Populus tremuloides* enzyme. In another aspect the nucleic acid is codon optimized. In still another aspect, expression of the isoprene synthase is under the transcriptional control of a promoter for a pyruvate: ferredoxin oxidoreductase gene from *Clostridium autoethanogenum*.

Another embodiment provides a process for converting CO and/or $CO_2$ into isopentyldiphosphate (IPP). The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isopentyldiphosphate (IPP), and recovering the IPP from the bioreactor. The carboxydotrophic acetogenic bacteria are genetically engineered to express a isopentyldiphosphate delta isomerase.

Still another embodiment provides isolated, genetically engineered, carboxydotrophic, acetogenic bacteria which comprise a nucleic acid encoding an isopentyldiphosphate delta isomerase. The bacteria express the isopentyldiphosphate delta isomerase and the bacteria are able to convert dimethylallyldiphosphate to isopentyldiphosphate. In some aspects the nucleic acid encodes a *Clostridium beijerinckii* isopentyldiphosphate delta isomerase. In other aspects, the nucleic acid is under the transcriptional control of a promoter for a pyruvate: ferredoxin oxidoreductase gene from *Clostridium autoethanogenum*. In still other aspects, the nucleic acid is under the transcriptional control of a promoter for a pyruvate: ferredoxin oxidoreductase gene from *Clostridium autoethanogenum* and downstream of a second nucleic acid encoding an isoprene synthase.

Still another embodiment provides a process for converting CO and/or $CO_2$ into isopentyldiphosphate (IPP) and/or isoprene. The process comprises: passing a gaseous CO-containing and/or $CO_2$-containing substrate to a bioreactor containing a culture of carboxydotrophic, acetogenic bacteria in a culture medium such that the bacteria convert the CO and/or $CO_2$ to isopentyldiphosphate (IPP) and/or isoprene, and recovering the IPP and/or isoprene from the bioreactor. The carboxydotrophic acetogenic bacteria are genetically engineered to have an increased copy number of a nucleic acid encoding a deoxyxylulose 5-phosphate synthase (DXS) enzyme, wherein the increased copy number is greater than 1 per genome.

Yet another embodiment provides isolated, genetically engineered, carboxydotrophic, acetogenic bacteria which comprise a copy number of greater than 1 per genome of a nucleic acid encoding a deoxyxylulose 5-phosphate synthase (DXS) enzyme. In some aspects, the isolated, genetically engineered, carboxydotrophic, acetogenic bacteria may further comprise a nucleic acid encoding an isoprene synthase. In other aspects, the isolated, genetically engineered, carboxydotrophic, acetogenic bacteria of may further comprise a nucleic acid encoding an isopentyldiphosphate delta isomerase. In still other aspects the isolated, genetically engineered, carboxydotrophic, acetogenic bacteria may further comprise a nucleic acid encoding an isopentyldiphosphate delta isomerase and a nucleic acid encoding an isoprene synthase.

Another embodiment provides isolated, genetically engineered, carboxydotrophic, acetogenic bacteria which comprise a nucleic acid encoding a phosphomevalonate kinase (PMK). The bacteria express the encoded enzyme and the enzyme is not native to the bacteria. In some aspects the enzymes are *Staphylococcus aureus* enzymes. In some aspects the enzyme is expressed under the control of one or more *C. autoethanogenum* promoters. In some aspects the bacteria further comprise a nucleic acid encoding thiolase (th1A/vraB), a nucleic acid encoding an HMG-CoA synthase (HMGS), and a nucleic acid encoding an HMG-CoA reductase (HMGR). In some aspects the thiolase is *Clostridium acetobutylicum* thiolase. In some aspects the bacteria further comprise a nucleic acid encoding a mevalonate diphosphate decarboxylase (PMD).

Still another embodiment provides isolated, genetically engineered, carboxydotrophic, acetogenic bacteria which comprise an exogenous nucleic acid encoding alpha-farnesene synthase. In some aspects the nucleic acid is codon optimized for expression in *C. autoethanogenum*. In some aspects the alpha-farnesene synthase is a *Malus×*

*domestica* alpha-farnesene synthase. In some aspects the bacteria further comprise a nucleic acid segment encoding geranyltranstransferase. In some aspects the geranyltranstransferase is an *E. coli* geranyltranstransferase.

Suitable isolated, genetically engineered, carboxydotrophic, acetogenic bacteria for any of the aspects or embodiments of the invention may be selected from the group consisting of *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kivui.*

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures.

DETAILED DESCRIPTION OF THE INVENTION

Figure 1:
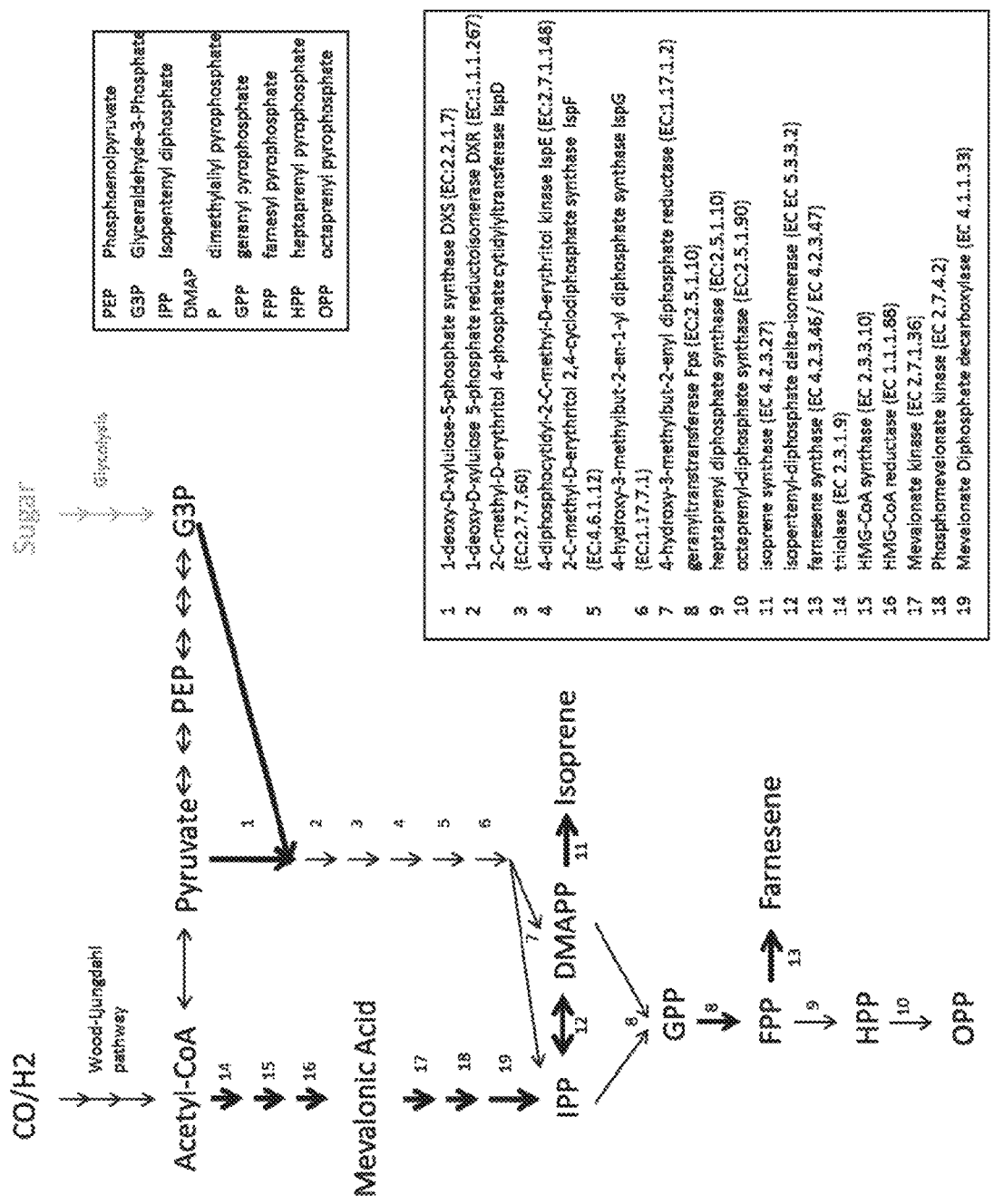
FIG. 1: Pathway diagram for production of terpenes, gene targets described in this application are highlighted with bold arrows.

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventors have surprisingly been able to engineer a carboxydotrophic acetogenic microorganism to produce terpene and precursors thereof including isoprene and farnesene by fermentation of a substrate comprising CO. This offers an alternative means for the production of these products which may have benefits over the current methods for their production. In addition, it offers a means of using carbon monoxide from industrial processes which would otherwise be released into the atmosphere and pollute the environment.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx. 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced (for example in a parental microorganism from which the recombinant microorganism is derived), strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

"Exogenous" may also be used to refer to proteins. This refers to a protein that is not present in the parental microorganism from which the recombinant microorganism is derived.

The term "endogenous" as used herein in relation to a recombinant microorganism and a nucleic acid or protein refers to any nucleic acid or protein that is present in a parental microorganism from which the recombinant microorganism is derived.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium acetobutylicum, Clostridium beijerinckii, C. saccharobutylicum* and *C. saccharoperbutylacetonicum*, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods described by Silver et al. (1991, *Plant Physiol.* 97: 1588-1591) or Zhao et al. (2011, *Appl Microbiol Biotechnol*, 90:1915-1922) for the isoprene synthase enzyme, by Green et al. (2007, *Phytochemistry*; 68:176-188) for the farnesene synthase enzyme, by Kuzuyama et al. (2000, *J. Bacteriol.* 182, 891-897) for the 1-deoxy-D-xylulose 5-phosphate synthase Dxs, by Berndt and Schlegel (1975, *Arch. Microbiol.* 103, 21-30) or by Stim-Herndon et al. (1995, *Gene* 154: 81-85) for the thiolase, by Cabano et al. (1997, *Insect Biochem. Mol. Biol.* 27: 499-505) for the HMG-CoA synthase, by Ma et al. (2011, *Metab. Engin.*, 13:588-597) for the HMG-CoA reductase and mevalonate kinase enzyme, by Herdendorf and Miziorko (2007, *Biochemistry*, 46: 11780-8) for the phosphomevalonate kinase, and by Krepkiy et al. (2004, *Protein Sci.* 13: 1875-1881) for the mevalonate diphosphate decarboxylase. It is also possible to identify genes of DXS and mevalonate pathway using inhibitors like fosmidomycin or mevinoline as described by Trutko et al. (2005, *Microbiology* 74: 153-158).

"Over-express", "over expression" and like terms and phrases when used in relation to the invention should be taken broadly to include any increase in expression of one or more proteins (including expression of one or more nucleic acids encoding same) as compared to the expression level of the protein (including nucleic acids) of a parental microorganism under the same conditions. It should not be taken to mean that the protein (or nucleic acid) is expressed at any particular level.

A "parental microorganism" is a microorganism used to generate a recombinant microorganism of the invention. The parental microorganism may be one that occurs in nature (i.e. a wild type microorganism) or one that has been previously modified but which does not express or over-express one or more of the enzymes that are the subject of the present invention. Accordingly, the recombinant microorganisms of the invention may have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

A "terpene" as referred to herein should be taken broadly to include any compound made up of $C_5$ isoprene units joined together including simple and complex terpenes and oxygen-containing terpene compounds such as alcohols, aldehydes and ketones. Simple terpenes are found in the essential oils and resins of plants such as conifers. More complex terpenes include the terpenoids and vitamin A, carotenoid pigments (such as lycopene), squalene, and rubber. Examples of monoterpenes include, but are not limited to isoprene, pinene, nerol, citral, camphor, menthol, limonene. Examples of sesquiterpenes include but are not limited to nerolidol, farnesol. Examples of diterpenes include but are not limited to phytol, vitamin $A_1$. Squalene is an example of a triterpene, and carotene (provitamin $A_1$) is a tetraterpene.

A "terpene precursor" is a compound or intermediate produced during the reaction to form a terpene starting from Acetyl CoA and optionally pyruvate. The term refers to a precursor compound or intermediate found in the mevalonate (MVA) pathway and optionally the DXS pathway as well as downstream precursors of longer chain terpenes, such as FPP and GPP. In particular embodiments, it includes but is not limited to mevalonic acid, IPP, dimethylallyl pyrophosphate (DMAPP), geranyl pyrophosphate (GPP) and farnesyl pyrophosphate (FPP).

The "DXS pathway" is the enzymatic pathway from pyruvate and D-glyceraldehyde-3-phosphate to DMAPP or IPP. It is also known as the deoxyxylulose 5-phosphate (DXP/DXPS/DOXP or DXS)/methylerythritol phosphate (MEP) pathway.

The "mevalonate (MVA) pathway" is the enzymatic pathway from acetyl-CoA to IPP.

Microorganisms

Two pathways for production of terpenes are known, the deoxyxylulose 5-phosphate (DXP/DXPS/DOXP or DXS)/methylerythritol phosphate (MEP) pathway (Hunter et al., 2007, *J. Biol. chem.* 282: 21573-77) starting from pyruvate and D-glyceraldehyde-3-phosphate (G3P), the two key intermediates in the glycolysis, and the mevalonate (MVA) pathway (Miziorko, 2011, *Arch Biochem Biophys*, 505: 131-143) starting from acetyl-CoA. Many different classes of microorganisms have been investigated for presence of either of these pathways (Lange et al., 2000, PNAS, 97: 13172-77; Trutko et al., 2005, *Microbiology*, 74: 153-158; Julsing et al., 2007, *Appl Microbiol Biotechnol*, 75: 1377-84), but not carboxydotrophic acetogens. The DXS pathway for example was found to be present in *E. coli, Bacillus*, or *Mycobacterium*, while the mevalonate pathway is present in yeast *Saccharomyces*, Cloroflexus, or *Myxococcus*.

Genomes of carboxydotrophic acetogens *C. autoethanogenum, C. ljungdahlii* were analysed by the inventors for presence of either of the two pathways. All genes of the DXS pathway were identified in *C. autoethanogenum* and *C. ljungdahlii* (Table 1), while the mevalonate pathway is absent. Additionally, carboxydotrophic acetogens such as *C. autoethanogenum* or *C. ljungdahlii* are not known to produce any terpenes as metabolic end products.

TABLE 1

Terpene biosynthesis genes of the DXS pathway identified in *C. autoethanogenum* and *C. ljungdahlii*:

| Gene/Enzyme | C. autoethanogenum | C. ljungdahlii |
|---|---|---|
| 1-deoxy-D-xylulose-5-phosphate synthase DXS (EC: 2.2.1.7) | SEQ ID NO: 1-2 | YP_003779286.1; GI: 300854302, CLJU_c11160 |
| 1-deoxy-D-xylulose 5-phosphate reductoisomerase DXR (EC: 1.1.1.267) | SEQ ID NO: 3-4 | YP_003779478.1; GI: 300854494, CLJU_c13080 |

TABLE 1-continued

Terpene biosynthesis genes of the DXS pathway identified in *C. autoethanogenum* and *C. ljungdahlii*:

| Gene/Enzyme | C. autoethanogenum | C. ljungdahlii |
|---|---|---|
| 2-C-methyl-D-erythritol 4-phosphate cytidylyltransferase IspD (EC: 2.7.7.60) | SEQ ID NO: 5-6 | YP_003782252.1 GI: 300857268, CLJU_c41280 |
| 4-diphosphocytidyl-2-C-methyl-D-erythritol kinase IspE (EC: 2.7.1.148) | SEQ ID NO: 7-8 | YP_003778403.1; GI: 300853419, CLJU_c02110 |
| 2-C-methyl-D-erythritol 2,4-cyclodiphosphate synthase IspF (EC: 4.6.1.12) | SEQ ID NO: 9-10 | YP_003778349.1; GI: 300853365, CLJU_c01570 |
| 4-hydroxy-3-methylbut-2-en-1-yl diphosphate synthase IspG (EC: 1.17.7.1) | SEQ ID NO: 11-12 | YP_003779480.1; GI: 300854496, CLJU_c13100 |
| 4-hydroxy-3-methylbut-2-enyl diphosphate reductase (EC: 1.17.1.2) | SEQ ID NO: 13-14 | YP_003780294.1; GI: 300855310, CLJU_c21320 |

Genes for downstream synthesis of terpenes from isoprene units were also identified in both organisms (Table 2).

| Gene/Enzyme | C. autoethanogenum | C. ljungdahlii |
|---|---|---|
| geranyltranstransferase Fps (EC: 2.5.1.10) | SEQID NO: 15-16 | YP_003779285.1; GI: 300854301, CLJU_c11150 |
| heptaprenyl diphosphate synthase (EC: 2.5.1.10) | SEQID NO: 17-18 | YP_003779312.1; GI: 300854328, CLJU_c11420 |
| octaprenyl-diphosphate synthase [EC: 2.5.1.90] | SEQ ID NO: 19-20 | YP_003782157.1; GI: 300857173, CLJU_c40310 |

Terpenes are energy dense compounds, and their synthesis requires the cell to invest energy in the form of nucleoside triphosphates such as ATP. Using sugar as a substrate requires sufficient energy to be supplied from glycolysis to yield several molecules of ATP. The production of terpenes and/or their precursors via the DXS pathway using sugar as a substrate proceeds in a relatively straightforward manner due to the availability of pyruvate and D-glyceraldehyde-3-phosphate (G3P), G3P being derived from C5 pentose and C6 hexose sugars. These C5 and C6 molecules are thus relatively easily converted into C5 isoprene units from which terpenes are composed.

For anaerobic acetogens using a C1 substrate like CO or CO2, it is more difficult to synthesise long molecules such as hemiterpenoids from C1 units. This is especially true for longer chain terpenes like C10 monoterpenes, C15 sesquiterpenes, or C40 tetraterpenes. To date the product with most carbon atoms reported in acetogens (both native and recombinant organisms) are C4 compounds butanol (Köpke et al., 2011, *Curr. Opin. Biotechnol.* 22: 320-325; Schiel-Bengelsdorf and Dürre, 2012, *FEBS Letters:* 10.1016/j.febslet.2012.04.043; Köpke et al., 2011, *Proc. Nat. Sci. U.S.A.* 107: 13087-92; US patent 2011/0236941) and 2,3-butanediol (Kopke et al., 2011, Appl. Environ. Microbiol. 77:5467-75). The inventors have shown that it is surprisingly possible to anaerobically produce these longer chain terpene molecules using the C1 feedstock CO via the acetyl CoA intermediate.

Energetics of the Wood-Ljungdahl pathway of anaerobic acetogens are just emerging, but unlike under aerobic growth conditions or glycolysis of sugar fermenting organisms no ATP is gained in the Wood-Ljungdahl pathway by substrate level phosphorylation, in fact activation of $CO_2$ to formate actually requires one molecule of ATP and a membrane gradient is required. The inventors note that it is important that a pathway for product formation is energy efficient. The inventors note that in acetogens the substrate CO or $CO_2$ is channeled directly into acetyl-CoA, which represents the most direct route to terpenes and/or their precursors, especially when compared to sugar based systems, with only six reactions required (FIG. 1). Though less ATP is available in carboxydotrophic acetogens, the inventors believe that this more direct pathway may sustain a higher metabolic flux (owing to higher chemical motive force of intermediate reactions). A highly effective metabolic flux is important as several intermediates in the terpene biosynthesis pathway, such as key intermediates Mevalonate and FPP, are toxic to most bacteria when not turned over efficiently. Despite having a higher ATP availability, this problem of intermediate toxicity can be a bottleneck in production of terpenes from sugar.

Figure 6:
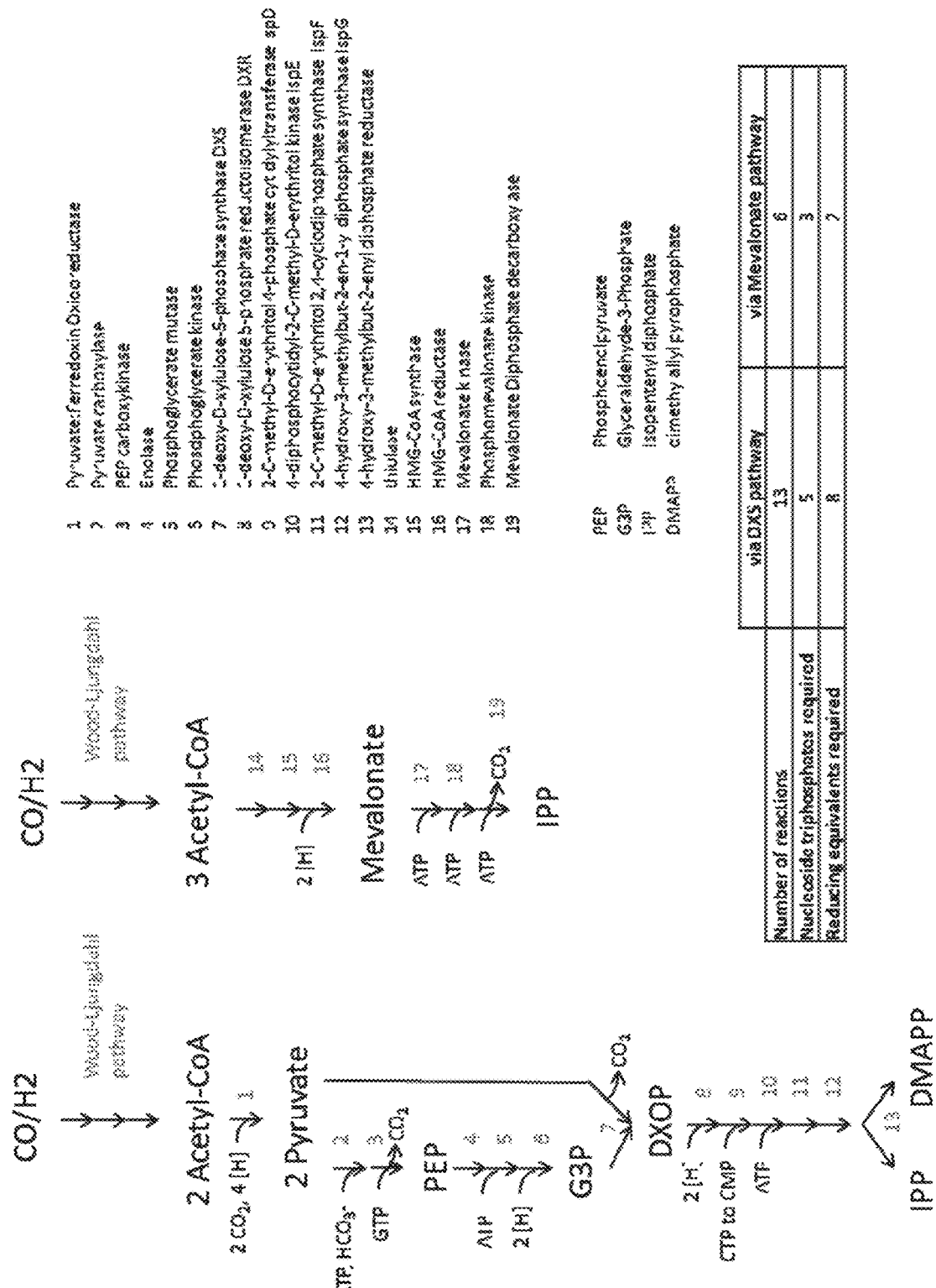
FIG. 6: Comparison of energetics for production of terpenes from CO via DXS and mevalonate pathway

When comparing the energetics of terpene precursor IPP and DMAPP production from CO (FIG. 6) via the mevalonate pathway versus the DXS pathway, the inventors noted that the mevalonate pathway requires less nucleoside triposphates as ATP, less reducing equivalents, and is also more direct when compared to the DXS pathway with only six necessary reaction steps from acetyl-CoA. This provides advantages in the speed of the reactions and metabolic fluxes and increases overall energy efficiency. Additionally, the lower number of enzymes required simplifies the recombination method required to produce a recombinant microorganism.

No acetogens with a mevalonate pathway have been identified, but the inventors have shown that it is possible to introduce the mevalonate pathway and optionally the DXS pathway into a carboxytrophic acetogen such as *Clostridium autoethanogenum* or *C. ljungdahlii* to efficiently produce terpenes and/or precursors thereof from the C1 carbon substrate CO. They contemplate that this is applicable to all carboxydotrophic acetogenic microorganisms.

Additionally, the production of terpenes and/or precursors thereof has never been shown to be possible using recombinant microorganisms under anaerobic conditions. Anaerobic production of isoprene has the advantage of providing a safer operating environment because isoprene is extremely flammable in the presence of oxygen and has a lower flammable limit (LFL) of 1.5-2.0% and an upper flammable (UFL) limit of 2.0-12% at room temperature and atmospheric pressure. As flames cannot occur in the absence of oxygen, the inventors believe that an anaerobic fermentation process is desirable as it would be safer across all product concentrations, gas compositions, temperature and pressure ranges.

As discussed hereinbefore, the invention provides a recombinant microorganism capable of producing one or more terpenes and/or precursors thereof, and optionally one or more other products, by fermentation of a substrate comprising CO.

In a further embodiment, the microorganism is adapted to:
express one or more exogenous enzymes from the mevalonate (MVA) pathway and/or overexpress one or more endogenous enzyme from the mevalonate (MVA) pathway; and
a) express one or more exogenous enzymes from the DXS pathway and/or overexpress one or more endogenous enzymes from the DXS pathway.

In one embodiment, the parental microorganism from which the recombinant microorganism is derived is capable of fermenting a substrate comprising CO to produce Acetyl CoA, but not of converting Acetyl CoA to mevalonic acid or isopentenyl pyrophosphate (IPP) and the recombinant microorganism is adapted to express one or more enzymes involved in the mevalonate pathway.

The microorganism may be adapted to express or over-express the one or more enzymes by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not naturally present within the parental microorganism.

In one embodiment, the one or more enzymes are from the mevalonate (MVA) pathway and are selected from the group consisting of:
a) thiolase (EC 2.3.1.9),
b) HMG-CoA synthase (EC 2.3.3.10),
c) HMG-CoA reductase (EC 1.1.1.88),
d) Mevalonate kinase (EC 2.7.1.36),
e) Phosphomevalonate kinase (EC 2.7.4.2),
f) Mevalonate Diphosphate decarboxylase (EC 4.1.1.33), and
g) a functionally equivalent variant of any one thereof.

In a further embodiment, the optional one or more enzymes are from the DXS pathway is selected from the group consisting of:
a) 1-deoxy-D-xylulose-5-phosphate synthase DXS (EC: 2.2.1.7),
b) 1-deoxy-D-xylulose 5-phosphate reductoisomerase DXR (EC:1.1.1.267),
c) 2-C-methyl-D-erythritol 4-phosphate cytidylyltransferase IspD (EC:2.7.7.60),
d) 4-diphosphocytidyl-2-C-methyl-D-erythritol kinase IspE (EC:2.7.1.148),
e) 2-C-methyl-D-erythritol 2,4-cyclodiphosphate synthase IspF (EC:4.6.1.12),
f) 4-hydroxy-3-methylbut-2-en-1-yl diphosphate synthase IspG (EC:1.17.7.1),
g) 4-hydroxy-3-methylbut-2-enyl diphosphate reductase (EC:1.17.1.2), and
h) a functionally equivalent variant of any one thereof.

In a further embodiment, one or more exogenous or endogenous further enzymes are expressed or over-expressed to result in the production of a terpene compound and/or precursor thereof wherein the exogenous enzyme that is expressed, or the endogenous enzyme that is overexpressed is selected from the group consisting of:
a) geranyltranstransferase Fps (EC:2.5.1.10),
b) heptaprenyl diphosphate synthase (EC:2.5.1.10),
c) octaprenyl-diphosphate synthase (EC:2.5.1.90),
d) isoprene synthase (EC 4.2.3.27),
e) isopentenyl-diphosphate delta-isomerase (EC 5.3.3.2),
f) farnesene synthase (EC 4.2.3.46/EC 4.2.3.47), and
g) a functionally equivalent variant of any one thereof.

By way of example only, sequence information for each of the enzymes is listed in the figures herein.

The enzymes of use in the microorganisms of the invention may be derived from any appropriate source, including different genera and species of bacteria, or other organisms. However, in one embodiment, the enzymes are derived from *Staphylococcus aureus*.

In one embodiment, the enzyme isoprene synthase (ispS) is derived from *Poplar tremuloides*. In a further embodiment, it has the nucleic acid sequence exemplified in SEQ ID NO: 21 hereinafter, or it is a functionally equivalent variant thereof.

In one embodiment, the enzyme deoxyxylulose 5-phosphate synthase is derived from *C. autoethanogenum*, encoded by the nucleic acid sequence exemplified in SEQ ID NO: 1 and/or with the amino acid sequence exemplified in SEQ ID NO: 2 hereinafter, or it is a functionally equivalent variant thereof.

In one embodiment, the enzyme 1-deoxy-D-xylulose 5-phosphate reductoisomerase DXR is derived from *C. autoethanogenum* and is encoded by the nucleic acid sequence exemplified in SEQ ID NO: 3 or is a functionally equivalent variant thereof.

In one embodiment, the enzyme 2-C-methyl-D-erythritol 4-phosphate cytidylyltransferase IspD is derived from *C. autoethanogenum* and is encoded by the nucleic acid sequence exemplified in SEQ ID NO: 5 or is a functionally equivalent variant thereof.

In one embodiment, the enzyme 4-diphosphocytidyl-2-C-methyl-D-erythritol kinase IspE is derived from *C. autoethanogenum* and is encoded by the nucleic acid sequence exemplified in SEQ ID NO: 7 or is a functionally equivalent variant thereof.

In one embodiment, the enzyme 2-C-methyl-D-erythritol 2,4-cyclodiphosphate synthase IspF is derived from *C. autoethanogenum* and is encoded by the nucleic acid sequence exemplified in SEQ ID NO: 9 or is a functionally equivalent variant thereof.

In one embodiment, the enzyme 4-hydroxy-3-methylbut-2-en-1-yl diphosphate synthase IspG is derived from *C. autoethanogenum* and is encoded by the nucleic acid sequence exemplified in SEQ ID NO: 11 or is a functionally equivalent variant thereof.

In one embodiment, the enzyme 4-hydroxy-3-methylbut-2-enyl diphosphate reductase is derived from *C. autoethanogenum* and is encoded by the nucleic acid sequence exemplified in SEQ ID NO: 13 or is a functionally equivalent variant thereof.

In one embodiment, the enzyme mevalonate kinase (MK) is derived from *Staphylococcus aureus* subsp. *aureus* Mu50 and is encoded by the nucleic acid sequence exemplified in SEQ ID NO: 51 hereinafter, or it is a functionally equivalent variant thereof.

In one embodiment, the enzyme phosphomevalonate kinase (PMK) is derived from *Staphylococcus aureus* subsp. *aureus* Mu50 and is encoded by the nucleic acid sequence exemplified in SEQ ID NO: 52 hereinafter, or it is a functionally equivalent variant thereof.

In one embodiment, the enzyme mevalonate diphosphate decarboxylase (PMD) is derived from *Staphylococcus aureus* subsp. *aureus* Mu50 and is encoded by the nucleic acid sequence exemplified in SEQ ID NO: 53 hereinafter, or it is a functionally equivalent variant thereof.

In one embodiment, the enzyme Isopentenyl-diphosphate delta-isomerase (idi) is derived from *Clostridium beijerinckii* and is encoded by the nucleic acid sequence exemplified in SEQ ID NO: 54 hereinafter, or it is a functionally equivalent variant thereof.

In one embodiment, the enzyme thiolase (thIA) is derived from *Clostridium acetobutylicum* ATCC824 and is encoded by the nucleic acid sequence exemplified in SEQ ID NO: 40 hereinafter, or it is a functionally equivalent variant thereof.

In one embodiment, the enzyme is a thiolase enzyme, and is an acetyl-CoA c-acetyltransferase (vraB) derived from *Staphylococcus aureus* subsp. *aureus* Mu50 and is encoded by the nucleic acid sequence exemplified in SEQ ID NO: 41 hereinafter, or it is a functionally equivalent variant thereof.

In one embodiment, the enzyme 3-hydroxy-3-methylglutaryl-CoA synthase (HMGS) is derived from *Staphylococcus aureus* subsp. *aureus* Mu50 and is encoded by the nucleic acid sequence exemplified in SEQ ID NO: 42 hereinafter, or it is a functionally equivalent variant thereof.

In one embodiment, the enzyme Hydroxymethylglutaryl-CoA reductase (HMGR) is derived from *Staphylococcus aureus* subsp. *aureus* Mu50 and is encoded by the nucleic acid sequence exemplified in SEQ ID NO: 43 hereinafter, or it is a functionally equivalent variant thereof.

In one embodiment, the enzyme Geranyltranstransferase (ispA) is derived from *Escherichia coli* str. K-12 substr. MG1655 is encoded by the nucleic acid sequence exemplified in SEQ ID NO: 56 hereinafter, or it is a functionally equivalent variant thereof.

In one embodiment, the enzyme heptaprenyl diphosphate synthase is derived from *C. autoethanogenum* and is encoded by the nucleic acid sequence exemplified in SEQ ID NO: 17 or is a functionally equivalent variant thereof.

In one embodiment, the enzyme polyprenyl synthetase is derived from *C. autoethanogenum* and is encoded by the nucleic acid sequence exemplified in SEQ ID NO: 19 or is a functionally equivalent variant thereof.

In one embodiment, the enzyme Alpha-farnesene synthase (FS) is derived from *Malus×domestica* and is encoded by the nucleic acid sequence exemplified in SEQ ID NO: 57 hereinafter, or it is a functionally equivalent variant thereof.

The enzymes and functional variants of use in the microorganisms may be identified by assays known to one of skill in the art. In particular embodiments, the enzyme isoprene synthase may be identified by the method outlined Silver et al. (1991, *Plant Physiol.* 97: 1588-1591) or Zhao et al. (2011, *Appl Microbiol Biotechnol*, 90:1915-1922). In a further particular embodiment, the enzyme farnesene synthase may be identified by the method outlined in Green et al., 2007, Phytochemistry; 68:176-188. In further particular embodiments, enzymes from the mevalonate pathway may be identified by the method outlined in Cabano et al. (1997, *Insect Biochem. Mol. Biol.* 27: 499-505) for the HMG-CoA synthase, Ma et al. (2011, *Metab. Engin.*, 13:588-597) for the HMG-CoA reductase and mevalonate kinase enzyme, Herdendorf and Miziorko (2007, *Biochemistry*, 46: 11780-8) for the phosphomevalonate kinase, and Krepkiy et al. (2004, *Protein Sci.* 13: 1875-1881) for the mevalonate diphosphate decarboxylase. Ma et al., 2011, *Metab. Engin.*, 13:588-597. The 1-deoxy-D-xylulose 5-phosphate synthase of the DXS pathway can be assayed using the method outlined in Kuzuyama et al. (2000, *J. Bacteriol.* 182, 891-897). It is also possible to identify genes of DXS and mevalonate pathway using inhibitors like fosmidomycin or mevinoline as described by Trutko et al. (2005, *Microbiology* 74: 153-158).

In one embodiment, the microorganism comprises one or more exogenous nucleic acids adapted to increase expression of one or more endogenous nucleic acids and which one or more endogenous nucleic acids encode one or more of the enzymes referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or Phosphotransacetylase/Acetate kinase operon promoters. It will be appreciated by those of skill in the art that other promoters which can direct expression, preferably a high level of expression under appropriate fermentation conditions, would be effective as alternatives to the exemplified embodiments.

In one embodiment, the microorganism comprises one or more exogenous nucleic acids encoding and adapted to express one or more of the enzymes referred to herein before. In one embodiment, the microorganisms comprise one or more exogenous nucleic acid encoding and adapted to express at least two, at least of the enzymes. In other embodiments, the microorganism comprises one or more exogenous nucleic acid encoding and adapted to express at least three, at least four, at least five, at least six, at least seven, at least eight, at least nine or more of the enzymes.

In one particular embodiment, the microorganism comprises one or more exogenous nucleic acid encoding an enzyme of the invention or a functionally equivalent variant thereof.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination.

The exogenous nucleic acids may remain extra-chromosomal upon transformation of the parental microorganism or may integrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

In one particular embodiment, the parental microorganism is selected from the group of carboxydotrophic acetogenic bacteria. In certain embodiments the microorganism is selected from the group comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Sporomusa ovata*, *Sporomusa silvacetica*, *Sporomusa sphaeroides*, *Oxobacter pfennigii*, and *Thermoanaerobacter kivui*.

In one particular embodiment, the parental microorganism is selected from the cluster of ethanologenic, acetogenic Clostridia comprising the species *C. autoethanogenum*, *C. ljungdahlii*, and *C. ragsdalei* and related isolates. These include but are not limited to strains *C. autoethanogenum* JAI-1$^T$ (DSM10061) [Abrini J, Naveau H, Nyns E-J: *Clostridium autoethanogenum*, sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* PETC$^T$ (DSM13528=ATCC 55383) [Tanner R S, Miller L M, Yang D: *Clostridium ljungdahlii* sp. nov., an Acetogenic Species in Clostridial rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. US patent 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. US patent, 2002, U.S. Pat. No. 6,368,819], *C. ljungdahlii* 0-52 (ATCC 55989) [Gaddy J L, Clausen E C, Ko C-W: Microbial process for the preparation of acetic acid as well as solvent for its extraction from the fermentation broth. US patent, 2002, U.S. Pat. No. 6,368,819], *C. ragsdalei* P11$^T$ (ATCC BAA-622) [Huhnke R L, Lewis R S, Tanner R S: Isolation and Characterization of novel Clostridial Species. International patent 2008, WO 2008/028055], related isolates such as "C. coskatii" [Zahn et al—Novel ethanologenic species *Clostridium* coskatii (US Patent Application number US20110229947)] and "*Clostridium* sp." (Tyurin et al., 2012, J. Biotech Res. 4: 1-12), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a sub-cluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel Clostridial Species. International patent 2008, WO 2008/028055].

All species of this cluster have a similar morphology and size (logarithmic growing cells are between 0.5-0.7×3-5 μm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel Clostridial Species. International patent 2008, WO 2008/028055]. Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover, some of the species were found to be auxotroph to certain vitamins (e.g. thiamine, biotin) while others were not.

In one embodiment, the parental carboxydotrophic acetogenic microorganism is selected from the group consisting of *Clostridium autoethanogenum*, *Clostridium ljungdahlii*, *Clostridium ragsdalei*, *Clostridium carboxidivorans*, *Clostridium drakei*, *Clostridium scatologenes*, *Butyribacterium limosum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Oxobacter pfennigii*, and *Thermoanaerobacter kivui*.

In one particular embodiment of the first or second aspects, the parental microorganism is selected from the group of carboxydotrophic Clostridia comprising *Clostridium autoethanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*.

In a one embodiment, the microorganism is selected from a cluster of carboxydotrophic Clostridia comprising the species *C. autoethanogenum*, *C. ljungdahlii*, and "*C. ragsdalei*" and related isolates. These include but are not limited to strains *C. autoethanogenum* JAI-1T (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), or "*C. ragsdalei* P11$^T$" (ATCC BAA-622) (WO 2008/028055), and related isolates such as "*C. coskatii*" (US patent 2011/0229947), "*Clostridium* sp. MT351" (Michael Tyurin & Kiriukhin, 2012) and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Köpke et al., 2010) and a GC composition of around 32% mol (Abrini et al., 1994; Kopke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Kopke et al., 2010, 2011). The organization and number of Wood-Ljungdahl pathway genes, responsible for gas uptake, has been found to be the same in all species, despite differences in nucleic and amino acid sequences (Kopke et al., 2011).

The strains all have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993)(WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Kopke et al., 2011; Tanner et al., 1993) However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

The recombinant carboxydotrophic acetogenic microorganisms of the invention may be prepared from a parental carboxydotrophic acetogenic microorganism and one or more exogenous nucleic acids using any number of techniques known in the art for producing recombinant microorganisms. By way of example only, transformation (including transduction or transfection) may be achieved by electroporation, electrofusion, ultrasonication, polyethylene glycol-mediated transformation, conjugation, or chemical and natural competence. Suitable transformation techniques are described for example in Sambrook J, Fritsch E F, Maniatis T: Molecular Cloning: A laboratory Manual, Cold Spring Harbour Laboratory Press, Cold Spring Harbour, 1989.

Electroporation has been described for several carboxydotrophic acetogens as *C. ljungdahlii* (Köpke et al., 2010; Leang, Ueki, Nevin, & Lovley, 2012) (PCT/NZ2011/000203; WO2012/053905), *C. autoethanogenum* (PCT/NZ2011/000203; WO2012/053905), *Acetobacterium woodii* (Strätz, Sauer, Kuhn, & Dürre, 1994) or *Moorella thermoacetica* (Kita et al., 2012) and is a standard method used in many Clostridia such as *C. acetobutylicum* (Mermelstein, Welker, Bennett, & Papoutsakis, 1992), *C. cellulolyticum* (Jennert, Tardif, Young, & Young, 2000) or *C. thermocellum* (MV Tyurin, Desai, & Lynd, 2004).

Electrofusion has been described for acetogenic *Clostridium* sp. MT351 (Tyurin and Kiriukhin, 2012).

Prophage induction has been described for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University).

Conjugation has been described as method of choice for acetogen *Clostridium difficile* (Herbert, O'Keeffe, Purdy, Elmore, & Minton, 2003) and many other Clostridia including *C. acetobutylicum* (Williams, Young, & Young, 1990).

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

Nucleic Acids

The invention also provides one or more nucleic acids or nucleic acid constructs of use in generating a recombinant microorganism of the invention.

In one embodiment, the nucleic acid comprises sequences encoding one or more of the enzymes in the mevalonate (MVA) pathway and optionally the DXS pathway which when expressed in a microorganism allows the microorganism to produce one or more terpenes and/or precursors thereof by fermentation of a substrate comprising CO. In one particular embodiment, the invention provides a nucleic acid encoding two or more enzymes which when expressed in a microorganism allows the microorganism to produce one or more terpene and/or precursor thereof by fermentation of substrate comprising CO. In one embodiment, a nucleic acid of the invention encodes three, four, five or more of such enzymes.

In one embodiment, the one or more enzymes encoded by the nucleic acid are from the mevalonate (MVA) pathway and are selected from the group consisting of:
  a) thiolase (EC 2.3.1.9),
  b) HMG-CoA synthase (EC 2.3.3.10),
  c) HMG-CoA reductase (EC 1.1.1.88),
  d) Mevalonate kinase (EC 2.7.1.36),
  e) Phosphomevalonate kinase (EC 2.7.4.2),
  f) Mevalonate Diphosphate decarboxylase (EC 4.1.1.33), and
  g) a functionally equivalent variant of any one thereof.

In a further embodiment, the one or more optional enzymes encoded by the nucleic acid are from the DXS pathway are selected from the group consisting of:
  a) 1-deoxy-D-xylulose-5-phosphate synthase DXS (EC: 2.2.1.7),
  b) 1-deoxy-D-xylulose 5-phosphate reductoisomerase DXR (EC:1.1.1.267),
  c) 2-C-methyl-D-erythritol 4-phosphate cytidylyltransferase IspD (EC:2.7.7.60),
  d) 4-diphosphocytidyl-2-C-methyl-D-erythritol kinase IspE (EC:2.7.1.148),
  e) 2-C-methyl-D-erythritol 2,4-cyclodiphosphate synthase IspF (EC:4.6.1.12),
  f) 4-hydroxy-3-methylbut-2-en-1-yl diphosphate synthase IspG (EC:1.17.7.1),
  g) 4-hydroxy-3-methylbut-2-enyl diphosphate reductase (EC:1.17.1.2), and
  h) a functionally equivalent variant of any one thereof.

In a further embodiment, the nucleic acid encodes one or more further enzymes that are expressed or over-expressed to result in the production of a terpene compound and/or precursor thereof wherein the exogenous enzyme that is expressed, or the endogenous enzyme that is overexpressed is selected from the group consisting of:
  a) geranyltranstransferase Fps (EC:2.5.1.10),
  b) heptaprenyl diphosphate synthase (EC:2.5.1.10),
  c) octaprenyl-diphosphate synthase (EC:2.5.1.90),
  d) isoprene synthase (EC 4.2.3.27),
  e) isopentenyl-diphosphate delta-isomerase (EC 5.3.3.2),
  f) farnesene synthase (EC 4.2.3.46/EC 4.2.3.47), and
  g) a functionally equivalent variant of any one thereof.

Exemplary amino acid sequences and nucleic acid sequences encoding each of the above enzymes are provided herein or can be obtained from GenBank as mentioned hereinbefore. However, skilled persons will readily appreciate alternative nucleic acid sequences encoding the enzymes or functionally equivalent variants thereof, having regard to the information contained herein, in GenBank and other databases, and the genetic code.

In a further embodiment, the nucleic acid encoding thiolase (thlA) derived from *Clostridium acetobutylicum* ATCC824 is encoded by the nucleic acid sequence exemplified in SEQ ID NO: 40 hereinafter, or it is a functionally equivalent variant thereof.

In a further embodiment, the nucleic acid encoding thiolase wherein the thiolase is acetyl-CoA c-acetyltransferase (vraB) derived from *Staphylococcus aureus* subsp. *aureus* Mu50 is encoded by the nucleic acid sequence exemplified in SEQ ID NO: 41 hereinafter, or it is a functionally equivalent variant thereof.

In a further embodiment, the nucleic acid encoding 3-hydroxy-3-methylglutaryl-CoA synthase (HMGS) derived from *Staphylococcus aureus* subsp. *aureus* Mu50 is encoded by the nucleic acid sequence exemplified in SEQ ID NO: 42 hereinafter, or it is a functionally equivalent variant thereof.

In a further embodiment, the nucleic acid encoding Hydroxymethylglutaryl-CoA reductase (HMGR) derived from *Staphylococcus aureus* subsp. *aureus* Mu50 is encoded by the nucleic acid sequence exemplified in SEQ ID NO: 43 hereinafter, or it is a functionally equivalent variant thereof.

In a further embodiment, the nucleic acid encoding mevalonate kinase (MK) derived from *Staphylococcus aureus* subsp. *aureus* Mu50 is encoded by the nucleic acid sequence exemplified in SEQ ID NO: 51 hereinafter, or it is a functionally equivalent variant thereof.

In a further embodiment, the nucleic acid encoding phosphomevalonate kinase (PMK) derived from *Staphylococcus aureus* subsp. *aureus* Mu50 is encoded by the nucleic acid sequence exemplified in SEQ ID NO: 52 hereinafter, or it is a functionally equivalent variant thereof.

In a further embodiment, the nucleic acid encoding mevalonate diphosphate decarboxylase (PMD) derived from *Staphylococcus aureus* subsp. *aureus* Mu50 is encoded by the nucleic acid sequence exemplified in SEQ ID NO: 53 hereinafter, or it is a functionally equivalent variant thereof.

In a further embodiment, the nucleic acid encoding deoxyxylulose 5-phosphate synthase derived from *C. autoethanogenum*, is encoded by the nucleic acid sequence exemplified in SEQ ID NO: 1 and/or with the amino acid sequence exemplified in SEQ ID NO: 2 hereinafter, or it is a functionally equivalent variant thereof.

In one embodiment, the nucleic acid encoding 1-deoxy-D-xylulose 5-phosphate reductoisomerase DXR (EC: 1.1.1.267) has the sequence SEQ ID NO: 3 or is a functionally equivalent variant thereof.

In one embodiment, the nucleic acid encoding 2-C-methyl-D-erythritol 4-phosphate cytidylyltransferase IspD (EC:2.7.7.60) has the sequence SEQ ID NO: 5 or is a functionally equivalent variant thereof.

In one embodiment, the nucleic acid encoding 4-diphosphocytidyl-2-C-methyl-D-erythritol kinase IspE (EC: 2.7.1.148) has the sequence SEQ ID NO: 7 or is a functionally equivalent variant thereof.

In one embodiment, the nucleic acid encoding 2-C-methyl-D-erythritol 2,4-cyclodiphosphate synthase IspF (EC:4.6.1.12) has the sequence SEQ ID NO: 9 or is a functionally equivalent variant thereof.

In one embodiment, the nucleic acid encoding 4-hydroxy-3-methylbut-2-en-1-yl diphosphate synthase IspG (EC: 1.17.7.1) has the sequence SEQ ID NO: 11 or is a functionally equivalent variant thereof.

In one embodiment, the nucleic acid encoding 4-hydroxy-3-methylbut-2-enyl diphosphate reductase (EC:1.17.1.2) has the sequence SEQ ID NO: 13 or is a functionally equivalent variant thereof.

In a further embodiment, the nucleic acid encoding Geranyltranstransferase (ispA) derived from *Escherichia coli* str. K-12 substr. MG1655 is encoded by the nucleic acid sequence exemplified in SEQ ID NO: 56 hereinafter, or it is a functionally equivalent variant thereof.

In one embodiment, the nucleic acid encoding heptaprenyl diphosphate synthase has the sequence SEQ ID NO: 17, or it is a functionally equivalent variant thereof.

In one embodiment, the nucleic acid encoding octaprenyl-diphosphate synthase (EC:2.5.1.90) wherein the octaprenyl-diphosphate synthase is polyprenyl synthetase is encoded by sequence SEQ ID NO: 19, or it is a functionally equivalent variant thereof.

In one embodiment, the nucleic acid encoding isoprene synthase (ispS) derived from Poplar *tremuloides* is exemplified in SEQ ID NO: 21 hereinafter, or it is a functionally equivalent variant thereof.

In a further embodiment, the nucleic acid encoding Isopentenyl-diphosphate delta-isomerase (idi) derived from *Clostridium beijerinckii* is encoded by the nucleic acid sequence exemplified in SEQ ID NO: 54 hereinafter, or it is a functionally equivalent variant thereof.

In a further embodiment, the nucleic acid encoding Alpha-farnesene synthase (FS) derived from *Malus×domestica* is encoded by the nucleic acid sequence exemplified in SEQ ID NO: 57 hereinafter, or it is a functionally equivalent variant thereof.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kinase promoter is used. In another embodiment a pyruvate:ferredoxin oxidoreductase promoter, an Rnf complex operon promoter or an ATP synthase operon promoter. In one particular embodiment, the promoter is from *C. autoethanogenum*.

The nucleic acids of the invention may remain extra-chromosomal upon transformation of a parental microorganism or may be adapted for integration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, NY, 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

Methods of Producing Organisms

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:
b) introduction into a shuttle microorganism of (i) of an expression construct/vector as described herein and (ii) a methylation construct/vector comprising a methyltransferase gene;
c) expression of the methyltransferase gene;
d) isolation of one or more constructs/vectors from the shuttle microorganism; and,
e) introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli*, *Bacillus subtilis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ ID NO: 60 or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ ID NO: 63, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used.

Methods of Production

The invention provides a method for the production of one or more terpenes and/or precursors thereof, and optionally one or more other products, by microbial fermentation comprising fermenting a substrate comprising CO using a recombinant microorganism of the invention. Preferably, the one or more terpene and/or precursor thereof is the main fermentation product. The methods of the invention may be used to reduce the total atmospheric carbon emissions from an industrial process.

Preferably, the fermentation comprises the steps of anaerobically fermenting a substrate in a bioreactor to produce at least one or more terpenes and/or a precursor thereof using a recombinant microorganism of the invention.

In one embodiment, the one or more terpene and/or precursor thereof is chosen from mevalonic acid, IPP, dimethylallyl pyrophosphate (DMAPP), isoprene, geranyl pyrophosphate (GPP), farnesyl pyrophosphate (FPP) and farnesene.

Instead of producing isoprene directly from terpenoid key intermediates IPP and DMAPP then using this to synthesise longer chain terpenes, it is also possible to synthesise longer chain terpenes, such as C10 Monoterpenoids or C15 Sesquiterpenoids, directly via a geranyltransferase (see Table 6). From C15 Sesquiterpenoid building block farnesyl-PP it is possible to produce farnesene, which, similarly to ethanol, can be used as a transportation fuel.

In one embodiment the method comprises the steps of:
(a) providing a substrate comprising CO to a bioreactor containing a culture of one or more microorganism of the invention; and
(b) anaerobically fermenting the culture in the bioreactor to produce at least one or more terpene and/or precursor thereof.

In one embodiment the method comprises the steps of:
a) capturing CO-containing gas produced as a result of the industrial process;
b) anaerobic fermentation of the CO-containing gas to produce the at least one or more terpene and/or precursor thereof by a culture containing one or more microorganism of the invention.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing a terpene for use as a biofuel. Depending on the composition of the gaseous CO—containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and CO-to-at least one or more terpene and/or precursor thereof to occur, in addition to the CO-containing substrate gas, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce a terpene and/or a precursor thereof using CO are known in the art. For example, suitable media are described Biebel (2001). In one embodiment of the invention the media is as described in the Examples section herein after.

The fermentation should desirably be carried out under appropriate conditions for the CO-to-the at least one or more terpene and/or precursor thereof fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of at least one or more terpene and/or precursor thereof. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-at least one or more terpene and/or precursor thereof conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Terpenes and/or precursors thereof, or a mixed stream containing one or more terpenes, precursors thereof and/or one or more other products, may be recovered from the fermentation broth by methods known in the art, such as fractional distillation or evaporation, pervaporation, gas stripping and extractive fermentation, including for example, liquid-liquid extraction.

In certain preferred embodiments of the invention, the one or more terpene and/or precursor thereof and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.

Example 1—Expression of Isoprene Synthase in *C. autoethanogenum* for Production of Isoprene from CO The inventors have identified terpene biosynthesis genes in carboxydotrophic acetogens such as *C. autoethanogenum* and *C. ljungdahlii*. A recombinant organism was engineered to produce isoprene. Isoprene is naturally emitted by some plant such as poplar to protect its leave from UV radiation. Isoprene synthase (EC 4.2.3.27) gene of Poplar was codon optimized and introduced into a carboxydotrophic acetogen *C. autoethanogenum* to produce isoprene from CO. The enzyme takes key intermediate DMAPP (Dimethylallyl diphosphate) of terpenoid biosynthesis to isoprene in an irreversible reaction (FIG. 1).

Strains and Growth Conditions:

All subcloning steps were performed in *E. coli* using standard strains and growth conditions as described earlier (Sambrook et al, Molecular Cloning: A laboratory Manual, Cold Spring Harbour Laboratory Press, Cold Spring Harbour, 1989; Ausubel et al, Current protocols in molecular biology, John Wiley & Sons, Ltd., Hoboken, 1987).

*C. autoethanogenum* DSM10061 and DSM23693 (a derivative of DSM10061) were obtained from DSMZ (The German Collection of Microorganisms and Cell Cultures, Inhoffenstraβe 7 B, 38124 Braunschweig, Germany). Growth was carried out at 37° C. using strictly anaerobic conditions and techniques (Hungate, 1969, Methods in Microbiology, vol. 3B. Academic Press, New York: 117-132; Wolfe, 1971, *Adv. Microb. Physiol.*, 6: 107-146). Chemically defined PETC media without yeast extract (Table 1) and 30 psi carbon monoxide containing steel mill waste gas (collected from New Zealand Steel site in Glenbrook, NZ; composition: 44% CO, 32% $N_2$, 22% $CO_2$, 2% $H_2$) as sole carbon and energy source was used.

TABLE 1

| Media component | Concentration per 1.0 L of media |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Resazurin (2 g/L stock) | 0.5 ml |
| $NaHCO_3$ | 2 g |
| Reducing agent | 0.006-0.008 % (v/v) |
| Distilled water | Up to 1 L, pH 5.5 (adjusted with HCl) |
| Wolfe's vitamin solution | per L of Stock |
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Lipoic acid | 5 mg |
| Thiamine | 5 mg |
| Distilled water | To 1 L |
| Trace metal solution | per L of stock |
| Nitrilo triacetic Acid | 2 g |
| $MnSO_4 \cdot H_2O$ | 1 g |
| Fe $(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1 L |
| Reducing agent stock | per 100 mL of stock |
| NaOH | 0.9 g |
| Cystein•HCl | 4 g |
| $Na_2S$ | 4 g |
| Distilled water | To 166 mL |

Construction of Expression Plasmid:

Standard Recombinant DNA and molecular cloning techniques were used in this invention (Sambrook J, Fritsch E F, Maniatis T: Molecular Cloning: A laboratory Manual, Cold Spring Harbour Laboratory Press, Cold Spring Harbour, 1989; Ausubel F M, Brent R, Kingston R E, Moore D D, Seidman J G, Smith J A, Struhl K: Current protocols in molecular biology. John Wiley & Sons, Ltd., Hoboken, 1987). The isoprene synthase of Poplar *tremuloides* (AAQ16588.1; GI:33358229) was codon-optimized (SEQ ID NO: 21) and synthesized. A promoter region of the Pyruvate:ferredoxin oxidoreductase of *C. autoethanogenum* (SEQ ID NO: 22) was used to express the gene.

Genomic DNA from *Clostridium autoethanogenum* DSM23693 was isolated using a modified method by Bertram and Dürre (1989). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 µl lysozyme (~100,000 U) was added and the mixture was incubated at 37° C. for 30 min, followed by addition of 280 µl of a 10% (w/v) SDS solution and another incubation for 10 min. RNA was digested at room temperature by addition of 240 µl of an EDTA solution (0.5 M, pH 8), 20 µl Tris-HCl (1 M, pH 7.5), and 10 µl RNase A (Fermentas Life Sciences). Then, 100 µl Proteinase K (0.5 U) was added and proteolysis took place for 1-3 h at 37° C. Finally, 600 µl of sodium perchlorate (5 M) was added, followed by a phenol-chloroform extraction and an isopropanol precipitation. DNA quantity and quality was inspected spectrophotometrically. The Pyruvate:ferredoxin oxidoreductase promoter sequence was amplified by PCR using oligonucleotides Ppfor-NotI-F (SEQ ID NO: 23: AAGCGGCCGCAAAATAGTTGATAATAATGC) and Ppfor-NdeI-R (SEQ ID NO: 24: TACGCATATGAAT-TCCTCTCCTTTTCAAGC) using iProof High Fidelity DNA Polymerase (Bio-Rad Laboratories) and the following program: initial denaturation at 98° C. for 30 seconds, followed by 32 cycles of denaturation (98° C. for 10 seconds), annealing (50-62° C. for 30-120 seconds) and elongation (72° C. for 30-90 seconds), before a final extension step (72° C. for 10 minutes).

Figure 2:
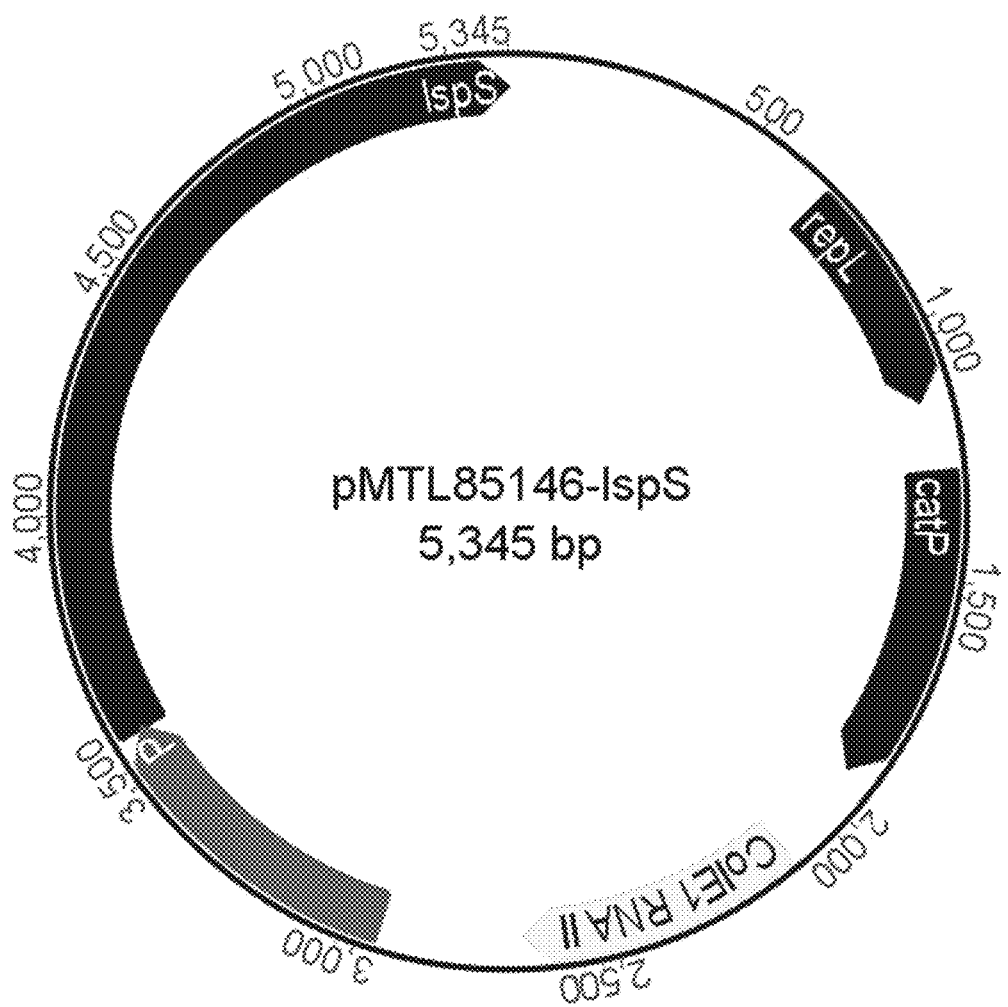
FIG. 2: Genetic map of plasmid pMTL 85146-ispS

Construction of Isoprene Synthase Expression Plasmid:

Construction of an expression plasmid was performed in *E. coli* DH5α-T1$^R$ (Invitrogen) and XL1-Blue MRF' Kan (Stratagene). In a first step, the amplified $P_{pfor}$ promoter region was cloned into the *E. coli-Clostridium* shuttle vector pMTL85141 (FJ797651.1; Nigel Minton, University of Nottingham; Heap et al., 2009) using NotI and NdeI restriction sites, generating plasmid pMTL85146. As a second step, ispS was cloned into pMTL85146 using restriction sites NdeI and EcoRI, resulting in plasmid pMTL 85146-ispS (FIG. 2, SEQ ID NO: 25).

Transformation and Expression in *C. autoethanogenum*

Prior to transformation, DNA was methylated in vivo in *E. coli* using a synthesized hybrid Type II methyltransferase (SEQ ID NO: 63) co-expressed on a methylation plasmid (SEQ ID NO: 64) designed from methyltransferase genes from *C. autoethanogenum*, *C. ragsdalei* and *C. ljungdahlii* as described in US patent 2011/0236941.

Both expression plasmid and methylation plasmid were transformed into same cells of restriction negative *E. coli* XL1-Blue MRF' Kan (Stratagene), which is possible due to their compatible Gram-(−) origins of replication (high copy ColE1 in expression plasmid and low copy p15A in methylation plasmid). In vivo methylation was induced by addition of 1 mM IPTG, and methylated plasmids were isolated using QIAGEN Plasmid Midi Kit (QIAGEN). The resulting mixture was used for transformation experiments with *C. autoethanogenum* DSM23693, but only the abundant (high-copy) expression plasmid has a Gram-(+) replication origin (repL) allowing it to replicate in Clostridia.

Transformation into *C. autoethanogenum*:

During the complete transformation experiment, *C. autoethanogenum* DSM23693 was grown in PETC media (Table 1) supplemented with 1 g/L yeast extract and 10 g/l fructose as well as 30 psi steel mill waste gas (collected from New Zealand Steel site in Glenbrook, NZ; composition: 44% CO, 32% $N_2$, 22% $CO_2$, 2% $H_2$) as carbon source.

To make competent cells, a 50 ml culture of *C. autoethanogenum* DSM23693 was subcultured to fresh media for 3 consecutive days. These cells were used to inoculate 50 ml PETC media containing 40 mM DL-threonine at an $OD_{600nm}$ of 0.05. When the culture reached an $OD_{600nm}$ of 0.4, the cells were transferred into an anaerobic chamber and harvested at 4,700×g and 4° C. The culture was twice washed with ice-cold electroporation buffer (270 mM sucrose, 1 mM MgCl2, 7 mM sodium phosphate, pH 7.4) and finally suspended in a volume of 600 µl fresh electroporation buffer. This mixture was transferred into a pre-cooled electroporation cuvette with a 0.4 cm electrode gap containing 1 µg of the methylated plasmid mixture and immediately pulsed using the Gene pulser Xcell electroporation system (Bio-Rad) with the following settings: 2.5 kV, 600Ω, and 25 µF. Time constants of 3.7-4.0 ms were achieved. The culture was transferred into 5 ml fresh media. Regeneration of the cells was monitored at a wavelength of 600 nm using a Spectronic Helios Epsilon Spectrophotometer (Thermo) equipped with a tube holder. After an initial drop in biomass, the cells started growing again. Once the biomass has doubled from that point, the cells were harvested, suspended in 200 µl fresh media and plated on selective PETC plates (containing 1.2% Bacto™ Agar (BD)) with appropriate antibiotics 4 µg/ml Clarithromycin or 15 µg/ml thiamphenicol. After 4-5 days of inoculation with 30 psi steel mill gas at 37° C., colonies were visible.

The colonies were used to inoculate 2 ml PETC media with antibiotics. When growth occurred, the culture was scaled up into a volume of 5 ml and later 50 ml with 30 psi steel mill gas as sole carbon source.

Confirmation of the Successful Transformation:

To verify the DNA transfer, a plasmid mini prep was performed from 10 ml culture volume using Zyppy plasmid miniprep kit (Zymo). Since the quality of the isolated plasmid was not sufficient for a restriction digest due to Clostridial exonuclease activity [Burchhardt and Dürre, 1990], a PCR was performed with the isolated plasmid with oligonucleotide pairs colE1-F (SEQ ID NO: 65: CGTCA-GACCCCGTAGAAA) plus colE1-R (SEQ ID NO: 66: CTCTCCTGTTCCGACCCT). PCR was carried out using iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes).

To confirm the identity of the clones, genomic DNA was isolated (see above) from 50 ml cultures of *C. autoethanogenum* DSM23693. A PCR was performed against the 16s rRNA gene using oligonucleotides fD1 (SEQ ID NO: 67: CCGAATTCGTCGACAACAGAGTTTGATCCTGG-CTCAG) and rP2 (SEQ ID NO: 68: CCCGGGATC-CAAGCTTACGGCTACCTTGTTACGACTT) [Weisberg et al., 1991] and iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes). Sequencing results were at least 99.9% identity against the 16s rRNA gene (rrsA) of *C. autoethanogenum* (Y18178, GI:7271109).

Expression of Isoprene Synthase Gene qRT-PCR experiments were performed to confirm successful expression of introduced isoprene synthase gene in *C. autoethanogenum*.

A culture harboring isoprene synthase plasmid pMTL 85146-ispS and a control culture without plasmid was grown in 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and carbon source. 0.8 mL samples were taken during logarithmic growth phase at an $OD_{600nm}$ of around 0.5 and mixed with 1.6 mL RNA protect reagent (Qiagen). The mixture was centrifuged (6,000×g, 5 min, 4° C.), and the cell sediment snap frozen in liquid nitrogen and stored at −80° C. until RNA extraction. Total RNA was isolated using RNeasy Mini Kit (Qiagen) according to protocol 5 of the manual. Disruption of the cells was carried out by passing the mixture through a syringe 10 times and eluted in 50 µL of RNase/DNase-free water. After DNase I treatment using DNA-free™ Kit (Ambion), the reverse transcription step was then carried out using Super-Script III Reverse Transcriptase Kit (Invitrogen, Carlsbad, CA, USA). RNA was checked using an Agilent Bioanalyzer 2100 (Agilent Technologies, Santa Clara, CA, USA), Qubit Fluorometer (Invitrogen, Carlsbad, CA, USA) and by gel electrophoresis. A non-RT control was performed for every oligonucleotide pair. All qRT-PCR reactions were performed in duplicate using a MyiQ™ Single Colour Detection System (Bio-Rad Laboratories, Carlsbad, CA, USA) in a total reaction volume of 15 µL with 25 ng of cDNA template, 67 nM of each oligonucleotide (Table 2), and 1× iQ™ SYBR® Green Supermix (Bio-Rad Laboratories, Carlsbad, CA, USA). The reaction conditions were 95° C. for 3 min, followed by 40 cycles of 95° C. for 15 s, 55° C. for 15 s and 72° C. for 30 s. For detection of oligonucleotide dimerisation or other artifacts of amplification, a melting-curve analysis was performed immediately after completion of the qPCR (38 cycles of 58° C. to 95° C. at 1° C./s). Two housekeeping genes (guanylate kinase and formate tetrahydrofolate ligase) were included for each cDNA sample for normalization. Determination of relative gene expression was conducted using Relative Expression Software Tool (REST©) 2008 V2.0.7 (38). Dilution series of cDNA spanning 4 log units were used to generate standard curves and the resulting amplification efficiencies to calculate concentration of mRNA.

synthesizes both IPP and DMAPP equally, in the mevalonate pathway the only product is IPP. Production of isoprene requires only the precursor DMAPP to be present in conjunction with an isoprene synthase, while for production of higher terpenes and terpenoids, it is required to have equal amounts of IPP and DMAPP available to produce Geranyl-PP by a geranyltransferase.

Figure 3:
FIG. 3: Genetic map of plasmid pMTL 85246-ispS-idi

Construction of Isopentenyl-Diphosphate Delta-Isomerase Expression Plasmid:

An Isopentenyl-diphosphate delta-isomerase gene idi from *C. beijerinckii* (Gene ID:5294264), encoding an Isopentenyl-diphosphate delta-isomerase (YP_001310174.1), was cloned downstream of ispS. The gene was amplified using oligonucleotide Idi-Cbei-SacI-F (SEQ ID NO: 26: GTGAGCTCGAAAGGGGAAAT-TAAATG) and Idi-Cbei-KpnI-R (SEQ ID NO: 27: ATGGTACCCCAAATCTTTATTTAGACG) from genomic DNA of *C. beijerinckii* NCIMB8052, obtained using the same method as described above for *C. autoethanogenum*. The PCR product was cloned into vector pMTL 85146-ispS using SacI and KpnI restriction sites to yield plasmid pMTL85146-ispS-idi (SEQ ID NO: 28). The antibiotic resistance marker was exchanged from catP to ermB (released from vector pMTL82254 (FJ797646.1; Nigel Minton, University of Nottingham; Heap et al., 2009) using restriction enzymes PmeI and FseI to form plasmid pMTL85246-ispS-idi (FIG. 3).

Transformation and expression in *C. autoethanogenum* was carried out as described for plasmid pMTL 85146-ispS. After successful transformation, growth experiment was carried out in 50 mL 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and

TABLE 2

Oligonucleotides for qRT-PCR

| Target | Oligonucleotide Name | DNA Sequence (5' to 3') | SEQ ID NO: |
|---|---|---|---|
| Guanylate kinase (gnk) | GnK-F | TCAGGACCTTCTGGAACTGG | 108 |
| | GnK-R | ACCTCCCCTTTTCTTGGAGA | 109 |
| Formate tetrahydrofolate ligase (FoT4L) | FoT4L-F | CAGGTTTCGGTGCTGACCTA | 110 |
| | FoT4L-F | AACTCCGCCGTTGTATTTCA | 111 |
| Isoprene Synthase | ispS-F | AGG CTG AAT TTC TTA CAC TTC TTG A | 69 |
| | ispS-R | GTA ACT CCA TCA AAT CCT CCA CTA C | 70 |

While no amplification was observed with the wild-type strain using oligonucleotide pair ispS, a signal with the ispS oligonucleotide pair was measured for the strain carrying plasmid pMTL 85146-ispS, confirming successful expression of the ispS gene.

Example 2—Expression of Isopentenyl-Diphosphate Delta-Isomerase to Convert Between Key Terpene Precursors DMAPP (Dimethylallyl Diphosphate) and IPP (Isopentenyl Diphosphate)

Figure 8:
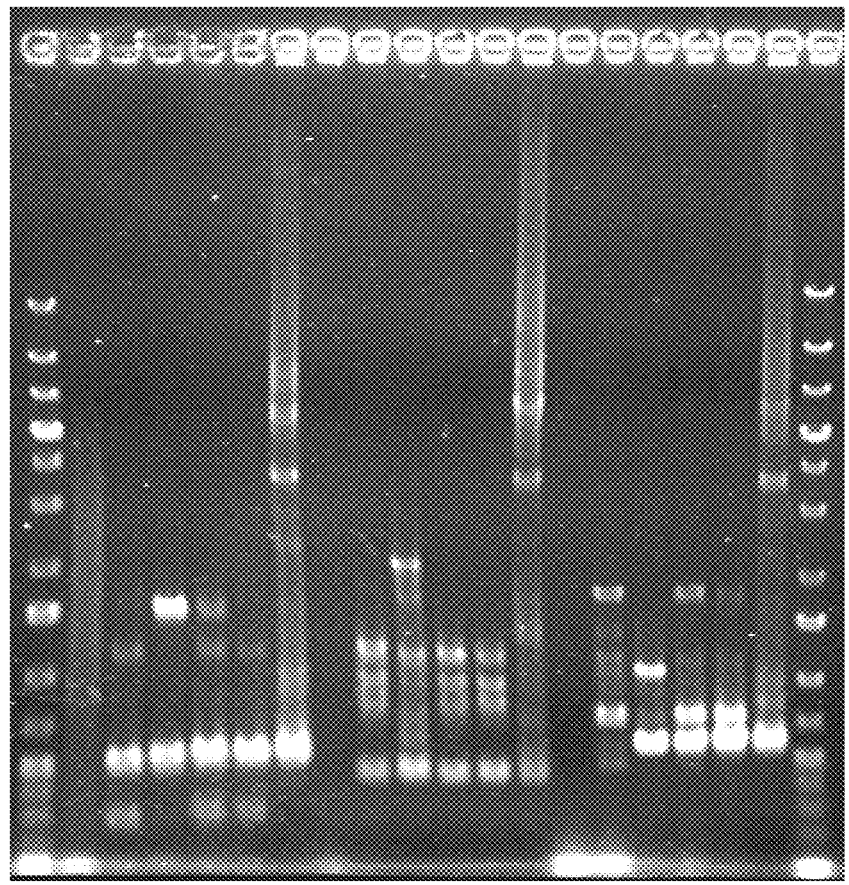
FIG. 8: Agarose gel electrophoresis image confirming presence of isoprene expression plasmid pMTL 85246-ispS-idi in *C. autoethanogenum* transformants. Lanes 1, and 20 show 100 bp Plus DNA Ladder. Lane 3-6, 9-12, 15-18 show PCR with isolated plasmids from 4 different clones as template, each in the following order: colE1, ermB, and idi. Lanes 2, 8, and 14 show PCR without template as negative control, each in the following order: colE1, ermB, and idi. Lanes 7, 13, and 19 show PCR with pMTL 85246-ispS-idi from *E. coli* as positive control, each in the following order: colE1, ermB, and idi.
Figure 9:
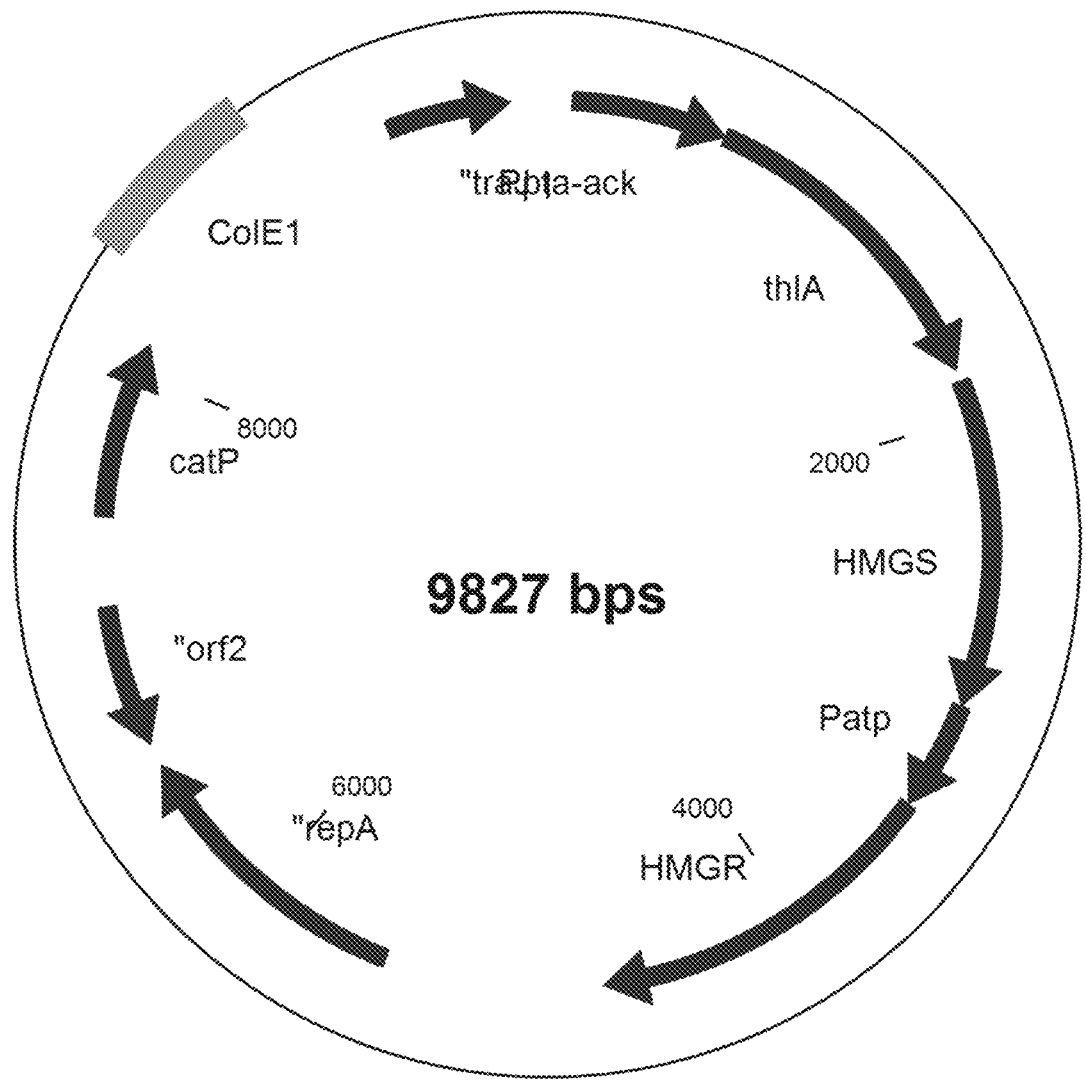
FIG. 9—Mevalonate expression plasmid pMTL8215-Pptaack-th1A-HMGS-Patp-HMGR

Availability and balance of precursors DMAPP (Dimethylallyl diphosphate) and IPP (Isopentenyl diphosphate) is crucial for production of terpenes. While the DXS pathway carbon source. To confirm that the plasmid has been successfully introduced, plasmid mini prep DNA was carried out from transformants as described previously. PCR against the isolated plasmid using oligonucleotide pairs that target colE1 (colE1-F: SEQ ID NO: 65: CGTCA-GACCCCGTAGAAA and colE1-R: SEQ ID NO: 66: CTCTCCTGTTCCGACCCT), ermB (ermB-F: SEQ ID NO: 106: TTTGTAATTAAGAAGGAG and ermB-R: SEQ ID NO: 107:

GTAGAATCCTTCTTCAAC) and idi (Idi-Cbei-SacI-F: SEQ ID NO: 26: GTGAGCTCGAAAGGGGAAAT-TAAATG and Idi-Cbei-KpnI-R: SEQ ID NO: 27: ATGGTACCCCAAATCTTTATTTAGACG) confirmed transformation success (FIG. 8). Similarly, genomic DNA from these transformants were extracted, and the resulting 16s rRNA amplicon using oligonucleotides fD1 and rP2 (see above) confirmed 99.9% identity against the 16S rRNA gene of *C. autoethanogenum* (Y18178, GI:7271109).

Figure 14:
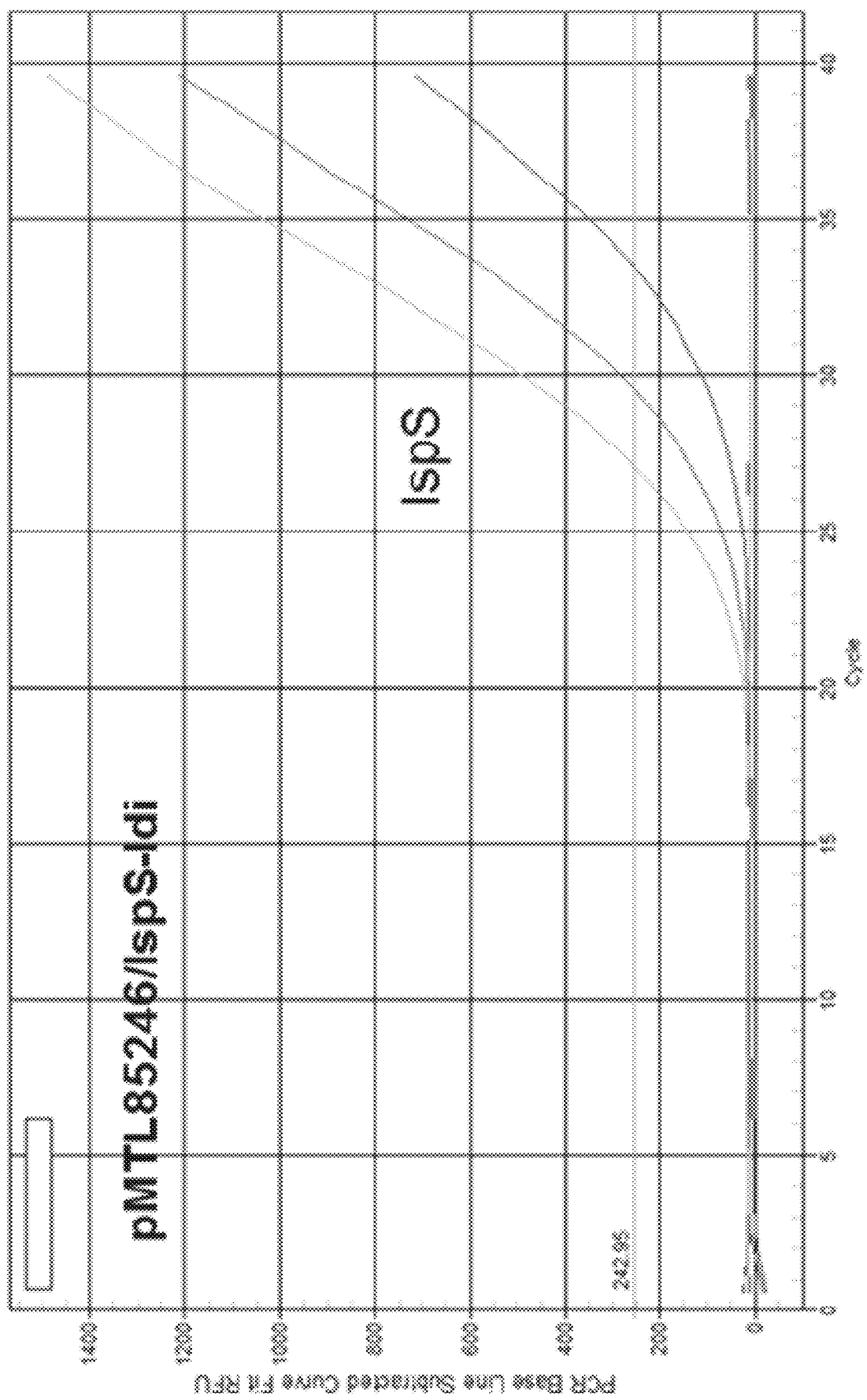

Successful confirmation of gene expression was carried out as described above using a oligonucleotide pair against Isopentenyl-diphosphate delta-isomerase gene idi (idi-F, SEQ ID NO: 71: ATA CGT GCT GTA GTC ATC CAA GAT A and idiR, SEQ ID NO: 72: TCT TCA AGT TCA CAT GTA AAA CCC A) and a sample from a serum bottle growth experiment with *C. autoethanogenum* carrying plasmid pMTL 85146-ispS-idi. A signal for the isoprene synthase gene ispS was also observed (FIG. 14).

Example 3—Overexpression of DXS Pathway

To improve flow through the DXS pathway, genes of the pathway were overexpressed. The initial step of the pathway, converting pyruvate and D-glyceraldehyde-3-phosphate (G3P) into deoxyxylulose 5-phosphate (DXP/DXPS/DOXP), is catalyzed by an deoxyxylulose 5-phosphate synthase (DXS).

Figure 4:
FIG. 4: Genetic map of plasmid pMTL 85246-ispS-idi-dxs
Figure 5:
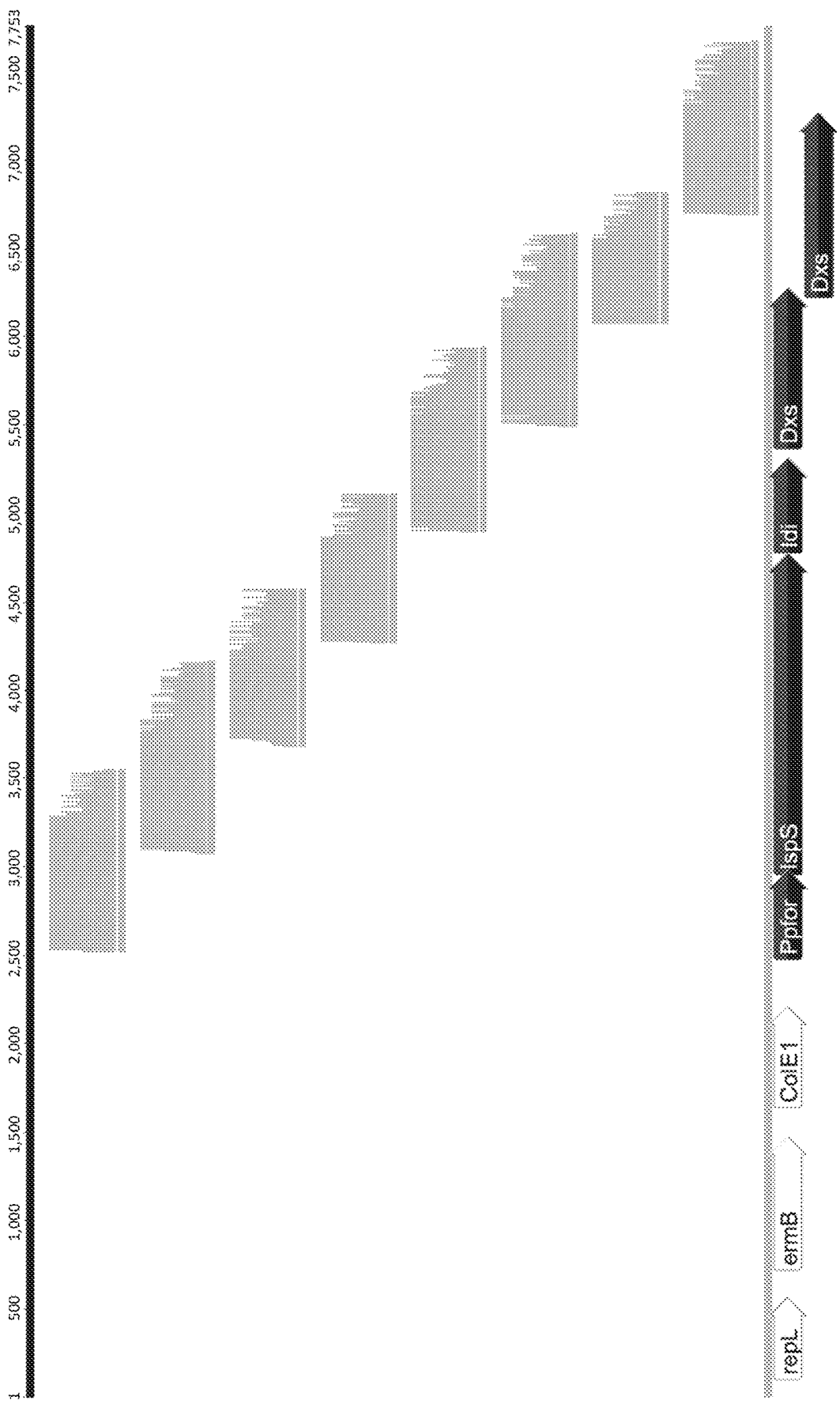
FIG. 5: Sequencing results for plasmid pMTL 85246-ispS-idi-dxs

Construction of DXS Overexpression Expression Plasmid:

The dxs gene of *C. autoethanogenum* was amplified from genomic DNA with oligonucleotides Dxs-SalI-F (SEQ ID NO: 29: GCAGTCGACTTTATTAAAGGGATAGATAA) and Dxs-XhoI-R (SEQ ID NO: 30: TGCTCGAGT-TAAAATATATGACTTACCTCTG) as described for other genes above. The amplified gene was then cloned into plasmid pMTL85246-ispS-idi with SalI and XhoI to produce plasmid pMTL85246-ispS-idi-dxs (SEQ ID NO: 31 and FIG. 4). DNA sequencing using oligonucleotides given in Table 3 confirmed successful cloning of ispS, idi, and dxs without mutations (FIG. 5). The ispS and idi genes are as described in example 1 and 2 respectively.

TABLE 3

Oligonucleotides for sequencing

| Oligonucleotide Name | DNA Sequence (5' to 3') | SEQ ID NO: |
|---|---|---|
| M13R | CAGGAAACAGCTATGAC | 32 |
| Isoprene-seq1 | GTTATTCAAGCTACACCTTT | 33 |
| Isoprene-seq2 | GATTGGTAAAGAATTAGCTG | 34 |
| Isoprene-seq3 | TCAAGAAGCTAAGTGGCT | 35 |
| Isoprene-seq4 | CTCACCGTAAAGGAACA | 36 |
| Isoprene-seq5 | GCTAGCTAGAGAAATTAGAA | 37 |
| Isoprene-seq6 | GGAATGGCAAAATATCTTGA | 38 |
| Isoprene-seq7 | GAAACACATCAGGGAATATT | 39 |

Transformation and Expression in *C. autoethanogenum*

Figure 15:
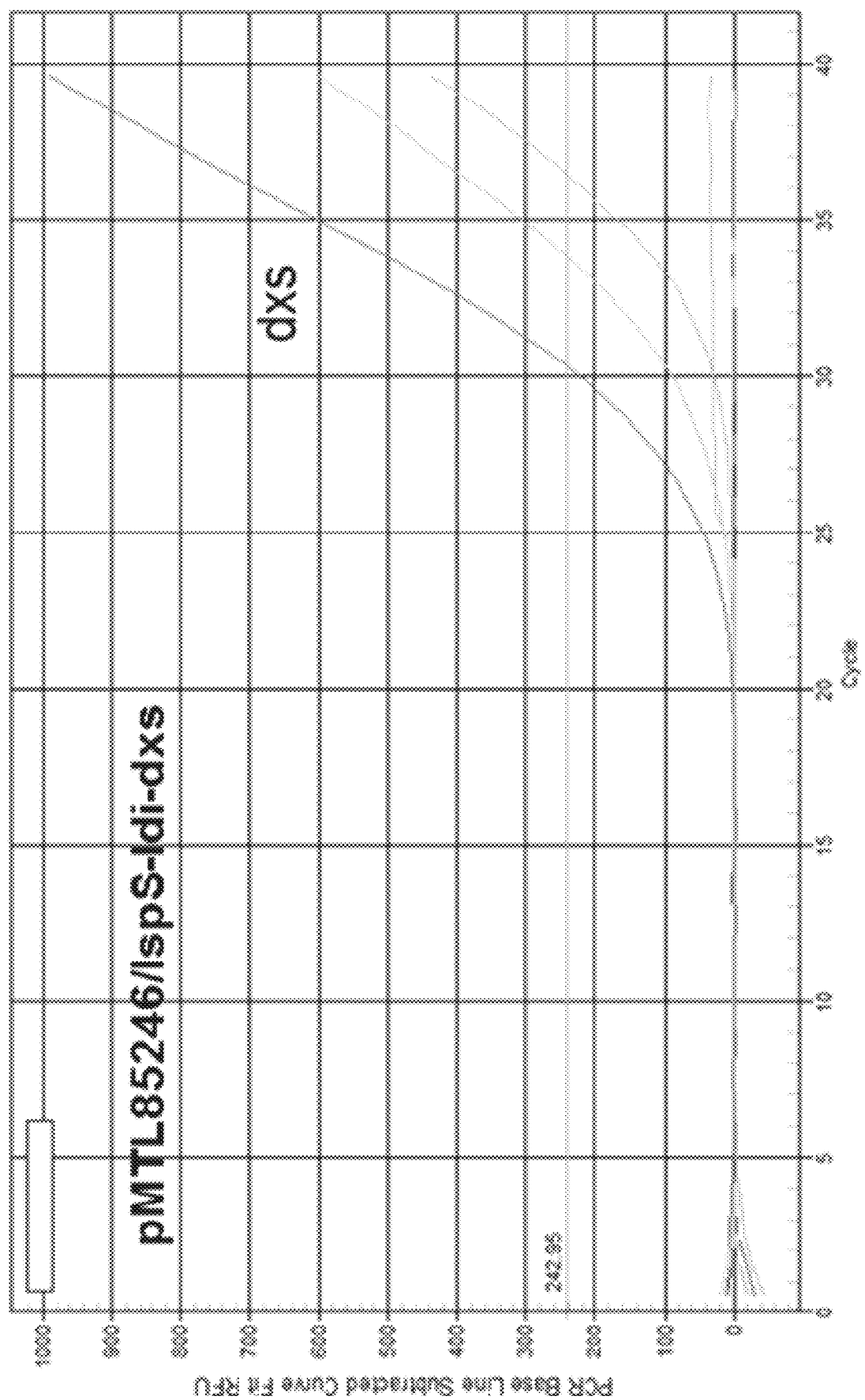

Transformation and expression in *C. autoethanogenum* was carried out as described for plasmid pMTL 85146-ispS. After successful transformation, a growth experiment was carried out in 50 mL 50 mL serum bottles and PETC media (Table 1) with 30 psi steel mill waste gas (collected from New Zealand Steel site in Glenbrook, NZ; composition: 44% CO, 32% $N_2$, 22% $CO_2$, 2% $H_2$) as sole energy and carbon source. Confirmation of gene expression was carried out as described above from a sample collected at $OD_{600nm}$=0.75. Oligonucleotide pair dxs-F (SEQ ID NO: 73: ACAAAGTATCTAAGACAGGAGGTCA) and dxs-R (SEQ ID NO: 74: GATGTCCCACATCCCATATAAGTTT) was used to measure expression of gene dxs in both wild-type strain and strain carrying plasmid pMTL 85146-ispS-idi-dxs. mRNA levels in the strain carrying the plasmid were found to be over 3 times increased compared to the wild-type (FIG. 15). Biomass was normalized before RNA extraction.

Example 4—Introduction and Expression of Mevalonate Pathway

Figure 7:
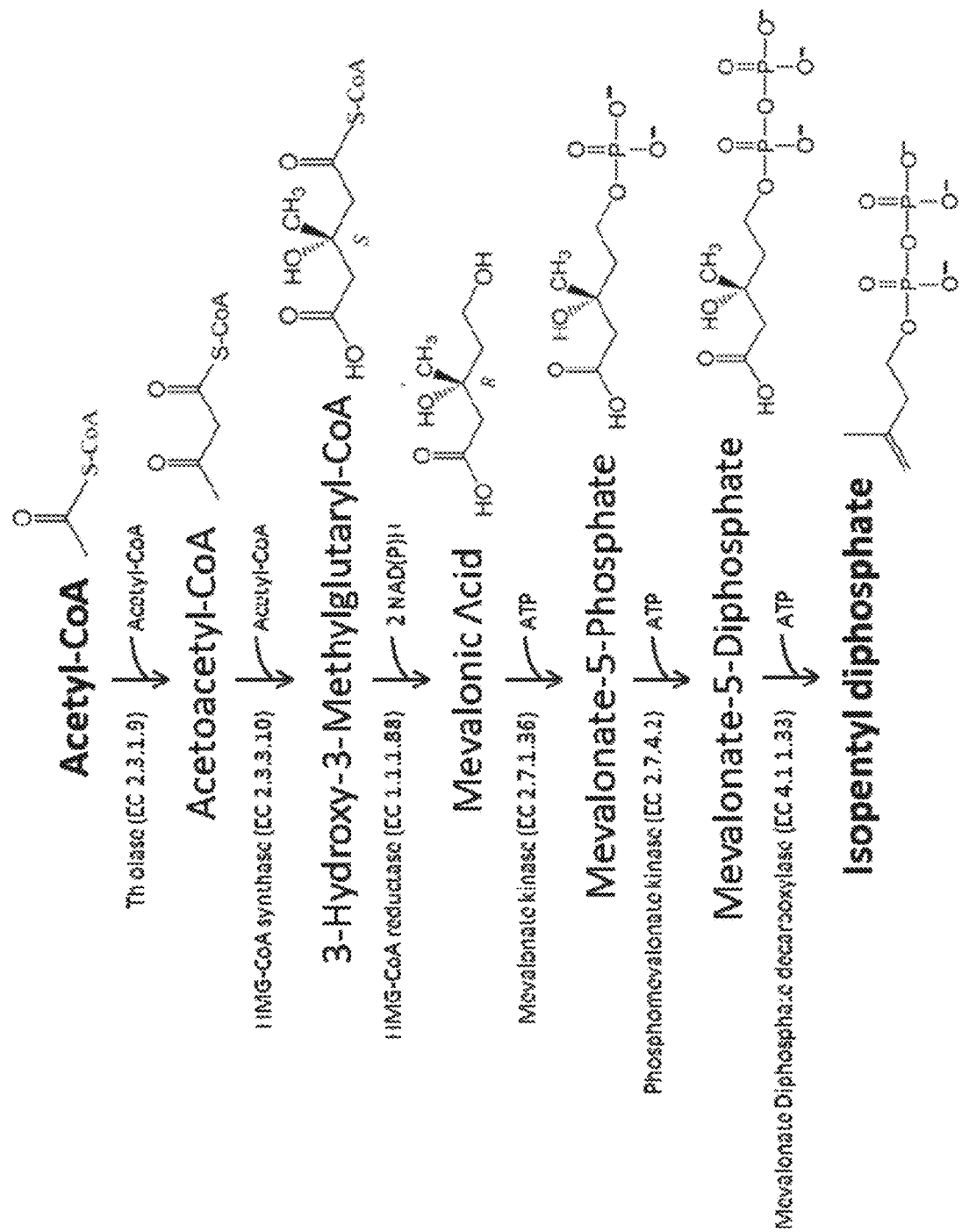
FIG. 7: Mevalonate pathway

The first step of the mevalonate pathway (FIG. 7) is catalyzed by a thiolase that converts two molecules of acetyl-CoA into acetoacetyl-CoA (and HS-CoA). This enzyme has been successfully expressed in carboxydotrophic acetogens *Clostridium autoethanogenum* and *C. ljungdahlii* by the same inventors (US patent 2011/0236941). Constructs for the remaining genes of the mevalonate pathway have been designed.

Construction of Mevalonate Expression Plasmid:

Standard recombinant DNA and molecular cloning techniques were used (Sambrook, J., and Russell, D., Molecular cloning: A Laboratory Manual 3rd Ed., Cold Spring Harbour Lab Press, Cold Spring Harbour, N Y, 2001). The three genes required for mevalonate synthesis via the upper part of the mevalonate pathway, i.e., thiolase (thlA/vraB), HMG-CoA synthase (HMGS) and HMG-CoA reductase (HMGR), were codon-optimised as an operon ($P_{ptaack}$-thlA/vraB-HMGS-$P_{atp}$-HMGR).

The Phosphotransacetylase/Acetate kinase operon promoter ($P_{pta-ack}$) of *C. autoethanogenum* (SEQ ID NO: 61) was used for expression of the thiolase and HMG-CoA synthase while a promoter region of the ATP synthase ($P_{atp}$) of *C. autoethanogenum* was used for expression of the HMG-CoA reductase. Two variants of thiolase, thlA from *Clostridium acetobutylicum* and vraB from *Staphylococcus aureus*, were synthesised and flanked by NdeI and EcoRI restriction sites for further sub-cloning. Both HMG-CoA synthase (HMGS) and HMG-CoA reductase (HMGR) were synthesised from *Staphylococcus aureus* and flanked by EcoRI-SacI and KpnI-XbaI restriction sites respectively for further sub-cloning. All optimized DNA sequences used are given in Table 4.

TABLE 4

Sequences of mevalonate expression plasmid

| Description | Source | SEQ ID NO: |
|---|---|---|
| Thiolase (thlA) | *Clostridium acetobutylicum* ATCC 824; NC_003030.1; GI: 1119056 | 40 |
| Acetyl-CoA c-acetyltransferase (vraB) | *Staphylococcus aureus* subsp. *aureus* Mu50; NC_002758.2; region: 652965 . . . 654104; including GI: 15923566 | 41 |
| 3-hydroxy-3-methylglutaryl-CoA synthase (HMGS) | *Staphylococcus aureus* subsp. *aureus* Mu50; NC_002758.2; region: 2689180 . . . 2690346; including GI: 15925536 | 42 |
| Hydroxymethyl-glutaryl-CoA reductase (HMGR) | *Staphylococcus aureus* subsp. *aureus* Mu50; NC_002758.2; region: complement(2687648 . . . 2688925); including GI: 15925535 | 43 |

TABLE 4-continued

Sequences of mevalonate expression plasmid

| Description | Source | SEQ ID NO: |
|---|---|---|
| Phosphotrans-acetylase-acetate kinase operon ($P_{pta\text{-}ack}$) | *Clostridium autoethanogenum* DSM10061 | 44 |
| ATP synthase promoter ($P_{atp}$) | *Clostridium autoethanogenum* DSM10061 | 45 |

The ATP synthase promoter ($P_{atp}$) together with the hydroxymethylglutaryl-CoA reductase (HMGR) was amplified using oligonucleotides pUC57-F (SEQ ID NO: 46: AGCAGATTGTACTGAGAGTGC) and pUC57-R (SEQ ID NO: 47: ACAGCTATGACCATGATTACG) and pUC57-Patp-HMGR as a template. The 2033 bp amplified fragment was digested with SacI and XbaI and ligated into the *E. coli-Clostridium* shuttle vector pMTL 82151 (FJ7976; Nigel Minton, University of Nottingham, UK; Heap et al., 2009, *J Microbiol Methods*. 78: 79-85) resulting in plasmid pMTL 82151-Patp-HMGR (SEQ ID NO: 76).

3-hydroxy-3-methylglutaryl-CoA synthase (HMGS) was amplified from the codon-synthesised plasmid pGH-seq3.2 using oligonucleotides EcoRI-HMGS_F (SEQ ID NO: 77: AGCCGTGAATTCGAGGCTTTTACTAAAAACA) and EcoRI-HMGS_R (SEQ ID NO: 78: AGGCGTCTA-GATGTTCGTCTCTACAAATAATT). The 1391 bp amplified fragment was digested with SacI and EcoRI and ligated into the previously created plasmid pMTL 82151-Patp-HMGR to give pMTL 82151-HMGS-Patp-HMGR (SEQ ID NO: 79). The created plasmid pMTL 82151-HMGS-Patp-HMGR (SEQ ID NO: 79) and the 1768 bp codon-optimised operon of $P_{ptaack}$-thlA/vraB were both cut with NotI and EcoRI. A ligation was performed and subsequently transformed into *E. coli* XL1-Blue MRF' Kan resulting in plasmid pMTL8215-$P_{ptaack}$-thlA/vraB-HMGS-$P_{atp}$-HMGR (SEQ ID NO: 50).

The five genes required for synthesis of terpenoid key intermediates from mevalonate via the bottom part of the mevalonate pathway, i.e., mevalonate kinase (MK), phosphomevalonate kinase (PMK), mevalonate diphosphate decarboxylase (PMD), isopentenyl-diphosphate delta-isomerase (idi) and isoprene synthase (ispS) were codon-optimised by ATG:Biosynthetics GmbH (Merzhausen, Germany). Mevalonate kinase (MK), phosphomevalonate kinase (PMK) and mevalonate diphosphate decarboxylase (PMD) were obtained from *Staphylococcus aureus*.

The promoter region of the RNF Complex ($P_{rnf}$) of *C. autoethanogenum* (SEQ ID NO: 62) was used for expression of mevalonate kinase (MK), phosphomevalonate kinase (PMK) and mevalonate diphosphate decarboxylase (PMD), while the promoter region of the Pyruvate:ferredoxin oxidoreductase ($P_{for}$) of *C. autoethanogenum* (SEQ ID NO: 22) was used for expression of isopentenyl-diphosphate delta-isomerase (idi) and isoprene synthase (ispS). All DNA sequences used are given in Table 5. The codon-optimised Prnf-MK was amplified from the synthesised plasmid pGH-Prnf-MK-PMK-PMD with oligonucleotides NotI-XbaI-Prnf-MK_F (SEQ ID NO: 80: ATGCGCGGCCGCTAGGTCTAGAATATCGATACAGA-TAAAAAATATATAATACA G) and SalI-Prnf-MK_R (SEQ ID NO: 81: TGGTTCTGTAACAGCGTATT-CACCTGC). The amplified gene was then cloned into plasmid pMTL83145 (SEQ ID NO: 49) with NotI and SalI to produce plasmid pMTL8314-Prnf-MK (SEQ ID NO: 82).

This resulting plasmid and the 2165 bp codon optimised fragment PMK-PMD was subsequently digested with SalI and HindIII. A ligation was performed resulting in plasmid pMTL 8314-Prnf-MK-PMK-PMD (SEQ ID NO: 83).

Figure 10:
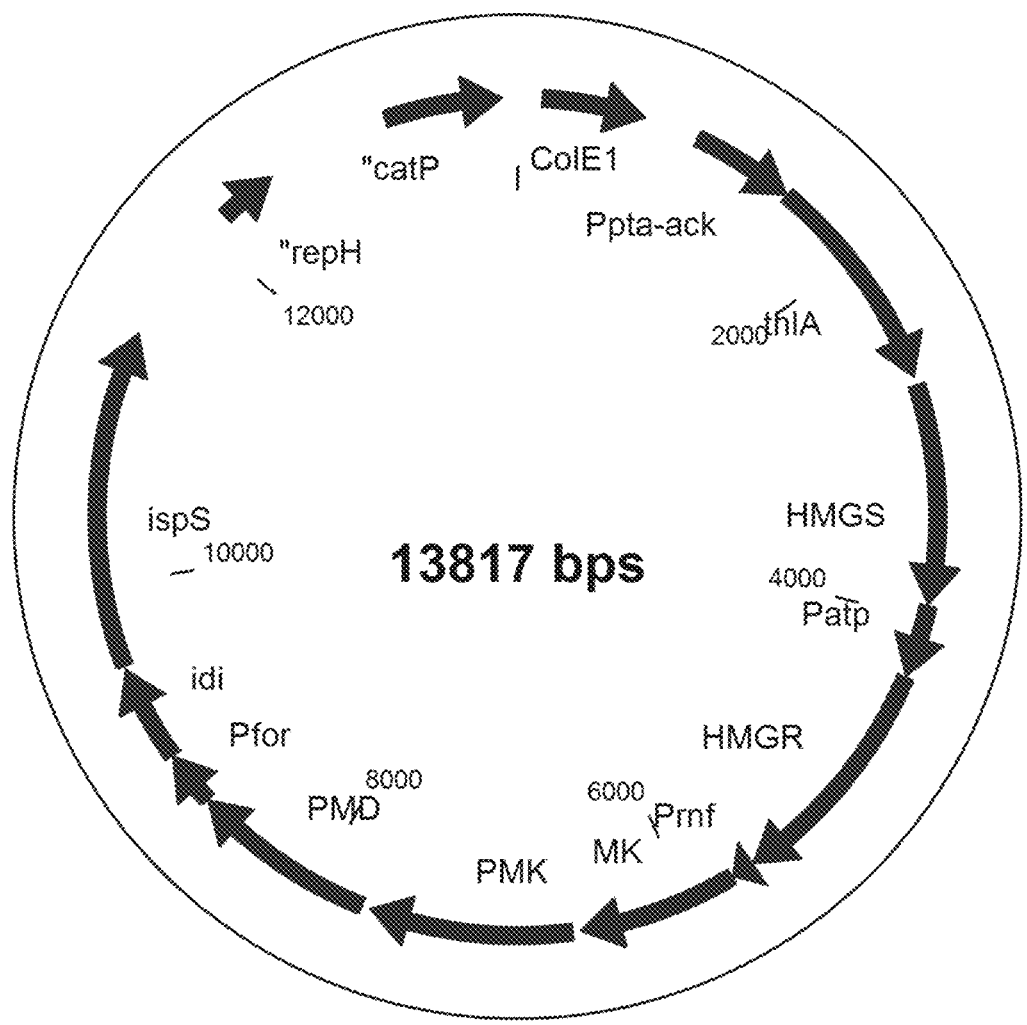
FIG. 10—Isoprene expression plasmid pMTL 8314-Pptaack-th1A-HMGS-Patp-HMGR-Prnf-MK-PMK-PMD-Pfor-idi-ispS FIG. 11—Farnesene expression plasmid pMTL8314-Pptaack-th1A-HMGS-Patp-HMGR-Prnf-MK-PMK-PMD-Pfor-idi-ispA-FS FIG. 12—Genetic map of plasmid pMTL 85246-ispS-idi-dxs FIG. 13—Amplification chart for gene expression experiment with *C. autoethanogenum* carrying plasmid pMTL 85146-ispS FIG. 14—Amplification chart for gene expression experiment with *C. autoethanogenum* carrying plasmid pMTL 85246-ispS-idi FIG. 15—Amplification chart for gene expression experiment with *C. autoethanogenum* carrying plasmid pMTL 85246-ispS-idi-dxs FIG. 16—PCR check for the presence of the plasmid pMTL8314Prnf-MK-PMK-PMD-Pfor-idi-ispA-FS. Expected band size 1584 bp. The DNA marker Fermentas 1 kb DNA ladder.
Figure 11:
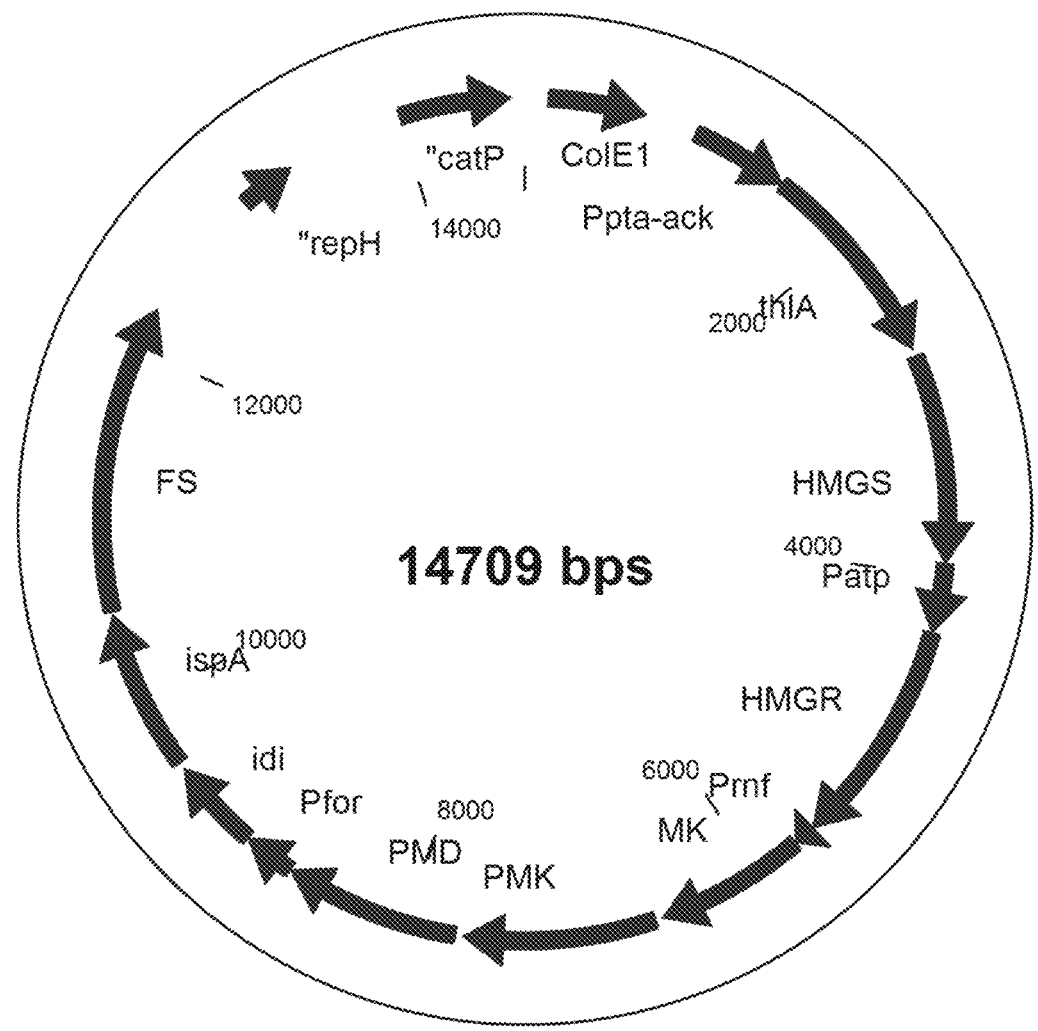
Figure 12:
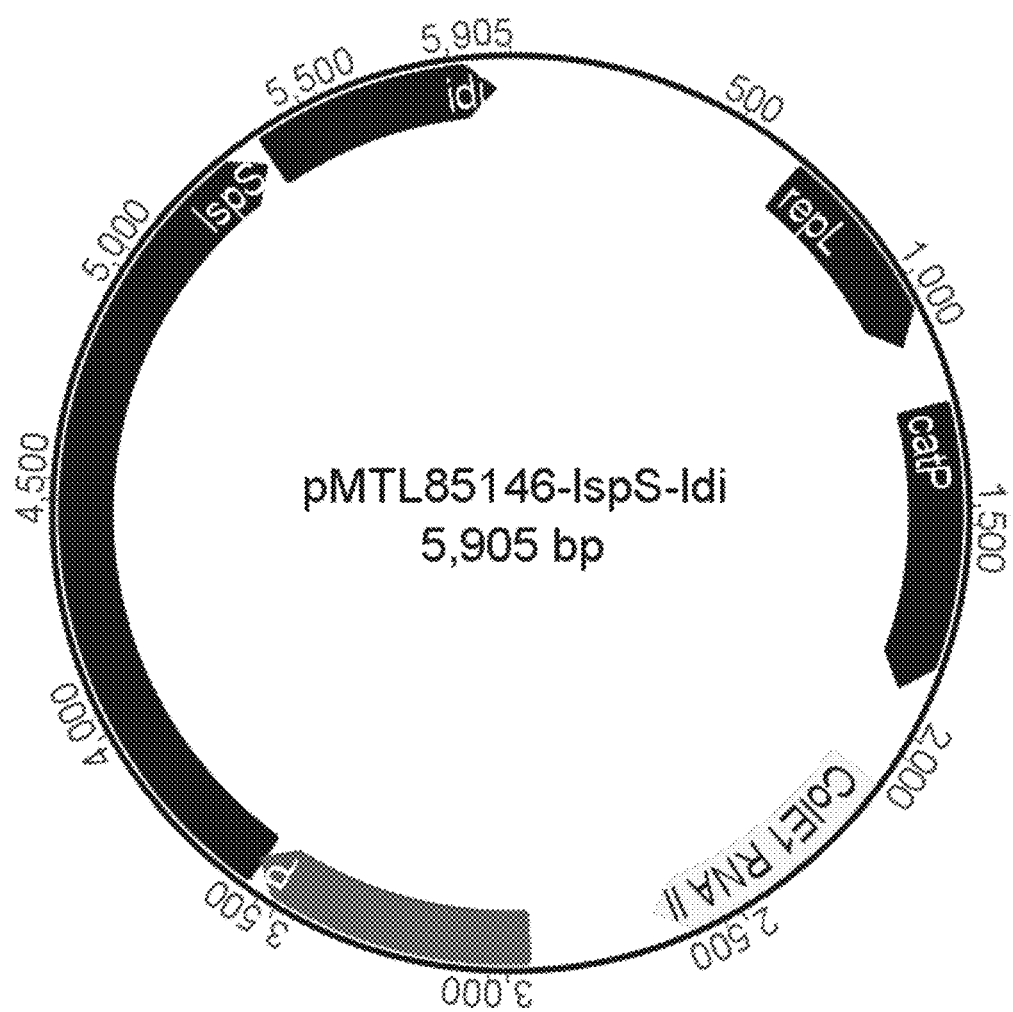
Figure 13:
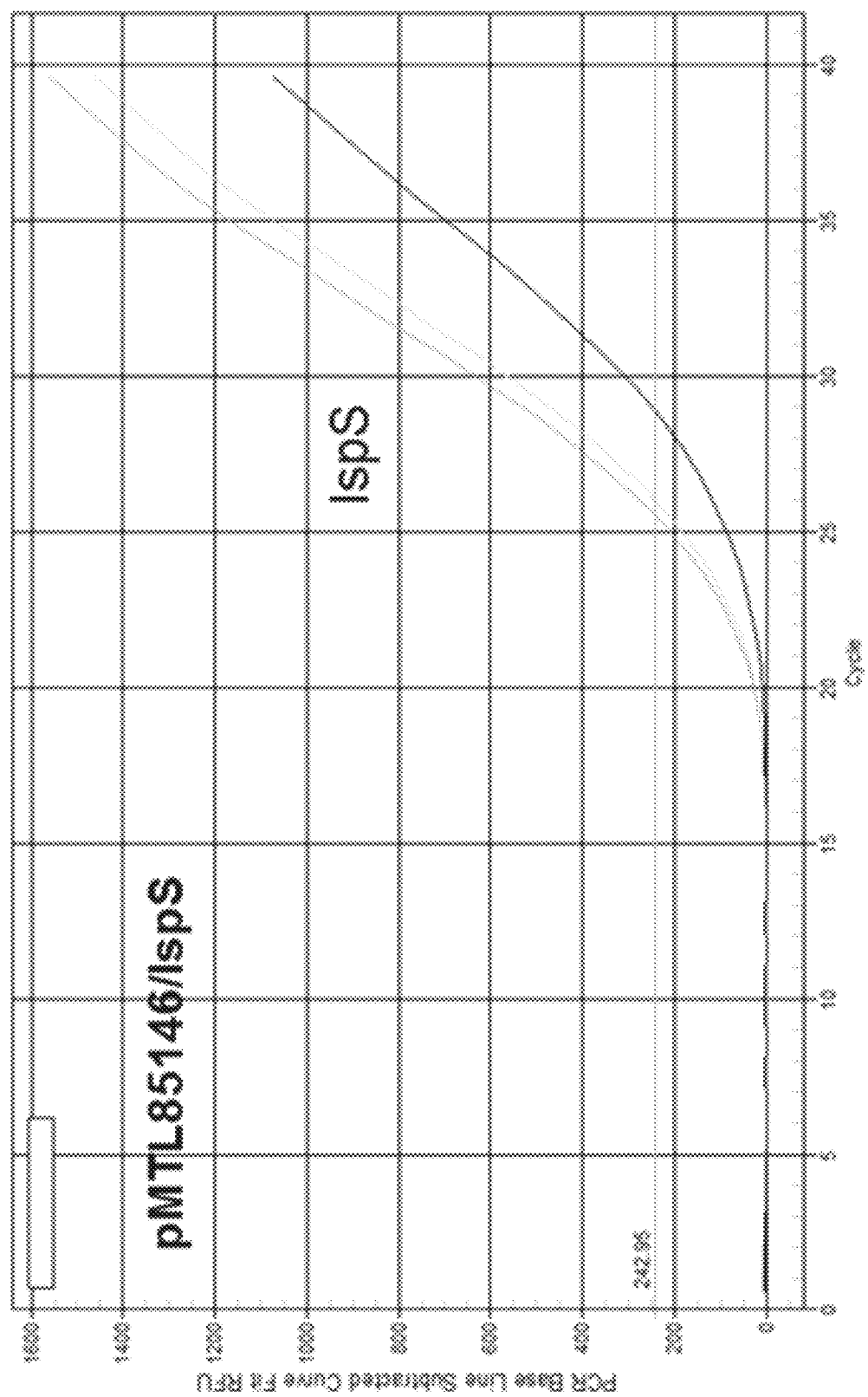

The isoprene expression plasmid without the mevalonate pathway was created by ligating the isoprene synthase (ispS) flanked by restriction sites AgeI and NheI to the previously created farnesene plasmid, pMTL 8314-Prnf-MK-PMK-PMD-Pfor-idi-ispA-FS (SEQ ID NO:91) to result in plasmid pMTL8314-Prnf-MK-PMK-PMD-Pfor-idi-ispS (SEQ ID NO:84). The final isoprene expression plasmid, pMTL 8314-Pptaack-th1A-HMGS-Patp-HMGR-Prnf-MK-PMK-PMD-Pfor-idi-ispS (SEQ ID NO: 58, FIG. 10) is created by ligating the 4630 bp fragment of Pptaack-th1A-HMGS-Patp-HMGR from pMTL8215-Pptaack-th1A-HMGS-Patp-HMGR (SEQ ID NO: 50) with pMTL 8314-Prnf-MK-PMK-PMD-Pfor-idi-ispS (SEQ ID NO: 84) using restriction sites NotI and XbaI.

TABLE 5

Sequences of isoprene expression plasmid from mevalonate pathway

| Description | Source | SEQ ID NO: |
|---|---|---|
| Mevalonate kinase (MK) | *Staphylococcus aureus* subsp. *aureus* Mu50; NC_002758.2; region: 665080 . . . 665919; including GI: 15923580 | 51 |
| Phosphomevalonate kinase (PMK) | *Staphylococcus aureus* subsp. *aureus* Mu50; NC_002758.2; region: 666920 . . . 667996; including GI: 15923582 | 52 |
| Mevalonate diphosphate decarboxylase (PMD) | *Staphylococcus aureus* subsp. *aureus* Mu50; NC_002758.2; region: 665924 . . . 666907; including GI: 15923581 | 53 |
| Isoprene synthase (isIS) | isoprene synthase of *Poplar tremuloides* (AAQ16588.1; GI:33358229) | 21 |
| Isopentenyl-diphosphate delta-isomerase (idi) | *Clostridium beijerinckii* NCIMB 8052; YP_001310174.1; region: complement(3597793..3598308); including GI: 150017920 | 54 |
| RNF Complex promoter ($P_{rnf}$) | *Clostridium autoethanogenum* DSM10061 | 55 |

Example 5—Introduction of Farnesene Synthase in *C. autoethanogenum* for Production of Farnesene from CO Via the Mevalonate Pathway Instead of producing isoprene directly from terpenoid key intermediates IPP and DMAPP then using this to synthesise longer chain terpenes, it is also possible to synthesise longer chain terpenes, such as C10 Monoterpenoids or C15 Sesquiterpenoids, directly via a geranyltransferase (see Table 6). From C15 Sesquiterpenoid building block farnesyl-PP it is possible to produce farnesene, which, similarly to ethanol, can be used as a transportation fuel.

Construction of Farnesene Expression Plasmid

The two genes required for farnesene synthesis from IPP and DMAPP via the mevalonate pathway, i.e., geranyltranstransferase (ispA) and alpha-farnesene synthase (FS) were codon-optimised. Geranyltranstransferase (ispA) was obtained from *Escherichia coli* str. K-12 substr. MG1655 and alpha-farnesene synthase (FS) was obtained from *Malus×domestica*. All DNA sequences used are given in Table 6. The codon-optimised idi was amplified from the synthesised plasmid pMTL83245-Pfor-FS-idi (SEQ ID NO: 85) with via the mevalonate pathways idi_F (SEQ ID NO: 86: AGGCACTCGAGATGGCAGAGTATATAATAGCA-GTAG) and idi_R2 (SEQ ID NO:87: AGGCGC-AAGCTTGGCGCACCGGTTTATTTAAATATCTTAT-TTTCAGC). The amplified gene was then cloned into plasmid pMTL83245-Pfor with XhoI and HindIII to produce plasmid pMTL83245-Pfor-idi (SEQ ID NO: 88). This resulting plasmid and the 1754 bp codon optimised fragment of farnesene synthase (FS) was subsequently digested with HindIII and NheI. A ligation was performed resulting in plasmid pMTL83245-Pfor-idi-FS (SEQ ID NO: 89). The 946 bp fragment of ispA and pMTL83245-Pfor-idi-FS was subsequently digested with AgeI and HindIII and ligated to create the resulting plasmid pMTL83245-Pfor-idi-ispA-FS (SEQ ID NO: 90). The farnesene expression plasmid without the upper mevalonate pathway was created by ligating the 2516 bp fragment of Pfor-idi-ispA-FS from pMTL83245-Pfor-idi-ispA-FS to pMTL 8314-Prnf-MK-PMK-PMD to result in plasmid pMTL 8314-Prnf-MK-PMK-PMD-Pfor-idi-ispA-FS (SEQ ID NO: 91). The final farnesene expression plasmid pMTL83145-th1A-HMGS-Patp-HMGR-Prnf-MK-PMK-PMD-Pfor-idi-ispA-FS (SEQ ID NO: 59 and FIG. 18) is created by ligating the 4630 bp fragment of Pptaack-th1A-HMGS-Patp-HMGR from pMTL8215-Pptaack-th1A-HMGS-Patp-HMGR (SEQ ID NO: 50) with pMTL 8314-Prnf-MK-PMK-PMD-Pfor-idi-ispA-FS (SEQ ID NO: 91) using restriction sites NotI and XbaI.

TABLE 6

Sequences of farnesene expression plasmid from mevalonate pathway

| Description | Source | SEQ ID NO: |
|---|---|---|
| Geranyltransferase (ispA) | Escherichia coli str. K-12 substr. MG1655; NC_000913.2; region: complement(439426 . . . 440325); including GI: 16128406 | 56 |
| Alpha-farnesene synthase (FS) | Malus x domestica: AY787633.1; GF60418690 | 57 |

Figure 16:
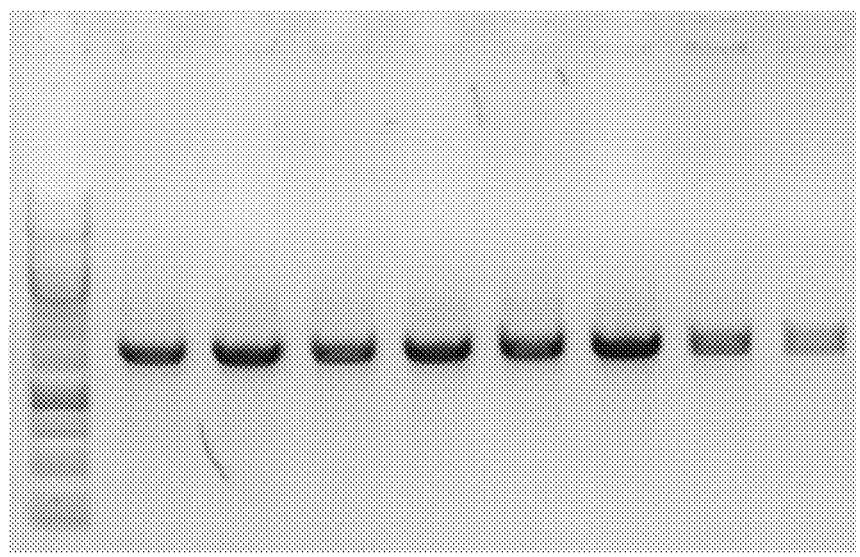

Transformation into C. autoethanogenum
Transformation and expression in C. autoethanogenum was carried out as described in example 1.
Confirmation of Successful Transformation
The presence of pMTL8314-Prnf-MK-PMK-PMD-Pfor-idi-ispA-FS (SEQ ID NO: 59) was confirmed by colony PCR using oligonucleotides repHF (SEQ ID NO: 92:AAGAAGGGCGTATATGAAAACTTGT) andcatR (SEQ ID NO: 93: TTCGTTTA-CAAAACGGCAAATGTGA) which selectively amplifies a portion of the garm+ve perplicon and most of the cat gene on the pMTL83 lxxx series plasmids. Yielding a band of 1584 bp (FIG. 16).
Expression of Lower Mevalonate Pathway in C. autoethanogenum
Confirmation of expression of the lower mevalonate pathway genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi; SEQ ID NO: 54), Geranyltranstransferase (ispA; SEQ ID NO: 56) and Farnesene synthase (FS SEQ ID NO: 57) was done as described above in example 1. Using oligonucleotides listed in table 7.

TABLE 7

List of oligonucleotides used for the detection of expression of the genes in the lower mevalonate pathway carried on plasmid pMTL8314Prnf-MK-PMK-PMD-Pfor-idi-ispA-FS (SEQ ID NO: 91)

| Target | Oligonucleotide Name | DNA Sequence (5' to 3') | SEQ ID NO: |
|---|---|---|---|
| Mevalonate kinase | MK-RTPCR-F | GTGCTGGTAGAGGTGGTTCA | 94 |
|  | MK-RTPCR-R | CCAAGTATGTGCTGCACCAG | 95 |
| Phosphomevalonate Kinase | PMK-RTPCR-F | ATATCAGACCCACACGCAGC | 96 |
|  | PMK-RTPCR-R | AATGCTTCATTGCTATGTCACATG | 97 |
| Mevalonate Diphosphate Decarboxylase | PMD-RTPCR-F | GCAGAAGCAAAGGCAGCAAT | 98 |
|  | PMD-RTPCR-R | TTGATCCAAGATTTGTAGCATGC | 99 |
| Isopentyl-diphosphate Delta-isomerase | idi-RTPCR-F | GGACAAACACTTGTTGTAGTCACC | 100 |
|  | idi-RTPCR-R | TCAAGTTCGCAAGTAAATCCCA | 101 |
| Geranyltranstransferase | ispA-RTPCR-F | ACCAGCAATGGATGACGATG | 102 |
|  | ispA-RTPCR-R | AGTTTGTAAAGCGTCACCTGC | 103 |
| Farnesene synthase | FS-RTPCR-F | AAGCTAGTAGATGGTGGGCT | 104 |
|  | FS-RTPCR-R | AATGCTACACCTACTGCGCA | 105 |

Figure 18:
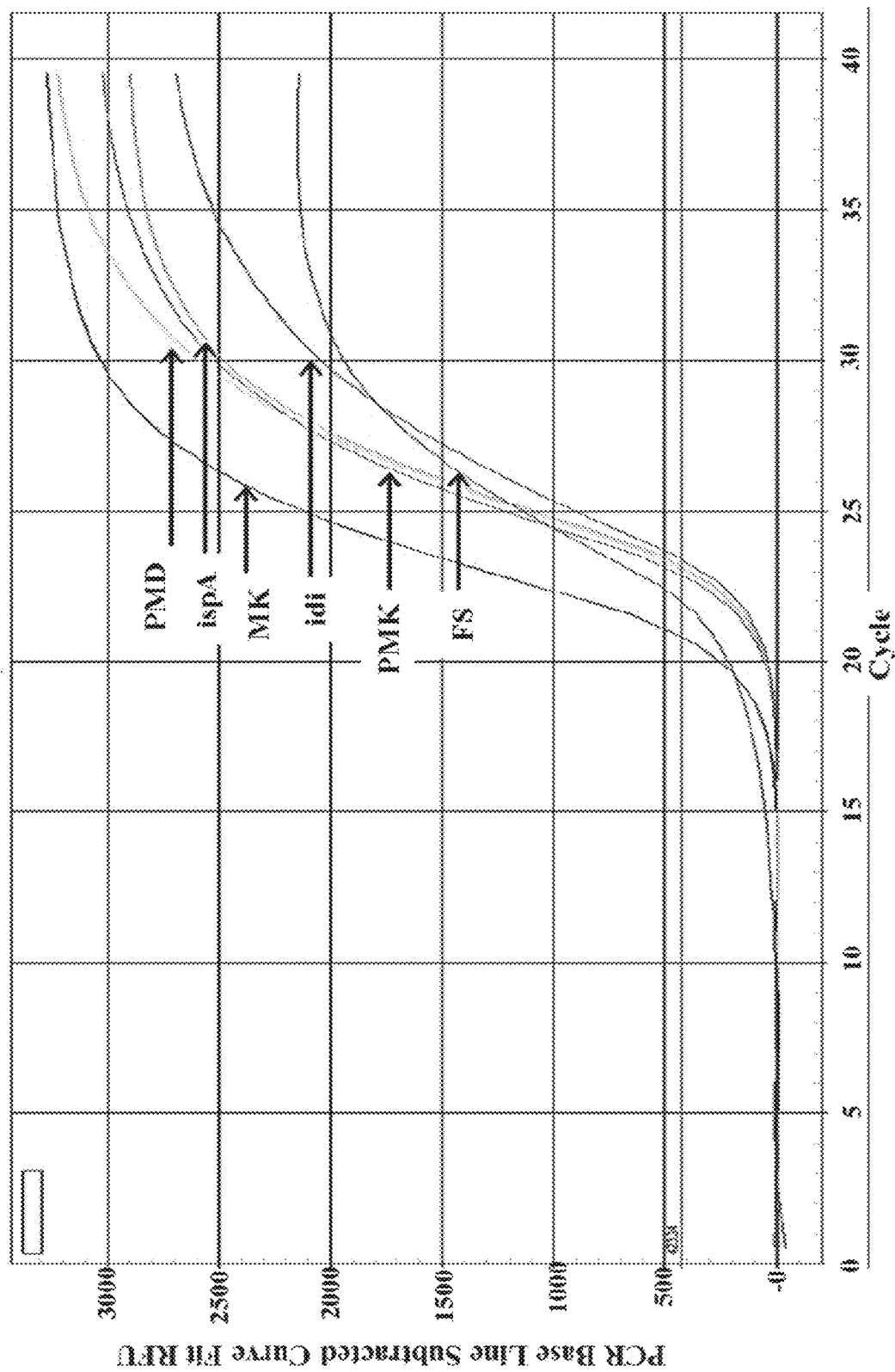
FIG. 18—RT-PRC data showing the expression of the genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi SEQ ID NO: 54), Geranyltranstransferase (ispA SEQ ID NO: 56) and Farnesene synthase (FS SEQ ID NO: 57).

Rt-PCR data confirming expression of all genes in the lower mevalonate pathway is shown in FIG. 18, this data is also summarised in Table 8.

TABLE 8

Average CT values for the genes genes Mevalonate kinase (MK SEQ ID NO: 51), Phosphomevalonate Kinase (PMK SEQ ID NO: 52), Mevalonate Diphosphate Decarboxylase (PMD SEQ ID NO: 53), Isopentyl-diphosphate Delta-isomerase (idi SEQ ID NO: 54), Geranyltranstransferase (ispA SEQ ID NO: 56) and Farnesene synthase (FS SEQ ID NO: 57). for two independent samples taken from the two starter cultures for the mevalonate feeding experiment (see below).

| Gene | Sample 1 (Ct Mean) | Sample 2 (Ct Mean) |
| --- | --- | --- |
| MK | 21.9 | 20.82 |
| PMK | 23.64 | 22.81 |
| PMD | 24 | 22.83 |
| Idi | 24.23 | 27.54 |
| ispA | 23.92 | 23.22 |
| FS | 21.28 | 21.95 |
|  | (single Ct) | (single Ct) |
| HK (rho) | 31.5 | 28.88 |

Production of Alpha-Farnesene from Mevalonate

Figure 17:
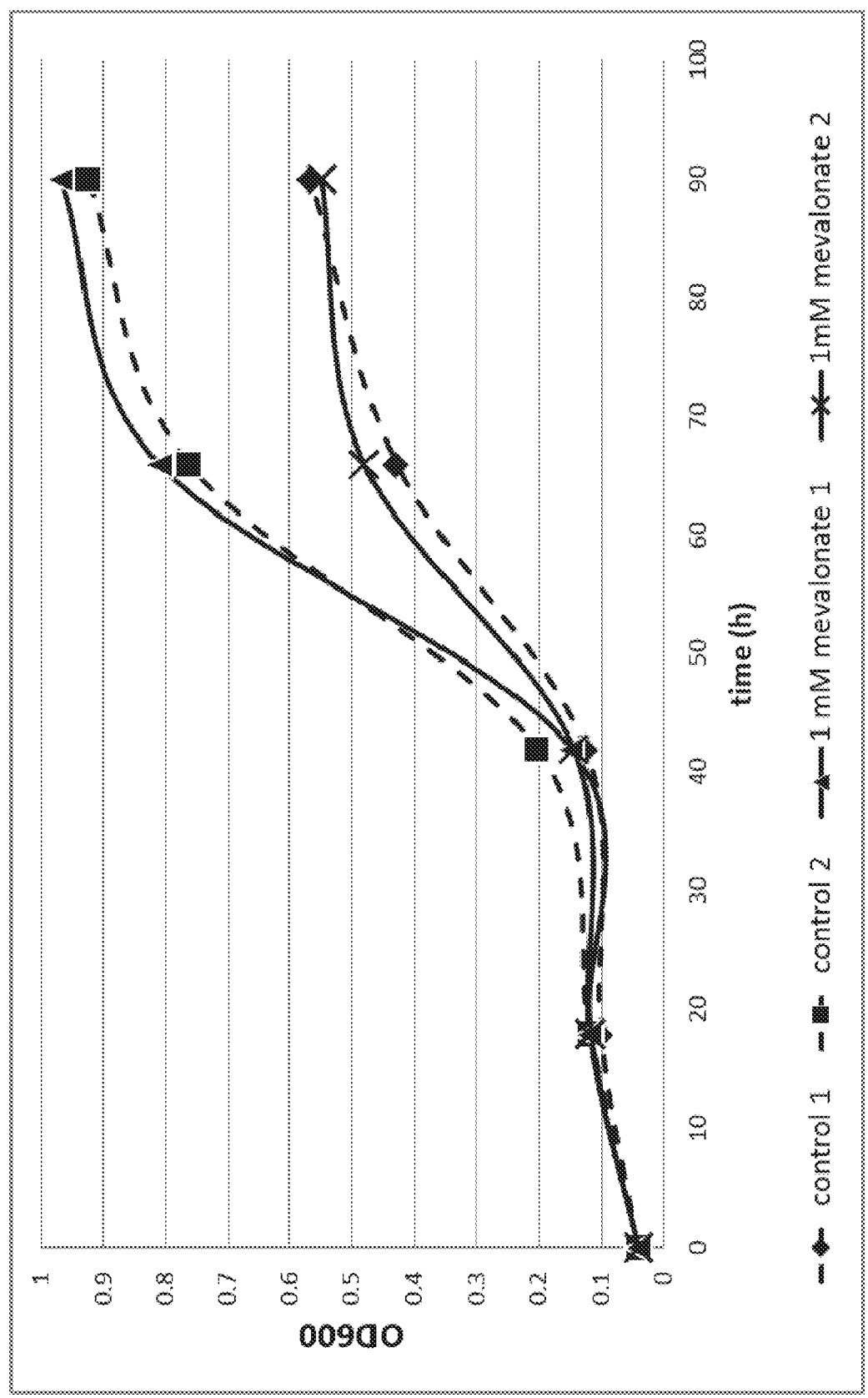
FIG. 17—Growth curve for transformed *C. autoethanogenum* carrying plasmid pMTL8314Prnf-MK-PMK-PMD-Pfor-idi-ispA-FS.
Figure 19:
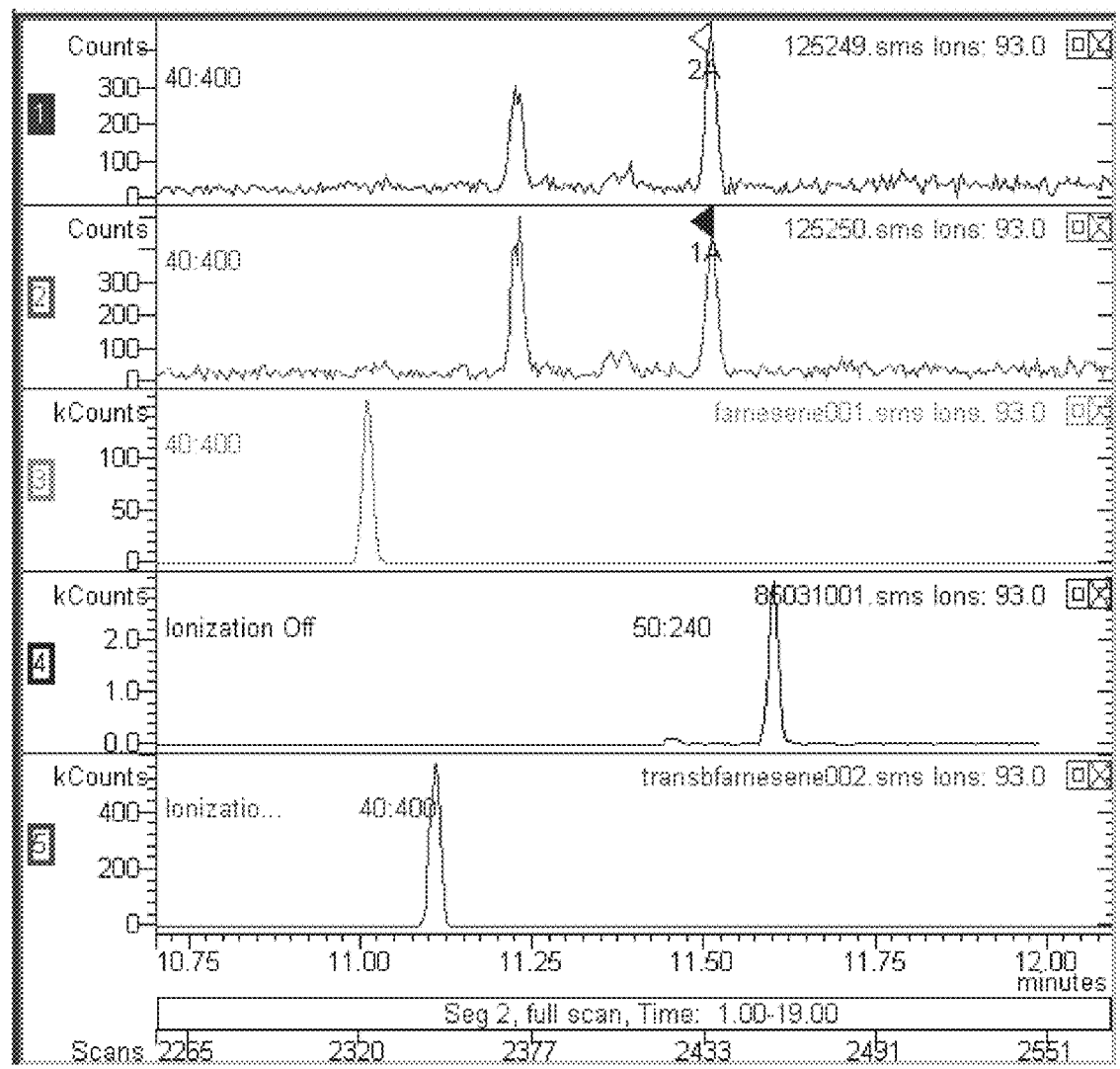
FIG. 19—GC-MS detection and conformation of the presence of farnesene in 1 mM mevalonate spiked cultures carrying pMTL8314Prnf-MK-PMK-PMD-Pfor-idi-ispA-FS. GC-MS chromatogram scanned for peaks containing ions with a mass of 93. Chromatogram 1 and 2 are transformed *C. autoethanogenum,* 3 is beta-farnesene standard run at the same time as the *C. autoethanogenum* samples. 4 is *E. coli* carrying the plasmids pMTL8314Prnf-MK-PMK-PMD-Pfor-idi-ispA-FS grown on M9 Glucose showing alpha-farnesene production and 5 is beta-farnesene standard run at the time of the *E. coli* samples. The difference in retention time between the *E. coli* and the *C. autoethanogenum* samples are due to minor changes to the instrument. However, the difference in retention time between the beta-farnesene standard and the produced alpha-farnesene are the exact same in both cases, which together with the match in mass spectra's confirm the production of alpha-farnesene in *C. autoethanogenum.*
Figure 20:
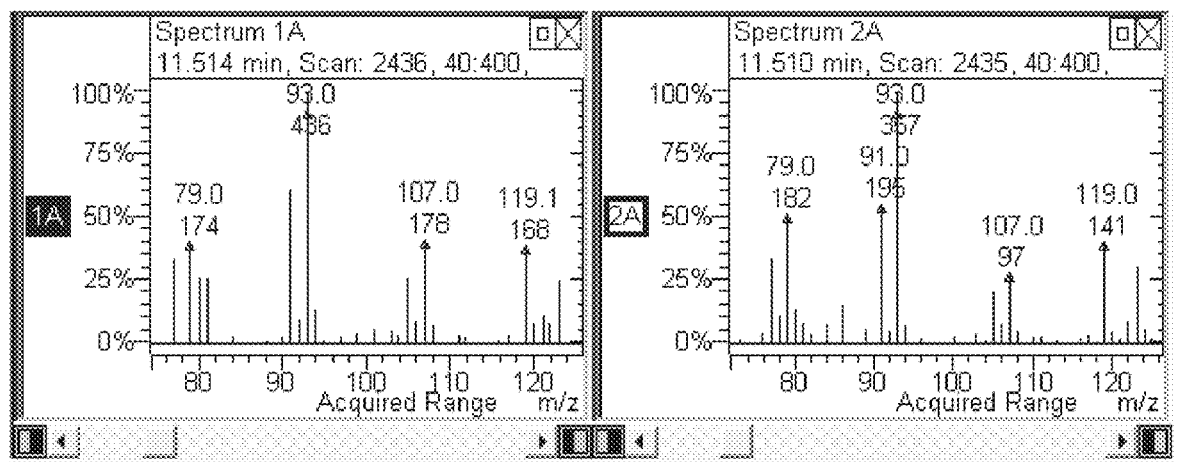
FIG. 20—MS spectrums for peaks labeled 1A and 2A in FIG. 19. The MS spectra's matches up with the NIST database spectra (FIG. 21) confirming the peak is alpha-farnesene.
Figure 21:
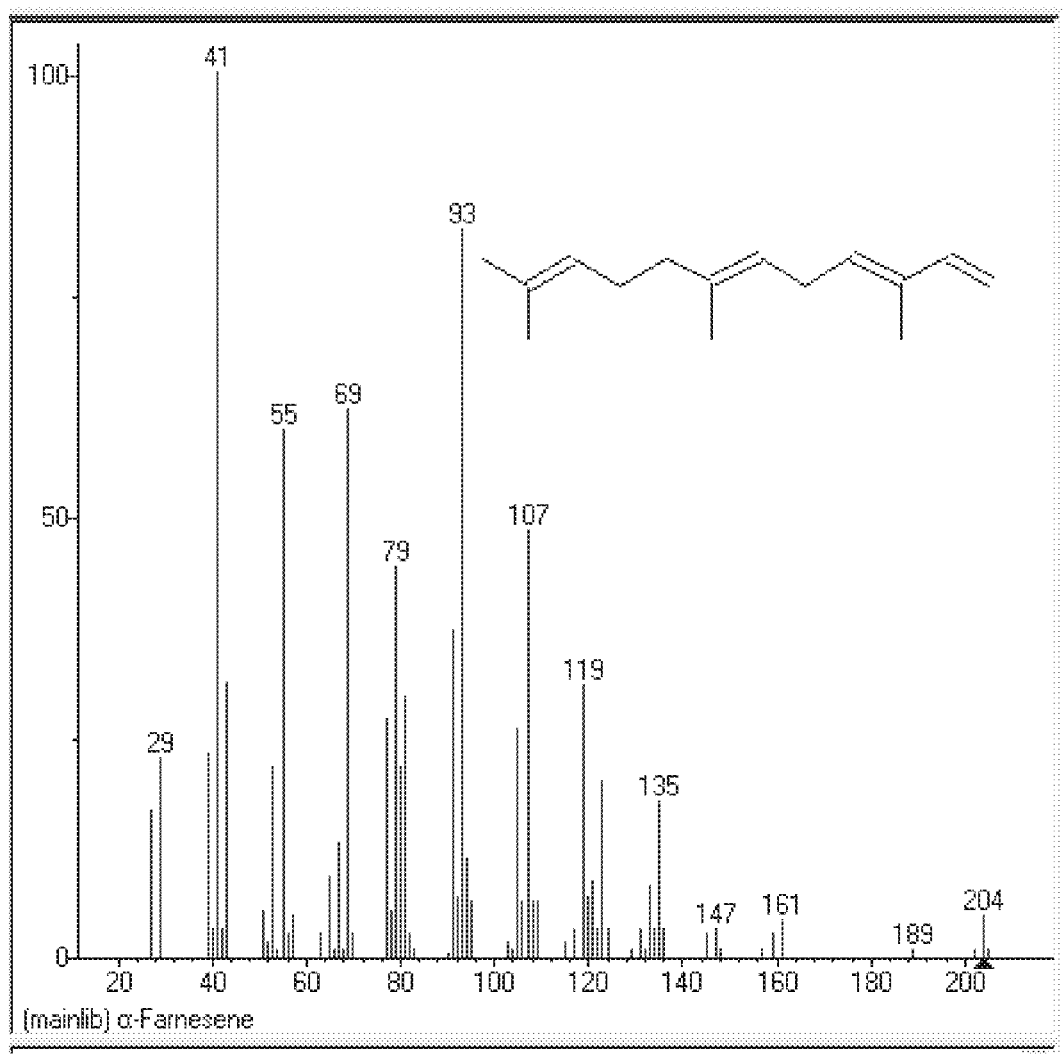
FIG. 21—MS spectrum for alpha-farnesene from the NIST Mass Spectral Database.

After conformation of successfully transformed of the plasmid pMTL8314-Prnf-MK-PMK-PMD-Pfor-idi-ispA-FS, a growth experiment was carried out in 50 ml PETC media (Table 1) in 250 ml serum bottles with 30 psi Real Mill Gas (collected from New Zealand Steel site in Glenbrook, NZ; composition: 44% CO, 32% $N_2$, 22% $CO_2$, 2% $H_2$) as sole energy and carbon source. All cultures were incubated at 37° C. on an orbital shaker adapted to hold serum bottles. Transformants were first grown up to an OD600 of ~0.4 before being subcultured into fresh media supplemented with 1 mM mevalonic acid. Controls without mevalonic acid were set up at the same time from the same culture. Samples for GC-MS (Gas Chromatography—Mass Spectroscopy) were taken at each time point. FIG. 17 shows a representative growth curve for 2 control cultures and two cultures fed 1 mM mevalonate. Farnesene was detected in the samples taken at 66 h and 90 h after start of experiment (FIGS. 19-21).

Detection of Alpha-Farnesene by Gas Chromatography—Mass Spectroscopy

For GC-MS detection of alpha-farnesene hexane extraction was performed on 5 ml of culture by adding 2 ml hexane and shaking vigorously to mix in a sealed glass balch tube. The tubes were then incubated in a sonicating water bath for 5 min to encourage phase separation. 400 μl hexane extract were transferred to a GC vail and loaded on to the auto loader. The samples was analysed on a VARIAN GC3800 MS4000 iontrap GC/MS (Varian Inc, CA, USA. Now Agilent Technologies) with a EC-1000 column 0.25 μm film thickness (Grace Davidson, OR, USA) Varian MS workstation (Varian Inc, Ca. Now Agilent Technologies, CA, USA) and NIST MS Search 2.0 (Agilent Technologies, CA, USA). Injection volume of 1 μl with Helium carrier gas flow rate of 1 ml per min.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to."

The invention claimed is:

1. A method for producing isoprene by providing at least one C1 compound selected from the group consisting of carbon monoxide and carbon dioxide into contact with a recombinant C1-fixing microorganism comprising a nucleic acid encoding a group of exogenous enzymes comprising thiolase, 3-hydroxy-3-methylglutaryl coenzyme A (HMG-CoA) synthase, and HMG-CoA reductase, mevalonate kinase, phosphomevalonate kinase, mevalonate diphosphate decarboxylase, isopentenyl-diphosphate delta-isomerase, and isoprene synthase, wherein the microorganism is *Clostridium* or *Moorella*, to allow the microorganism to produce isoprene from the C1 compound, and converting the isoprene into synthetic rubber tires.

2. The method according to claim 1, wherein the microorganism is provided with a gas comprising hydrogen.

* * * * *